US011970539B2

(12) United States Patent
Macoin et al.

(10) Patent No.: US 11,970,539 B2
(45) Date of Patent: Apr. 30, 2024

(54) ANTIBODIES THAT BIND TO IL1RAP AND USES THEREOF

(71) Applicant: Ichnos Sciences SA, La Chaux-de-Fonds (CH)

(72) Inventors: Julie Macoin, La Chaux-de-Fonds (CH); Amelie Croset, La Chaux-de-Fonds (CH); Jeremy Loyau, La Chaux-de-Fonds (CH); Thierry Monney, La Chaux-de-Fonds (CH); Lamine Mbow, La Chaux-de-Fonds (CH); Marie-Agnes Doucey, La Chaux-de-Fonds (CH); Valentina Labanca, La Chaux-de-Fonds (CH)

(73) Assignee: Ichnos Sciences SA, La Chaux-de-Fonds (CH)

( * ) Notice: Subject to any disclaimer, the term of this patent is extended or adjusted under 35 U.S.C. 154(b) by 0 days.

(21) Appl. No.: 17/474,837

(22) Filed: Sep. 14, 2021

(65) Prior Publication Data

US 2022/0089754 A1 Mar. 24, 2022

(30) Foreign Application Priority Data

| Sep. 14, 2020 | (EP) | 20195961 |
| Jan. 12, 2021 | (EP) | 21151218 |
| Feb. 26, 2021 | (EP) | 21159485 |
| Jun. 16, 2021 | (EP) | 21179711 |

(51) Int. Cl.
*C07K 16/28* (2006.01)
*A61P 29/00* (2006.01)

(52) U.S. Cl.
CPC .......... *C07K 16/2866* (2013.01); *A61P 29/00* (2018.01); *C07K 2317/31* (2013.01); *C07K 2317/33* (2013.01); *C07K 2317/565* (2013.01); *C07K 2317/92* (2013.01)

(58) Field of Classification Search
CPC ............ C07K 16/2866; C07K 2317/31; C07K 2317/33; C07K 2317/565; C07K 2317/92; C07K 2317/76; A61P 29/00
See application file for complete search history.

(56) References Cited

U.S. PATENT DOCUMENTS

| 4,676,980 A | 6/1987 | Segal et al. |
| 4,816,567 A | 3/1989 | Cabilly et al. |
| 5,500,362 A | 3/1996 | Robinson et al. |
| 5,571,894 A | 11/1996 | Wels et al. |
| 5,587,458 A | 12/1996 | King et al. |
| 5,595,756 A * | 1/1997 | Bally .................. A61K 9/1272 264/4.1 |
| 5,624,821 A | 4/1997 | Winter et al. |
| 5,648,260 A | 7/1997 | Winter et al. |
| 5,770,429 A | 6/1998 | Lonberg et al. |
| 5,821,337 A | 10/1998 | Carter et al. |
| 5,869,046 A | 2/1999 | Presta et al. |
| 5,959,177 A | 9/1999 | Hein et al. |
| 6,040,498 A | 3/2000 | Stomp et al. |
| 6,075,181 A | 6/2000 | Kucherlapati et al. |
| 6,150,584 A | 11/2000 | Kucherlapati et al. |
| 6,171,586 B1 | 1/2001 | Lam et al. |
| 6,194,551 B1 | 2/2001 | Idusogie et al. |
| 6,248,516 B1 | 6/2001 | Winter et al. |
| 6,267,958 B1 | 7/2001 | Andya et al. |
| 6,420,548 B1 | 7/2002 | Vezina et al. |
| 6,737,056 B1 | 5/2004 | Presta |
| 6,982,321 B2 | 1/2006 | Winter |
| 7,041,870 B2 | 5/2006 | Tomizuka et al. |
| 7,087,409 B2 | 8/2006 | Barbas, III et al. |
| 7,125,978 B1 | 10/2006 | Vezina et al. |
| 7,189,826 B2 | 3/2007 | Rodman |
| 7,332,581 B2 | 2/2008 | Presta |
| 7,521,541 B2 | 4/2009 | Eigenbrot et al. |
| 7,527,791 B2 | 5/2009 | Adams et al. |
| 7,658,921 B2 | 2/2010 | Dall'Acqua et al. |
| 8,664,475 B2 * | 3/2014 | Puzio .................. C07K 14/415 800/278 |
| 2002/0164328 A1 | 11/2002 | Shinkawa et al. |
| 2003/0115614 A1 | 6/2003 | Kanda et al. |
| 2003/0157108 A1 | 8/2003 | Presta |
| 2004/0093621 A1 | 5/2004 | Shitara et al. |
| 2004/0109865 A1 | 6/2004 | Niwa et al. |
| 2004/0110282 A1 | 6/2004 | Kanda et al. |
| 2004/0110704 A1 | 6/2004 | Yamane et al. |

(Continued)

FOREIGN PATENT DOCUMENTS

| EP | 0404097 B1 | 9/1996 |
| WO | WO-9301161 A1 | 1/1993 |

(Continued)

OTHER PUBLICATIONS

Heppner et al., Tumor heterogeneity: biological implications and therapeutic consequences, 1983, Cancer Metastasis Reviews 2: 5-23 (Year: 1983).*
Wang et al., Structural insights into the assembly and activation of IL-1beta with its receptors, 2010, Nature Immunology, 11: 905-912 (Year: 2010).*
Merriam-Webster.com, 2023, pp. 1 (Year: 2023).*
MaineHealth.org, Orthopedic Surgery, pp. 1-3 (Year: 2023).*
Lazar et al., Mol. Cell. Biol., 8:1247-1252, 1988 (Year: 1988).*
Bowie et al., Science, 1990, 247:1306-1310 (Year: 1990).*
Burgess et al., J. Cell Biol. 111:2129-2138, 1990 (Year: 1990).*
Jain RK, Barriers to Drug Delivery in Solid Tumors, 1994, Scientific American, pp. 58-645 (Year: 1994).*
MacCallum et al., 1996, J. Mol. Biol. 262: 732-745 (Year: 1996).*
Gura T, Systems for Identifying New Drugs are Often Faulty, Science, 1997, 278(5340): 1041-1042 (Year: 1997).*

(Continued)

*Primary Examiner* — Vanessa L. Ford
*Assistant Examiner* — Danaya L Middleton
(74) *Attorney, Agent, or Firm* — Sterne, Kessler, Goldstein & Fox P.L.L.C.

(57) ABSTRACT

The present invention relates to antibodies which specifically bind to human IL1RAP and may also bind to cynomolgus monkey and/or mouse IL1RAP. The present invention also relates to the use of such antibodies to diagnose and treat human disease.

11 Claims, 29 Drawing Sheets

Specification includes a Sequence Listing.

(56) References Cited

U.S. PATENT DOCUMENTS

| | | |
|---|---|---|
| 2004/0132140 A1 | 7/2004 | Satoh et al. |
| 2005/0014934 A1 | 1/2005 | Hinton et al. |
| 2005/0260186 A1 | 11/2005 | Bookbinder et al. |
| 2006/0104968 A1 | 5/2006 | Bookbinder et al. |
| 2007/0061900 A1 | 3/2007 | Murphy et al. |

FOREIGN PATENT DOCUMENTS

| | | | |
|---|---|---|---|
| WO | WO-9316185 A2 | 8/1993 | |
| WO | WO-9429351 A2 | 12/1994 | |
| WO | WO-9951642 A1 | 10/1999 | |
| WO | WO-0061739 A1 | 10/2000 | |
| WO | WO-0129246 A1 | 4/2001 | |
| WO | WO-0231140 A1 | 4/2002 | |
| WO | WO-03084570 A1 | 10/2003 | |
| WO | WO-03085107 A1 | 10/2003 | |
| WO | WO-03085119 A1 | 10/2003 | |
| WO | WO-2004056312 A2 | 7/2004 | |
| WO | WO-2005012359 A2 | 2/2005 | |
| WO | WO-2005035586 A1 | 4/2005 | |
| WO | WO-2005035778 A1 | 4/2005 | |
| WO | WO-2005053742 A1 | 6/2005 | |
| WO | WO-2005063816 A2 | 7/2005 | |
| WO | WO-2005100402 A1 | 10/2005 | |
| WO | WO-2006029879 A2 | 3/2006 | |
| WO | WO-2006044908 A2 | 4/2006 | |
| WO | WO-2007048037 A2 | 4/2007 | |
| WO | WO-2007059782 A1 | 5/2007 | |
| WO | WO-2008077546 A1 | 7/2008 | |
| WO | WO-2008145137 A2 | 12/2008 | |
| WO | WO-2008145138 A1 | 12/2008 | |
| WO | WO-2009089004 A1 | 7/2009 | |
| WO | WO-2012098407 A1 | 7/2012 | |
| WO | WO-2012131555 A2 | 10/2012 | |
| WO | WO-2014100772 A1 | 6/2014 | |
| WO | WO-2015132602 A1 * | 9/2015 | ........... A61K 39/395 |
| WO | WO-2016020502 A1 | 2/2016 | |
| WO | WO-2016207304 A2 | 12/2016 | |
| WO | WO-2017079121 A2 | 5/2017 | |
| WO | WO-2017191325 A9 | 1/2018 | |
| WO | WO-2018071910 A2 | 4/2018 | |
| WO | WO-2018231827 A1 | 12/2018 | |
| WO | WO-2019028190 A1 | 2/2019 | |
| WO | WO-2019175359 A1 | 9/2019 | |
| WO | WO-2020035577 A1 | 2/2020 | |
| WO | WO-2020037154 A1 | 2/2020 | |
| WO | WO-2022053715 A1 | 3/2022 | |

OTHER PUBLICATIONS

Greenspan et al. 1999 Defining epitopes: It's not as easy as it seems; Nature Biotechnology, 17:936-937 (Year: 1999).*
Bork. Powers and Pitfalls in Sequence Analysis: The 70% Hurdle. Genome Research, 2000, 10:398-400 (Year: 2000).*
Sporn et al. Chemoprevention of Cancer, Carcinogenesis, vol. 21 (2000), 525-530 (Year: 2000).*
Auerbach et al, Angiogenesis assays: Problems and pitfalls, Cancer and Metastasis Reviews, 2000, 19: 167-172 (Year: 2000).*
Vajdos et al., 2002, J. Mol. Biol. 320: 415-428 (Year: 2002).*
Paul, Fundamental Immunology, 2003, 5th Edition, Raven Press, New York, Chapter 3, pp. 109-147 (Year: 2003).*
Casset et al., 2003, Biochemical and Biophysical Research Communications 307:198-205 (Year: 2003).*
Hait., Anticancer drug development: the grand challenges, Nature Reviews/Drug Discovery, 2010, 9, pp. 253-254 (Year: 2010).*
Sela-Culang et al., 2013, Frontiers in Immunology 4(302): 1-13 (Year: 2013).*
Gravanis et al., The changing world of cancer drug development: the regulatory bodies' perspective, Chin Clin Oncol, 2014, 3, pp. 1-5 (Year: 2014).*
Beans, Targeting metastasis to halt cancer's spread, PNAS 2018; 115(50): 12539-12543 (Year: 2018).*

Almagro, J. C., and Fransson, J., "Humanization of antibodies," *Frontiers in Bioscience* 13:1619-1633, Frontiers In Bioscience Publications, United States (Jan. 2008).
Baca, M., et al., "Antibody Humanization Using Monovalent Phage Display," *The Journal of Biological Chemistry* 272(16):10678-10684, American Society for Biochemistry and Molecular Biology, United States (1997).
Binz, H. K., et al., "Engineering novel binding proteins from nonimmunoglobulin domains," *Nature Biotechnology* 23(10):1257-1268, Nature America Publishing, United Kingdom (Oct. 2005).
Boerner, P., et al., "Production of Antigen-specific Human Monoclonal Antibodies from in Vitro-primed Human Splenocytes," *Journal of Immunology* 147(1):86-95, The American Association of Immunologists, United States (Jul. 1991).
Brennan, M., et al., "Preparation of Bispecific Antibodies by Chemical Recombination of Monoclonal Immunoglobulin G1 Fragments," *Science* 229(4708):81-83, American Association for the Advancement of Science, United States (Jul. 1985).
Brodeur, B. R., et al., "Mouse-Human Myeloma Partners for the Production of Heterohybridomas," in *Monoclonal Antibody Production Techniques and Applications*, Schook, L. B., ed., pp. 51-63, Marcel Dekker, Inc., United States (1987).
Bruggemann, M., et al., "Comparison of the effector functions of human immunoglobulins using a matched set of chimeric antibodies," *The Journal of Experimental Medicine* 166(5): 1351-1361, Rockefeller University Press, United States (Nov. 1987).
Capel, P. J., et al., "Heterogeneity of human IgG Fc receptors," *Immunomethods* 4(1):25-34, Academic Press, United States (Feb. 1994).
Carter, P., et al., "Humanization of an anti-p185HER2 antibody for human cancer therapy," *Proc Natl Acad Sci USA* 89(10):4285-4289, National Academy of Sciences, United States (May 1992).
Chothia, C., and Lesk, A. M., "Canonical Structures for the Hypervariable Regions of Immunoglobulins," *Journal of Molecular Biology* 196(4):901-917, Elsevier Science, United States (Aug. 1987).
Chothia, C., et al., "Conformations of Immunoglobulin Hypervariable Regions," *Nature* 342(6252):877-883, Nature Publishing Group, United Kingdom (Dec. 1989).
Chowdhury, P. S., "Engineering hot spots for affinity enhancement of antibodies," *Methods in Molecular Biology* 207:179-196, Welschof, M., and Krauss, J., eds., Humana Press, United States (2003).
Clackson, T., et al., "Making antibody fragments using phage display libraries," *Nature* 352(6336):624-628, Nature Publishing Group, United Kingdom (Aug. 1991).
Clynes, R., et al., "Fc receptors are required in passive and active immunity to melanoma," *Proc Natl Acad Sci USA* 95(2):652-656, National Academy of Sciences, United States (Jan. 1998).
Cragg, M. S., and Glennie, M. J., "Antibody specificity controls in vivo effector mechanisms of anti-CD20 reagents," Blood 103(7):2738-2743, Elsevier, United States (Apr. 2004).
Cragg, M. S., et al., "Complement-mediated lysis by anti-CD20 mAb correlates with segregation into lipid rafts," *Blood* 101(3):1045-1052, American Society of Hematology, United States (Feb. 2003).
Cunningham, B. C., and Wells, J. A., "High-resolution epitope mapping of hGH-receptor interactions by alanine-scanning mutagenesis," *Science* 244(4908):1081-1085, American Association for the Advancement of Science, United States (Jun. 1989).
Daeron, M., "Fc receptor biology," *Annual Review of Immunology* 15:203-234, Annual Reviews Inc., United States (1997).
Dall'Acqua, W. F., et al., "Antibody humanization by framework shuffling," *Methods* 36(1):43-60, Academic Press, United States (2005).
Fellouse F. A., et al., "Synthetic antibodies from a four-amino-acid code: a dominant role for tyrosine in antigen recognition," *Proc Natl Acad Sci USA* 101(34):12467-12472, National Academy of Sciences, United States (Aug. 2004).
Fiedler, M., and Skerra, A., "Chapter 17: Non-Antibody Scaffolds as Alternative Therapeutic Agents," in *Handbook of Therapeutic Antibodies*, pp. 435-474, Dobel, S., and Reichert, J. M., eds., Wiley-VCH Verlag, Germany (Aug. 2014).
Flatman, S., et al., "Process analytics for purification of monoclonal antibodies," *J Chromatogr B Analyt Technol Biomed Life Sci* 848(1):79-87, Elsevier, Netherlands (Mar. 2007).

(56) References Cited

OTHER PUBLICATIONS

Garlanda, C., "The interleukin-1 family: back to the future," *Immunity* 39(6):1003-1018, Cell Press, United States (Dec. 2013).
Gazzano-Santoro, H., et al., "A non-radioactive complement-dependent cytotoxicity assay for anti-CD20 monoclonal antibody," *Journal of Immunological Methods* 202(2):163-171, Elsevier, Netherlands (Mar. 1997).
Gebauer, M., and Skerra, A., "Engineered protein scaffolds as next-generation antibody therapeutics," *Current Opinion in Chemical Biology* 13(3):245-255, Elsevier, United Kingdom (Jun. 2009).
GenBank, "interleukin-1 receptor accessory protein isoform X7 [Gallus gallus]," Accession No. XP_422719.4, accessed at URL:[https://www.ncbi.nlm.nih.gov/protein/XP_422719.4] on Dec. 27, 2021, 2 pages.
Gerngross, T. U., "Advances in the production of human therapeutic proteins in yeasts and filamentous fungi," *Nature Biotechnology* 22(11):1409-1414, Nature America Publishing, United States (Nov. 2004).
Graham, F. L., et al., "Characteristics of a human cell line transformed by DNA from human adenovirus type 5," *The Journal of General Virology* 36(1):59-72, Society For General Microbiology, United Kingdom (Jul. 1977).
Gruber, M., et al., "Efficient tumor cell lysis mediated by a bispecific single chain antibody expressed in *Escherichia coli*," *The Journal of Immunology* 152(11):5368-5374, The American Association of Immunologists, Inc., United States (Jun. 1994).
Guyer, R. L., et al., "Immunoglobulin binding by mouse intestinal epithelial cell receptors," *Journal of Immunology* 117(2):587-93, American Association of Immunologists, United States (Aug. 1976).
De Haas, M., et al., "Fc gamma receptors of phagocytes," The *Journal of Laboratory and Clinical Medicine* 126(4):330-341, Elsevier, United States (Oct. 1995).
Hellstrom, I., et al., "Strong antitumor activities of IgG3 antibodies to a human melanoma-associated ganglioside," *Proc Natl Acad Sci USA* 82(5):1499-1502, National Academy of Sciences, United States (Mar. 1985).
Hellstrom, I., et al., "Antitumor effects of L6, an IgG2a antibody that reacts with most human carcinomas," *Proc Natl Acad Sci USA* 83(18):7059-7063, National Academy of Sciences, United States (Sep. 1986).
Holliger, P., et al., "'Diabodies': small bivalent and bispecific antibody fragments," *Proc Natl Acad Sci USA* 90(14):6444-6448, National Academy of Sciences, United States (Jul. 1993).
Hoogenboom, H. R., "Overview of antibody phage-display technology and its applications," *Methods in Molecular Biology* 178:1-37, Humana Press, United States (2002).
Hudson, P. J., and Souriau, C., "Engineered antibodies," *Nature Medicine* 9(1):129-134, Nature Publishing Company, United States (Jan. 2003).
Idusogie, E. E., et al., "Mapping of the C1q binding site on rituxan, a chimeric antibody with a human IgG1 Fc," *The Journal of Immunology* 164(8):4178-4184, American Association of Immunologists, United States (Apr. 2000).
Kabat, E. A., et al., "Sequences of Proteins of Immunological Interest," 5th Edition, U.S. Department of Public Health and Human Services, Public Health Service, NIH publication No. 91-3242, National Institutes of Health, United States (1991).
Kanda, Y., et al., "Comparison of cell lines for stable production of fucose-negative antibodies with enhanced ADCC," *Biotechnol Bioeng* 94(4):680-688, Wiley, United States (Jul. 2006).
Kashmiri, S. V. S., et al., "SDR grafting—a new approach to antibody humanization," *Methods* 36(1):25-34, Academic Press, United States (May 2005).
Kim, J. K., et al., "Localization of the site of the murine IgG1 molecule that is involved in binding to the murine intestinal Fc receptor," *European Journal of Immunology* 24(10):2429-2434, Wiley-VCH, Germany (Oct. 1994).

Klimka, A., et al., "Human anti-CD30 recombinant antibodies by guided phage antibody selection using cell panning," *British Journal of Cancer* 83(2):252-260, Nature Publishing Group, United Kingdom (Jul. 2000).
Kostelny, S. A., et al., "Formation of a bispecific antibody by the use of leucine zippers," *The Journal of Immunology* 148(5):1547-1553, American Association of Immunologists, United States (Mar. 1992).
Kozbor, D., et al., "A human hybrid myeloma for production of human monoclonal antibodies," *Journal of Immunology* 133(6):3001-3005, American Association of Immunologists, United States (Dec. 1984).
Lee, C. V., et al., "Bivalent antibody phage display mimics natural immunoglobulin," *J Immunological Methods* 284(1-2):119-132, Elsevier, Netherlands (Jan. 2004).
Lee, C. V., et al., "High-affinity human antibodies from phage-displayed synthetic Fab libraries with a single framework scaffold," *Journal of Molecular Biology* 340(5):1073-1093, Academic Press, United Kingdom (Jul. 2004).
Lefranc, M. P., et al., "IMGT, the international ImMunoGeneTics database," *Nucleic Acids Research* 27(1):209-212, Oxford University Press, United Kingdom (Jan. 1999).
Li, H., et al., "Optimization of Humanized IgGs In Glycoengineered Pichia Pastoris," Nature Biotechnology 24(2):210-215, Nature America Publishing, United States (Feb. 2006).
Li, J., et al., "Human antibodies for immunotherapy development generated via a human B cell hybridoma technology," *Proc Natl Acad Sci USA* 103(10):3557-3562, National Academy of Sciences, United States (Mar. 2006).
Lonberg, N., "Fully human antibodies from transgenic mouse and phage display platforms," *Curr Opin Immunol* 20(4):450-459, Elsevier, Netherlands (Aug. 2008).
Lonberg, N., "Human antibodies from transgenic animals," *Nature Biotechnology* 23(9):1117-1125, Nature America Publishing, United States (Sep. 2005).
Marks, J. D., and Bradbury, A., "Selection of human antibodies from phage display libraries," *Methods in Molecular Biology* 248:161-176, Humana Press, United States (2004).
Marks, J. D., et al., "By-passing immunization. Human antibodies from V-gene libraries displayed on phage," *Journal of Molecular Biology* 222(3):581-597, Academic Press Limited, United States (Dec. 1991).
Mather, J. P., "Establishment and characterization of two distinct mouse testicular epithelial cell lines," *Biology of Reproduction* 23(1):243-252, Oxford University Press, United Kingdom (Aug. 1980).
Mather, J. P., et al., "Culture of testicular cells in hormone-supplemented serum-free medium," *Annals of the New York Academy of Sciences* 383:44-68, Blackwell, United States (1982).
McCafferty, J., et al., "Phage antibodies: filamentous phage displaying antibody variable domains," *Nature* 348(6301):552-554, Nature Publishing Group, United Kingdom (Dec. 1990).
Migliorini, P., et al., "The IL-1 family cytokines and receptors in autoimmune diseases," *Autoimmun Rev* 19(9):102617, 13 pages, Elsevier, Netherlands (Sep. 2020).
Morrison, S. L., et al., "Chimeric human antibody molecules: mouse antigen-binding domains with human constant region domains," *Proc Natl Acad Sci USA* 81(21):6851-6855, National Academy of Sciences, United States (Nov. 1984).
Okazaki A., et al., "Fucose depletion from human IgG1 oligosaccharide enhances binding enthalpy and association rate between IgG1 and FcgammaRIIIa," *Journal Of Molecular Biology* 336(5):1239-1249, Academic Press, United Kingdom (Mar. 2004).
Osbourn, J., et al., "From rodent reagents to human therapeutics using antibody guided selection," *Methods* 36(1):61-68, Academic Press, United States (May 2005).
Padlan, E. A., "A possible procedure for reducing the immunogenicity of antibody variable domains while preserving their ligand-binding properties," *Molecular Immunology* 28(4-5):489-498, Pergamon Press, United Kingdom (Apr. 1991).
Petkova, S. B., et al., "Enhanced half-life of genetically engineered human IgG1 antibodies in a humanized FcRn mouse model: poten-

(56) References Cited

OTHER PUBLICATIONS tial application in humorally mediated autoimmune disease," *International Immunology* 18(12):1759-1769, Oxford University Press, United Kingdom (2006).

Pluckthun, A., "Chapter 11: Antibodies from *Escherichia coli*," in *Handbook of Experimental Pharmacology, vol. 113: The Pharmacology of Monoclonal Antibodies*, pp. 269-315, Rosenburg, M., and Moore, G. P., eds., Springer-Verlag, Germany (1994).

Portolano, S., et al., "Lack of promiscuity in autoantigen-specific H and L chain combinations as revealed by human H and L chain 'roulette'," *The Journal of Immunology* 150(3):880-887, The American Association of Immunologists, United States (Feb. 1993).

Presta, L. G., et al., "Humanization of an antibody directed against IgE," *The Journal of Immunology* 151(5):2623-2632, The American Association of Immunologists, Inc., United States (Sep. 1993).

Queen, C., et al., "A humanized antibody that binds to the interleukin 2 receptor," *Proc Natl Acad Sci USA* 86(24):10029-10033, National Academy of Sciences, United States (Dec. 1989).

Ravetch, J. V., and Kinet, J. P., "Fc receptors," *Annual Review of Immunology* 9:457-492, Annual Reviews Inc., United States (1991).

Riechmann, L., et al., "Reshaping human antibodies for therapy," *Nature* 332(6162):323-327, Nature Publishing Group, United States (Mar. 1988).

Ripka, J., et al., "Two Chinese hamster ovary glycosylation mutants affected in the conversion of GDP-mannose to GDP-fucose," *Arch Biochem Biophys* 249(2):533-545, Academic Press, United States (Sep. 1986).

Rosok, M. J., et al., "A combinatorial library strategy for the rapid humanization of anticarcinoma BR96 Fab," *The Journal of Biological Chemistry* 271(37):22611-22618, American Society for Biochemistry and Molecular Biology, United States (Sep. 1996).

Shields, R. L., et al., "High resolution mapping of the binding site on human IgG1 for Fc gamma RI, Fc gamma RII, Fc gamma RIII, and FcRn and design of IgG1 variants with improved binding to the Fc gamma R," *The Journal of Biological Chemistry* 276(9):6591-6604, American Society for Biochemistry and Molecular Biology, United States (Mar. 2001).

Sidhu, S. S., et al., "Phage-displayed antibody libraries of synthetic heavy chain complementarity determining regions," *Journal of Molecular Biology* 338(2):299-310, Elsevier, United Kingdom (Apr. 2004).

Sims, M. J., et al., "A humanized CD18 antibody can block function without cell destruction," *The Journal of Immunology* 151(4):2296-2308, The American Association of Immunologists, United States (Aug. 1993).

Tutt, A., et al., "Trispecific F(ab')3 derivatives that use cooperative signaling via the TCR/CD3 complex and CD2 to activate and redirect resting cytotoxic T cells," *Journal of Immunology* 147(1):60-69, American Association of Immunologists, United States (Jul. 1991).

UniProt, "Interleukin-1 receptor accessory protein," Accession No. P59822, accessed at URL:[https://www.uniprot.org/uniprot/P59822] on Dec. 27, 2021, 8 pages.

UniProt, "Interleukin-1 receptor accessory protein," Accession No. Q9NPH3, accessed at URL:[https://www.uniprot.org/uniprot/Q9NPH3] on Dec. 27, 2021, 14 pages.

Urlaub, G., and Chasin, L. A., "Isolation of Chinese hamster cell mutants deficient in dihydrofolate reductase activity," *Proc Natl Acad Sci USA* 77(7):4216-4220, National Academy of Sciences, United States (Jul. 1980).

Van Dijk, M. A., and Van De Winkel, J. G., "Human antibodies as next generation therapeutics," *Current Opinion in Chemical Biology* 5(4):368-374, Elsevier Ltd., United Kingdom (Aug. 2001).

Vollmers, H. P., and Brandlein, S., "Death by stress: natural IgM-induced apoptosis," *Methods & Findings in Experimental & Clinical Pharmacology* 27(3): 185-91, Prous Science, Spain (Apr. 2005).

Vollmers H. P., and Brandlein, S., "The 'early birds': natural IgM antibodies and immune surveillance," *Histology & Histopathology* 20(3):927-937, University of Murcia, Spain (Jul. 2005).

Wright, A., and Morrison, S. L., "Effect of glycosylation on antibody function: implications for genetic engineering," *Trends in Biotechnology* 15(1):26-32, Elsevier Science Publishers, United Kingdom (Jan. 1997).

Yamane-Ohnuki, N., et al., "Establishment of FUT8 knockout Chinese hamster ovary cells: an ideal host cell line for producing completely defucosylated antibodies with enhanced antibody-dependent cellular cytotoxicity," *Biotechnology and Bioengineering* 87(5):614-622, Wiley, United States (Sep. 2004).

Yazaki, P. J., and Wu, A. M., "Chapter 15: Expression of Recombinant Antibodies in Mammalian Cell Lines," in *Methods in Molecular Biology* 248, pp. 255-268, Lo, B. K. C., ed., Humana Press, United States (2003).

Zapata, G., et al., "Engineering linear F(ab')2 fragments for efficient production in *Escherichia coli* and enhanced antiproliferative activity," *Protein Engineering* 8(10):1057-1062, Oxford University Press, United Kingdom (Oct. 1995).

Zola, H., "Chapter 6—Using Monoclonal Antibodies: Soluble Antigens," in *Monoclonal Antibodies: A Manual of Techniques*, pp. 147-181, CRC Press Inc., United States (Jul. 1987).

Cacia, J., et al., "Isomerization of an aspartic acid residue in the complementarity-determining regions of a recombinant antibody to human IgE: identification and effect on binding affinity," Biochemistry 35(6):1897-1903, American Chemical Society, United States (1996).

International Search Report and Written Opinion for International Application No. PCT/EP2021/075235, dated Mar. 1, 2022, European Patent Office, Netherlands, 20 pages.

Lo, M., et al., "Effector-attenuating Substitutions That Maintain Antibody Stability and Reduce Toxicity in Mice," J. Biol. Chem. 292(9):3900-3908, Elsevier, Netherlands (2017).

Rudikoff, S., et al., "Single amino acid substitution altering antigen-binding specificity," Proc. Natl. Acad. Sci. 79(6):1979-1983, National Academy of Sciences, United States (1982).

\* cited by examiner

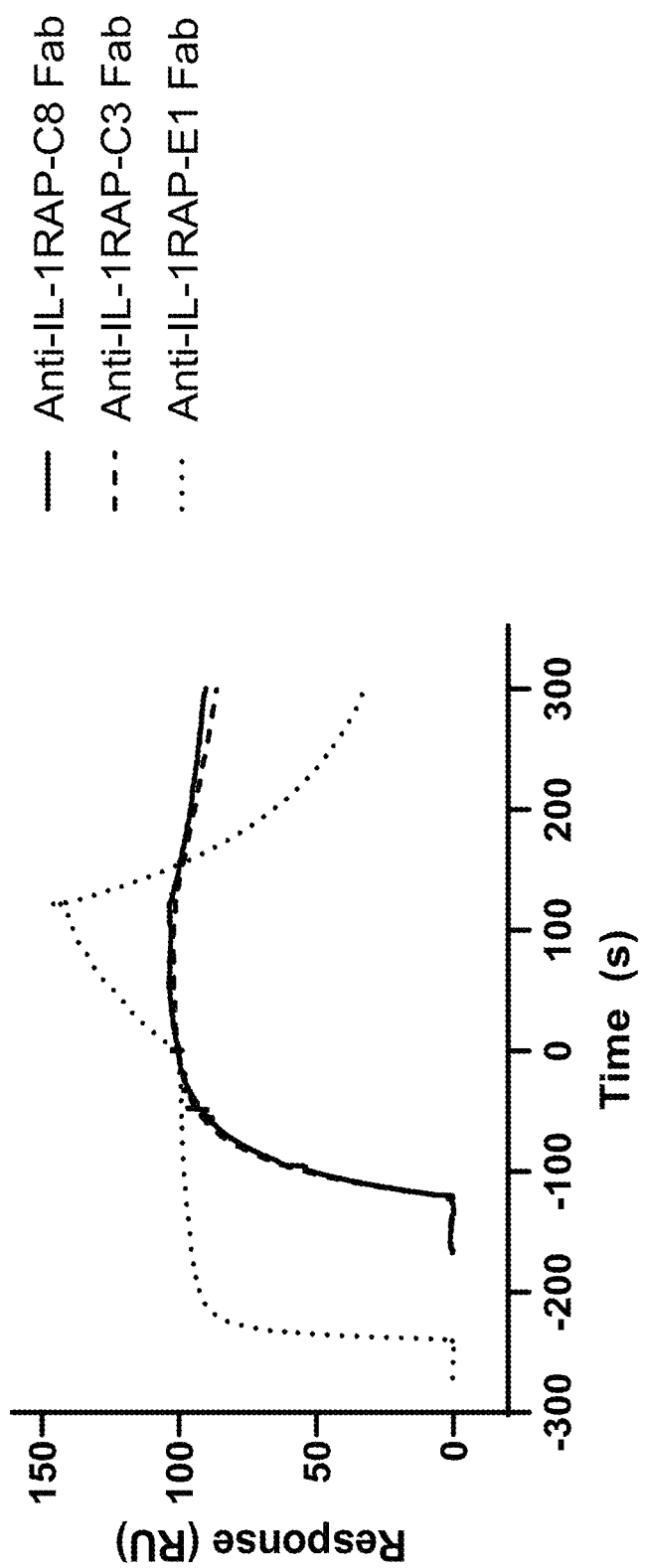

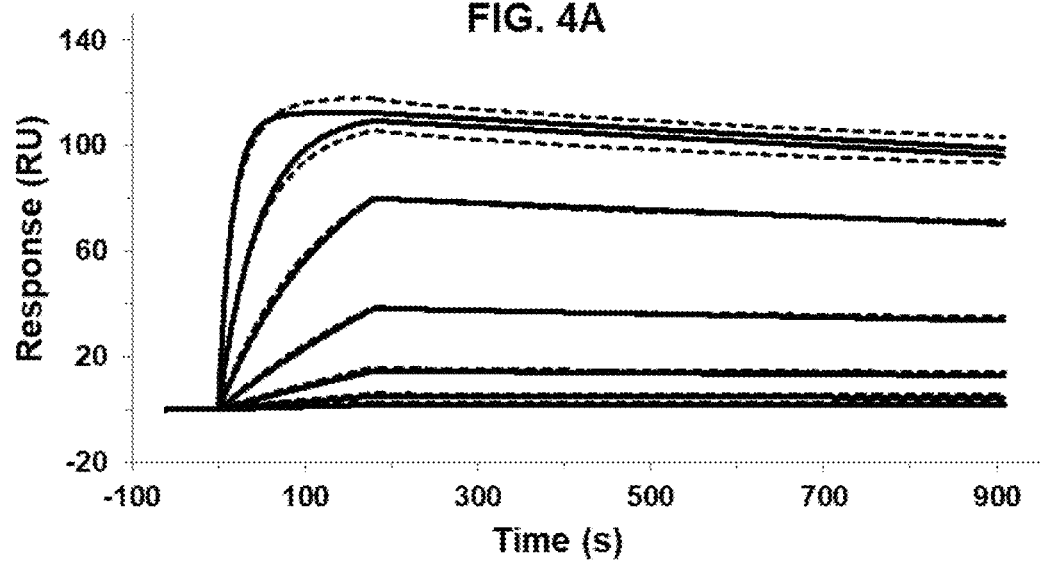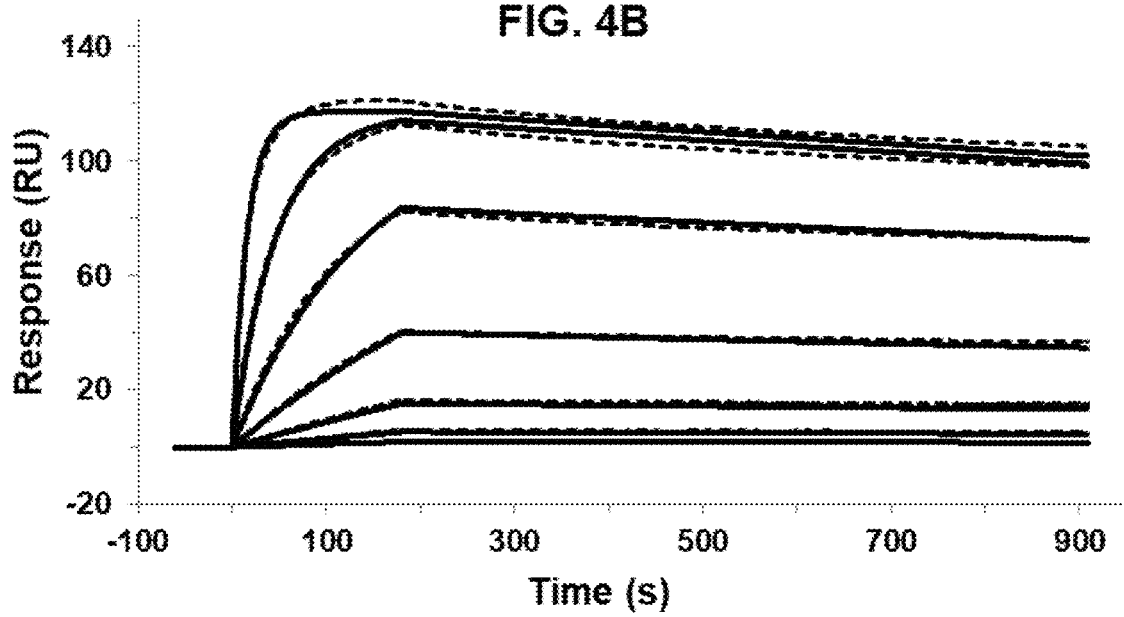

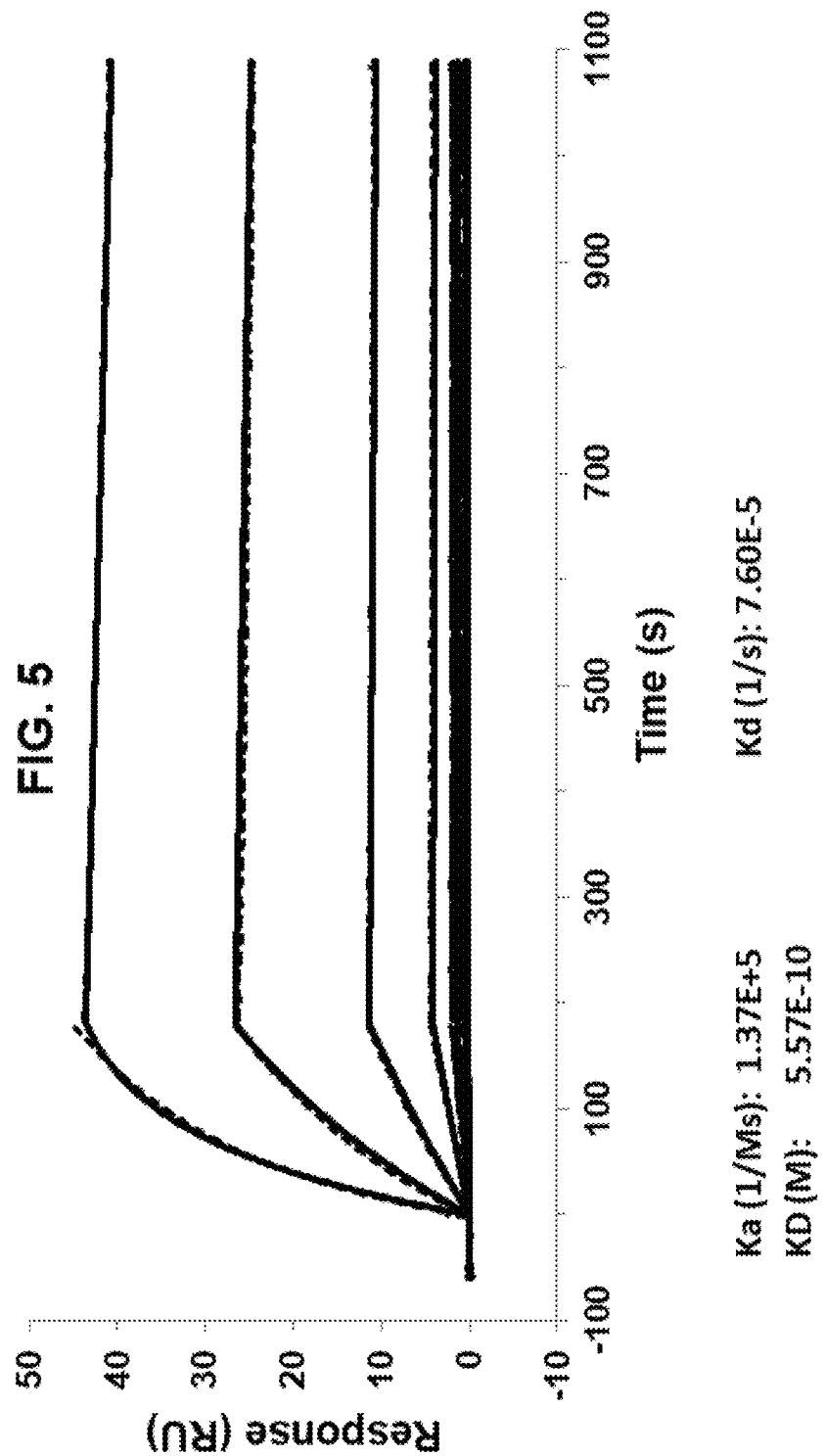

Normal Human Dermal Fibroblasts

Human Neutrophils

IL-1β stimulation
IL-8 release

IL-12/IL-33 stimulation
IFNg release

- Isotype control_4
- Anti-human IL-1RAP_candidate_1

- Isotype control_4 + sIL-1RAP
- Anti-human IL-1RAP_candidate_1 + sIL-1RAP

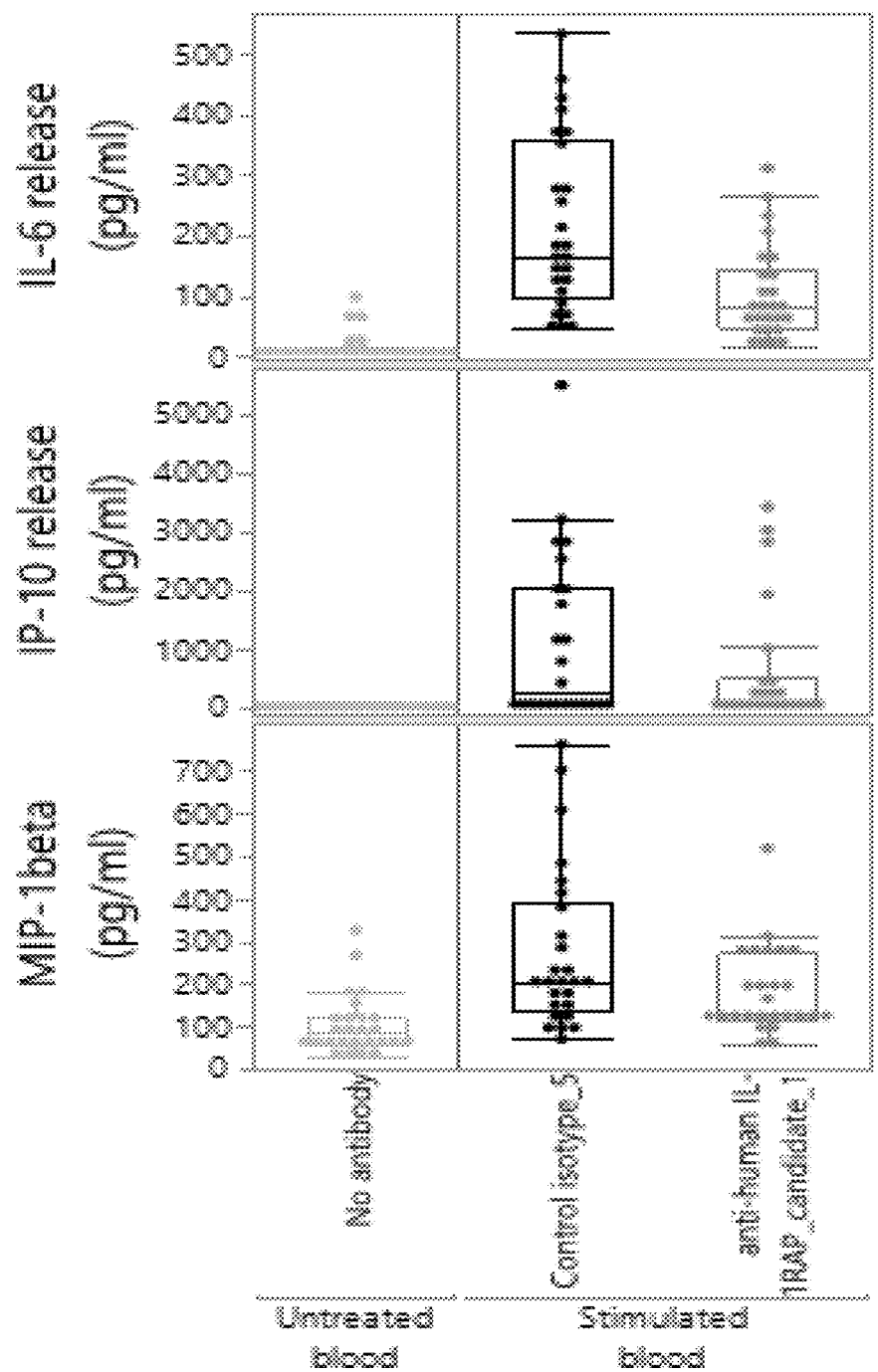

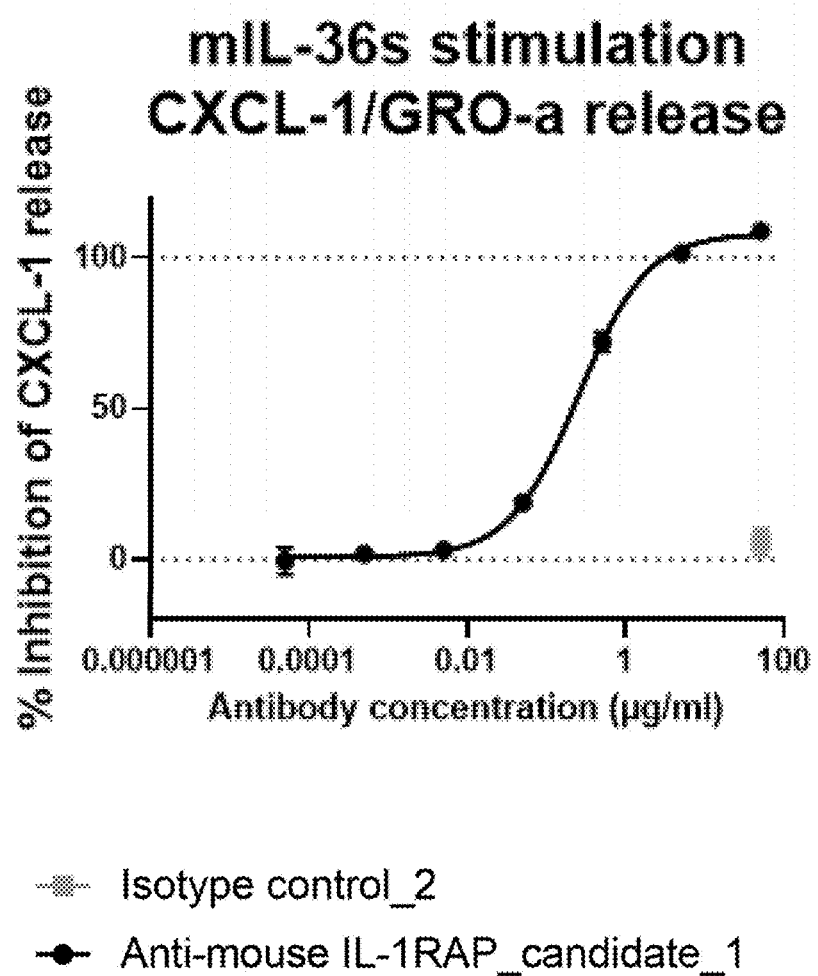

FIG. 19B

| Number of responder donors | IL-6 | IL-8 | MCP-1 | MIP-1alpha | MIP-1beta |
|---|---|---|---|---|---|
| IL-1α Stimulation | 13 | 11 | 10 | 8 | 10 |
| IL-1β Stimulation | 15 | 15 | 10 | 10 | 11 |

SEQUENCE LISTING

```
<160> NUMBER OF SEQ ID NOS: 349

<210> SEQ ID NO 1
<211> LENGTH: 373
<212> TYPE: PRT
<213> ORGANISM: Artificial Sequence
<220> FEATURE:
<223> OTHER INFORMATION: >SEQ ID NO: 1 - human (hs)IL-1RAP-ECD(S21-
      E359)-Avi-His

<400> SEQUENCE: 1

Ser Glu Arg Cys Asp Asp Trp Gly Leu Asp Thr Met Arg Gln Ile Gln
1               5                   10                  15

Val Phe Glu Asp Glu Pro Ala Arg Ile Lys Cys Pro Leu Phe Glu His
            20                  25                  30

Phe Leu Lys Phe Asn Tyr Ser Thr Ala His Ser Ala Gly Leu Thr Leu
        35                  40                  45

Ile Trp Tyr Trp Thr Arg Gln Asp Arg Asp Leu Glu Glu Pro Ile Asn
    50                  55                  60

Phe Arg Leu Pro Glu Asn Arg Ile Ser Lys Glu Lys Asp Val Leu Trp
65                  70                  75                  80

Phe Arg Pro Thr Leu Leu Asn Asp Thr Gly Asn Tyr Thr Cys Met Leu
                85                  90                  95

Arg Asn Thr Thr Tyr Cys Ser Lys Val Ala Phe Pro Leu Glu Val Val
            100                 105                 110

Gln Lys Asp Ser Cys Phe Asn Ser Pro Met Lys Leu Pro Val His Lys
        115                 120                 125

Leu Tyr Ile Glu Tyr Gly Ile Gln Arg Ile Thr Cys Pro Asn Val Asp
    130                 135                 140

Gly Tyr Phe Pro Ser Ser Val Lys Pro Thr Ile Thr Trp Tyr Met Gly
145                 150                 155                 160

Cys Tyr Lys Ile Gln Asn Phe Asn Asn Val Ile Pro Glu Gly Met Asn
                165                 170                 175

Leu Ser Phe Leu Ile Ala Leu Ile Ser Asn Asn Gly Asn Tyr Thr Cys
            180                 185                 190

Val Val Thr Tyr Pro Glu Asn Gly Arg Thr Phe His Leu Thr Arg Thr
        195                 200                 205

Leu Thr Val Lys Val Val Gly Ser Pro Lys Asn Ala Val Pro Pro Val
    210                 215                 220

Ile His Ser Pro Asn Asp His Val Val Tyr Glu Lys Glu Pro Gly Glu
225                 230                 235                 240

Glu Leu Leu Ile Pro Cys Thr Val Tyr Phe Ser Phe Leu Met Asp Ser
                245                 250                 255

Arg Asn Glu Val Trp Trp Thr Ile Asp Gly Lys Lys Pro Asp Asp Ile
            260                 265                 270

Thr Ile Asp Val Thr Ile Asn Glu Ser Ile Ser His Ser Arg Thr Glu
        275                 280                 285

Asp Glu Thr Arg Thr Gln Ile Leu Ser Ile Lys Lys Val Thr Ser Glu
    290                 295                 300

Asp Leu Lys Arg Ser Tyr Val Cys His Ala Arg Ser Ala Lys Gly Glu
305                 310                 315                 320
```

```
Val Ala Lys Ala Ala Lys Val Lys Gln Lys Val Pro Ala Pro Arg Tyr
                325                 330                 335

Thr Val Glu Gly Gly Gly Gly Thr Gly Gly Leu Asn Asp Ile Phe Glu
            340                 345                 350

Ala Gln Lys Ile Glu Trp His Glu Gly Gly His His His His His
        355                 360                 365

His His His His His
        370

<210> SEQ ID NO 2
<211> LENGTH: 373
<212> TYPE: PRT
<213> ORGANISM: Artificial Sequence
<220> FEATURE:
<223> OTHER INFORMATION: >SEQ ID NO: 2 - cynomolgus monkey
      (cyno)IL-1RAP-ECD(S21-E359)-Avi-His

<400> SEQUENCE: 2

Ser Glu Arg Cys Asp Asp Trp Gly Leu Asp Thr Met Arg Gln Ile Gln
1               5                   10                  15

Val Phe Glu Asp Glu Pro Ala Arg Ile Lys Cys Pro Leu Phe Glu His
            20                  25                  30

Phe Leu Lys Phe Asn Tyr Ser Thr Ala His Ser Ala Gly Leu Thr Leu
        35                  40                  45

Ile Trp Tyr Trp Thr Arg Gln Asp Arg Asp Leu Glu Glu Pro Ile Asn
    50                  55                  60

Phe Arg Leu Pro Glu Asn Arg Ile Ser Lys Glu Lys Asp Val Leu Trp
65                  70                  75                  80

Phe Arg Pro Thr Leu Leu Asn Asp Thr Gly Asn Tyr Thr Cys Met Leu
                85                  90                  95

Arg Asn Thr Thr Tyr Cys Ser Lys Val Ala Phe Pro Leu Glu Val Val
            100                 105                 110

Gln Lys Asp Ser Cys Phe Asn Ser Pro Met Lys Leu Pro Val His Lys
        115                 120                 125

Leu Tyr Ile Glu Tyr Gly Ile Gln Arg Ile Thr Cys Pro Asn Val Asp
    130                 135                 140

Gly Tyr Phe Pro Ser Ser Val Lys Pro Thr Ile Thr Trp Tyr Met Gly
145                 150                 155                 160

Cys Tyr Lys Ile Gln Asn Phe Asn Asn Val Ile Pro Glu Gly Met Asn
                165                 170                 175

Leu Ser Phe Leu Ile Ala Phe Ile Ser Asn Asn Gly Asn Tyr Thr Cys
            180                 185                 190

Val Val Thr Tyr Pro Glu Asn Gly Arg Thr Phe His Leu Thr Arg Thr
        195                 200                 205

Leu Thr Val Lys Val Val Gly Ser Pro Lys Asn Ala Val Pro Pro Val
    210                 215                 220

Ile His Ser Pro Asn Asp His Val Val Tyr Glu Lys Glu Pro Gly Glu
225                 230                 235                 240

Glu Leu Leu Ile Pro Cys Thr Val Tyr Phe Ser Phe Leu Met Asp Ser
                245                 250                 255

Arg Asn Glu Val Trp Trp Thr Ile Asp Gly Lys Lys Pro Asp Asp Ile
            260                 265                 270

Pro Ile Asp Val Thr Ile Asn Glu Ser Ile Ser His Ser Arg Thr Glu
        275                 280                 285

Asp Glu Thr Arg Thr Gln Ile Leu Ser Ile Lys Lys Val Thr Ser Glu
    290                 295                 300
```

```
Asp Leu Lys Arg Ser Tyr Val Cys His Ala Arg Ser Ala Lys Gly Glu
305                 310                 315                 320

Val Ala Lys Ala Ala Thr Val Lys Gln Lys Val Pro Ala Pro Arg Tyr
            325                 330                 335

Thr Val Glu Gly Gly Gly Thr Gly Leu Asn Asp Ile Phe Glu
        340                 345                 350

Ala Gln Lys Ile Glu Trp His Glu Gly Gly His His His His
        355                 360                 365

His His His His His
    370

<210> SEQ ID NO 3
<211> LENGTH: 373
<212> TYPE: PRT
<213> ORGANISM: Artificial Sequence
<220> FEATURE:
<223> OTHER INFORMATION: >SEQ ID NO: 3 - chicken (gg)IL-1RAP-ECD(S139-
      E478)-Avi-His

<400> SEQUENCE: 3

Ser Glu Arg Cys Asp Asp Trp Gly Val Asp Thr Met Lys Gln Ile Gln
1               5                   10                  15

Ile Tyr Asp Gly Glu Pro Ala Lys Ile Lys Cys Pro Leu Phe Glu Thr
            20                  25                  30

Phe Leu Lys Tyr Asn Tyr Ser Thr Ala His Ser Ala Gly Leu Thr Leu
        35                  40                  45

Ile Trp Tyr Arg Ile Gly Gln Asp Arg Asp Leu Glu Glu Pro Ile Asn
50                  55                  60

Phe Arg Leu Pro Asp Asn Arg Ile Ser Lys Glu Lys Asp Thr Leu Trp
65                  70                  75                  80

Phe Trp Pro Ala Leu Leu Asn Asp Thr Gly Asn Tyr Thr Cys Met Leu
                85                  90                  95

Arg Asn Thr Thr Tyr Cys Ser Lys Val Ala Phe Pro Leu Glu Val Val
            100                 105                 110

Pro Lys Asp Gln Gly Ser Cys Val Ser His Ser Ile Lys Pro Val Glu
        115                 120                 125

Gln Met Phe Tyr Leu Glu Tyr Ala Asn Glu Lys Ile Thr Cys Pro Asp
    130                 135                 140

Ile Asp Gly Phe Tyr Pro Ala Ser Val Thr Pro Thr Val Lys Trp Tyr
145                 150                 155                 160

Gln Ser Cys Arg Leu Val Asp Gly Phe Asn Glu Arg His Pro Gln Gly
                165                 170                 175

Ser Lys Leu Val Ile Gly Val Val Arg Ser Ala Tyr Glu Gly Asn Tyr
            180                 185                 190

Thr Cys Ile Val Thr Phe Lys Asp His Gly Arg Thr Tyr Asn Leu Thr
        195                 200                 205

Arg Thr Val Lys Met Lys Val Val Gly Ser Pro Asn Lys Ala Leu Pro
    210                 215                 220

Pro Gln Phe Thr Ser Pro Asn Glu Lys Val Val Tyr Glu Leu Glu Ala
225                 230                 235                 240

Gly Asp Asp Leu Val Leu Pro Cys Glu Val Phe Phe Thr Phe Leu Lys
                245                 250                 255

Asp Ser Arg Thr Glu Val Trp Trp Thr Ile Asp Gly Lys Asn Thr Asp
            260                 265                 270

Asp Ile Val Asp Ala Lys Val Thr Gln Ser Glu Ile Pro Arg Arg Phe
```

```
                275                 280                 285
Glu Asp Lys Thr Ile Ile Arg Thr Leu Thr Val Ala Lys Ala Thr Pro
    290                 295                 300
Glu Asp Leu Lys Arg Asn Tyr Thr Cys Tyr Ala Arg Asn Ala Lys Gly
305                 310                 315                 320
Glu Gly His Ser Gln Ala Ile Val His Met Lys Val Ala Ala Pro Lys
                325                 330                 335
Tyr Thr Val Glu Gly Gly Gly Thr Gly Gly Leu Asn Asp Ile Phe
            340                 345                 350
Glu Ala Gln Lys Ile Glu Trp His Glu Gly Gly Gly His His His
        355                 360                 365
His His His His His
        370
```

<210> SEQ ID NO 4
<211> LENGTH: 373
<212> TYPE: PRT
<213> ORGANISM: Artificial Sequence
<220> FEATURE:
<223> OTHER INFORMATION: >SEQ ID NO: 4 - IL-1RAP-ECD(ggD1(S139-P246)-
    hsD2(V132-V233)-hsD3(V234-E359))-Avi-His

<400> SEQUENCE: 4

```
Ser Glu Arg Cys Asp Asp Trp Gly Val Asp Thr Met Lys Gln Ile Gln
1               5                   10                  15
Ile Tyr Asp Gly Glu Pro Ala Lys Ile Lys Cys Pro Leu Phe Glu Thr
            20                  25                  30
Phe Leu Lys Tyr Asn Tyr Ser Thr Ala His Ser Ala Gly Leu Thr Leu
        35                  40                  45
Ile Trp Tyr Arg Ile Gly Gln Asp Arg Asp Leu Glu Glu Pro Ile Asn
    50                  55                  60
Phe Arg Leu Pro Asp Asn Arg Ile Ser Lys Glu Lys Asp Thr Leu Trp
65                  70                  75                  80
Phe Trp Pro Ala Leu Leu Asn Asp Thr Gly Asn Tyr Thr Cys Met Leu
                85                  90                  95
Arg Asn Thr Thr Tyr Cys Ser Lys Val Ala Phe Pro Leu Glu Val Val
            100                 105                 110
Gln Lys Asp Ser Cys Phe Asn Ser Pro Met Lys Leu Pro Val His Lys
        115                 120                 125
Leu Tyr Ile Glu Tyr Gly Ile Gln Arg Ile Thr Cys Pro Asn Val Asp
    130                 135                 140
Gly Tyr Phe Pro Ser Ser Val Lys Pro Thr Ile Thr Trp Tyr Met Gly
145                 150                 155                 160
Cys Tyr Lys Ile Gln Asn Phe Asn Asn Val Ile Pro Glu Gly Met Asn
                165                 170                 175
Leu Ser Phe Leu Ile Ala Leu Ile Ser Asn Asn Gly Asn Tyr Thr Cys
            180                 185                 190
Val Val Thr Tyr Pro Glu Asn Gly Arg Thr Phe His Leu Thr Arg Thr
        195                 200                 205
Leu Thr Val Lys Val Val Gly Ser Pro Lys Asn Ala Val Pro Pro Val
    210                 215                 220
Ile His Ser Pro Asn Asp His Val Val Tyr Glu Lys Glu Pro Gly Glu
225                 230                 235                 240
Glu Leu Leu Ile Pro Cys Thr Val Tyr Phe Ser Phe Leu Met Asp Ser
                245                 250                 255
```

```
Arg Asn Glu Val Trp Trp Thr Ile Asp Gly Lys Lys Pro Asp Ile
            260                 265                 270

Thr Ile Asp Val Thr Ile Asn Glu Ser Ile Ser His Ser Arg Thr Glu
    275                 280                 285

Asp Glu Thr Arg Thr Gln Ile Leu Ser Ile Lys Lys Val Thr Ser Glu
    290                 295                 300

Asp Leu Lys Arg Ser Tyr Val Cys His Ala Arg Ser Ala Lys Gly Glu
305                 310                 315                 320

Val Ala Lys Ala Ala Lys Val Lys Gln Lys Val Pro Ala Pro Arg Tyr
                325                 330                 335

Thr Val Glu Gly Gly Gly Gly Thr Gly Gly Leu Asn Asp Ile Phe Glu
            340                 345                 350

Ala Gln Lys Ile Glu Trp His Glu Gly Gly Gly His His His His His
            355                 360                 365

His His His His His
    370

<210> SEQ ID NO 5
<211> LENGTH: 373
<212> TYPE: PRT
<213> ORGANISM: Artificial Sequence
<220> FEATURE:
<223> OTHER INFORMATION: >SEQ ID NO: 5 - IL-1RAP-ECD(ggD1(S139-H260)-
      ggD2(S261-V349)-hsD3(V243-E359))-Avi-His

<400> SEQUENCE: 5

Ser Glu Arg Cys Asp Asp Trp Gly Val Asp Thr Met Lys Gln Ile Gln
1               5                   10                  15

Ile Tyr Asp Gly Glu Pro Ala Lys Ile Lys Cys Pro Leu Phe Glu Thr
            20                  25                  30

Phe Leu Lys Tyr Asn Tyr Ser Thr Ala His Ser Ala Gly Leu Thr Leu
        35                  40                  45

Ile Trp Tyr Arg Ile Gly Gln Asp Arg Asp Leu Glu Glu Pro Ile Asn
    50                  55                  60

Phe Arg Leu Pro Asp Asn Arg Ile Ser Lys Glu Lys Asp Thr Leu Trp
65                  70                  75                  80

Phe Trp Pro Ala Leu Leu Asn Asp Thr Gly Asn Tyr Thr Cys Met Leu
                85                  90                  95

Arg Asn Thr Thr Tyr Cys Ser Lys Val Ala Phe Pro Leu Glu Val Val
            100                 105                 110

Pro Lys Asp Gln Gly Ser Cys Val Ser His Ser Ile Lys Pro Val Glu
        115                 120                 125

Gln Met Phe Tyr Leu Glu Tyr Ala Asn Glu Lys Ile Thr Cys Pro Asp
    130                 135                 140

Ile Asp Gly Phe Tyr Pro Ala Ser Val Thr Pro Thr Val Lys Trp Tyr
145                 150                 155                 160

Gln Ser Cys Arg Leu Val Asp Gly Phe Asn Glu Arg His Pro Gln Gly
                165                 170                 175

Ser Lys Leu Val Ile Gly Val Val Arg Ser Ala Tyr Glu Gly Asn Tyr
            180                 185                 190

Thr Cys Ile Val Thr Phe Lys Asp His Gly Arg Thr Tyr Asn Leu Thr
        195                 200                 205

Arg Thr Val Lys Val Val Gly Ser Pro Lys Asn Ala Val Pro Pro Val
    210                 215                 220

Ile His Ser Pro Asn Asp His Val Val Tyr Glu Lys Glu Pro Gly Glu
225                 230                 235                 240
```

```
Glu Leu Leu Ile Pro Cys Thr Val Tyr Phe Ser Phe Leu Met Asp Ser
                245                 250                 255

Arg Asn Glu Val Trp Trp Thr Ile Asp Gly Lys Lys Pro Asp Asp Ile
            260                 265                 270

Thr Ile Asp Val Thr Ile Asn Glu Ser Ile Ser His Ser Arg Thr Glu
        275                 280                 285

Asp Glu Thr Arg Thr Gln Ile Leu Ser Ile Lys Lys Val Thr Ser Glu
    290                 295                 300

Asp Leu Lys Arg Ser Tyr Val Cys His Ala Arg Ser Ala Lys Gly Glu
305                 310                 315                 320

Val Ala Lys Ala Ala Lys Val Lys Gln Lys Val Pro Ala Pro Arg Tyr
                325                 330                 335

Thr Val Glu Gly Gly Gly Gly Thr Gly Gly Leu Asn Asp Ile Phe Glu
            340                 345                 350

Ala Gln Lys Ile Glu Trp His Glu Gly Gly Gly His His His His His
        355                 360                 365

His His His His His
    370

<210> SEQ ID NO 6
<211> LENGTH: 550
<212> TYPE: PRT
<213> ORGANISM: Homo sapiens
<220> FEATURE:
<221> NAME/KEY: MISC_FEATURE
<222> LOCATION: (1)..(550)
<223> OTHER INFORMATION: >SEQ ID NO: 6 - human IL-1RAP, full length

<400> SEQUENCE: 6

Ser Glu Arg Cys Asp Asp Trp Gly Leu Asp Thr Met Arg Gln Ile Gln
1               5                   10                  15

Val Phe Glu Asp Glu Pro Ala Arg Ile Lys Cys Pro Leu Phe Glu His
            20                  25                  30

Phe Leu Lys Phe Asn Tyr Ser Thr Ala His Ser Ala Gly Leu Thr Leu
        35                  40                  45

Ile Trp Tyr Trp Thr Arg Gln Asp Arg Asp Leu Glu Glu Pro Ile Asn
    50                  55                  60

Phe Arg Leu Pro Glu Asn Arg Ile Ser Lys Glu Lys Asp Val Leu Trp
65                  70                  75                  80

Phe Arg Pro Thr Leu Leu Asn Asp Thr Gly Asn Tyr Thr Cys Met Leu
                85                  90                  95

Arg Asn Thr Thr Tyr Cys Ser Lys Val Ala Phe Pro Leu Glu Val Val
            100                 105                 110

Gln Lys Asp Ser Cys Phe Asn Ser Pro Met Lys Leu Pro Val His Lys
        115                 120                 125

Leu Tyr Ile Glu Tyr Gly Ile Gln Arg Ile Thr Cys Pro Asn Val Asp
    130                 135                 140

Gly Tyr Phe Pro Ser Ser Val Lys Pro Thr Ile Thr Trp Tyr Met Gly
145                 150                 155                 160

Cys Tyr Lys Ile Gln Asn Phe Asn Asn Val Ile Pro Glu Gly Met Asn
                165                 170                 175

Leu Ser Phe Leu Ile Ala Leu Ile Ser Asn Asn Gly Asn Tyr Thr Cys
            180                 185                 190

Val Val Thr Tyr Pro Glu Asn Gly Arg Thr Phe His Leu Thr Arg Thr
        195                 200                 205
```

```
Leu Thr Val Lys Val Val Gly Ser Pro Lys Asn Ala Val Pro Val
210                 215                 220

Ile His Ser Pro Asn Asp His Val Val Tyr Glu Lys Glu Pro Gly Glu
225                 230                 235                 240

Glu Leu Leu Ile Pro Cys Thr Val Tyr Phe Ser Phe Leu Met Asp Ser
            245                 250                 255

Arg Asn Glu Val Trp Trp Thr Ile Asp Gly Lys Lys Pro Asp Asp Ile
        260                 265                 270

Thr Ile Asp Val Thr Ile Asn Glu Ser Ile Ser His Ser Arg Thr Glu
    275                 280                 285

Asp Glu Thr Arg Thr Gln Ile Leu Ser Ile Lys Lys Val Thr Ser Glu
290                 295                 300

Asp Leu Lys Arg Ser Tyr Val Cys His Ala Arg Ser Ala Lys Gly Glu
305                 310                 315                 320

Val Ala Lys Ala Ala Lys Val Lys Gln Lys Val Pro Ala Pro Arg Tyr
                325                 330                 335

Thr Val Glu Leu Ala Cys Gly Phe Gly Ala Thr Val Leu Leu Val Val
            340                 345                 350

Ile Leu Ile Val Val Tyr His Val Tyr Trp Leu Glu Met Val Leu Phe
        355                 360                 365

Tyr Arg Ala His Phe Gly Thr Asp Glu Thr Ile Leu Asp Gly Lys Glu
370                 375                 380

Tyr Asp Ile Tyr Val Ser Tyr Ala Arg Asn Ala Glu Glu Glu Glu Phe
385                 390                 395                 400

Val Leu Leu Thr Leu Arg Gly Val Leu Glu Asn Glu Phe Gly Tyr Lys
                405                 410                 415

Leu Cys Ile Phe Asp Arg Asp Ser Leu Pro Gly Gly Ile Val Thr Asp
            420                 425                 430

Glu Thr Leu Ser Phe Ile Gln Lys Ser Arg Arg Leu Leu Val Val Leu
        435                 440                 445

Ser Pro Asn Tyr Val Leu Gln Gly Thr Gln Ala Leu Leu Glu Leu Lys
450                 455                 460

Ala Gly Leu Glu Asn Met Ala Ser Arg Gly Asn Ile Asn Val Ile Leu
465                 470                 475                 480

Val Gln Tyr Lys Ala Val Lys Glu Thr Lys Val Lys Glu Leu Lys Arg
                485                 490                 495

Ala Lys Thr Val Leu Thr Val Ile Lys Trp Lys Gly Glu Lys Ser Lys
            500                 505                 510

Tyr Pro Gln Gly Arg Phe Trp Lys Gln Leu Gln Val Ala Met Pro Val
        515                 520                 525

Lys Lys Ser Pro Arg Arg Ser Ser Ser Asp Glu Gln Gly Leu Ser Tyr
530                 535                 540

Ser Ser Leu Lys Asn Val
545                 550

<210> SEQ ID NO 7
<211> LENGTH: 550
<212> TYPE: PRT
<213> ORGANISM: Macaca fascicularis
<220> FEATURE:
<221> NAME/KEY: MISC_FEATURE
<222> LOCATION: (1)..(550)
<223> OTHER INFORMATION: >SEQ ID NO: 7 - cynomolgus monkey IL-1RAP, full
      length

<400> SEQUENCE: 7
```

-continued

```
Ser Glu Arg Cys Asp Asp Trp Gly Leu Asp Thr Met Arg Gln Ile Gln
  1               5                  10                  15

Val Phe Glu Asp Glu Pro Ala Arg Ile Lys Cys Pro Leu Phe Glu His
             20                  25                  30

Phe Leu Lys Phe Asn Tyr Ser Thr Ala His Ser Ala Gly Leu Thr Leu
         35                  40                  45

Ile Trp Tyr Trp Thr Arg Gln Asp Arg Asp Leu Glu Glu Pro Ile Asn
 50                  55                  60

Phe Arg Leu Pro Glu Asn Arg Ile Ser Lys Glu Lys Asp Val Leu Trp
 65                  70                  75                  80

Phe Arg Pro Thr Leu Leu Asn Asp Thr Gly Asn Tyr Thr Cys Met Leu
             85                  90                  95

Arg Asn Thr Thr Tyr Cys Ser Lys Val Ala Phe Pro Leu Glu Val Val
            100                 105                 110

Gln Lys Asp Ser Cys Phe Asn Ser Pro Met Lys Leu Pro Val His Lys
            115                 120                 125

Leu Tyr Ile Glu Tyr Gly Ile Gln Arg Ile Thr Cys Pro Asn Val Asp
    130                 135                 140

Gly Tyr Phe Pro Ser Ser Val Lys Pro Thr Ile Thr Trp Tyr Met Gly
145                 150                 155                 160

Cys Tyr Lys Ile Gln Asn Phe Asn Asn Val Ile Pro Glu Gly Met Asn
                165                 170                 175

Leu Ser Phe Leu Ile Ala Phe Ile Ser Asn Asn Gly Asn Tyr Thr Cys
            180                 185                 190

Val Val Thr Tyr Pro Glu Asn Gly Arg Thr Phe His Leu Thr Arg Thr
        195                 200                 205

Leu Thr Val Lys Val Val Gly Ser Pro Lys Asn Ala Val Pro Pro Val
    210                 215                 220

Ile His Ser Pro Asn Asp His Val Val Tyr Glu Lys Glu Pro Gly Glu
225                 230                 235                 240

Glu Leu Leu Ile Pro Cys Thr Val Tyr Phe Ser Phe Leu Met Asp Ser
                245                 250                 255

Arg Asn Glu Val Trp Trp Thr Ile Asp Gly Lys Lys Pro Asp Asp Ile
            260                 265                 270

Pro Ile Asp Val Thr Ile Asn Glu Ser Ile Ser His Ser Arg Thr Glu
    275                 280                 285

Asp Glu Thr Arg Thr Gln Ile Leu Ser Ile Lys Lys Val Thr Ser Glu
        290                 295                 300

Asp Leu Lys Arg Ser Tyr Val Cys His Ala Arg Ser Ala Lys Gly Glu
305                 310                 315                 320

Val Ala Lys Ala Ala Thr Val Lys Gln Lys Val Pro Ala Pro Arg Tyr
                325                 330                 335

Thr Val Glu Leu Ala Cys Gly Phe Gly Ala Thr Val Leu Leu Val Val
            340                 345                 350

Ile Leu Ile Val Val Tyr His Val Tyr Trp Leu Glu Met Val Leu Phe
        355                 360                 365

Tyr Arg Ala His Phe Gly Thr Asp Glu Thr Ile Leu Asp Gly Lys Glu
    370                 375                 380

Tyr Asp Ile Tyr Val Ser Tyr Ala Arg Asn Ala Glu Glu Glu Glu Phe
385                 390                 395                 400

Val Leu Leu Thr Leu Arg Gly Val Leu Glu Asn Glu Phe Gly Tyr Lys
                405                 410                 415

Leu Cys Ile Phe Asp Arg Asp Ser Leu Pro Gly Gly Ile Val Thr Asp
```

```
                420                 425                 430
Glu Thr Leu Ser Phe Ile Gln Lys Ser Arg Arg Leu Leu Val Val Leu
                435                 440                 445

Ser Pro Asn Tyr Val Leu Gln Gly Thr Gln Ala Leu Leu Glu Leu Lys
            450                 455                 460

Ala Gly Leu Glu Asn Met Ala Ser Gln Gly Asn Ile Asn Val Ile Leu
465                 470                 475                 480

Val Gln Tyr Lys Ala Val Lys Glu Thr Lys Val Lys Glu Leu Lys Arg
                485                 490                 495

Ala Lys Thr Val Leu Thr Val Ile Lys Trp Lys Gly Glu Lys Ser Lys
            500                 505                 510

Tyr Pro Gln Gly Arg Phe Trp Lys Gln Leu Gln Val Ala Met Pro Val
            515                 520                 525

Lys Lys Ser Pro Arg Arg Ser Ser Ser Asp Glu Gln Gly Leu Ser Tyr
530                 535                 540

Ser Ser Leu Lys Asn Val
545                 550

<210> SEQ ID NO 8
<211> LENGTH: 222
<212> TYPE: PRT
<213> ORGANISM: Artificial Sequence
<220> FEATURE:
<223> OTHER INFORMATION: >SEQ ID NO: 8 - anti-IL-1Rap-UCP02-A4 FAB heavy
      chain

<400> SEQUENCE: 8

Gln Val Gln Leu Val Gln Ser Gly Ala Glu Val Lys Lys Pro Gly Ser
1               5                   10                  15

Ser Val Lys Val Ser Cys Lys Ala Ser Gly Gly Val Phe Ser Tyr Tyr
            20                  25                  30

Ala Ile Ser Trp Val Arg Gln Ala Pro Gly Gln Gly Leu Glu Trp Met
        35                  40                  45

Gly Ala Ile Ile Pro Asp Phe Gly His Thr Ile Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Ser Pro Tyr Lys Gly Trp Trp Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys
    210                 215                 220
```

<210> SEQ ID NO 9
<211> LENGTH: 224
<212> TYPE: PRT
<213> ORGANISM: Artificial Sequence
<220> FEATURE:
<223> OTHER INFORMATION: >SEQ ID NO: 9 - anti-IL-1Rap-UCP02-A6 FAB heavy chain

<400> SEQUENCE: 9

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Ala Phe Arg Ile Tyr
            20                  25                  30

Ala Ile His Trp Val Arg Gln Ala Pro Gly Gln Gly Leu Glu Trp Met
        35                  40                  45

Gly Gly Ile Leu Ala Ser Gly Gly Ala Val Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Lys Asp Ile Tyr Gly Tyr Gly Tyr Gly Asp Ile Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220
```

<210> SEQ ID NO 10
<211> LENGTH: 222
<212> TYPE: PRT
<213> ORGANISM: Artificial Sequence
<220> FEATURE:
<223> OTHER INFORMATION: >SEQ ID NO: 10 - anti-IL-1Rap-UCP02-B11 FAB heavy chain

<400> SEQUENCE: 10

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly His Phe Ser Gln Phe
            20                  25                  30

Ala Ile Ser Trp Val Arg Gln Ala Pro Gly Gln Gly Leu Glu Trp Met
        35                  40                  45

Gly Gly Ile Ala Pro Gly Leu Gly Ser Thr Arg Tyr Ala Gln Lys Phe
    50                  55                  60

Gln Gly Arg Val Thr Ile Thr Ala Asp Glu Ser Thr Ser Thr Ala Tyr
65                  70                  75                  80
```

```
Met Glu Leu Ser Ser Leu Arg Ser Glu Asp Thr Ala Val Tyr Tyr Cys
                85                  90                  95

Ala Arg Asp Ser Ile Tyr Ser Ala Trp Leu Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys
210                 215                 220

<210> SEQ ID NO 11
<211> LENGTH: 223
<212> TYPE: PRT
<213> ORGANISM: Artificial Sequence
<220> FEATURE:
<223> OTHER INFORMATION: >SEQ ID NO: 11 - anti-IL-1Rap-UCP02-B5 FAB
      heavy chain

<400> SEQUENCE: 11

Gln Val Gln Leu Val Gln Ser Gly Ala Glu Val Lys Lys Pro Gly Ser
1               5                   10                  15

Ser Val Lys Val Ser Cys Lys Ala Ser Gly Gly Tyr Phe Ser Ala Tyr
            20                  25                  30

Ile Ile Ser Trp Val Arg Gln Ala Pro Gly Gln Gly Leu Glu Trp Met
        35                  40                  45

Gly Gly Ile Val Pro Gln Tyr Gly Tyr Ala Thr Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Arg Ser Thr Thr Tyr Tyr Gly Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys
210                 215                 220
```

<210> SEQ ID NO 12
<211> LENGTH: 221
<212> TYPE: PRT
<213> ORGANISM: Artificial Sequence
<220> FEATURE:
<223> OTHER INFORMATION: >SEQ ID NO: 12 - anti-IL-1Rap-UCP02-C3 FAB
      heavy chain

<400> SEQUENCE: 12

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Asp Tyr
            20                  25                  30

Ala Met Gly Trp Val Arg Gln Ala Pro Gly Lys Gly Leu Glu Trp Val
        35                  40                  45

Ser Ala Ile Ser Tyr Asp Gly Glu Gly Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Arg Tyr Tyr Thr Ala Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys
    210                 215                 220

<210> SEQ ID NO 13
<211> LENGTH: 222
<212> TYPE: PRT
<213> ORGANISM: Artificial Sequence
<220> FEATURE:
<223> OTHER INFORMATION: >SEQ ID NO: 13 - anti-IL-1Rap-UCP02-C5 FAB
      heavy chain

<400> SEQUENCE: 13

Gln Val Gln Leu Val Gln Ser Gly Ala Glu Val Lys Lys Pro Gly Ser
1               5                   10                  15

Ser Val Lys Val Ser Cys Lys Ala Ser Gly Gly His Phe Asn Ile Tyr
            20                  25                  30

Ala Ile Ser Trp Val Arg Gln Ala Pro Gly Gln Gly Leu Glu Trp Met
        35                  40                  45

Gly Tyr Ile Ile Pro Ser Leu Gly Ala Val Asp Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Ser Ile Tyr His Gly Trp Met Ala Tyr Trp Gly Gln Gly
                100                 105                 110

Thr Leu Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Lys Val Glu Pro Lys Ser Cys
                210                 215                 220

<210> SEQ ID NO 14
<211> LENGTH: 225
<212> TYPE: PRT
<213> ORGANISM: Artificial Sequence
<220> FEATURE:
<223> OTHER INFORMATION: >SEQ ID NO: 14 - anti-IL-1Rap-UCP02-C8 FAB
      heavy chain

<400> SEQUENCE: 14

Gln Val Gln Leu Val Gln Ser Gly Ala Glu Val Lys Lys Pro Gly Ser
1               5                   10                  15

Ser Val Lys Val Ser Cys Lys Ala Ser Gly Gly Gln Phe Ser Glu Tyr
                20                  25                  30

Ala Ile Gln Trp Val Arg Gln Ala Pro Gly Gln Gly Leu Glu Trp Met
                35                  40                  45

Gly Tyr Ile Ile Pro Leu His Gly Gln Val Asp Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gln Thr Leu Tyr Asp Ser Gly Arg Gln Phe Asp Ile Trp
                100                 105                 110

Gly Gln Gly Thr Leu Val Thr Val Ser Ser Ala Ser Thr Lys Gly Pro
                115                 120                 125

Ser Val Phe Pro Leu Ala Pro Ser Ser Lys Ser Thr Ser Gly Gly Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Gln Thr Tyr Ile Cys Asn Val Asn
                195                 200                 205

His Lys Pro Ser Asn Thr Lys Val Asp Lys Lys Val Glu Pro Lys Ser

<210> SEQ ID NO 15
<211> LENGTH: 223
<212> TYPE: PRT
<213> ORGANISM: Artificial Sequence
<220> FEATURE:
<223> OTHER INFORMATION: >SEQ ID NO: 15 - anti-IL-1Rap-UCP02-C9 FAB
      heavy chain

<400> SEQUENCE: 15

Gln Val Gln Leu Val Gln Ser Gly Ala Glu Val Lys Lys Pro Gly Ser
1               5                   10                  15

Ser Val Lys Val Ser Cys Lys Ala Ser Gly Gly Val Phe Ser Tyr Tyr
            20                  25                  30

Ala Phe His Trp Val Arg Gln Ala Pro Gly Gln Gly Leu Glu Trp Met
        35                  40                  45

Gly Gly Ile Ile Pro Gly Tyr Gly Ala Thr Phe Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Pro Val Ser Tyr Ser Ser Gly Trp Tyr Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys
    210                 215                 220

<210> SEQ ID NO 16
<211> LENGTH: 226
<212> TYPE: PRT
<213> ORGANISM: Artificial Sequence
<220> FEATURE:
<223> OTHER INFORMATION: >SEQ ID NO: 16 - anti-IL-1Rap-UCP02-D2 FAB
      heavy chain

<400> SEQUENCE: 16

Gln Val Gln Leu Val Gln Ser Gly Ala Glu Val Lys Lys Pro Gly Ser
1               5                   10                  15

Ser Val Lys Val Ser Cys Lys Ala Ser Gly Gly Arg Phe Ser Asp Ser
            20                  25                  30

Ala Ile His Trp Val Arg Gln Ala Pro Gly Gln Gly Leu Glu Trp Met
        35                  40                  45

Gly Tyr Ile Leu Pro Gln Phe Gly Ala Pro Leu Tyr Ala Gln Lys Phe

```
                50                  55                  60
Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                     85                  90                  95

Ala Arg Gly Ser Tyr Tyr Gly Val Val Gly Tyr Val Pro Asp Asp Tyr
                100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
        210                 215                 220

Ser Cys
225

<210> SEQ ID NO 17
<211> LENGTH: 222
<212> TYPE: PRT
<213> ORGANISM: Artificial Sequence
<220> FEATURE:
<223> OTHER INFORMATION: >SEQ ID NO: 17 - anti-IL-1Rap-UCP02-G11 FAB
      heavy chain

<400> SEQUENCE: 17

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Gln Phe Asn Asp Tyr
                20                  25                  30

Ala Ile His Trp Val Arg Gln Ala Pro Gly Gln Gly Leu Glu Trp Met
            35                  40                  45

Gly Tyr Ile Ile Pro Ala Tyr Gly Gln Ala Glu Tyr Ala Gln Lys Phe
        50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                     85                  90                  95

Ala Arg Val Pro Tyr Ser Thr Ala Tyr Phe Asp Tyr Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175
```

```
Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys
    210                 215                 220
```

<210> SEQ ID NO 18
<211> LENGTH: 223
<212> TYPE: PRT
<213> ORGANISM: Artificial Sequence
<220> FEATURE:
<223> OTHER INFORMATION: >SEQ ID NO: 18 - anti-IL-1Rap-UCP02-G3 FAB
    heavy chain

<400> SEQUENCE: 18

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Tyr Leu Asn Glu Tyr
            20                  25                  30

Ala Ile His Trp Val Arg Gln Ala Pro Gly Gln Gly Leu Glu Trp Met
        35                  40                  45

Gly Ala Val Ile Pro Arg Tyr Gly Gln Thr Tyr Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Pro Leu Gly Tyr Ser Tyr Gly Trp Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys
    210                 215                 220
```

<210> SEQ ID NO 19
<211> LENGTH: 227
<212> TYPE: PRT
<213> ORGANISM: Artificial Sequence
<220> FEATURE:
<223> OTHER INFORMATION: >SEQ ID NO: 19 - anti-IL-1Rap-UCP02-G8 FAB
    heavy chain

<400> SEQUENCE: 19

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Phe Phe Ser Ile Tyr
            20                  25                  30
```

-continued

```
Ala Ile Ser Trp Val Arg Gln Ala Pro Gly Gln Gly Leu Glu Trp Met
            35                  40                  45

Gly Gly Ile Ala Pro Ala Ala Gly Ile Ala Glu Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gln Ser Pro Gly Arg Val Arg Glu Tyr Trp Tyr Asp
            100                 105                 110

Tyr Trp Gly Gln Gly Thr Leu Val Thr Val Ser Ser Ala Ser Thr Lys
            115                 120                 125

Gly Pro Ser Val Phe Pro Leu Ala Pro Ser Ser Lys Ser Thr Ser Gly
        130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
            195                 200                 205

Val Asn His Lys Pro Ser Asn Thr Lys Val Asp Lys Lys Val Glu Pro
        210                 215                 220

Lys Ser Cys
225

<210> SEQ ID NO 20
<211> LENGTH: 223
<212> TYPE: PRT
<213> ORGANISM: Artificial Sequence
<220> FEATURE:
<223> OTHER INFORMATION: >SEQ ID NO: 20 - anti-IL-1Rap-UCP02-H8 FAB
      heavy chain

<400> SEQUENCE: 20

Gln Val Gln Leu Val Gln Ser Gly Ala Glu Val Lys Lys Pro Gly Ser
1               5                   10                  15

Ser Val Lys Val Ser Cys Lys Ala Ser Gly Gly Val Phe Ser Gly Tyr
            20                  25                  30

Ala Ile Ser Trp Val Arg Gln Ala Pro Gly Gln Gly Leu Glu Trp Met
            35                  40                  45

Gly Gly Ile Ile Pro Glu Phe Gly Ala Thr Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Ser Ser Ala Tyr Ser Pro Trp Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160
```

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys
            210                 215                 220

<210> SEQ ID NO 21
<211> LENGTH: 223
<212> TYPE: PRT
<213> ORGANISM: Artificial Sequence
<220> FEATURE:
<223> OTHER INFORMATION: >SEQ ID NO: 21 - anti-IL-1Rap-UCP02-H9 FAB
      heavy chain

<400> SEQUENCE: 21

Gln Val Gln Leu Val Gln Ser Gly Ala Glu Val Lys Lys Pro Gly Ser
1               5                   10                  15

Ser Val Lys Val Ser Cys Lys Ala Ser Gly Gly Pro Phe Ser Ser Tyr
            20                  25                  30

Ala Leu Ser Trp Val Arg Gln Ala Pro Gly Gln Gly Leu Glu Trp Met
        35                  40                  45

Gly Gly Ile Ile Pro His His Gly Ala Thr Tyr Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Pro Asp Val Tyr Thr Pro Trp Phe Asp Val Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys
            210                 215                 220

<210> SEQ ID NO 22
<211> LENGTH: 223
<212> TYPE: PRT
<213> ORGANISM: Artificial Sequence
<220> FEATURE:
<223> OTHER INFORMATION: >SEQ ID NO: 22 - anti-IL-1Rap-UCP03-A2 FAB
      heavy chain

<400> SEQUENCE: 22

Gln Val Gln Leu Val Gln Ser Gly Ala Glu Val Lys Lys Pro Gly Ser
1               5                   10                  15

```
Ser Val Lys Val Ser Cys Lys Ala Ser Gly Gly Lys Phe Asn Phe Asp
            20                  25                  30

Val Ile His Trp Val Arg Gln Ala Pro Gly Gln Gly Leu Glu Trp Met
        35                  40                  45

Gly Gly Ile Ile Pro Asp Phe Ala Ser Thr His Tyr Ala Gln Lys Phe
 50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Pro Asp Tyr Tyr Thr Gly Trp Met Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys
210                 215                 220

<210> SEQ ID NO 23
<211> LENGTH: 222
<212> TYPE: PRT
<213> ORGANISM: Artificial Sequence
<220> FEATURE:
<223> OTHER INFORMATION: >SEQ ID NO: 23 - anti-IL-1Rap-UCP03-A3 FAB
      heavy chain

<400> SEQUENCE: 23

Gln Val Gln Leu Val Gln Ser Gly Ala Glu Val Lys Lys Pro Gly Ser
1               5                   10                  15

Ser Val Lys Val Ser Cys Lys Ala Ser Gly Gly Leu Phe Asn Glu Asn
            20                  25                  30

Ala Ile His Trp Val Arg Gln Ala Pro Gly Gln Gly Leu Glu Trp Met
        35                  40                  45

Gly Gly Ile Ile Pro Asp Val Gly Ala Ala Phe Tyr Ala Gln Lys Phe
 50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Ile Tyr Thr Ala Trp Phe Ala Val Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
```

```
                145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
                180                 185                 190
Ser Ser Leu Gly Thr Gln Thr Tyr Ile Cys Asn Val Asn His Lys Pro
                195                 200                 205
Ser Asn Thr Lys Val Asp Lys Lys Val Glu Pro Lys Ser Cys
            210                 215                 220

<210> SEQ ID NO 24
<211> LENGTH: 222
<212> TYPE: PRT
<213> ORGANISM: Artificial Sequence
<220> FEATURE:
<223> OTHER INFORMATION: >SEQ ID NO: 24 - anti-IL-1Rap-UCP03-B4 FAB
      heavy chain

<400> SEQUENCE: 24

Gln Val Gln Leu Val Gln Ser Gly Ala Glu Val Lys Lys Pro Gly Ser
1               5                   10                  15
Ser Val Lys Val Ser Cys Lys Ala Ser Gly Gly Pro Phe Ser Gln His
                20                  25                  30
Ala Ile Ser Trp Val Arg Gln Ala Pro Gly Gln Gly Leu Glu Trp Met
            35                  40                  45
Gly Gly Ile Ile Pro Phe Glu Gly Val Ala Phe Tyr Ala Gln Lys Phe
        50                  55                  60
Gln Gly Arg Val Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Ser Ser Ser Tyr Tyr Ser Trp Leu Asp Tyr Trp Gly Gln Gly
            100                 105                 110
Thr Leu Val Thr Val Ser Ser Ala Ser Thr Lys Gly Pro Ser Val Phe
        115                 120                 125
Pro Leu Ala Pro Ser Ser Lys Ser Thr Ser Gly Gly Thr Ala Ala Leu
    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
                180                 185                 190
Ser Ser Leu Gly Thr Gln Thr Tyr Ile Cys Asn Val Asn His Lys Pro
                195                 200                 205
Ser Asn Thr Lys Val Asp Lys Lys Val Glu Pro Lys Ser Cys
            210                 215                 220

<210> SEQ ID NO 25
<211> LENGTH: 223
<212> TYPE: PRT
<213> ORGANISM: Artificial Sequence
<220> FEATURE:
<223> OTHER INFORMATION: >SEQ ID NO: 25 - anti-IL-1Rap-UCP03-B6 FAB
      heavy chain

<400> SEQUENCE: 25

Gln Val Gln Leu Val Gln Ser Gly Ala Glu Val Lys Lys Pro Gly Ser
```

```
                1               5                   10                  15
            Ser Val Lys Val Ser Cys Lys Ala Ser Gly Asp Pro Phe Ser Val Tyr
                            20                  25                  30

Ile Ile His Trp Val Arg Gln Ala Pro Gly Gln Gly Leu Glu Trp Met
                            35                  40                  45

Gly Tyr Ile Ile Ala Gln Gln Gly Ser Ala Ser Tyr Ala Gln Lys Phe
                            50                  55                  60

Gln Gly Arg Val Thr Ile Thr Ala Asp Glu Ser Thr Ser Thr Ala Tyr
            65                  70                  75                  80

Met Glu Leu Ser Ser Leu Arg Ser Glu Asp Thr Ala Val Tyr Tyr Cys
                            85                  90                  95

Ala Arg Val Pro Asp Pro Tyr Ser Gly His Phe Asp Tyr Trp Gly Gln
                            100                 105                 110

Gly Thr Leu Val Thr Val Ser Ser Ala Ser Thr Lys Gly Pro Ser Val
                            115                 120                 125

Phe Pro Leu Ala Pro Ser Ser Lys Ser Thr Ser Gly Gly Thr Ala Ala
                            130                 135                 140

Leu Gly Cys Leu Val Lys Asp Tyr Phe Pro Glu Pro Val Thr Val Ser
            145                 150                 155                 160

Trp Asn Ser Gly Ala Leu Thr Ser Gly Val His Thr Phe Pro Ala Val
                            165                 170                 175

Leu Gln Ser Ser Gly Leu Tyr Ser Leu Ser Ser Val Val Thr Val Pro
                            180                 185                 190

Ser Ser Ser Leu Gly Thr Gln Thr Tyr Ile Cys Asn Val Asn His Lys
                            195                 200                 205

Pro Ser Asn Thr Lys Val Asp Lys Lys Val Glu Pro Lys Ser Cys
                            210                 215                 220

<210> SEQ ID NO 26
<211> LENGTH: 222
<212> TYPE: PRT
<213> ORGANISM: Artificial Sequence
<220> FEATURE:
<223> OTHER INFORMATION: >SEQ ID NO: 26 - anti-IL-1Rap-UCP03-C1 FAB
      heavy chain

<400> SEQUENCE: 26

Gln Val Gln Leu Val Gln Ser Gly Ala Glu Val Lys Lys Pro Gly Ser
            1               5                   10                  15

Ser Val Lys Val Ser Cys Lys Ala Ser Gly Gly Arg Phe Ser Ser Asn
                            20                  25                  30

Ala Ile Ser Trp Val Arg Gln Ala Pro Gly Gln Gly Leu Glu Trp Met
                            35                  40                  45

Gly Gly Ile Ile Pro His Phe Gly Ala Val Tyr Tyr Ala Gln Lys Phe
                            50                  55                  60

Gln Gly Arg Val Thr Ile Thr Ala Asp Glu Ser Thr Ser Thr Ala Tyr
            65                  70                  75                  80

Met Glu Leu Ser Ser Leu Arg Ser Glu Asp Thr Ala Val Tyr Tyr Cys
                            85                  90                  95

Ala Arg Gly Ser Val Tyr Thr Gly Trp Phe Asp Asn Trp Gly Gln Gly
                            100                 105                 110

Thr Leu Val Thr Val Ser Ser Ala Ser Thr Lys Gly Pro Ser Val Phe
                            115                 120                 125

Pro Leu Ala Pro Ser Ser Lys Ser Thr Ser Gly Gly Thr Ala Ala Leu
                            130                 135                 140
```

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys
    210                 215                 220

<210> SEQ ID NO 27
<211> LENGTH: 222
<212> TYPE: PRT
<213> ORGANISM: Artificial Sequence
<220> FEATURE:
<223> OTHER INFORMATION: >SEQ ID NO: 27 - anti-IL-1Rap-UCP03-C2 FAB
      heavy chain

<400> SEQUENCE: 27

Gln Val Gln Leu Val Gln Ser Gly Ala Glu Val Lys Lys Pro Gly Ser
1               5                   10                  15

Ser Val Lys Val Ser Cys Lys Ala Ser Gly Asp Pro Phe Lys Arg Tyr
            20                  25                  30

Ala Ile Gly Trp Val Arg Gln Ala Pro Gly Gln Gly Leu Glu Trp Met
        35                  40                  45

Gly Gly Ile Ile Pro Thr Thr Gly Glu Ala Ile Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Gly Thr Thr Tyr Ala Ala Phe Asp His Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys
    210                 215                 220

<210> SEQ ID NO 28
<211> LENGTH: 222
<212> TYPE: PRT
<213> ORGANISM: Artificial Sequence
<220> FEATURE:
<223> OTHER INFORMATION: >SEQ ID NO: 28 - anti-IL-1Rap-UCP03-F4 FAB
      heavy chain

<400> SEQUENCE: 28

Gln Val Gln Leu Val Gln Ser Gly Ala Glu Val Lys Lys Pro Gly Ser
1               5                   10                  15

Ser Val Lys Val Ser Cys Lys Ala Ser Gly Gly Phe Ser Glu Tyr
            20                  25                  30

Ala Ile His Trp Val Arg Gln Ala Pro Gly Gln Gly Leu Glu Trp Met
        35                  40                  45

Gly Ala Ile Leu Pro Glu Gln Gly Ala Ala Tyr Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Gly Leu Tyr Val Pro Tyr Met Asp Ile Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys
    210                 215                 220

<210> SEQ ID NO 29
<211> LENGTH: 222
<212> TYPE: PRT
<213> ORGANISM: Artificial Sequence
<220> FEATURE:
<223> OTHER INFORMATION: >SEQ ID NO: 29 - anti-IL-1Rap-UCP03-G3 FAB
      heavy chain

<400> SEQUENCE: 29

Gln Val Gln Leu Val Gln Ser Gly Ala Glu Val Lys Lys Pro Gly Ser
1               5                   10                  15

Ser Val Lys Val Ser Cys Lys Ala Ser Gly Gly Pro Leu Ser Gly Tyr
            20                  25                  30

Ala Phe His Trp Val Arg Gln Ala Pro Gly Gln Gly Leu Glu Trp Met
        35                  40                  45

Gly Gly Ile Ile Pro Asn Phe Ala Gln Thr Asp Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Phe Ser Ile Tyr Ser Gly Trp Ser Asp Val Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

```
Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys
            210                 215                 220

<210> SEQ ID NO 30
<211> LENGTH: 222
<212> TYPE: PRT
<213> ORGANISM: Artificial Sequence
<220> FEATURE:
<223> OTHER INFORMATION: >SEQ ID NO: 30 - anti-IL-1Rap-UCP03-G4 FAB
      heavy chain

<400> SEQUENCE: 30

Gln Val Gln Leu Val Gln Ser Gly Ala Glu Val Lys Lys Pro Gly Ser
1               5                   10                  15

Ser Val Lys Val Ser Cys Lys Ala Ser Gly Gly Arg Phe Ser His Tyr
            20                  25                  30

Val Phe Ser Trp Val Arg Gln Ala Pro Gly Gln Gly Leu Glu Trp Met
        35                  40                  45

Gly Gly Ile Ile Pro Tyr Glu Gly Lys Pro Phe Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Asp Tyr Phe Tyr Tyr Phe Asp Pro Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys
            210                 215                 220

<210> SEQ ID NO 31
<211> LENGTH: 221
<212> TYPE: PRT
<213> ORGANISM: Artificial Sequence
<220> FEATURE:
<223> OTHER INFORMATION: >SEQ ID NO: 31 - anti-IL-1Rap-UCP04-C1 FAB
      heavy chain

<400> SEQUENCE: 31
```

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Thr Met Ser Trp Val Arg Gln Ala Pro Gly Lys Gly Leu Glu Trp Val
        35                  40                  45

Ser Ala Ile Ser Tyr Glu Gly Asp Gly Thr Leu Tyr Ala Asp Ser Val
50                  55                  60

Lys Gly Arg Phe Thr Ile Ser Arg Asp Asn Ser Lys Asn Thr Leu Tyr
65              70                  75                  80

Leu Gln Met Asn Ser Leu Arg Ala Glu Asp Thr Ala Val Tyr Tyr Cys
                85                  90                  95

Ala Arg Ser Leu Tyr Trp Ser Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys
210                 215                 220

<210> SEQ ID NO 32
<211> LENGTH: 225
<212> TYPE: PRT
<213> ORGANISM: Artificial Sequence
<220> FEATURE:
<223> OTHER INFORMATION: >SEQ ID NO: 32 - anti-IL-1Rap-C8-H1A-C4 FAB
      heavy chain

<400> SEQUENCE: 32

Gln Val Gln Leu Val Gln Ser Gly Ala Glu Val Lys Lys Pro Gly Ser
1               5                   10                  15

Ser Val Lys Val Ser Cys Lys Ala Ser Gly Gly Lys Leu Asn Ala Tyr
            20                  25                  30

Ala Ile Gln Trp Val Arg Gln Ala Pro Gly Gln Gly Leu Glu Trp Met
        35                  40                  45

Gly Tyr Ile Ile Pro Leu His Gly Gln Val Asp Tyr Ala Gln Lys Phe
50                  55                  60

Gln Gly Arg Val Thr Ile Thr Ala Asp Glu Ser Thr Ser Thr Ala Tyr
65              70                  75                  80

Met Glu Leu Ser Ser Leu Arg Ser Glu Asp Thr Ala Val Tyr Tyr Cys
                85                  90                  95

Ala Arg Gly Gln Thr Leu Tyr Asp Ser Gly Arg Gln Phe Asp Ile Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
```

```
                130             135             140
Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys
225

<210> SEQ ID NO 33
<211> LENGTH: 225
<212> TYPE: PRT
<213> ORGANISM: Artificial Sequence
<220> FEATURE:
<223> OTHER INFORMATION: >SEQ ID NO: 33 - anti-IL-1Rap-C8-H1A-C8 FAB
      heavy chain

<400> SEQUENCE: 33

Gln Val Gln Leu Val Gln Ser Gly Ala Glu Val Lys Lys Pro Gly Ser
1               5                   10                  15

Ser Val Lys Val Ser Cys Lys Ala Ser Gly Gly Leu Phe Ser Asp Tyr
            20                  25                  30

Ala Ile Gln Trp Val Arg Gln Ala Pro Gly Gln Gly Leu Glu Trp Met
        35                  40                  45

Gly Tyr Ile Ile Pro Leu His Gly Gln Val Asp Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gln Thr Leu Tyr Asp Ser Gly Arg Gln Phe Asp Ile Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys
225

<210> SEQ ID NO 34
<211> LENGTH: 225
```

```
<212> TYPE: PRT
<213> ORGANISM: Artificial Sequence
<220> FEATURE:
<223> OTHER INFORMATION: >SEQ ID NO: 34 - anti-IL-1Rap-C8-H1A-D8 FAB
      heavy chain

<400> SEQUENCE: 34

Gln Val Gln Leu Val Gln Ser Gly Ala Glu Val Lys Lys Pro Gly Ser
1               5                   10                  15

Ser Val Lys Val Ser Cys Lys Ala Ser Gly Gly His Phe Asn Asn Tyr
            20                  25                  30

Ala Ile Gln Trp Val Arg Gln Ala Pro Gly Gln Gly Leu Glu Trp Met
        35                  40                  45

Gly Tyr Ile Ile Pro Leu His Gly Gln Val Asp Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gln Thr Leu Tyr Asp Ser Gly Arg Gln Phe Asp Ile Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys
225

<210> SEQ ID NO 35
<211> LENGTH: 225
<212> TYPE: PRT
<213> ORGANISM: Artificial Sequence
<220> FEATURE:
<223> OTHER INFORMATION: >SEQ ID NO: 35 - anti-IL-1Rap-C8-H1A-F1 FAB
      heavy chain

<400> SEQUENCE: 35

Gln Val Gln Leu Val Gln Ser Gly Ala Glu Val Lys Lys Pro Gly Ser
1               5                   10                  15

Ser Val Lys Val Ser Cys Lys Ala Ser Gly Gly Ile Phe Ser Asn Tyr
            20                  25                  30

Ala Ile Gln Trp Val Arg Gln Ala Pro Gly Gln Gly Leu Glu Trp Met
        35                  40                  45

Gly Tyr Ile Ile Pro Leu His Gly Gln Val Asp Tyr Ala Gln Lys Phe
    50                  55                  60

Gln Gly Arg Val Thr Ile Thr Ala Asp Glu Ser Thr Ser Thr Ala Tyr
65                  70                  75                  80
```

```
Met Glu Leu Ser Ser Leu Arg Ser Glu Asp Thr Ala Val Tyr Tyr Cys
                85                  90                  95

Ala Arg Gly Gln Thr Leu Tyr Asp Ser Gly Arg Gln Phe Asp Ile Trp
            100                 105                 110

Gly Gln Gly Thr Leu Val Thr Val Ser Ser Ala Ser Thr Lys Gly Pro
            115                 120                 125

Ser Val Phe Pro Leu Ala Pro Ser Ser Lys Ser Thr Ser Gly Gly Thr
            130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Lys Val Glu Pro Lys Ser
            210                 215                 220

Cys
225

<210> SEQ ID NO 36
<211> LENGTH: 225
<212> TYPE: PRT
<213> ORGANISM: Artificial Sequence
<220> FEATURE:
<223> OTHER INFORMATION: >SEQ ID NO: 36 - anti-IL-1Rap-C8-H1A-G11 FAB
      heavy chain

<400> SEQUENCE: 36

Gln Val Gln Leu Val Gln Ser Gly Ala Glu Val Lys Lys Pro Gly Ser
1               5                   10                  15

Ser Val Lys Val Ser Cys Lys Ala Ser Gly Gly Arg Phe His Gln Tyr
            20                  25                  30

Ala Ile Gln Trp Val Arg Gln Ala Pro Gly Gln Gly Leu Glu Trp Met
        35                  40                  45

Gly Tyr Ile Ile Pro Leu His Gly Gln Val Asp Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gln Thr Leu Tyr Asp Ser Gly Arg Gln Phe Asp Ile Trp
            100                 105                 110

Gly Gln Gly Thr Leu Val Thr Val Ser Ser Ala Ser Thr Lys Gly Pro
            115                 120                 125

Ser Val Phe Pro Leu Ala Pro Ser Ser Lys Ser Thr Ser Gly Gly Thr
            130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
            195                 200                 205
```

His Lys Pro Ser Asn Thr Lys Val Asp Lys Lys Val Glu Pro Lys Ser
    210                 215                 220

Cys
225

<210> SEQ ID NO 37
<211> LENGTH: 225
<212> TYPE: PRT
<213> ORGANISM: Artificial Sequence
<220> FEATURE:
<223> OTHER INFORMATION: >SEQ ID NO: 37 - anti-IL-1Rap-C8-H1A-G1 FAB
      heavy chain

<400> SEQUENCE: 37

Gln Val Gln Leu Val Gln Ser Gly Ala Glu Val Lys Lys Pro Gly Ser
1               5                   10                  15

Ser Val Lys Val Ser Cys Lys Ala Ser Gly Gly Ala Ser Arg Ala Tyr
            20                  25                  30

Ala Ile His Trp Val Arg Gln Ala Pro Gly Gln Gly Leu Glu Trp Met
        35                  40                  45

Gly Tyr Ile Ile Pro Leu His Gly Gln Val Asp Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gln Thr Leu Tyr Asp Ser Gly Arg Gln Phe Asp Ile Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys
225

<210> SEQ ID NO 38
<211> LENGTH: 225
<212> TYPE: PRT
<213> ORGANISM: Artificial Sequence
<220> FEATURE:
<223> OTHER INFORMATION: >SEQ ID NO: 38 - anti-IL-1Rap-C8-H1A-G3 FAB
      heavy chain

<400> SEQUENCE: 38

Gln Val Gln Leu Val Gln Ser Gly Ala Glu Val Lys Lys Pro Gly Ser
1               5                   10                  15

Ser Val Lys Val Ser Cys Lys Ala Ser Gly Gly Pro Phe Ser Asp Tyr
            20                  25                  30

-continued

Ala Ile Gln Trp Val Arg Gln Ala Pro Gly Gln Gly Leu Glu Trp Met
        35                  40                  45

Gly Tyr Ile Ile Pro Leu His Gly Gln Val Asp Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gln Thr Leu Tyr Asp Ser Gly Arg Gln Phe Asp Ile Trp
            100                 105                 110

Gly Gln Gly Thr Leu Val Thr Val Ser Ser Ala Ser Thr Lys Gly Pro
            115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys
225

<210> SEQ ID NO 39
<211> LENGTH: 225
<212> TYPE: PRT
<213> ORGANISM: Artificial Sequence
<220> FEATURE:
<223> OTHER INFORMATION: >SEQ ID NO: 39 - anti-IL-1Rap-C8-H1B-A8 FAB
      heavy chain

<400> SEQUENCE: 39

Gln Val Gln Leu Val Gln Ser Gly Ala Glu Val Lys Lys Pro Gly Ser
1               5                   10                  15

Ser Val Lys Val Ser Cys Lys Ala Ser Gly Glu Gly Ser Tyr Pro Tyr
            20                  25                  30

Ala Ile Gln Trp Val Arg Gln Ala Pro Gly Gln Gly Leu Glu Trp Met
        35                  40                  45

Gly Tyr Ile Ile Pro Leu His Gly Gln Val Asp Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gln Thr Leu Tyr Asp Ser Gly Arg Gln Phe Asp Ile Trp
            100                 105                 110

Gly Gln Gly Thr Leu Val Thr Val Ser Ser Ala Ser Thr Lys Gly Pro
            115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr

```
                145                 150                 155                 160
Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Gln Thr Tyr Ile Cys Asn Val Asn
                195                 200                 205

His Lys Pro Ser Asn Thr Lys Val Asp Lys Lys Val Glu Pro Lys Ser
                210                 215                 220

Cys
225

<210> SEQ ID NO 40
<211> LENGTH: 225
<212> TYPE: PRT
<213> ORGANISM: Artificial Sequence
<220> FEATURE:
<223> OTHER INFORMATION: >SEQ ID NO: 40 - anti-IL-1Rap-C8-H1B-B10 FAB
      heavy chain

<400> SEQUENCE: 40

Gln Val Gln Leu Val Gln Ser Gly Ala Glu Val Lys Lys Pro Gly Ser
1               5                   10                  15

Ser Val Lys Val Ser Cys Lys Ala Ser Gly Val Thr His Thr Ser Tyr
                20                  25                  30

Ala Ile Gln Trp Val Arg Gln Ala Pro Gly Gln Gly Leu Glu Trp Met
            35                  40                  45

Gly Tyr Ile Ile Pro Leu His Gly Gln Val Asp Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gln Thr Leu Tyr Asp Ser Gly Arg Gln Phe Asp Ile Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Gln Thr Tyr Ile Cys Asn Val Asn
                195                 200                 205

His Lys Pro Ser Asn Thr Lys Val Asp Lys Lys Val Glu Pro Lys Ser
                210                 215                 220

Cys
225

<210> SEQ ID NO 41
<211> LENGTH: 225
<212> TYPE: PRT
<213> ORGANISM: Artificial Sequence
<220> FEATURE:
```

<223> OTHER INFORMATION: >SEQ ID NO: 41 - anti-IL-1Rap-C8-H1B-B8 FAB heavy chain

<400> SEQUENCE: 41

Gln Val Gln Leu Val Gln Ser Gly Ala Glu Val Lys Lys Pro Gly Ser
1               5                   10                  15

Ser Val Lys Val Ser Cys Lys Ala Ser Gly Ser Pro Ala Glu Pro Tyr
            20                  25                  30

Ala Ile Gln Trp Val Arg Gln Ala Pro Gly Gln Gly Leu Glu Trp Met
        35                  40                  45

Gly Tyr Ile Ile Pro Leu His Gly Gln Val Asp Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gln Thr Leu Tyr Asp Ser Gly Arg Gln Phe Asp Ile Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys
225

<210> SEQ ID NO 42
<211> LENGTH: 225
<212> TYPE: PRT
<213> ORGANISM: Artificial Sequence
<220> FEATURE:
<223> OTHER INFORMATION: >SEQ ID NO: 42 - anti-IL-1Rap-C8-H1B-D8 FAB heavy chain

<400> SEQUENCE: 42

Gln Val Gln Leu Val Gln Ser Gly Ala Glu Val Lys Lys Pro Gly Ser
1               5                   10                  15

Ser Val Lys Val Ser Cys Lys Ala Ser Gly Pro Ser Asn Pro Val Tyr
            20                  25                  30

Ala Ile Gln Trp Val Arg Gln Ala Pro Gly Gln Gly Leu Glu Trp Met
        35                  40                  45

Gly Tyr Ile Ile Pro Leu His Gly Gln Val Asp Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gln Thr Leu Tyr Asp Ser Gly Arg Gln Phe Asp Ile Trp
            100                 105                 110

Gly Gln Gly Thr Leu Val Thr Val Ser Ser Ala Ser Thr Lys Gly Pro
            115                 120                 125

Ser Val Phe Pro Leu Ala Pro Ser Ser Lys Ser Thr Ser Gly Gly Thr
            130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Lys Val Glu Pro Lys Ser
            210                 215                 220

Cys
225

<210> SEQ ID NO 43
<211> LENGTH: 225
<212> TYPE: PRT
<213> ORGANISM: Artificial Sequence
<220> FEATURE:
<223> OTHER INFORMATION: >SEQ ID NO: 43 - anti-IL-1Rap-C8-H1B-E7 FAB
      heavy chain

<400> SEQUENCE: 43

Gln Val Gln Leu Val Gln Ser Gly Ala Glu Val Lys Lys Pro Gly Ser
1               5                   10                  15

Ser Val Lys Val Ser Cys Lys Ala Ser Gly Ser Lys His Gly Asn Tyr
            20                  25                  30

Ala Ile Gln Trp Val Arg Gln Ala Pro Gly Gln Gly Leu Glu Trp Met
            35                  40                  45

Gly Tyr Ile Ile Pro Leu His Gly Gln Val Asp Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Gly Gln Thr Leu Tyr Asp Ser Gly Arg Gln Phe Asp Ile Trp
            100                 105                 110

Gly Gln Gly Thr Leu Val Thr Val Ser Ser Ala Ser Thr Lys Gly Pro
            115                 120                 125

Ser Val Phe Pro Leu Ala Pro Ser Ser Lys Ser Thr Ser Gly Gly Thr
            130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Lys Val Glu Pro Lys Ser
            210                 215                 220

Cys
225

<210> SEQ ID NO 44
<211> LENGTH: 225
<212> TYPE: PRT
<213> ORGANISM: Artificial Sequence
<220> FEATURE:
<223> OTHER INFORMATION: >SEQ ID NO: 44 - anti-IL-1Rap-C8-H1B-F3 FAB
      heavy chain

<400> SEQUENCE: 44

Gln Val Gln Leu Val Gln Ser Gly Ala Glu Val Lys Lys Pro Gly Ser
1               5                   10                  15

Ser Val Lys Val Ser Cys Lys Ala Ser Gly Gly Pro His Thr Ala His
                20                  25                  30

Ala Ile Gln Trp Val Arg Gln Ala Pro Gly Gln Gly Leu Glu Trp Met
            35                  40                  45

Gly Tyr Ile Ile Pro Leu His Gly Gln Val Asp Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gln Thr Leu Tyr Asp Ser Gly Arg Gln Phe Asp Ile Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys
225

<210> SEQ ID NO 45
<211> LENGTH: 225
<212> TYPE: PRT
<213> ORGANISM: Artificial Sequence
<220> FEATURE:
<223> OTHER INFORMATION: >SEQ ID NO: 45 - anti-IL-1Rap-C8-H1B-G10 FAB
      heavy chain

<400> SEQUENCE: 45

Gln Val Gln Leu Val Gln Ser Gly Ala Glu Val Lys Lys Pro Gly Ser
1               5                   10                  15

Ser Val Lys Val Ser Cys Lys Ala Ser Gly Gly Pro Arg Arg Ala Tyr
                20                  25                  30

Ala Ile Gln Trp Val Arg Gln Ala Pro Gly Gln Gly Leu Glu Trp Met
            35                  40                  45

```
Gly Tyr Ile Ile Pro Leu His Gly Gln Val Asp Tyr Ala Gln Lys Phe
             50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Gln Thr Leu Tyr Asp Ser Gly Arg Gln Phe Asp Ile Trp
            100                 105                 110

Gly Gln Gly Thr Leu Val Thr Val Ser Ser Ala Ser Thr Lys Gly Pro
            115                 120                 125

Ser Val Phe Pro Leu Ala Pro Ser Ser Lys Ser Thr Ser Gly Gly Thr
            130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Lys Val Glu Pro Lys Ser
            210                 215                 220

Cys
225

<210> SEQ ID NO 46
<211> LENGTH: 225
<212> TYPE: PRT
<213> ORGANISM: Artificial Sequence
<220> FEATURE:
<223> OTHER INFORMATION: >SEQ ID NO: 46 - anti-IL-1Rap-C8-H1B-H10 FAB
      heavy chain

<400> SEQUENCE: 46

Gln Val Gln Leu Val Gln Ser Gly Ala Glu Val Lys Lys Pro Gly Ser
 1               5                  10                  15

Ser Val Lys Val Ser Cys Lys Ala Ser Gly Ser Thr Trp Glu Pro Tyr
             20                  25                  30

Ala Ile Gln Trp Val Arg Gln Ala Pro Gly Gln Gly Leu Glu Trp Met
            35                  40                  45

Gly Tyr Ile Ile Pro Leu His Gly Gln Val Asp Tyr Ala Gln Lys Phe
             50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Gln Thr Leu Tyr Asp Ser Gly Arg Gln Phe Asp Ile Trp
            100                 105                 110

Gly Gln Gly Thr Leu Val Thr Val Ser Ser Ala Ser Thr Lys Gly Pro
            115                 120                 125

Ser Val Phe Pro Leu Ala Pro Ser Ser Lys Ser Thr Ser Gly Gly Thr
            130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
```

```
                    165                 170                 175
Ala Val Leu Gln Ser Ser Gly Leu Tyr Ser Leu Ser Val Val Thr
                180                 185                 190

Val Pro Ser Ser Leu Gly Thr Gln Thr Tyr Ile Cys Asn Val Asn
            195                 200                 205

His Lys Pro Ser Asn Thr Lys Val Asp Lys Lys Val Glu Pro Lys Ser
        210                 215                 220

Cys
225

<210> SEQ ID NO 47
<211> LENGTH: 225
<212> TYPE: PRT
<213> ORGANISM: Artificial Sequence
<220> FEATURE:
<223> OTHER INFORMATION: >SEQ ID NO: 47 - anti-IL-1Rap-C8-H2B-B5 FAB
      heavy chain

<400> SEQUENCE: 47

Gln Val Gln Leu Val Gln Ser Gly Ala Glu Val Lys Lys Pro Gly Ser
1               5                   10                  15

Ser Val Lys Val Ser Cys Lys Ala Ser Gly Gln Phe Ser Glu Tyr
            20                  25                  30

Ala Ile Gln Trp Val Arg Gln Ala Pro Gly Gln Gly Leu Glu Trp Met
        35                  40                  45

Gly Tyr Ile Ile Pro Thr Val Gly Gly Phe Asp Tyr Ala Gln Lys Phe
    50                  55                  60

Gln Gly Arg Val Thr Ile Thr Ala Asp Glu Ser Thr Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gln Thr Leu Tyr Asp Ser Gly Arg Gln Phe Asp Ile Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Val Val Thr
            180                 185                 190

Val Pro Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys
225

<210> SEQ ID NO 48
<211> LENGTH: 225
<212> TYPE: PRT
<213> ORGANISM: Artificial Sequence
<220> FEATURE:
<223> OTHER INFORMATION: >SEQ ID NO: 48 - anti-IL-1Rap-C8-H2B-C10 FAB
      heavy chain
```

<400> SEQUENCE: 48

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Gln Phe Ser Glu Tyr
            20                  25                  30

Ala Ile Gln Trp Val Arg Gln Ala Pro Gly Gln Gly Leu Glu Trp Met
        35                  40                  45

Gly Tyr Ile Ile Pro Ser Leu Gly Gly Tyr Asp Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gln Thr Leu Tyr Asp Ser Gly Arg Gln Phe Asp Ile Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys
225
```

<210> SEQ ID NO 49
<211> LENGTH: 225
<212> TYPE: PRT
<213> ORGANISM: Artificial Sequence
<220> FEATURE:
<223> OTHER INFORMATION: >SEQ ID NO: 49 - anti-IL-1Rap-C8-recA FAB heavy chain

<400> SEQUENCE: 49

```
Gln Val Gln Leu Val Gln Ser Gly Ala Glu Val Lys Lys Pro Gly Ser
1               5                   10                  15

Ser Val Lys Val Ser Cys Lys Ala Ser Gly Ser Thr Trp Glu Pro Tyr
            20                  25                  30

Ala Ile Gln Trp Val Arg Gln Ala Pro Gly Gln Gly Leu Glu Trp Met
        35                  40                  45

Gly Tyr Ile Ile Pro Ser Leu Gly Gly Tyr Asp Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gln Thr Leu Tyr Asp Ser Gly Arg Gln Phe Asp Ile Trp
            100                 105                 110
```

```
Gly Gln Gly Thr Leu Val Thr Val Ser Ser Ala Ser Thr Lys Gly Pro
            115                 120                 125

Ser Val Phe Pro Leu Ala Pro Ser Ser Lys Ser Thr Ser Gly Gly Thr
            130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Lys Val Glu Pro Lys Ser
            210                 215                 220

Cys
225

<210> SEQ ID NO 50
<211> LENGTH: 225
<212> TYPE: PRT
<213> ORGANISM: Artificial Sequence
<220> FEATURE:
<223> OTHER INFORMATION: >SEQ ID NO: 50 - anti-IL-1Rap-C8-recB FAB heavy
      chain

<400> SEQUENCE: 50

Gln Val Gln Leu Val Gln Ser Gly Ala Glu Val Lys Lys Pro Gly Ser
1               5                   10                  15

Ser Val Lys Val Ser Cys Lys Ala Ser Gly Gly Pro Arg Arg Ala Tyr
            20                  25                  30

Ala Ile Gln Trp Val Arg Gln Ala Pro Gly Gln Gly Leu Glu Trp Met
        35                  40                  45

Gly Tyr Ile Ile Pro Ser Leu Gly Gly Tyr Asp Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gln Thr Leu Tyr Asp Ser Gly Arg Gln Phe Asp Ile Trp
            100                 105                 110

Gly Gln Gly Thr Leu Val Thr Val Ser Ser Ala Ser Thr Lys Gly Pro
            115                 120                 125

Ser Val Phe Pro Leu Ala Pro Ser Ser Lys Ser Thr Ser Gly Gly Thr
            130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Lys Val Glu Pro Lys Ser
            210                 215                 220

Cys
225
```

```
<210> SEQ ID NO 51
<211> LENGTH: 225
<212> TYPE: PRT
<213> ORGANISM: Artificial Sequence
<220> FEATURE:
<223> OTHER INFORMATION: >SEQ ID NO: 51 - anti-IL-1Rap-C8-recC FAB heavy
      chain

<400> SEQUENCE: 51
```

Gln Val Gln Leu Val Gln Ser Gly Ala Glu Val Lys Lys Pro Gly Ser
1               5                   10                  15

Ser Val Lys Val Ser Cys Lys Ala Ser Gly Ser Pro Ala Glu Pro Tyr
            20                  25                  30

Ala Ile Gln Trp Val Arg Gln Ala Pro Gly Gln Gly Leu Glu Trp Met
        35                  40                  45

Gly Tyr Ile Ile Pro Ser Leu Gly Gly Tyr Asp Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gln Thr Leu Tyr Asp Ser Gly Arg Gln Phe Asp Ile Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys
225

```
<210> SEQ ID NO 52
<211> LENGTH: 452
<212> TYPE: PRT
<213> ORGANISM: Artificial Sequence
<220> FEATURE:
<223> OTHER INFORMATION: >SEQ ID NO: 52 - anti-IL-1Rap-UCP02-C8 IgG1
      LALA heavy chain

<400> SEQUENCE: 52
```

Gln Val Gln Leu Val Gln Ser Gly Ala Glu Val Lys Lys Pro Gly Ser
1               5                   10                  15

Ser Val Lys Val Ser Cys Lys Ala Ser Gly Gly Gln Phe Ser Glu Tyr
            20                  25                  30

Ala Ile Gln Trp Val Arg Gln Ala Pro Gly Gln Gly Leu Glu Trp Met
        35                  40                  45

Gly Tyr Ile Ile Pro Leu His Gly Gln Val Asp Tyr Ala Gln Lys Phe
    50                  55                  60

```
Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Gln Thr Leu Tyr Asp Ser Gly Arg Gln Phe Asp Ile Trp
            100                 105                 110

Gly Gln Gly Thr Leu Val Thr Val Ser Ser Ala Ser Thr Lys Gly Pro
            115                 120                 125

Ser Val Phe Pro Leu Ala Pro Ser Ser Lys Ser Thr Ser Gly Gly Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 53
<211> LENGTH: 448
```

```
<212> TYPE: PRT
<213> ORGANISM: Artificial Sequence
<220> FEATURE:
<223> OTHER INFORMATION: >SEQ ID NO: 53 - anti-IL-1Rap-UCP02-C3 IgG1
      LALA heavy chain

<400> SEQUENCE: 53
```

| | | | | | | | | | | | | | | |
|---|---|---|---|---|---|---|---|---|---|---|---|---|---|---|
| Glu | Val | Gln | Leu | Leu | Glu | Ser | Gly | Gly | Gly | Leu | Val | Gln | Pro | Gly | Gly |
| 1 | | | | 5 | | | | | 10 | | | | | 15 |

| Ser | Leu | Arg | Leu | Ser | Cys | Ala | Ala | Ser | Gly | Phe | Thr | Phe | Arg | Asp | Tyr |
| | | | 20 | | | | | 25 | | | | | 30 | | |

| Ala | Met | Gly | Trp | Val | Arg | Gln | Ala | Pro | Gly | Lys | Gly | Leu | Glu | Trp | Val |
| | | 35 | | | | | 40 | | | | | 45 | | | |

| Ser | Ala | Ile | Ser | Tyr | Asp | Gly | Glu | Gly | Thr | Leu | Tyr | Ala | Asp | Ser | Val |
| 50 | | | | | 55 | | | | | 60 | | | | | |

| Lys | Gly | Arg | Phe | Thr | Ile | Ser | Arg | Asp | Asn | Ser | Lys | Asn | Thr | Leu | Tyr |
| 65 | | | | | 70 | | | | | 75 | | | | | 80 |

| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |

| Ala | Arg | Phe | Arg | Tyr | Tyr | Thr | Ala | Phe | Asp | Tyr | Trp | Gly | Gln | Gly | Thr |
| | | | 100 | | | | | 105 | | | | | 110 | | |

| Leu | Val | Thr | Val | Ser | Ser | Ala | Ser | Thr | Lys | Gly | Pro | Ser | Val | Phe | Pro |
| | | 115 | | | | | 120 | | | | | 125 | | | |

| Leu | Ala | Pro | Ser | Ser | Lys | Ser | Thr | Ser | Gly | Gly | Thr | Ala | Ala | Leu | Gly |
| 130 | | | | | 135 | | | | | 140 | | | | | |

| Cys | Leu | Val | Lys | Asp | Tyr | Phe | Pro | Glu | Pro | Val | Thr | Val | Ser | Trp | Asn |
| 145 | | | | | 150 | | | | | 155 | | | | | 160 |

| Ser | Gly | Ala | Leu | Thr | Ser | Gly | Val | His | Thr | Phe | Pro | Ala | Val | Leu | Gln |
| | | | | 165 | | | | | 170 | | | | | 175 | |

| Ser | Ser | Gly | Leu | Tyr | Ser | Leu | Ser | Val | Val | Thr | Val | Pro | Ser | Ser |
| | | | 180 | | | | | 185 | | | | | 190 | |

| Ser | Leu | Gly | Thr | Gln | Thr | Tyr | Ile | Cys | Asn | Val | Asn | His | Lys | Pro | Ser |
| | | 195 | | | | | 200 | | | | | 205 | | | |

| Asn | Thr | Lys | Val | Asp | Lys | Lys | Val | Glu | Pro | Lys | Ser | Cys | Asp | Lys | Thr |
| 210 | | | | | 215 | | | | | 220 | | | | | |

| His | Thr | Cys | Pro | Pro | Cys | Pro | Ala | Pro | Glu | Ala | Ala | Gly | Gly | Pro | Ser |
| 225 | | | | | 230 | | | | | 235 | | | | | 240 |

| Val | Phe | Leu | Phe | Pro | Pro | Lys | Pro | Lys | Asp | Thr | Leu | Met | Ile | Ser | Arg |
| | | | | 245 | | | | | 250 | | | | | 255 | |

| Thr | Pro | Glu | Val | Thr | Cys | Val | Val | Val | Asp | Val | Ser | His | Glu | Asp | Pro |
| | | | 260 | | | | | 265 | | | | | 270 | | |

| Glu | Val | Lys | Phe | Asn | Trp | Tyr | Val | Asp | Gly | Val | Glu | Val | His | Asn | Ala |
| | | 275 | | | | | 280 | | | | | 285 | | | |

| Lys | Thr | Lys | Pro | Arg | Glu | Glu | Gln | Tyr | Asn | Ser | Thr | Tyr | Arg | Val | Val |
| | | 290 | | | | | 295 | | | | | 300 | | | |

| Ser | Val | Leu | Thr | Val | Leu | His | Gln | Asp | Trp | Leu | Asn | Gly | Lys | Glu | Tyr |
| 305 | | | | | 310 | | | | | 315 | | | | | 320 |

| Lys | Cys | Lys | Val | Ser | Asn | Lys | Ala | Leu | Pro | Ala | Pro | Ile | Glu | Lys | Thr |
| | | | | 325 | | | | | 330 | | | | | 335 | |

| Ile | Ser | Lys | Ala | Lys | Gly | Gln | Pro | Arg | Glu | Pro | Gln | Val | Tyr | Thr | Leu |
| | | | 340 | | | | | 345 | | | | | 350 | | |

| Pro | Pro | Ser | Arg | Asp | Glu | Leu | Thr | Lys | Asn | Gln | Val | Ser | Leu | Thr | Cys |
| | | | 355 | | | | | 360 | | | | | 365 | | |

| Leu | Val | Lys | Gly | Phe | Tyr | Pro | Ser | Asp | Ile | Ala | Val | Glu | Trp | Glu | Ser |
| | | 370 | | | | | 375 | | | | | 380 | | | |

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
        420                 425                 430

Leu His Asn His Tyr Thr Gln Lys Ser Leu Ser Leu Ser Pro Gly Lys
        435                 440                 445

<210> SEQ ID NO 54
<211> LENGTH: 452
<212> TYPE: PRT
<213> ORGANISM: Artificial Sequence
<220> FEATURE:
<223> OTHER INFORMATION: >SEQ ID NO: 54 - anti-IL-1Rap-C8-RecC IgG1 LALA
      heavy chain

<400> SEQUENCE: 54

Gln Val Gln Leu Val Gln Ser Gly Ala Glu Val Lys Lys Pro Gly Ser
1               5                   10                  15

Ser Val Lys Val Ser Cys Lys Ala Ser Gly Ser Pro Ala Glu Pro Tyr
            20                  25                  30

Ala Ile Gln Trp Val Arg Gln Ala Pro Gly Gln Gly Leu Glu Trp Met
        35                  40                  45

Gly Tyr Ile Ile Pro Ser Leu Gly Tyr Asp Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Gly Gln Thr Leu Tyr Asp Ser Gly Arg Gln Phe Asp Ile Trp
        100                 105                 110

Gly Gln Gly Thr Leu Val Thr Val Ser Ser Ala Ser Thr Lys Gly Pro
    115                 120                 125

Ser Val Phe Pro Leu Ala Pro Ser Ser Lys Ser Thr Ser Gly Gly Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
        180                 185                 190

Val Pro Ser Ser Ser Leu Gly Thr Gln Thr Tyr Ile Cys Asn Val Asn
    195                 200                 205

His Lys Pro Ser Asn Thr Lys Val Asp Lys Lys Val Glu Pro Lys Ser
210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
        260                 265                 270

His Glu Asp Pro Glu Val Lys Phe Asn Trp Tyr Val Asp Gly Val Glu
    275                 280                 285

Val His Asn Ala Lys Thr Lys Pro Arg Glu Glu Gln Tyr Asn Ser Thr

```
            290                 295                 300
Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 55
<211> LENGTH: 452
<212> TYPE: PRT
<213> ORGANISM: Artificial Sequence
<220> FEATURE:
<223> OTHER INFORMATION: >SEQ ID NO: 55 - anti-IL-1Rap-C8-RecC-AA IgG1
      LALA heavy chain

<400> SEQUENCE: 55

Gln Val Gln Leu Val Gln Ser Gly Ala Glu Val Lys Lys Pro Gly Ser
1               5                   10                  15

Ser Val Lys Val Ser Cys Lys Ala Ser Gly Ser Pro Ala Glu Pro Tyr
            20                  25                  30

Ala Ile Gln Trp Val Arg Gln Ala Pro Gly Gln Gly Leu Glu Trp Met
        35                  40                  45

Gly Tyr Ile Ile Pro Ser Leu Gly Gly Tyr Asp Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gln Thr Leu Tyr Ala Ala Gly Arg Gln Phe Asp Ile Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190
```

```
Val Pro Ser Ser Ser Leu Gly Thr Gln Thr Tyr Ile Cys Asn Val Asn
            195                 200                 205

His Lys Pro Ser Asn Thr Lys Val Asp Lys Val Glu Pro Lys Ser
    210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
        260                 265                 270

His Glu Asp Pro Glu Val Lys Phe Asn Trp Tyr Val Asp Gly Val Glu
    275                 280                 285

Val His Asn Ala Lys Thr Lys Pro Arg Glu Glu Gln Tyr Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
        340                 345                 350

Val Tyr Thr Leu Pro Pro Ser Arg Asp Glu Leu Thr Lys Asn Gln Val
    355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
        420                 425                 430

Met His Glu Ala Leu His Asn His Tyr Thr Gln Lys Ser Leu Ser Leu
    435                 440                 445

Ser Pro Gly Lys
    450

<210> SEQ ID NO 56
<211> LENGTH: 452
<212> TYPE: PRT
<213> ORGANISM: Artificial Sequence
<220> FEATURE:
<223> OTHER INFORMATION: >SEQ ID NO: 56 - anti-IL-1Rap-C8-RecC-DA IgG1
      LALA heavy chain

<400> SEQUENCE: 56

Gln Val Gln Leu Val Gln Ser Gly Ala Glu Val Lys Lys Pro Gly Ser
1               5                   10                  15

Ser Val Lys Val Ser Cys Lys Ala Ser Gly Ser Pro Ala Glu Pro Tyr
            20                  25                  30

Ala Ile Gln Trp Val Arg Gln Ala Pro Gly Gln Gly Leu Glu Trp Met
        35                  40                  45

Gly Tyr Ile Ile Pro Ser Leu Gly Gly Tyr Asp Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

Ala Arg Gly Gln Thr Leu Tyr Asp Ala Gly Arg Gln Phe Asp Ile Trp
            100                 105                 110

Gly Gln Gly Thr Leu Val Thr Val Ser Ser Ala Ser Thr Lys Gly Pro
            115                 120                 125

Ser Val Phe Pro Leu Ala Pro Ser Ser Lys Ser Thr Ser Gly Gly Thr
            130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Lys Val Glu Pro Lys Ser
            210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
            290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
            325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
            355                 360                 365

Ser Leu Thr Cys Leu Val Lys Gly Phe Tyr Pro Ser Asp Ile Ala Val
            370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly Lys
    450

<210> SEQ ID NO 57
<211> LENGTH: 452
<212> TYPE: PRT
<213> ORGANISM: Artificial Sequence
<220> FEATURE:
<223> OTHER INFORMATION: >SEQ ID NO: 57 - anti-IL-1Rap-C8-RecC-AS IgG1
      LALA heavy chain

<400> SEQUENCE: 57

Gln Val Gln Leu Val Gln Ser Gly Ala Glu Val Lys Lys Pro Gly Ser
1               5                   10                  15

Ser Val Lys Val Ser Cys Lys Ala Ser Gly Ser Pro Ala Glu Pro Tyr
            20                  25                  30

Ala Ile Gln Trp Val Arg Gln Ala Pro Gly Gln Gly Leu Glu Trp Met
        35                  40                  45

Gly Tyr Ile Ile Pro Ser Leu Gly Gly Tyr Asp Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gln Thr Leu Tyr Ala Ser Gly Arg Gln Phe Asp Ile Trp
            100                 105                 110

Gly Gln Gly Thr Leu Val Thr Val Ser Ala Ser Thr Lys Gly Pro
        115                 120                 125

Ser Val Phe Pro Leu Ala Pro Ser Ser Lys Ser Thr Ser Gly Gly Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

-continued

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly Lys
        450

<210> SEQ ID NO 58
<211> LENGTH: 452
<212> TYPE: PRT
<213> ORGANISM: Artificial Sequence
<220> FEATURE:
<223> OTHER INFORMATION: >SEQ ID NO: 58 - anti-IL-1Rap-C8-RecC-ES IgG1
      LALA heavy chain

<400> SEQUENCE: 58

Gln Val Gln Leu Val Gln Ser Gly Ala Glu Val Lys Lys Pro Gly Ser
1               5                   10                  15

Ser Val Lys Val Ser Cys Lys Ala Ser Gly Ser Pro Ala Glu Pro Tyr
            20                  25                  30

Ala Ile Gln Trp Val Arg Gln Ala Pro Gly Gln Gly Leu Glu Trp Met
        35                  40                  45

Gly Tyr Ile Ile Pro Ser Leu Gly Gly Tyr Asp Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gln Thr Leu Tyr Glu Ser Gly Arg Gln Phe Asp Ile Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn

```
                305                 310                 315                 320
Gly Lys Glu Tyr Lys Cys Lys Val Ser Asn Lys Ala Leu Pro Ala Pro
                    325                 330                 335

Ile Glu Lys Thr Ile Ser Lys Ala Lys Gly Gln Pro Arg Glu Pro Gln
                340                 345                 350

Val Tyr Thr Leu Pro Pro Ser Arg Asp Glu Leu Thr Lys Asn Gln Val
                355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
                435                 440                 445

Ser Pro Gly Lys
        450

<210> SEQ ID NO 59
<211> LENGTH: 452
<212> TYPE: PRT
<213> ORGANISM: Artificial Sequence
<220> FEATURE:
<223> OTHER INFORMATION: >SEQ ID NO: 59 - anti-IL-1Rap-C8-RecC-ET IgG1
      LALA heavy chain

<400> SEQUENCE: 59

Gln Val Gln Leu Val Gln Ser Gly Ala Glu Val Lys Lys Pro Gly Ser
1               5                   10                  15

Ser Val Lys Val Ser Cys Lys Ala Ser Gly Ser Pro Ala Glu Pro Tyr
                20                  25                  30

Ala Ile Gln Trp Val Arg Gln Ala Pro Gly Gln Gly Leu Glu Trp Met
            35                  40                  45

Gly Tyr Ile Ile Pro Ser Leu Gly Gly Tyr Asp Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gln Thr Leu Tyr Glu Thr Gly Arg Gln Phe Asp Ile Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205
```

```
His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 60
<211> LENGTH: 221
<212> TYPE: PRT
<213> ORGANISM: Artificial Sequence
<220> FEATURE:
<223> OTHER INFORMATION: >SEQ ID NO: 60 - anti-IL-1Rap-C3-MP01-A2 FAB
      heavy chain

<400> SEQUENCE: 60

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala Glu Tyr
            20                  25                  30

Ala Met Asn Trp Val Arg Gln Ala Pro Gly Lys Gly Leu Glu Trp Val
        35                  40                  45

Ser Ala Ile Ser Tyr Asp Gly Glu Gly Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Arg Tyr Tyr Thr Ala Phe Asp Tyr Trp Gly Gln Gly Thr
            100                 105                 110
```

-continued

Leu Val Thr Val Ser Ser Ala Ser Thr Lys Gly Pro Ser Val Phe Pro
              115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys
    210                 215                 220

<210> SEQ ID NO 61
<211> LENGTH: 221
<212> TYPE: PRT
<213> ORGANISM: Artificial Sequence
<220> FEATURE:
<223> OTHER INFORMATION: >SEQ ID NO: 61 - anti-IL-1Rap-C3-MP01-A3 FAB
      heavy chain

<400> SEQUENCE: 61

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ile Phe Ser His Tyr
            20                  25                  30

Gly Met Ser Trp Val Arg Gln Ala Pro Gly Lys Gly Leu Glu Trp Val
        35                  40                  45

Ser Ala Ile Ser Tyr Asp Gly Glu Gly Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Arg Tyr Tyr Thr Ala Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys
    210                 215                 220

<210> SEQ ID NO 62
<211> LENGTH: 221
<212> TYPE: PRT

<213> ORGANISM: Artificial Sequence
<220> FEATURE:
<223> OTHER INFORMATION: >SEQ ID NO: 62 - anti-IL-1Rap-C3-MP01-B5 FAB heavy chain

<400> SEQUENCE: 62

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ile Phe Ser Thr Tyr
            20                  25                  30

Gly Met Gly Trp Val Arg Gln Ala Pro Gly Lys Gly Leu Glu Trp Val
        35                  40                  45

Ser Ala Ile Ser Tyr Asp Gly Glu Gly Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Arg Tyr Tyr Thr Ala Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys
    210                 215                 220

<210> SEQ ID NO 63
<211> LENGTH: 221
<212> TYPE: PRT
<213> ORGANISM: Artificial Sequence
<220> FEATURE:
<223> OTHER INFORMATION: >SEQ ID NO: 63 - anti-IL-1Rap-C3-MP01-B7 FAB heavy chain

<400> SEQUENCE: 63

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Leu Ser Gly Phe
            20                  25                  30

Ser Met Ser Trp Val Arg Gln Ala Pro Gly Lys Gly Leu Glu Trp Val
        35                  40                  45

Ser Ala Ile Ser Tyr Asp Gly Glu Gly Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Arg Tyr Tyr Thr Ala Phe Asp Tyr Trp Gly Gln Gly Thr

```
                    100                 105                 110
Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys
    210                 215                 220

<210> SEQ ID NO 64
<211> LENGTH: 221
<212> TYPE: PRT
<213> ORGANISM: Artificial Sequence
<220> FEATURE:
<223> OTHER INFORMATION: >SEQ ID NO: 64 - anti-IL-1Rap-C3-MP01-D2 FAB
      heavy chain

<400> SEQUENCE: 64

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gln Phe
            20                  25                  30

Gly Met Thr Trp Val Arg Gln Ala Pro Gly Lys Gly Leu Glu Trp Val
        35                  40                  45

Ser Ala Ile Ser Tyr Asp Gly Glu Gly Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Arg Tyr Tyr Thr Ala Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys
    210                 215                 220

<210> SEQ ID NO 65
<211> LENGTH: 221
```

```
<212> TYPE: PRT
<213> ORGANISM: Artificial Sequence
<220> FEATURE:
<223> OTHER INFORMATION: >SEQ ID NO: 65 - anti-IL-1Rap-C3-MP01-F5 FAB
      heavy chain

<400> SEQUENCE: 65

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Pro Leu Ser Asn Tyr
            20                  25                  30

Gly Met Ser Trp Val Arg Gln Ala Pro Gly Lys Gly Leu Glu Trp Val
        35                  40                  45

Ser Ala Ile Ser Tyr Asp Gly Glu Gly Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Arg Tyr Tyr Thr Ala Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys
    210                 215                 220

<210> SEQ ID NO 66
<211> LENGTH: 221
<212> TYPE: PRT
<213> ORGANISM: Artificial Sequence
<220> FEATURE:
<223> OTHER INFORMATION: >SEQ ID NO: 66 - anti-IL-1Rap-C3-MP01-G10 FAB
      heavy chain

<400> SEQUENCE: 66

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

Gly Met Ser Trp Val Arg Gln Ala Pro Gly Lys Gly Leu Glu Trp Val
        35                  40                  45

Ser Ala Ile Ser Tyr Asp Gly Glu Gly Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Arg Phe Arg Tyr Tyr Thr Ala Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys
    210                 215                 220

<210> SEQ ID NO 67
<211> LENGTH: 221
<212> TYPE: PRT
<213> ORGANISM: Artificial Sequence
<220> FEATURE:
<223> OTHER INFORMATION: >SEQ ID NO: 67 - anti-IL-1Rap-C3-MP02-B8 FAB
      heavy chain

<400> SEQUENCE: 67

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Glu His Ser
            20                  25                  30

Ser Ala Gly Trp Val Arg Gln Ala Pro Gly Lys Gly Leu Glu Trp Val
        35                  40                  45

Ser Ala Ile Ser Tyr Asp Gly Glu Gly Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Arg Tyr Tyr Thr Ala Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys
    210                 215                 220

<210> SEQ ID NO 68
```

```
<211> LENGTH: 221
<212> TYPE: PRT
<213> ORGANISM: Artificial Sequence
<220> FEATURE:
<223> OTHER INFORMATION: >SEQ ID NO: 68 - anti-IL-1Rap-C3-MP02-F6 FAB
      heavy chain

<400> SEQUENCE: 68
```

| Glu | Val | Gln | Leu | Leu | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Pro | Asp | Tyr |
|---|---|---|---|---|---|---|---|---|---|---|---|---|---|---|---|
| | | | 20 | | | | | 25 | | | | | 30 | | |

| Pro | Leu | Gly | Trp | Val | Arg | Gln | Ala | Pro | Gly | Lys | Gly | Leu | Glu | Trp | Val |
|---|---|---|---|---|---|---|---|---|---|---|---|---|---|---|---|
| | | 35 | | | | | 40 | | | | | 45 | | | |

| Ser | Ala | Ile | Ser | Tyr | Asp | Gly | Glu | Gly | Thr | Leu | Tyr | Ala | Asp | Ser | Val |
|---|---|---|---|---|---|---|---|---|---|---|---|---|---|---|---|
| 50 | | | | | 55 | | | | | 60 | | | | | |

| Lys | Gly | Arg | Phe | Thr | Ile | Ser | Arg | Asp | Asn | Ser | Lys | Asn | Thr | Leu | Tyr |
|---|---|---|---|---|---|---|---|---|---|---|---|---|---|---|---|
| 65 | | | | | 70 | | | | | 75 | | | | | 80 |

| Leu | Gln | Met | Asn | Ser | Leu | Arg | Ala | Glu | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Ala | Arg | Phe | Arg | Tyr | Tyr | Thr | Ala | Phe | Asp | Tyr | Trp | Gly | Gln | Gly | Thr |
|---|---|---|---|---|---|---|---|---|---|---|---|---|---|---|---|
| | | | 100 | | | | | 105 | | | | | 110 | | |

| Leu | Val | Thr | Val | Ser | Ser | Ala | Ser | Thr | Lys | Gly | Pro | Ser | Val | Phe | Pro |
|---|---|---|---|---|---|---|---|---|---|---|---|---|---|---|---|
| | | 115 | | | | | 120 | | | | | 125 | | | |

| Leu | Ala | Pro | Ser | Ser | Lys | Ser | Thr | Ser | Gly | Gly | Thr | Ala | Ala | Leu | Gly |
|---|---|---|---|---|---|---|---|---|---|---|---|---|---|---|---|
| | 130 | | | | | 135 | | | | | 140 | | | | |

| Cys | Leu | Val | Lys | Asp | Tyr | Phe | Pro | Glu | Pro | Val | Thr | Val | Ser | Trp | Asn |
|---|---|---|---|---|---|---|---|---|---|---|---|---|---|---|---|
| 145 | | | | | 150 | | | | | 155 | | | | | 160 |

| Ser | Gly | Ala | Leu | Thr | Ser | Gly | Val | His | Thr | Phe | Pro | Ala | Val | Leu | Gln |
|---|---|---|---|---|---|---|---|---|---|---|---|---|---|---|---|
| | | | | 165 | | | | | 170 | | | | | 175 | |

| Ser | Ser | Gly | Leu | Tyr | Ser | Leu | Ser | Ser | Val | Val | Thr | Val | Pro | Ser | Ser |
|---|---|---|---|---|---|---|---|---|---|---|---|---|---|---|---|
| | | | 180 | | | | | 185 | | | | | 190 | | |

| Ser | Leu | Gly | Thr | Gln | Thr | Tyr | Ile | Cys | Asn | Val | Asn | His | Lys | Pro | Ser |
|---|---|---|---|---|---|---|---|---|---|---|---|---|---|---|---|
| | | 195 | | | | | 200 | | | | | 205 | | | |

| Asn | Thr | Lys | Val | Asp | Lys | Lys | Val | Glu | Pro | Lys | Ser | Cys |
|---|---|---|---|---|---|---|---|---|---|---|---|---|
| | 210 | | | | | 215 | | | | | 220 | |

```
<210> SEQ ID NO 69
<211> LENGTH: 221
<212> TYPE: PRT
<213> ORGANISM: Artificial Sequence
<220> FEATURE:
<223> OTHER INFORMATION: >SEQ ID NO: 69 - anti-IL-1Rap-C3-MP02-G2 FAB
      heavy chain

<400> SEQUENCE: 69
```

| Glu | Val | Gln | Leu | Leu | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Tyr | Asp | Val | Ala |
|---|---|---|---|---|---|---|---|---|---|---|---|---|---|---|---|
| | | | 20 | | | | | 25 | | | | | 30 | | |

| Pro | Met | Gly | Trp | Val | Arg | Gln | Ala | Pro | Gly | Lys | Gly | Leu | Glu | Trp | Val |
|---|---|---|---|---|---|---|---|---|---|---|---|---|---|---|---|
| | | 35 | | | | | 40 | | | | | 45 | | | |

| Ser | Ala | Ile | Ser | Tyr | Asp | Gly | Glu | Gly | Thr | Leu | Tyr | Ala | Asp | Ser | Val |
|---|---|---|---|---|---|---|---|---|---|---|---|---|---|---|---|
| 50 | | | | | 55 | | | | | 60 | | | | | |

| Lys | Gly | Arg | Phe | Thr | Ile | Ser | Arg | Asp | Asn | Ser | Lys | Asn | Thr | Leu | Tyr |
|---|---|---|---|---|---|---|---|---|---|---|---|---|---|---|---|
| 65 | | | | | 70 | | | | | 75 | | | | | 80 |

| Leu | Gln | Met | Asn | Ser | Leu | Arg | Ala | Glu | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

```
Ala Arg Phe Arg Tyr Tyr Thr Ala Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys
    210                 215                 220
```

<210> SEQ ID NO 70
<211> LENGTH: 221
<212> TYPE: PRT
<213> ORGANISM: Artificial Sequence
<220> FEATURE:
<223> OTHER INFORMATION: >SEQ ID NO: 70 - anti-IL-1Rap-C3-UCP01-H4 FAB heavy chain

<400> SEQUENCE: 70

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Asp Tyr
            20                  25                  30

Ala Met Gly Trp Val Arg Gln Ala Pro Gly Lys Gly Leu Glu Trp Val
        35                  40                  45

Ser Ala Ile Ser Tyr Asp Gly Glu Gly Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe His Tyr Arg Ser Ala Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys
    210                 215                 220
```

```
<210> SEQ ID NO 71
<211> LENGTH: 214
<212> TYPE: PRT
<213> ORGANISM: Artificial Sequence
<220> FEATURE:
<223> OTHER INFORMATION: >SEQ ID NO: 71 - Vk3-15/Jk1-Ck light chain

<400> SEQUENCE: 71

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 72
<211> LENGTH: 451
<212> TYPE: PRT
<213> ORGANISM: Artificial Sequence
<220> FEATURE:
<223> OTHER INFORMATION: >SEQ ID NO: 72 - Anti-IL-1RAP C8-RecC-ES IgG1
      LALA heavy chain

<400> SEQUENCE: 72

Gln Val Gln Leu Val Gln Ser Gly Ala Glu Val Lys Lys Pro Gly Ser
1               5                   10                  15

Ser Val Lys Val Ser Cys Lys Ala Ser Gly Ser Pro Ala Glu Pro Tyr
            20                  25                  30

Ala Ile Gln Trp Val Arg Gln Ala Pro Gly Gln Gly Leu Glu Trp Met
        35                  40                  45

Gly Tyr Ile Ile Pro Ser Leu Gly Gly Tyr Asp Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

```
Ala Arg Gly Gln Thr Leu Tyr Glu Ser Gly Arg Gln Phe Asp Ile Trp
                100                 105                 110
Gly Gln Gly Thr Leu Val Thr Val Ser Ser Ala Ser Thr Lys Gly Pro
            115                 120                 125
Ser Val Phe Pro Leu Ala Pro Ser Ser Lys Ser Thr Ser Gly Gly Thr
        130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
            180                 185                 190
Val Pro Ser Ser Ser Leu Gly Thr Gln Thr Tyr Ile Cys Asn Val Asn
        195                 200                 205
His Lys Pro Ser Asn Thr Lys Val Asp Lys Lys Val Glu Pro Lys Ser
    210                 215                 220
Cys Asp Lys Thr His Thr Cys Pro Pro Cys Pro Ala Pro Glu Ala Ala
225                 230                 235                 240
Gly Gly Pro Ser Val Phe Leu Phe Pro Pro Lys Pro Lys Asp Thr Leu
                245                 250                 255
Met Ile Ser Arg Thr Pro Glu Val Thr Cys Val Val Val Asp Val Ser
            260                 265                 270
His Glu Asp Pro Glu Val Lys Phe Asn Trp Tyr Val Asp Gly Val Glu
        275                 280                 285
Val His Asn Ala Lys Thr Lys Pro Arg Glu Glu Gln Tyr Asn Ser Thr
    290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Ala Leu Pro Ala Pro
                325                 330                 335
Ile Glu Lys Thr Ile Ser Lys Ala Lys Gly Gln Pro Arg Glu Pro Gln
            340                 345                 350
Val Tyr Thr Leu Pro Pro Ser Arg Asp Glu Leu Thr Lys Asn Gln Val
        355                 360                 365
Ser Leu Thr Cys Leu Val Lys Gly Phe Tyr Pro Ser Asp Ile Ala Val
    370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Lys Leu Thr
                405                 410                 415
Val Asp Lys Ser Arg Trp Gln Gln Gly Asn Val Phe Ser Cys Ser Val
            420                 425                 430
Met His Glu Ala Leu His Asn His Tyr Thr Gln Lys Ser Leu Ser Leu
        435                 440                 445
Ser Pro Gly
    450

<210> SEQ ID NO 73
<211> LENGTH: 447
<212> TYPE: PRT
<213> ORGANISM: Artificial Sequence
<220> FEATURE:
<223> OTHER INFORMATION: >SEQ ID NO: 73 - Anti-IL-1RAP C3-A3 mmIgG2a
      LALA heavy chain
```

```
<400> SEQUENCE: 73

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ile Phe Ser His Tyr
            20                  25                  30

Gly Met Ser Trp Val Arg Gln Ala Pro Gly Lys Gly Leu Glu Trp Val
        35                  40                  45

Ser Ala Ile Ser Tyr Asp Gly Glu Gly Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Arg Tyr Tyr Thr Ala Phe Asp Tyr Trp Gly Gln Gly Thr
            100                 105                 110

Leu Val Thr Val Ser Ser Ala Lys Thr Thr Ala Pro Ser Val Tyr Pro
        115                 120                 125

Leu Ala Pro Val Cys Gly Asp Thr Thr Gly Ser Ser Val Thr Leu Gly
    130                 135                 140

Cys Leu Val Lys Gly Tyr Phe Pro Glu Pro Val Thr Leu Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Ser Val Thr Val Thr Ser Ser Thr
            180                 185                 190

Trp Pro Ser Gln Ser Ile Thr Cys Asn Val Ala His Pro Ala Ser Ser
        195                 200                 205

Thr Lys Val Asp Lys Lys Ile Glu Pro Arg Gly Pro Thr Ile Lys Pro
    210                 215                 220

Cys Pro Pro Cys Lys Cys Pro Ala Pro Asn Ala Ala Gly Gly Pro Ser
225                 230                 235                 240

Val Phe Ile Phe Pro Pro Lys Ile Lys Asp Val Leu Met Ile Ser Leu
                245                 250                 255

Ser Pro Ile Val Thr Cys Val Val Asp Val Ser Glu Asp Asp Pro
            260                 265                 270

Asp Val Gln Ile Ser Trp Phe Val Asn Asn Val Glu Val His Thr Ala
        275                 280                 285

Gln Thr Gln Thr His Arg Glu Asp Tyr Asn Ser Thr Leu Arg Val Val
    290                 295                 300

Ser Ala Leu Pro Ile Gln His Gln Asp Trp Met Ser Gly Lys Glu Phe
305                 310                 315                 320

Lys Cys Lys Val Asn Asn Lys Asp Leu Pro Ala Pro Ile Glu Arg Thr
                325                 330                 335

Ile Ser Lys Pro Lys Gly Ser Val Arg Ala Pro Gln Val Tyr Val Leu
            340                 345                 350

Pro Pro Pro Glu Glu Glu Met Thr Lys Lys Gln Val Thr Leu Thr Cys
        355                 360                 365

Met Val Thr Asp Phe Met Pro Glu Asp Ile Tyr Val Glu Trp Thr Asn
    370                 375                 380

Asn Gly Lys Thr Glu Leu Asn Tyr Lys Asn Thr Glu Pro Val Leu Asp
385                 390                 395                 400

Ser Asp Gly Ser Tyr Phe Met Tyr Ser Lys Leu Arg Val Glu Lys Lys
                405                 410                 415
```

```
Asn Trp Val Glu Arg Asn Ser Tyr Ser Cys Ser Val Val His Glu Gly
            420                 425                 430

Leu His Asn His His Thr Thr Lys Ser Phe Ser Arg Thr Pro Gly
            435                 440                 445

<210> SEQ ID NO 74
<211> LENGTH: 214
<212> TYPE: PRT
<213> ORGANISM: Artificial Sequence
<220> FEATURE:
<223> OTHER INFORMATION: >SEQ ID NO: 74 - Anti-IL-1RAP C3-A3 mmIgG2a
      LALA light chain

<400> SEQUENCE: 74

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Trp
                85                  90                  95

Thr Phe Gly Gln Gly Thr Lys Val Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 75
<211> LENGTH: 439
<212> TYPE: PRT
<213> ORGANISM: Artificial Sequence
<220> FEATURE:
<223> OTHER INFORMATION: >SEQ ID NO: 75 - ABC mmIgG1 heavy chain

<400> SEQUENCE: 75

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45
```

```
Ser Ala Ile Ser Gly Ser Gly Gly Ser Thr Tyr Tyr Ala Asp Ser Val
    50              55                  60

Lys Gly Arg Phe Thr Ile Ser Arg Asp Asn Ser Lys Asn Thr Leu Tyr
 65              70              75                  80

Leu Gln Met Asn Ser Leu Arg Ala Glu Asp Thr Ala Val Tyr Tyr Cys
             85                  90                  95

Ala Lys Ser Tyr Gly Ala Phe Asp Tyr Trp Gly Gln Gly Thr Leu Val
                100             105             110

Thr Val Ser Ser Ala Lys Thr Thr Pro Pro Ser Val Tyr Pro Leu Ala
            115             120             125

Pro Gly Ser Ala Ala Gln Thr Asn Ser Met Val Thr Leu Gly Cys Leu
130             135             140

Val Lys Gly Tyr Phe Pro Glu Pro Val Thr Val Thr Trp Asn Ser Gly
145             150             155             160

Ser Leu Ser Ser Gly Val His Thr Phe Pro Ala Val Leu Gln Ser Asp
                165             170             175

Leu Tyr Thr Leu Ser Ser Ser Val Thr Val Pro Ser Ser Thr Trp Pro
            180             185             190

Ser Glu Thr Val Thr Cys Asn Val Ala His Pro Ala Ser Ser Thr Lys
            195             200             205

Val Asp Lys Lys Ile Val Pro Arg Asp Cys Gly Cys Lys Pro Cys Ile
210             215             220

Cys Thr Val Pro Glu Val Ser Ser Val Phe Ile Phe Pro Pro Lys Pro
225             230             235             240

Lys Asp Val Leu Thr Ile Thr Leu Thr Pro Lys Val Thr Cys Val Val
            245             250             255

Val Asp Ile Ser Lys Asp Asp Pro Glu Val Gln Phe Ser Trp Phe Val
            260             265             270

Asp Asp Val Glu Val His Thr Ala Gln Thr Gln Pro Arg Glu Glu Gln
            275             280             285

Phe Asn Ser Thr Phe Arg Ser Val Ser Glu Leu Pro Ile Met His Gln
290             295             300

Asp Trp Leu Asn Gly Lys Glu Phe Lys Cys Arg Val Asn Ser Ala Ala
305             310             315             320

Phe Pro Ala Pro Ile Glu Lys Thr Ile Ser Lys Thr Lys Gly Arg Pro
            325             330             335

Lys Ala Pro Gln Val Tyr Thr Ile Pro Pro Lys Glu Gln Met Ala
            340             345             350

Lys Asp Lys Val Ser Leu Thr Cys Met Ile Thr Asp Phe Phe Pro Glu
            355             360             365

Asp Ile Thr Val Glu Trp Gln Trp Asn Gly Gln Pro Ala Glu Asn Tyr
370             375             380

Lys Asn Thr Gln Pro Ile Met Asp Thr Asp Gly Ser Tyr Phe Val Tyr
385             390             395             400

Ser Lys Leu Asn Val Gln Lys Ser Asn Trp Glu Ala Gly Asn Thr Phe
            405             410             415

Thr Cys Ser Val Leu His Glu Gly Leu His Asn His Thr Glu Lys
            420             425             430

Ser Leu Ser His Ser Pro Gly
            435

<210> SEQ ID NO 76
<211> LENGTH: 214
<212> TYPE: PRT
```

```
<213> ORGANISM: Artificial Sequence
<220> FEATURE:
<223> OTHER INFORMATION: >SEQ ID NO: 76 - ABC mmIgG light chain

<400> SEQUENCE: 76

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Asn
                85                  90                  95

Thr Phe Gly Gln Gly Thr Lys Val Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 77
<211> LENGTH: 445
<212> TYPE: PRT
<213> ORGANISM: Artificial Sequence
<220> FEATURE:
<223> OTHER INFORMATION: >SEQ ID NO: 77 - ABC mmIgG2a LALA heavy chain

<400> SEQUENCE: 77

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Tyr Gly Ala Phe Asp Tyr Trp Gly Gln Gly Thr Leu Val
            100                 105                 110
```

Thr Val Ser Ser Ala Lys Thr Thr Ala Pro Ser Val Tyr Pro Leu Ala
            115                 120                 125

Pro Val Cys Gly Asp Thr Thr Gly Ser Ser Val Thr Leu Gly Cys Leu
        130                 135                 140

Val Lys Gly Tyr Phe Pro Glu Pro Val Thr Leu Thr Trp Asn Ser Gly
145                 150                 155                 160

Ser Leu Ser Ser Gly Val His Thr Phe Pro Ala Val Leu Gln Ser Asp
                165                 170                 175

Leu Tyr Thr Leu Ser Ser Ser Val Thr Val Thr Ser Ser Thr Trp Pro
            180                 185                 190

Ser Gln Ser Ile Thr Cys Asn Val Ala His Pro Ala Ser Ser Thr Lys
        195                 200                 205

Val Asp Lys Lys Ile Glu Pro Arg Gly Pro Thr Ile Lys Pro Cys Pro
210                 215                 220

Pro Cys Lys Cys Pro Ala Pro Asn Ala Ala Gly Gly Pro Ser Val Phe
225                 230                 235                 240

Ile Phe Pro Pro Lys Ile Lys Asp Val Leu Met Ile Ser Leu Ser Pro
                245                 250                 255

Ile Val Thr Cys Val Val Val Asp Val Ser Glu Asp Asp Pro Asp Val
            260                 265                 270

Gln Ile Ser Trp Phe Val Asn Asn Val Glu Val His Thr Ala Gln Thr
        275                 280                 285

Gln Thr His Arg Glu Asp Tyr Asn Ser Thr Leu Arg Val Val Ser Ala
    290                 295                 300

Leu Pro Ile Gln His Gln Asp Trp Met Ser Gly Lys Glu Phe Lys Cys
305                 310                 315                 320

Lys Val Asn Asn Lys Asp Leu Pro Ala Pro Ile Glu Arg Thr Ile Ser
                325                 330                 335

Lys Pro Lys Gly Ser Val Arg Ala Pro Gln Val Tyr Val Leu Pro Pro
            340                 345                 350

Pro Glu Glu Glu Met Thr Lys Lys Gln Val Thr Leu Thr Cys Met Val
        355                 360                 365

Thr Asp Phe Met Pro Glu Asp Ile Tyr Val Glu Trp Thr Asn Asn Gly
    370                 375                 380

Lys Thr Glu Leu Asn Tyr Lys Asn Thr Glu Pro Val Leu Asp Ser Asp
385                 390                 395                 400

Gly Ser Tyr Phe Met Tyr Ser Lys Leu Arg Val Glu Lys Lys Asn Trp
                405                 410                 415

Val Glu Arg Asn Ser Tyr Ser Cys Ser Val Val His Glu Gly Leu His
            420                 425                 430

Asn His His Thr Thr Lys Ser Phe Ser Arg Thr Pro Gly
        435                 440                 445

<210> SEQ ID NO 78
<211> LENGTH: 446
<212> TYPE: PRT
<213> ORGANISM: Artificial Sequence
<220> FEATURE:
<223> OTHER INFORMATION: >SEQ ID NO: 78 - Human ABC IgG1 LALA heavy
      chain

<400> SEQUENCE: 78

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

```
Ala Met Ser Trp Val Arg Gln Ala Pro Gly Lys Gly Leu Glu Trp Val
        35                  40                  45

Ser Ala Ile Ser Gly Ser Gly Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Tyr Gly Ala Phe Asp Tyr Trp Gly Gln Gly Thr Leu Val
                100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
                435                 440                 445
```

```
<210> SEQ ID NO 79
<211> LENGTH: 214
<212> TYPE: PRT
<213> ORGANISM: Artificial Sequence
<220> FEATURE:
<223> OTHER INFORMATION: >SEQ ID NO: 79 - Human ABC IgG light chain

<400> SEQUENCE: 79

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Asn
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 80
<211> LENGTH: 154
<212> TYPE: PRT
<213> ORGANISM: Artificial Sequence
<220> FEATURE:
<223> OTHER INFORMATION: >SEQ ID NO: 80 - Anakinra

<400> SEQUENCE: 80

Met Met Arg Pro Ser Gly Arg Lys Ser Ser Lys Met Gln Ala Phe Arg
1               5                   10                  15

Ile Trp Asp Val Asn Gln Lys Thr Phe Tyr Leu Arg Asn Asn Gln Leu
            20                  25                  30

Val Ala Gly Tyr Leu Gln Gly Pro Asn Val Asn Leu Glu Glu Lys Ile
        35                  40                  45

Asp Val Val Pro Ile Glu Pro His Ala Leu Phe Leu Gly Ile His Gly
    50                  55                  60

Gly Lys Met Cys Leu Ser Cys Val Lys Ser Gly Asp Glu Thr Arg Leu
65                  70                  75                  80

Gln Leu Glu Ala Val Asn Ile Thr Asp Leu Ser Glu Asn Arg Lys Gln
                85                  90                  95
```

```
Asp Lys Arg Phe Ala Phe Ile Arg Ser Asp Ser Gly Pro Thr Thr Ser
            100                 105                 110

Phe Glu Ser Ala Ala Cys Pro Gly Trp Phe Leu Cys Thr Ala Met Glu
        115                 120                 125

Ala Asp Gln Pro Val Ser Leu Thr Asn Met Pro Asp Glu Gly Val Met
    130                 135                 140

Val Thr Lys Phe Tyr Phe Gln Glu Asp Glu
145                 150

<210> SEQ ID NO 81
<211> LENGTH: 10
<212> TYPE: PRT
<213> ORGANISM: Artificial Sequence
<220> FEATURE:
<223> OTHER INFORMATION: >SEQ ID NO: 81 - anti-IL-1Rap-UCP02-A4 CDRH1

<400> SEQUENCE: 81

Gly Gly Val Phe Ser Tyr Tyr Ala Ile Ser
1               5                   10

<210> SEQ ID NO 82
<211> LENGTH: 10
<212> TYPE: PRT
<213> ORGANISM: Artificial Sequence
<220> FEATURE:
<223> OTHER INFORMATION: >SEQ ID NO: 82 - anti-IL-1Rap-UCP02-A6 CDRH1

<400> SEQUENCE: 82

Gly Gly Ala Phe Arg Ile Tyr Ala Ile His
1               5                   10

<210> SEQ ID NO 83
<211> LENGTH: 10
<212> TYPE: PRT
<213> ORGANISM: Artificial Sequence
<220> FEATURE:
<223> OTHER INFORMATION: >SEQ ID NO: 83 - anti-IL-1Rap-UCP02-B11 CDRH1

<400> SEQUENCE: 83

Gly Gly His Phe Ser Gln Phe Ala Ile Ser
1               5                   10

<210> SEQ ID NO 84
<211> LENGTH: 10
<212> TYPE: PRT
<213> ORGANISM: Artificial Sequence
<220> FEATURE:
<223> OTHER INFORMATION: >SEQ ID NO: 84 - anti-IL-1Rap-UCP02-B5 CDRH1

<400> SEQUENCE: 84

Gly Gly Tyr Phe Ser Ala Tyr Ile Ile Ser
1               5                   10

<210> SEQ ID NO 85
<211> LENGTH: 10
<212> TYPE: PRT
<213> ORGANISM: Artificial Sequence
<220> FEATURE:
<223> OTHER INFORMATION: >SEQ ID NO: 85 - anti-IL-1Rap-UCP02-C3 CDRH1

<400> SEQUENCE: 85

Gly Phe Thr Phe Arg Asp Tyr Ala Met Gly
1               5                   10
```

```
<210> SEQ ID NO 86
<211> LENGTH: 10
<212> TYPE: PRT
<213> ORGANISM: Artificial Sequence
<220> FEATURE:
<223> OTHER INFORMATION: >SEQ ID NO: 86 - anti-IL-1Rap-UCP02-C5 CDRH1

<400> SEQUENCE: 86

Gly Gly His Phe Asn Ile Tyr Ala Ile Ser
1               5                   10

<210> SEQ ID NO 87
<211> LENGTH: 10
<212> TYPE: PRT
<213> ORGANISM: Artificial Sequence
<220> FEATURE:
<223> OTHER INFORMATION: >SEQ ID NO: 87 - anti-IL-1Rap-UCP02-C8 CDRH1

<400> SEQUENCE: 87

Gly Gly Gln Phe Ser Glu Tyr Ala Ile Gln
1               5                   10

<210> SEQ ID NO 88
<211> LENGTH: 10
<212> TYPE: PRT
<213> ORGANISM: Artificial Sequence
<220> FEATURE:
<223> OTHER INFORMATION: >SEQ ID NO: 88 - anti-IL-1Rap-UCP02-C9 CDRH1

<400> SEQUENCE: 88

Gly Gly Val Phe Ser Tyr Tyr Ala Phe His
1               5                   10

<210> SEQ ID NO 89
<211> LENGTH: 10
<212> TYPE: PRT
<213> ORGANISM: Artificial Sequence
<220> FEATURE:
<223> OTHER INFORMATION: >SEQ ID NO: 89 - anti-IL-1Rap-UCP02-D2 CDRH1

<400> SEQUENCE: 89

Gly Gly Arg Phe Ser Asp Ser Ala Ile His
1               5                   10

<210> SEQ ID NO 90
<211> LENGTH: 10
<212> TYPE: PRT
<213> ORGANISM: Artificial Sequence
<220> FEATURE:
<223> OTHER INFORMATION: >SEQ ID NO: 90 - anti-IL-1Rap-UCP02-G11 CDRH1

<400> SEQUENCE: 90

Gly Gly Gln Phe Asn Asp Tyr Ala Ile His
1               5                   10

<210> SEQ ID NO 91
<211> LENGTH: 10
<212> TYPE: PRT
<213> ORGANISM: Artificial Sequence
<220> FEATURE:
<223> OTHER INFORMATION: >SEQ ID NO: 91 - anti-IL-1Rap-UCP02-G3 CDRH1

<400> SEQUENCE: 91

Gly Gly Tyr Leu Asn Glu Tyr Ala Ile His
1               5                   10

<210> SEQ ID NO 92
```

```
<211> LENGTH: 10
<212> TYPE: PRT
<213> ORGANISM: Artificial Sequence
<220> FEATURE:
<223> OTHER INFORMATION: >SEQ ID NO: 92 - anti-IL-1Rap-UCP02-G8 CDRH1

<400> SEQUENCE: 92

Gly Gly Phe Phe Ser Ile Tyr Ala Ile Ser
1               5                   10

<210> SEQ ID NO 93
<211> LENGTH: 10
<212> TYPE: PRT
<213> ORGANISM: Artificial Sequence
<220> FEATURE:
<223> OTHER INFORMATION: >SEQ ID NO: 93 - anti-IL-1Rap-UCP02-H8 CDRH1

<400> SEQUENCE: 93

Gly Gly Val Phe Ser Gly Tyr Ala Ile Ser
1               5                   10

<210> SEQ ID NO 94
<211> LENGTH: 10
<212> TYPE: PRT
<213> ORGANISM: Artificial Sequence
<220> FEATURE:
<223> OTHER INFORMATION: >SEQ ID NO: 94 - anti-IL-1Rap-UCP02-H9 CDRH1

<400> SEQUENCE: 94

Gly Gly Pro Phe Ser Ser Tyr Ala Leu Ser
1               5                   10

<210> SEQ ID NO 95
<211> LENGTH: 10
<212> TYPE: PRT
<213> ORGANISM: Artificial Sequence
<220> FEATURE:
<223> OTHER INFORMATION: >SEQ ID NO: 95 - anti-IL-1Rap-UCP03-A2 CDRH1

<400> SEQUENCE: 95

Gly Gly Lys Phe Asn Phe Asp Val Ile His
1               5                   10

<210> SEQ ID NO 96
<211> LENGTH: 10
<212> TYPE: PRT
<213> ORGANISM: Artificial Sequence
<220> FEATURE:
<223> OTHER INFORMATION: >SEQ ID NO: 96 - anti-IL-1Rap-UCP03-A3 CDRH1

<400> SEQUENCE: 96

Gly Gly Leu Phe Asn Glu Asn Ala Ile His
1               5                   10

<210> SEQ ID NO 97
<211> LENGTH: 10
<212> TYPE: PRT
<213> ORGANISM: Artificial Sequence
<220> FEATURE:
<223> OTHER INFORMATION: >SEQ ID NO: 97 - anti-IL-1Rap-UCP03-B4 CDRH1

<400> SEQUENCE: 97

Gly Gly Pro Phe Ser Gln His Ala Ile Ser
1               5                   10

<210> SEQ ID NO 98
<211> LENGTH: 10
```

```
<212> TYPE: PRT
<213> ORGANISM: Artificial Sequence
<220> FEATURE:
<223> OTHER INFORMATION: >SEQ ID NO: 98 - anti-IL-1Rap-UCP03-B6 CDRH1

<400> SEQUENCE: 98

Gly Asp Pro Phe Ser Val Tyr Ile Ile His
1               5                   10

<210> SEQ ID NO 99
<211> LENGTH: 10
<212> TYPE: PRT
<213> ORGANISM: Artificial Sequence
<220> FEATURE:
<223> OTHER INFORMATION: >SEQ ID NO: 99 - anti-IL-1Rap-UCP03-C1 CDRH1

<400> SEQUENCE: 99

Gly Gly Arg Phe Ser Ser Asn Ala Ile Ser
1               5                   10

<210> SEQ ID NO 100
<211> LENGTH: 10
<212> TYPE: PRT
<213> ORGANISM: Artificial Sequence
<220> FEATURE:
<223> OTHER INFORMATION: >SEQ ID NO: 100 - anti-IL-1Rap-UCP03-C2 CDRH1

<400> SEQUENCE: 100

Gly Asp Pro Phe Lys Arg Tyr Ala Ile Gly
1               5                   10

<210> SEQ ID NO 101
<211> LENGTH: 10
<212> TYPE: PRT
<213> ORGANISM: Artificial Sequence
<220> FEATURE:
<223> OTHER INFORMATION: >SEQ ID NO: 101 - anti-IL-1Rap-UCP03-F4 CDRH1

<400> SEQUENCE: 101

Gly Gly Gly Phe Ser Glu Tyr Ala Ile His
1               5                   10

<210> SEQ ID NO 102
<211> LENGTH: 10
<212> TYPE: PRT
<213> ORGANISM: Artificial Sequence
<220> FEATURE:
<223> OTHER INFORMATION: >SEQ ID NO: 102 - anti-IL-1Rap-UCP03-G3 CDRH1

<400> SEQUENCE: 102

Gly Gly Pro Leu Ser Gly Tyr Ala Phe His
1               5                   10

<210> SEQ ID NO 103
<211> LENGTH: 10
<212> TYPE: PRT
<213> ORGANISM: Artificial Sequence
<220> FEATURE:
<223> OTHER INFORMATION: >SEQ ID NO: 103 - anti-IL-1Rap-UCP03-G4 CDRH1

<400> SEQUENCE: 103

Gly Gly Arg Phe Ser His Tyr Val Phe Ser
1               5                   10

<210> SEQ ID NO 104
<211> LENGTH: 10
<212> TYPE: PRT
```

```
<213> ORGANISM: Artificial Sequence
<220> FEATURE:
<223> OTHER INFORMATION: >SEQ ID NO: 104 - anti-IL-1Rap-UCP04-C1 CDRH1

<400> SEQUENCE: 104

Gly Phe Thr Phe Ser Ala Tyr Thr Met Ser
1               5                   10

<210> SEQ ID NO 105
<211> LENGTH: 10
<212> TYPE: PRT
<213> ORGANISM: Artificial Sequence
<220> FEATURE:
<223> OTHER INFORMATION: >SEQ ID NO: 105 - anti-IL-1Rap-C8-H1A-C4 CDRH1

<400> SEQUENCE: 105

Gly Gly Lys Leu Asn Ala Tyr Ala Ile Gln
1               5                   10

<210> SEQ ID NO 106
<211> LENGTH: 10
<212> TYPE: PRT
<213> ORGANISM: Artificial Sequence
<220> FEATURE:
<223> OTHER INFORMATION: >SEQ ID NO: 106 - anti-IL-1Rap-C8-H1A-C8 CDRH1

<400> SEQUENCE: 106

Gly Gly Leu Phe Ser Asp Tyr Ala Ile Gln
1               5                   10

<210> SEQ ID NO 107
<211> LENGTH: 10
<212> TYPE: PRT
<213> ORGANISM: Artificial Sequence
<220> FEATURE:
<223> OTHER INFORMATION: >SEQ ID NO: 107 - anti-IL-1Rap-C8-H1A-D8 CDRH1

<400> SEQUENCE: 107

Gly Gly His Phe Asn Asn Tyr Ala Ile Gln
1               5                   10

<210> SEQ ID NO 108
<211> LENGTH: 10
<212> TYPE: PRT
<213> ORGANISM: Artificial Sequence
<220> FEATURE:
<223> OTHER INFORMATION: >SEQ ID NO: 108 - anti-IL-1Rap-C8-H1A-F1 CDRH1

<400> SEQUENCE: 108

Gly Gly Ile Phe Ser Asn Tyr Ala Ile Gln
1               5                   10

<210> SEQ ID NO 109
<211> LENGTH: 10
<212> TYPE: PRT
<213> ORGANISM: Artificial Sequence
<220> FEATURE:
<223> OTHER INFORMATION: >SEQ ID NO: 109 - anti-IL-1Rap-C8-H1A-G11 CDRH1

<400> SEQUENCE: 109

Gly Gly Arg Phe His Gln Tyr Ala Ile Gln
1               5                   10

<210> SEQ ID NO 110
<211> LENGTH: 10
<212> TYPE: PRT
<213> ORGANISM: Artificial Sequence
```

```
<220> FEATURE:
<223> OTHER INFORMATION: >SEQ ID NO: 110 - anti-IL-1Rap-C8-H1A-G1 CDRH1

<400> SEQUENCE: 110

Gly Gly Ala Ser Arg Ala Tyr Ala Ile His
1               5                   10

<210> SEQ ID NO 111
<211> LENGTH: 10
<212> TYPE: PRT
<213> ORGANISM: Artificial Sequence
<220> FEATURE:
<223> OTHER INFORMATION: >SEQ ID NO: 111 - anti-IL-1Rap-C8-H1A-G3 CDRH1

<400> SEQUENCE: 111

Gly Gly Pro Phe Ser Asp Tyr Ala Ile Gln
1               5                   10

<210> SEQ ID NO 112
<211> LENGTH: 10
<212> TYPE: PRT
<213> ORGANISM: Artificial Sequence
<220> FEATURE:
<223> OTHER INFORMATION: >SEQ ID NO: 112 - anti-IL-1Rap-C8-H1B-A8 CDRH1

<400> SEQUENCE: 112

Gly Glu Gly Ser Tyr Pro Tyr Ala Ile Gln
1               5                   10

<210> SEQ ID NO 113
<211> LENGTH: 10
<212> TYPE: PRT
<213> ORGANISM: Artificial Sequence
<220> FEATURE:
<223> OTHER INFORMATION: >SEQ ID NO: 113 - anti-IL-1Rap-C8-H1B-B10 CDRH1

<400> SEQUENCE: 113

Gly Val Thr His Thr Ser Tyr Ala Ile Gln
1               5                   10

<210> SEQ ID NO 114
<211> LENGTH: 10
<212> TYPE: PRT
<213> ORGANISM: Artificial Sequence
<220> FEATURE:
<223> OTHER INFORMATION: >SEQ ID NO: 114 - anti-IL-1Rap-C8-H1B-B8 CDRH1

<400> SEQUENCE: 114

Gly Ser Pro Ala Glu Pro Tyr Ala Ile Gln
1               5                   10

<210> SEQ ID NO 115
<211> LENGTH: 10
<212> TYPE: PRT
<213> ORGANISM: Artificial Sequence
<220> FEATURE:
<223> OTHER INFORMATION: >SEQ ID NO: 115 - anti-IL-1Rap-C8-H1B-D8 CDRH1

<400> SEQUENCE: 115

Gly Pro Ser Asn Pro Val Tyr Ala Ile Gln
1               5                   10

<210> SEQ ID NO 116
<211> LENGTH: 10
<212> TYPE: PRT
<213> ORGANISM: Artificial Sequence
<220> FEATURE:
```

<223> OTHER INFORMATION: >SEQ ID NO: 116 - anti-IL-1Rap-C8-H1B-E7 CDRH1

<400> SEQUENCE: 116

Gly Ser Lys His Gly Asn Tyr Ala Ile Gln
1               5                   10

<210> SEQ ID NO 117
<211> LENGTH: 10
<212> TYPE: PRT
<213> ORGANISM: Artificial Sequence
<220> FEATURE:
<223> OTHER INFORMATION: >SEQ ID NO: 117 - anti-IL-1Rap-C8-H1B-F3 CDRH1

<400> SEQUENCE: 117

Gly Gly Pro His Thr Ala His Ala Ile Gln
1               5                   10

<210> SEQ ID NO 118
<211> LENGTH: 10
<212> TYPE: PRT
<213> ORGANISM: Artificial Sequence
<220> FEATURE:
<223> OTHER INFORMATION: >SEQ ID NO: 118 - anti-IL-1Rap-C8-H1B-G10 CDRH1

<400> SEQUENCE: 118

Gly Gly Pro Arg Arg Ala Tyr Ala Ile Gln
1               5                   10

<210> SEQ ID NO 119
<211> LENGTH: 10
<212> TYPE: PRT
<213> ORGANISM: Artificial Sequence
<220> FEATURE:
<223> OTHER INFORMATION: >SEQ ID NO: 119 - anti-IL-1Rap-C8-H1B-H10 CDRH1

<400> SEQUENCE: 119

Gly Ser Thr Trp Glu Pro Tyr Ala Ile Gln
1               5                   10

<210> SEQ ID NO 120
<211> LENGTH: 10
<212> TYPE: PRT
<213> ORGANISM: Artificial Sequence
<220> FEATURE:
<223> OTHER INFORMATION: >SEQ ID NO: 120 - anti-IL-1Rap-C8-H2B-B5 CDRH1

<400> SEQUENCE: 120

Gly Gly Gln Phe Ser Glu Tyr Ala Ile Gln
1               5                   10

<210> SEQ ID NO 121
<211> LENGTH: 10
<212> TYPE: PRT
<213> ORGANISM: Artificial Sequence
<220> FEATURE:
<223> OTHER INFORMATION: >SEQ ID NO: 121 - anti-IL-1Rap-C8-H2B-C10 CDRH1

<400> SEQUENCE: 121

Gly Gly Gln Phe Ser Glu Tyr Ala Ile Gln
1               5                   10

<210> SEQ ID NO 122
<211> LENGTH: 10
<212> TYPE: PRT
<213> ORGANISM: Artificial Sequence
<220> FEATURE:
<223> OTHER INFORMATION: >SEQ ID NO: 122 - anti-IL-1Rap-C8-recA CDRH1

```
<400> SEQUENCE: 122

Gly Ser Thr Trp Glu Pro Tyr Ala Ile Gln
1               5                   10

<210> SEQ ID NO 123
<211> LENGTH: 10
<212> TYPE: PRT
<213> ORGANISM: Artificial Sequence
<220> FEATURE:
<223> OTHER INFORMATION: >SEQ ID NO: 123 - anti-IL-1Rap-C8-recB CDRH1

<400> SEQUENCE: 123

Gly Gly Pro Arg Arg Ala Tyr Ala Ile Gln
1               5                   10

<210> SEQ ID NO 124
<211> LENGTH: 10
<212> TYPE: PRT
<213> ORGANISM: Artificial Sequence
<220> FEATURE:
<223> OTHER INFORMATION: >SEQ ID NO: 124 - anti-IL-1Rap-C8-recC CDRH1

<400> SEQUENCE: 124

Gly Ser Pro Ala Glu Pro Tyr Ala Ile Gln
1               5                   10

<210> SEQ ID NO 125
<211> LENGTH: 10
<212> TYPE: PRT
<213> ORGANISM: Artificial Sequence
<220> FEATURE:
<223> OTHER INFORMATION: >SEQ ID NO: 125 - anti-IL-1Rap-C8-RecC-AA CDRH1

<400> SEQUENCE: 125

Gly Ser Pro Ala Glu Pro Tyr Ala Ile Gln
1               5                   10

<210> SEQ ID NO 126
<211> LENGTH: 10
<212> TYPE: PRT
<213> ORGANISM: Artificial Sequence
<220> FEATURE:
<223> OTHER INFORMATION: >SEQ ID NO: 126 - anti-IL-1Rap-C8-RecC-DA CDRH1

<400> SEQUENCE: 126

Gly Ser Pro Ala Glu Pro Tyr Ala Ile Gln
1               5                   10

<210> SEQ ID NO 127
<211> LENGTH: 10
<212> TYPE: PRT
<213> ORGANISM: Artificial Sequence
<220> FEATURE:
<223> OTHER INFORMATION: >SEQ ID NO: 127 - anti-IL-1Rap-C8-RecC-AS CDRH1

<400> SEQUENCE: 127

Gly Ser Pro Ala Glu Pro Tyr Ala Ile Gln
1               5                   10

<210> SEQ ID NO 128
<211> LENGTH: 10
<212> TYPE: PRT
<213> ORGANISM: Artificial Sequence
<220> FEATURE:
<223> OTHER INFORMATION: >SEQ ID NO: 128 - anti-IL-1Rap-C8-RecC-ES CDRH1
```

```
<400> SEQUENCE: 128

Gly Ser Pro Ala Glu Pro Tyr Ala Ile Gln
1               5                   10

<210> SEQ ID NO 129
<211> LENGTH: 10
<212> TYPE: PRT
<213> ORGANISM: Artificial Sequence
<220> FEATURE:
<223> OTHER INFORMATION: >SEQ ID NO: 129 - anti-IL-1Rap-C8-RecC-ET CDRH1

<400> SEQUENCE: 129

Gly Ser Pro Ala Glu Pro Tyr Ala Ile Gln
1               5                   10

<210> SEQ ID NO 130
<211> LENGTH: 10
<212> TYPE: PRT
<213> ORGANISM: Artificial Sequence
<220> FEATURE:
<223> OTHER INFORMATION: >SEQ ID NO: 130 - anti-IL-1Rap-C3-MP01-A2 CDRH1

<400> SEQUENCE: 130

Gly Phe Thr Phe Ala Glu Tyr Ala Met Asn
1               5                   10

<210> SEQ ID NO 131
<211> LENGTH: 10
<212> TYPE: PRT
<213> ORGANISM: Artificial Sequence
<220> FEATURE:
<223> OTHER INFORMATION: >SEQ ID NO: 131 - anti-IL-1Rap-C3-MP01-A3 CDRH1

<400> SEQUENCE: 131

Gly Phe Ile Phe Ser His Tyr Gly Met Ser
1               5                   10

<210> SEQ ID NO 132
<211> LENGTH: 10
<212> TYPE: PRT
<213> ORGANISM: Artificial Sequence
<220> FEATURE:
<223> OTHER INFORMATION: >SEQ ID NO: 132 - anti-IL-1Rap-C3-MP01-B5 CDRH1

<400> SEQUENCE: 132

Gly Phe Ile Phe Ser Thr Tyr Gly Met Gly
1               5                   10

<210> SEQ ID NO 133
<211> LENGTH: 10
<212> TYPE: PRT
<213> ORGANISM: Artificial Sequence
<220> FEATURE:
<223> OTHER INFORMATION: >SEQ ID NO: 133 - anti-IL-1Rap-C3-MP01-B7 CDRH1

<400> SEQUENCE: 133

Gly Phe Thr Leu Ser Gly Phe Ser Met Ser
1               5                   10

<210> SEQ ID NO 134
<211> LENGTH: 10
<212> TYPE: PRT
<213> ORGANISM: Artificial Sequence
<220> FEATURE:
<223> OTHER INFORMATION: >SEQ ID NO: 134 - anti-IL-1Rap-C3-MP01-D2 CDRH1

<400> SEQUENCE: 134
```

Gly Phe Thr Phe Ser Gln Phe Gly Met Thr
1               5                   10

<210> SEQ ID NO 135
<211> LENGTH: 10
<212> TYPE: PRT
<213> ORGANISM: Artificial Sequence
<220> FEATURE:
<223> OTHER INFORMATION: >SEQ ID NO: 135 - anti-IL-1Rap-C3-MP01-F5 CDRH1

<400> SEQUENCE: 135

Gly Phe Pro Leu Ser Asn Tyr Gly Met Ser
1               5                   10

<210> SEQ ID NO 136
<211> LENGTH: 10
<212> TYPE: PRT
<213> ORGANISM: Artificial Sequence
<220> FEATURE:
<223> OTHER INFORMATION: >SEQ ID NO: 136 - anti-IL-1Rap-C3-MP01-G10
      CDRH1

<400> SEQUENCE: 136

Gly Phe Thr Phe Ser His Tyr Gly Met Ser
1               5                   10

<210> SEQ ID NO 137
<211> LENGTH: 10
<212> TYPE: PRT
<213> ORGANISM: Artificial Sequence
<220> FEATURE:
<223> OTHER INFORMATION: >SEQ ID NO: 137 - anti-IL-1Rap-C3-MP02-B8 CDRH1

<400> SEQUENCE: 137

Gly Phe Thr Phe Glu His Ser Ser Ala Gly
1               5                   10

<210> SEQ ID NO 138
<211> LENGTH: 10
<212> TYPE: PRT
<213> ORGANISM: Artificial Sequence
<220> FEATURE:
<223> OTHER INFORMATION: >SEQ ID NO: 138 - anti-IL-1Rap-C3-MP02-F6 CDRH1

<400> SEQUENCE: 138

Gly Phe Thr Phe Pro Asp Tyr Pro Leu Gly
1               5                   10

<210> SEQ ID NO 139
<211> LENGTH: 10
<212> TYPE: PRT
<213> ORGANISM: Artificial Sequence
<220> FEATURE:
<223> OTHER INFORMATION: >SEQ ID NO: 139 - anti-IL-1Rap-C3-MP02-G2 CDRH1

<400> SEQUENCE: 139

Gly Phe Thr Tyr Asp Val Ala Pro Met Gly
1               5                   10

<210> SEQ ID NO 140
<211> LENGTH: 10
<212> TYPE: PRT
<213> ORGANISM: Artificial Sequence
<220> FEATURE:
<223> OTHER INFORMATION: >SEQ ID NO: 140 - anti-IL-1Rap-C3-UCP01-H4
      CDRH1

```
<400> SEQUENCE: 140

Gly Phe Thr Phe Arg Asp Tyr Ala Met Gly
1               5                   10

<210> SEQ ID NO 141
<211> LENGTH: 10
<212> TYPE: PRT
<213> ORGANISM: Artificial Sequence
<220> FEATURE:
<223> OTHER INFORMATION: >SEQ ID NO: 141 - anti-IL-1Rap-UCP02-A4 CDRH2

<400> SEQUENCE: 141

Ala Ile Ile Pro Asp Phe Gly His Thr Ile
1               5                   10

<210> SEQ ID NO 142
<211> LENGTH: 10
<212> TYPE: PRT
<213> ORGANISM: Artificial Sequence
<220> FEATURE:
<223> OTHER INFORMATION: >SEQ ID NO: 142 - anti-IL-1Rap-UCP02-A6 CDRH2

<400> SEQUENCE: 142

Gly Ile Leu Ala Ser Gly Gly Gly Ala Val
1               5                   10

<210> SEQ ID NO 143
<211> LENGTH: 10
<212> TYPE: PRT
<213> ORGANISM: Artificial Sequence
<220> FEATURE:
<223> OTHER INFORMATION: >SEQ ID NO: 143 - anti-IL-1Rap-UCP02-B11 CDRH2

<400> SEQUENCE: 143

Gly Ile Ala Pro Gly Leu Gly Ser Thr Arg
1               5                   10

<210> SEQ ID NO 144
<211> LENGTH: 10
<212> TYPE: PRT
<213> ORGANISM: Artificial Sequence
<220> FEATURE:
<223> OTHER INFORMATION: >SEQ ID NO: 144 - anti-IL-1Rap-UCP02-B5 CDRH2

<400> SEQUENCE: 144

Gly Ile Val Pro Gln Tyr Gly Tyr Ala Thr
1               5                   10

<210> SEQ ID NO 145
<211> LENGTH: 10
<212> TYPE: PRT
<213> ORGANISM: Artificial Sequence
<220> FEATURE:
<223> OTHER INFORMATION: >SEQ ID NO: 145 - anti-IL-1Rap-UCP02-C3 CDRH2

<400> SEQUENCE: 145

Ala Ile Ser Tyr Asp Gly Glu Gly Thr Leu
1               5                   10

<210> SEQ ID NO 146
<211> LENGTH: 10
<212> TYPE: PRT
<213> ORGANISM: Artificial Sequence
<220> FEATURE:
<223> OTHER INFORMATION: >SEQ ID NO: 146 - anti-IL-1Rap-UCP02-C5 CDRH2

<400> SEQUENCE: 146
```

```
Tyr Ile Ile Pro Ser Leu Gly Ala Val Asp
1               5                   10

<210> SEQ ID NO 147
<211> LENGTH: 10
<212> TYPE: PRT
<213> ORGANISM: Artificial Sequence
<220> FEATURE:
<223> OTHER INFORMATION: >SEQ ID NO: 147 - anti-IL-1Rap-UCP02-C8 CDRH2

<400> SEQUENCE: 147

Tyr Ile Ile Pro Leu His Gly Gln Val Asp
1               5                   10

<210> SEQ ID NO 148
<211> LENGTH: 10
<212> TYPE: PRT
<213> ORGANISM: Artificial Sequence
<220> FEATURE:
<223> OTHER INFORMATION: >SEQ ID NO: 148 - anti-IL-1Rap-UCP02-C9 CDRH2

<400> SEQUENCE: 148

Gly Ile Ile Pro Gly Tyr Gly Ala Thr Phe
1               5                   10

<210> SEQ ID NO 149
<211> LENGTH: 10
<212> TYPE: PRT
<213> ORGANISM: Artificial Sequence
<220> FEATURE:
<223> OTHER INFORMATION: >SEQ ID NO: 149 - anti-IL-1Rap-UCP02-D2 CDRH2

<400> SEQUENCE: 149

Tyr Ile Leu Pro Gln Phe Gly Ala Pro Leu
1               5                   10

<210> SEQ ID NO 150
<211> LENGTH: 10
<212> TYPE: PRT
<213> ORGANISM: Artificial Sequence
<220> FEATURE:
<223> OTHER INFORMATION: >SEQ ID NO: 150 - anti-IL-1Rap-UCP02-G11 CDRH2

<400> SEQUENCE: 150

Tyr Ile Ile Pro Ala Tyr Gly Gln Ala Glu
1               5                   10

<210> SEQ ID NO 151
<211> LENGTH: 10
<212> TYPE: PRT
<213> ORGANISM: Artificial Sequence
<220> FEATURE:
<223> OTHER INFORMATION: >SEQ ID NO: 151 - anti-IL-1Rap-UCP02-G3 CDRH2

<400> SEQUENCE: 151

Ala Val Ile Pro Arg Tyr Gly Gln Thr Tyr
1               5                   10

<210> SEQ ID NO 152
<211> LENGTH: 10
<212> TYPE: PRT
<213> ORGANISM: Artificial Sequence
<220> FEATURE:
<223> OTHER INFORMATION: >SEQ ID NO: 152 - anti-IL-1Rap-UCP02-G8 CDRH2

<400> SEQUENCE: 152
```

```
Gly Ile Ala Pro Ala Ala Gly Ile Ala Glu
1               5                   10

<210> SEQ ID NO 153
<211> LENGTH: 10
<212> TYPE: PRT
<213> ORGANISM: Artificial Sequence
<220> FEATURE:
<223> OTHER INFORMATION: >SEQ ID NO: 153 - anti-IL-1Rap-UCP02-H8 CDRH2

<400> SEQUENCE: 153

Gly Ile Ile Pro Glu Phe Gly Ala Thr Asn
1               5                   10

<210> SEQ ID NO 154
<211> LENGTH: 10
<212> TYPE: PRT
<213> ORGANISM: Artificial Sequence
<220> FEATURE:
<223> OTHER INFORMATION: >SEQ ID NO: 154 - anti-IL-1Rap-UCP02-H9 CDRH2

<400> SEQUENCE: 154

Gly Ile Ile Pro His His Gly Ala Thr Tyr
1               5                   10

<210> SEQ ID NO 155
<211> LENGTH: 10
<212> TYPE: PRT
<213> ORGANISM: Artificial Sequence
<220> FEATURE:
<223> OTHER INFORMATION: >SEQ ID NO: 155 - anti-IL-1Rap-UCP03-A2 CDRH2

<400> SEQUENCE: 155

Gly Ile Ile Pro Asp Phe Ala Ser Thr His
1               5                   10

<210> SEQ ID NO 156
<211> LENGTH: 10
<212> TYPE: PRT
<213> ORGANISM: Artificial Sequence
<220> FEATURE:
<223> OTHER INFORMATION: >SEQ ID NO: 156 - anti-IL-1Rap-UCP03-A3 CDRH2

<400> SEQUENCE: 156

Gly Ile Ile Pro Asp Val Gly Ala Ala Phe
1               5                   10

<210> SEQ ID NO 157
<211> LENGTH: 10
<212> TYPE: PRT
<213> ORGANISM: Artificial Sequence
<220> FEATURE:
<223> OTHER INFORMATION: >SEQ ID NO: 157 - anti-IL-1Rap-UCP03-B4 CDRH2

<400> SEQUENCE: 157

Gly Ile Ile Pro Phe Glu Gly Val Ala Phe
1               5                   10

<210> SEQ ID NO 158
<211> LENGTH: 10
<212> TYPE: PRT
<213> ORGANISM: Artificial Sequence
<220> FEATURE:
<223> OTHER INFORMATION: >SEQ ID NO: 158 - anti-IL-1Rap-UCP03-B6 CDRH2

<400> SEQUENCE: 158

Tyr Ile Ile Ala Gln Gln Gly Ser Ala Ser
```

```
1               5                   10

<210> SEQ ID NO 159
<211> LENGTH: 10
<212> TYPE: PRT
<213> ORGANISM: Artificial Sequence
<220> FEATURE:
<223> OTHER INFORMATION: >SEQ ID NO: 159 - anti-IL-1Rap-UCP03-C1 CDRH2

<400> SEQUENCE: 159

Gly Ile Ile Pro His Phe Gly Ala Val Tyr
1               5                   10

<210> SEQ ID NO 160
<211> LENGTH: 10
<212> TYPE: PRT
<213> ORGANISM: Artificial Sequence
<220> FEATURE:
<223> OTHER INFORMATION: >SEQ ID NO: 160 - anti-IL-1Rap-UCP03-C2 CDRH2

<400> SEQUENCE: 160

Gly Ile Ile Pro Thr Thr Gly Glu Ala Ile
1               5                   10

<210> SEQ ID NO 161
<211> LENGTH: 10
<212> TYPE: PRT
<213> ORGANISM: Artificial Sequence
<220> FEATURE:
<223> OTHER INFORMATION: >SEQ ID NO: 161 - anti-IL-1Rap-UCP03-F4 CDRH2

<400> SEQUENCE: 161

Ala Ile Leu Pro Glu Gln Gly Ala Ala Tyr
1               5                   10

<210> SEQ ID NO 162
<211> LENGTH: 10
<212> TYPE: PRT
<213> ORGANISM: Artificial Sequence
<220> FEATURE:
<223> OTHER INFORMATION: >SEQ ID NO: 162 - anti-IL-1Rap-UCP03-G3 CDRH2

<400> SEQUENCE: 162

Gly Ile Ile Pro Asn Phe Ala Gln Thr Asp
1               5                   10

<210> SEQ ID NO 163
<211> LENGTH: 10
<212> TYPE: PRT
<213> ORGANISM: Artificial Sequence
<220> FEATURE:
<223> OTHER INFORMATION: >SEQ ID NO: 163 - anti-IL-1Rap-UCP03-G4 CDRH2

<400> SEQUENCE: 163

Gly Ile Ile Pro Tyr Glu Gly Lys Pro Phe
1               5                   10

<210> SEQ ID NO 164
<211> LENGTH: 10
<212> TYPE: PRT
<213> ORGANISM: Artificial Sequence
<220> FEATURE:
<223> OTHER INFORMATION: >SEQ ID NO: 164 - anti-IL-1Rap-UCP04-C1 CDRH2

<400> SEQUENCE: 164

Ala Ile Ser Tyr Glu Gly Asp Gly Thr Leu
1               5                   10
```

<210> SEQ ID NO 165
<211> LENGTH: 10
<212> TYPE: PRT
<213> ORGANISM: Artificial Sequence
<220> FEATURE:
<223> OTHER INFORMATION: >SEQ ID NO: 165 - anti-IL-1Rap-C8-H1A-C4 CDRH2

<400> SEQUENCE: 165

Tyr Ile Ile Pro Leu His Gly Gln Val Asp
1               5                   10

<210> SEQ ID NO 166
<211> LENGTH: 10
<212> TYPE: PRT
<213> ORGANISM: Artificial Sequence
<220> FEATURE:
<223> OTHER INFORMATION: >SEQ ID NO: 166 - anti-IL-1Rap-C8-H1A-C8 CDRH2

<400> SEQUENCE: 166

Tyr Ile Ile Pro Leu His Gly Gln Val Asp
1               5                   10

<210> SEQ ID NO 167
<211> LENGTH: 10
<212> TYPE: PRT
<213> ORGANISM: Artificial Sequence
<220> FEATURE:
<223> OTHER INFORMATION: >SEQ ID NO: 167 - anti-IL-1Rap-C8-H1A-D8 CDRH2

<400> SEQUENCE: 167

Tyr Ile Ile Pro Leu His Gly Gln Val Asp
1               5                   10

<210> SEQ ID NO 168
<211> LENGTH: 10
<212> TYPE: PRT
<213> ORGANISM: Artificial Sequence
<220> FEATURE:
<223> OTHER INFORMATION: >SEQ ID NO: 168 - anti-IL-1Rap-C8-H1A-F1 CDRH2

<400> SEQUENCE: 168

Tyr Ile Ile Pro Leu His Gly Gln Val Asp
1               5                   10

<210> SEQ ID NO 169
<211> LENGTH: 10
<212> TYPE: PRT
<213> ORGANISM: Artificial Sequence
<220> FEATURE:
<223> OTHER INFORMATION: >SEQ ID NO: 169 - anti-IL-1Rap-C8-H1A-G11 CDRH2

<400> SEQUENCE: 169

Tyr Ile Ile Pro Leu His Gly Gln Val Asp
1               5                   10

<210> SEQ ID NO 170
<211> LENGTH: 10
<212> TYPE: PRT
<213> ORGANISM: Artificial Sequence
<220> FEATURE:
<223> OTHER INFORMATION: >SEQ ID NO: 170 - anti-IL-1Rap-C8-H1A-G1 CDRH2

<400> SEQUENCE: 170

Tyr Ile Ile Pro Leu His Gly Gln Val Asp
1               5                   10

<210> SEQ ID NO 171
<211> LENGTH: 10
<212> TYPE: PRT
<213> ORGANISM: Artificial Sequence
<220> FEATURE:
<223> OTHER INFORMATION: >SEQ ID NO: 171 - anti-IL-1Rap-C8-H1A-G3 CDRH2

<400> SEQUENCE: 171

Tyr Ile Ile Pro Leu His Gly Gln Val Asp
1               5                   10

<210> SEQ ID NO 172
<211> LENGTH: 10
<212> TYPE: PRT
<213> ORGANISM: Artificial Sequence
<220> FEATURE:
<223> OTHER INFORMATION: >SEQ ID NO: 172 - anti-IL-1Rap-C8-H1B-A8 CDRH2

<400> SEQUENCE: 172

Tyr Ile Ile Pro Leu His Gly Gln Val Asp
1               5                   10

<210> SEQ ID NO 173
<211> LENGTH: 10
<212> TYPE: PRT
<213> ORGANISM: Artificial Sequence
<220> FEATURE:
<223> OTHER INFORMATION: >SEQ ID NO: 173 - anti-IL-1Rap-C8-H1B-B10 CDRH2

<400> SEQUENCE: 173

Tyr Ile Ile Pro Leu His Gly Gln Val Asp
1               5                   10

<210> SEQ ID NO 174
<211> LENGTH: 10
<212> TYPE: PRT
<213> ORGANISM: Artificial Sequence
<220> FEATURE:
<223> OTHER INFORMATION: >SEQ ID NO: 174 - anti-IL-1Rap-C8-H1B-B8 CDRH2

<400> SEQUENCE: 174

Tyr Ile Ile Pro Leu His Gly Gln Val Asp
1               5                   10

<210> SEQ ID NO 175
<211> LENGTH: 10
<212> TYPE: PRT
<213> ORGANISM: Artificial Sequence
<220> FEATURE:
<223> OTHER INFORMATION: >SEQ ID NO: 175 - anti-IL-1Rap-C8-H1B-D8 CDRH2

<400> SEQUENCE: 175

Tyr Ile Ile Pro Leu His Gly Gln Val Asp
1               5                   10

<210> SEQ ID NO 176
<211> LENGTH: 10
<212> TYPE: PRT
<213> ORGANISM: Artificial Sequence
<220> FEATURE:
<223> OTHER INFORMATION: >SEQ ID NO: 176 - anti-IL-1Rap-C8-H1B-E7 CDRH2

<400> SEQUENCE: 176

Tyr Ile Ile Pro Leu His Gly Gln Val Asp
1               5                   10

```
<210> SEQ ID NO 177
<211> LENGTH: 10
<212> TYPE: PRT
<213> ORGANISM: Artificial Sequence
<220> FEATURE:
<223> OTHER INFORMATION: >SEQ ID NO: 177 - anti-IL-1Rap-C8-H1B-F3 CDRH2

<400> SEQUENCE: 177

Tyr Ile Ile Pro Leu His Gly Gln Val Asp
1               5                   10

<210> SEQ ID NO 178
<211> LENGTH: 10
<212> TYPE: PRT
<213> ORGANISM: Artificial Sequence
<220> FEATURE:
<223> OTHER INFORMATION: >SEQ ID NO: 178 - anti-IL-1Rap-C8-H1B-G10 CDRH2

<400> SEQUENCE: 178

Tyr Ile Ile Pro Leu His Gly Gln Val Asp
1               5                   10

<210> SEQ ID NO 179
<211> LENGTH: 10
<212> TYPE: PRT
<213> ORGANISM: Artificial Sequence
<220> FEATURE:
<223> OTHER INFORMATION: >SEQ ID NO: 179 - anti-IL-1Rap-C8-H1B-H10 CDRH2

<400> SEQUENCE: 179

Tyr Ile Ile Pro Leu His Gly Gln Val Asp
1               5                   10

<210> SEQ ID NO 180
<211> LENGTH: 10
<212> TYPE: PRT
<213> ORGANISM: Artificial Sequence
<220> FEATURE:
<223> OTHER INFORMATION: >SEQ ID NO: 180 - anti-IL-1Rap-C8-H2B-B5 CDRH2

<400> SEQUENCE: 180

Tyr Ile Ile Pro Thr Val Gly Gly Phe Asp
1               5                   10

<210> SEQ ID NO 181
<211> LENGTH: 10
<212> TYPE: PRT
<213> ORGANISM: Artificial Sequence
<220> FEATURE:
<223> OTHER INFORMATION: >SEQ ID NO: 181 - anti-IL-1Rap-C8-H2B-C10 CDRH2

<400> SEQUENCE: 181

Tyr Ile Ile Pro Ser Leu Gly Gly Tyr Asp
1               5                   10

<210> SEQ ID NO 182
<211> LENGTH: 10
<212> TYPE: PRT
<213> ORGANISM: Artificial Sequence
<220> FEATURE:
<223> OTHER INFORMATION: >SEQ ID NO: 182 - anti-IL-1Rap-C8-recA CDRH2

<400> SEQUENCE: 182

Tyr Ile Ile Pro Ser Leu Gly Gly Tyr Asp
1               5                   10

<210> SEQ ID NO 183
```

```
<211> LENGTH: 10
<212> TYPE: PRT
<213> ORGANISM: Artificial Sequence
<220> FEATURE:
<223> OTHER INFORMATION: >SEQ ID NO: 183 - anti-IL-1Rap-C8-recB CDRH2

<400> SEQUENCE: 183

Tyr Ile Ile Pro Ser Leu Gly Gly Tyr Asp
1               5                   10

<210> SEQ ID NO 184
<211> LENGTH: 10
<212> TYPE: PRT
<213> ORGANISM: Artificial Sequence
<220> FEATURE:
<223> OTHER INFORMATION: >SEQ ID NO: 184 - anti-IL-1Rap-C8-recC CDRH2

<400> SEQUENCE: 184

Tyr Ile Ile Pro Ser Leu Gly Gly Tyr Asp
1               5                   10

<210> SEQ ID NO 185
<211> LENGTH: 10
<212> TYPE: PRT
<213> ORGANISM: Artificial Sequence
<220> FEATURE:
<223> OTHER INFORMATION: >SEQ ID NO: 185 - anti-IL-1Rap-C8-RecC-AA CDRH2

<400> SEQUENCE: 185

Tyr Ile Ile Pro Ser Leu Gly Gly Tyr Asp
1               5                   10

<210> SEQ ID NO 186
<211> LENGTH: 10
<212> TYPE: PRT
<213> ORGANISM: Artificial Sequence
<220> FEATURE:
<223> OTHER INFORMATION: >SEQ ID NO: 186 - anti-IL-1Rap-C8-RecC-DA CDRH2

<400> SEQUENCE: 186

Tyr Ile Ile Pro Ser Leu Gly Gly Tyr Asp
1               5                   10

<210> SEQ ID NO 187
<211> LENGTH: 10
<212> TYPE: PRT
<213> ORGANISM: Artificial Sequence
<220> FEATURE:
<223> OTHER INFORMATION: >SEQ ID NO: 187 - anti-IL-1Rap-C8-RecC-AS CDRH2

<400> SEQUENCE: 187

Tyr Ile Ile Pro Ser Leu Gly Gly Tyr Asp
1               5                   10

<210> SEQ ID NO 188
<211> LENGTH: 10
<212> TYPE: PRT
<213> ORGANISM: Artificial Sequence
<220> FEATURE:
<223> OTHER INFORMATION: >SEQ ID NO: 188 - anti-IL-1Rap-C8-RecC-ES CDRH2

<400> SEQUENCE: 188

Tyr Ile Ile Pro Ser Leu Gly Gly Tyr Asp
1               5                   10

<210> SEQ ID NO 189
<211> LENGTH: 10
```

```
<212> TYPE: PRT
<213> ORGANISM: Artificial Sequence
<220> FEATURE:
<223> OTHER INFORMATION: >SEQ ID NO: 189 - anti-IL-1Rap-C8-RecC-ET CDRH2

<400> SEQUENCE: 189

Tyr Ile Ile Pro Ser Leu Gly Gly Tyr Asp
1               5                   10

<210> SEQ ID NO 190
<211> LENGTH: 10
<212> TYPE: PRT
<213> ORGANISM: Artificial Sequence
<220> FEATURE:
<223> OTHER INFORMATION: >SEQ ID NO: 190 - anti-IL-1Rap-C3-MP01-A2 CDRH2

<400> SEQUENCE: 190

Ala Ile Ser Tyr Asp Gly Glu Gly Thr Leu
1               5                   10

<210> SEQ ID NO 191
<211> LENGTH: 10
<212> TYPE: PRT
<213> ORGANISM: Artificial Sequence
<220> FEATURE:
<223> OTHER INFORMATION: >SEQ ID NO: 191 - anti-IL-1Rap-C3-MP01-A3 CDRH2

<400> SEQUENCE: 191

Ala Ile Ser Tyr Asp Gly Glu Gly Thr Leu
1               5                   10

<210> SEQ ID NO 192
<211> LENGTH: 10
<212> TYPE: PRT
<213> ORGANISM: Artificial Sequence
<220> FEATURE:
<223> OTHER INFORMATION: >SEQ ID NO: 192 - anti-IL-1Rap-C3-MP01-B5 CDRH2

<400> SEQUENCE: 192

Ala Ile Ser Tyr Asp Gly Glu Gly Thr Leu
1               5                   10

<210> SEQ ID NO 193
<211> LENGTH: 10
<212> TYPE: PRT
<213> ORGANISM: Artificial Sequence
<220> FEATURE:
<223> OTHER INFORMATION: >SEQ ID NO: 193 - anti-IL-1Rap-C3-MP01-B7 CDRH2

<400> SEQUENCE: 193

Ala Ile Ser Tyr Asp Gly Glu Gly Thr Leu
1               5                   10

<210> SEQ ID NO 194
<211> LENGTH: 10
<212> TYPE: PRT
<213> ORGANISM: Artificial Sequence
<220> FEATURE:
<223> OTHER INFORMATION: >SEQ ID NO: 194 - anti-IL-1Rap-C3-MP01-D2 CDRH2

<400> SEQUENCE: 194

Ala Ile Ser Tyr Asp Gly Glu Gly Thr Leu
1               5                   10

<210> SEQ ID NO 195
<211> LENGTH: 10
<212> TYPE: PRT
```

```
<213> ORGANISM: Artificial Sequence
<220> FEATURE:
<223> OTHER INFORMATION: >SEQ ID NO: 195 - anti-IL-1Rap-C3-MP01-F5 CDRH2

<400> SEQUENCE: 195

Ala Ile Ser Tyr Asp Gly Glu Gly Thr Leu
1               5                   10

<210> SEQ ID NO 196
<211> LENGTH: 10
<212> TYPE: PRT
<213> ORGANISM: Artificial Sequence
<220> FEATURE:
<223> OTHER INFORMATION: >SEQ ID NO: 196 - anti-IL-1Rap-C3-MP01-G10
      CDRH2

<400> SEQUENCE: 196

Ala Ile Ser Tyr Asp Gly Glu Gly Thr Leu
1               5                   10

<210> SEQ ID NO 197
<211> LENGTH: 10
<212> TYPE: PRT
<213> ORGANISM: Artificial Sequence
<220> FEATURE:
<223> OTHER INFORMATION: >SEQ ID NO: 197 - anti-IL-1Rap-C3-MP02-B8 CDRH2

<400> SEQUENCE: 197

Ala Ile Ser Tyr Asp Gly Glu Gly Thr Leu
1               5                   10

<210> SEQ ID NO 198
<211> LENGTH: 10
<212> TYPE: PRT
<213> ORGANISM: Artificial Sequence
<220> FEATURE:
<223> OTHER INFORMATION: >SEQ ID NO: 198 - anti-IL-1Rap-C3-MP02-F6 CDRH2

<400> SEQUENCE: 198

Ala Ile Ser Tyr Asp Gly Glu Gly Thr Leu
1               5                   10

<210> SEQ ID NO 199
<211> LENGTH: 10
<212> TYPE: PRT
<213> ORGANISM: Artificial Sequence
<220> FEATURE:
<223> OTHER INFORMATION: >SEQ ID NO: 199 - anti-IL-1Rap-C3-MP02-G2 CDRH2

<400> SEQUENCE: 199

Ala Ile Ser Tyr Asp Gly Glu Gly Thr Leu
1               5                   10

<210> SEQ ID NO 200
<211> LENGTH: 10
<212> TYPE: PRT
<213> ORGANISM: Artificial Sequence
<220> FEATURE:
<223> OTHER INFORMATION: >SEQ ID NO: 200 - anti-IL-1Rap-C3-UCP01-H4
      CDRH2

<400> SEQUENCE: 200

Ala Ile Ser Tyr Asp Gly Glu Gly Thr Leu
1               5                   10

<210> SEQ ID NO 201
<211> LENGTH: 12
```

```
<212> TYPE: PRT
<213> ORGANISM: Artificial Sequence
<220> FEATURE:
<223> OTHER INFORMATION: >SEQ ID NO: 201 - anti-IL-1Rap-UCP02-A4 CDRH3

<400> SEQUENCE: 201

Ala Arg Ala Ser Pro Tyr Lys Gly Trp Trp Asp Tyr
1               5                   10

<210> SEQ ID NO 202
<211> LENGTH: 14
<212> TYPE: PRT
<213> ORGANISM: Artificial Sequence
<220> FEATURE:
<223> OTHER INFORMATION: >SEQ ID NO: 202 - anti-IL-1Rap-UCP02-A6 CDRH3

<400> SEQUENCE: 202

Ala Arg Ala Lys Asp Ile Tyr Gly Tyr Gly Tyr Gly Asp Ile
1               5                   10

<210> SEQ ID NO 203
<211> LENGTH: 12
<212> TYPE: PRT
<213> ORGANISM: Artificial Sequence
<220> FEATURE:
<223> OTHER INFORMATION: >SEQ ID NO: 203 - anti-IL-1Rap-UCP02-B11 CDRH3

<400> SEQUENCE: 203

Ala Arg Asp Ser Ile Tyr Ser Ala Trp Leu Ala Tyr
1               5                   10

<210> SEQ ID NO 204
<211> LENGTH: 13
<212> TYPE: PRT
<213> ORGANISM: Artificial Sequence
<220> FEATURE:
<223> OTHER INFORMATION: >SEQ ID NO: 204 - anti-IL-1Rap-UCP02-B5 CDRH3

<400> SEQUENCE: 204

Ala Arg Gly Arg Ser Thr Thr Tyr Tyr Gly Phe Ala Tyr
1               5                   10

<210> SEQ ID NO 205
<211> LENGTH: 11
<212> TYPE: PRT
<213> ORGANISM: Artificial Sequence
<220> FEATURE:
<223> OTHER INFORMATION: >SEQ ID NO: 205 - anti-IL-1Rap-UCP02-C3 CDRH3

<400> SEQUENCE: 205

Ala Arg Phe Arg Tyr Tyr Thr Ala Phe Asp Tyr
1               5                   10

<210> SEQ ID NO 206
<211> LENGTH: 12
<212> TYPE: PRT
<213> ORGANISM: Artificial Sequence
<220> FEATURE:
<223> OTHER INFORMATION: >SEQ ID NO: 206 - anti-IL-1Rap-UCP02-C5 CDRH3

<400> SEQUENCE: 206

Ala Arg Ala Ser Ile Tyr His Gly Trp Met Ala Tyr
1               5                   10

<210> SEQ ID NO 207
<211> LENGTH: 15
<212> TYPE: PRT
```

```
<213> ORGANISM: Artificial Sequence
<220> FEATURE:
<223> OTHER INFORMATION: >SEQ ID NO: 207 - anti-IL-1Rap-UCP02-C8 CDRH3

<400> SEQUENCE: 207

Ala Arg Gly Gln Thr Leu Tyr Asp Ser Gly Arg Gln Phe Asp Ile
1               5                   10                  15

<210> SEQ ID NO 208
<211> LENGTH: 13
<212> TYPE: PRT
<213> ORGANISM: Artificial Sequence
<220> FEATURE:
<223> OTHER INFORMATION: >SEQ ID NO: 208 - anti-IL-1Rap-UCP02-C9 CDRH3

<400> SEQUENCE: 208

Ala Arg Pro Val Ser Tyr Ser Ser Gly Trp Tyr Asp Tyr
1               5                   10

<210> SEQ ID NO 209
<211> LENGTH: 16
<212> TYPE: PRT
<213> ORGANISM: Artificial Sequence
<220> FEATURE:
<223> OTHER INFORMATION: >SEQ ID NO: 209 - anti-IL-1Rap-UCP02-D2 CDRH3

<400> SEQUENCE: 209

Ala Arg Gly Ser Tyr Tyr Gly Val Val Gly Tyr Val Pro Asp Asp Tyr
1               5                   10                  15

<210> SEQ ID NO 210
<211> LENGTH: 12
<212> TYPE: PRT
<213> ORGANISM: Artificial Sequence
<220> FEATURE:
<223> OTHER INFORMATION: >SEQ ID NO: 210 - anti-IL-1Rap-UCP02-G11 CDRH3

<400> SEQUENCE: 210

Ala Arg Val Pro Tyr Ser Thr Ala Tyr Phe Asp Tyr
1               5                   10

<210> SEQ ID NO 211
<211> LENGTH: 13
<212> TYPE: PRT
<213> ORGANISM: Artificial Sequence
<220> FEATURE:
<223> OTHER INFORMATION: >SEQ ID NO: 211 - anti-IL-1Rap-UCP02-G3 CDRH3

<400> SEQUENCE: 211

Ala Arg Pro Leu Gly Tyr Ser Tyr Gly Trp Phe Asp Tyr
1               5                   10

<210> SEQ ID NO 212
<211> LENGTH: 17
<212> TYPE: PRT
<213> ORGANISM: Artificial Sequence
<220> FEATURE:
<223> OTHER INFORMATION: >SEQ ID NO: 212 - anti-IL-1Rap-UCP02-G8 CDRH3

<400> SEQUENCE: 212

Ala Arg Gly Gln Ser Pro Gly Arg Val Arg Glu Glu Tyr Trp Tyr Asp
1               5                   10                  15

Tyr

<210> SEQ ID NO 213
<211> LENGTH: 13
```

```
<212> TYPE: PRT
<213> ORGANISM: Artificial Sequence
<220> FEATURE:
<223> OTHER INFORMATION: >SEQ ID NO: 213 - anti-IL-1Rap-UCP02-H8 CDRH3

<400> SEQUENCE: 213

Ala Arg His Ser Ser Ala Tyr Ser Pro Trp Phe Asp Tyr
1               5                   10

<210> SEQ ID NO 214
<211> LENGTH: 13
<212> TYPE: PRT
<213> ORGANISM: Artificial Sequence
<220> FEATURE:
<223> OTHER INFORMATION: >SEQ ID NO: 214 - anti-IL-1Rap-UCP02-H9 CDRH3

<400> SEQUENCE: 214

Ala Arg His Pro Asp Val Tyr Thr Pro Trp Phe Asp Val
1               5                   10

<210> SEQ ID NO 215
<211> LENGTH: 13
<212> TYPE: PRT
<213> ORGANISM: Artificial Sequence
<220> FEATURE:
<223> OTHER INFORMATION: >SEQ ID NO: 215 - anti-IL-1Rap-UCP03-A2 CDRH3

<400> SEQUENCE: 215

Ala Arg Val Pro Asp Tyr Tyr Thr Gly Trp Met Ala Tyr
1               5                   10

<210> SEQ ID NO 216
<211> LENGTH: 12
<212> TYPE: PRT
<213> ORGANISM: Artificial Sequence
<220> FEATURE:
<223> OTHER INFORMATION: >SEQ ID NO: 216 - anti-IL-1Rap-UCP03-A3 CDRH3

<400> SEQUENCE: 216

Ala Arg Gly Ser Ile Tyr Thr Ala Trp Phe Ala Val
1               5                   10

<210> SEQ ID NO 217
<211> LENGTH: 12
<212> TYPE: PRT
<213> ORGANISM: Artificial Sequence
<220> FEATURE:
<223> OTHER INFORMATION: >SEQ ID NO: 217 - anti-IL-1Rap-UCP03-B4 CDRH3

<400> SEQUENCE: 217

Ala Arg Ser Ser Ser Tyr Tyr Ser Trp Leu Asp Tyr
1               5                   10

<210> SEQ ID NO 218
<211> LENGTH: 13
<212> TYPE: PRT
<213> ORGANISM: Artificial Sequence
<220> FEATURE:
<223> OTHER INFORMATION: >SEQ ID NO: 218 - anti-IL-1Rap-UCP03-B6 CDRH3

<400> SEQUENCE: 218

Ala Arg Val Pro Asp Pro Tyr Ser Gly His Phe Asp Tyr
1               5                   10

<210> SEQ ID NO 219
<211> LENGTH: 12
<212> TYPE: PRT
```

```
<213> ORGANISM: Artificial Sequence
<220> FEATURE:
<223> OTHER INFORMATION: >SEQ ID NO: 219 - anti-IL-1Rap-UCP03-C1 CDRH3

<400> SEQUENCE: 219

Ala Arg Gly Ser Val Tyr Thr Gly Trp Phe Asp Asn
1               5                   10

<210> SEQ ID NO 220
<211> LENGTH: 12
<212> TYPE: PRT
<213> ORGANISM: Artificial Sequence
<220> FEATURE:
<223> OTHER INFORMATION: >SEQ ID NO: 220 - anti-IL-1Rap-UCP03-C2 CDRH3

<400> SEQUENCE: 220

Ala Arg His Gly Thr Thr Tyr Ala Ala Phe Asp His
1               5                   10

<210> SEQ ID NO 221
<211> LENGTH: 12
<212> TYPE: PRT
<213> ORGANISM: Artificial Sequence
<220> FEATURE:
<223> OTHER INFORMATION: >SEQ ID NO: 221 - anti-IL-1Rap-UCP03-F4 CDRH3

<400> SEQUENCE: 221

Ala Arg Val Gly Leu Tyr Val Pro Tyr Met Asp Ile
1               5                   10

<210> SEQ ID NO 222
<211> LENGTH: 12
<212> TYPE: PRT
<213> ORGANISM: Artificial Sequence
<220> FEATURE:
<223> OTHER INFORMATION: >SEQ ID NO: 222 - anti-IL-1Rap-UCP03-G3 CDRH3

<400> SEQUENCE: 222

Ala Arg Phe Ser Ile Tyr Ser Gly Trp Ser Asp Val
1               5                   10

<210> SEQ ID NO 223
<211> LENGTH: 12
<212> TYPE: PRT
<213> ORGANISM: Artificial Sequence
<220> FEATURE:
<223> OTHER INFORMATION: >SEQ ID NO: 223 - anti-IL-1Rap-UCP03-G4 CDRH3

<400> SEQUENCE: 223

Ala Arg Ser Asp Tyr Phe Tyr Tyr Tyr Phe Asp Pro
1               5                   10

<210> SEQ ID NO 224
<211> LENGTH: 11
<212> TYPE: PRT
<213> ORGANISM: Artificial Sequence
<220> FEATURE:
<223> OTHER INFORMATION: >SEQ ID NO: 224 - anti-IL-1Rap-UCP04-C1 CDRH3

<400> SEQUENCE: 224

Ala Arg Ser Leu Tyr Trp Ser Gly Phe Asp Tyr
1               5                   10

<210> SEQ ID NO 225
<211> LENGTH: 15
<212> TYPE: PRT
<213> ORGANISM: Artificial Sequence
```

```
<220> FEATURE:
<223> OTHER INFORMATION: >SEQ ID NO: 225 - anti-IL-1Rap-C8-H1A-C4 CDRH3

<400> SEQUENCE: 225

Ala Arg Gly Gln Thr Leu Tyr Asp Ser Gly Arg Gln Phe Asp Ile
1               5                   10                  15

<210> SEQ ID NO 226
<211> LENGTH: 15
<212> TYPE: PRT
<213> ORGANISM: Artificial Sequence
<220> FEATURE:
<223> OTHER INFORMATION: >SEQ ID NO: 226 - anti-IL-1Rap-C8-H1A-C8 CDRH3

<400> SEQUENCE: 226

Ala Arg Gly Gln Thr Leu Tyr Asp Ser Gly Arg Gln Phe Asp Ile
1               5                   10                  15

<210> SEQ ID NO 227
<211> LENGTH: 15
<212> TYPE: PRT
<213> ORGANISM: Artificial Sequence
<220> FEATURE:
<223> OTHER INFORMATION: >SEQ ID NO: 227 - anti-IL-1Rap-C8-H1A-D8 CDRH3

<400> SEQUENCE: 227

Ala Arg Gly Gln Thr Leu Tyr Asp Ser Gly Arg Gln Phe Asp Ile
1               5                   10                  15

<210> SEQ ID NO 228
<211> LENGTH: 15
<212> TYPE: PRT
<213> ORGANISM: Artificial Sequence
<220> FEATURE:
<223> OTHER INFORMATION: >SEQ ID NO: 228 - anti-IL-1Rap-C8-H1A-F1 CDRH3

<400> SEQUENCE: 228

Ala Arg Gly Gln Thr Leu Tyr Asp Ser Gly Arg Gln Phe Asp Ile
1               5                   10                  15

<210> SEQ ID NO 229
<211> LENGTH: 15
<212> TYPE: PRT
<213> ORGANISM: Artificial Sequence
<220> FEATURE:
<223> OTHER INFORMATION: >SEQ ID NO: 229 - anti-IL-1Rap-C8-H1A-G11 CDRH3

<400> SEQUENCE: 229

Ala Arg Gly Gln Thr Leu Tyr Asp Ser Gly Arg Gln Phe Asp Ile
1               5                   10                  15

<210> SEQ ID NO 230
<211> LENGTH: 15
<212> TYPE: PRT
<213> ORGANISM: Artificial Sequence
<220> FEATURE:
<223> OTHER INFORMATION: >SEQ ID NO: 230 - anti-IL-1Rap-C8-H1A-G1 CDRH3

<400> SEQUENCE: 230

Ala Arg Gly Gln Thr Leu Tyr Asp Ser Gly Arg Gln Phe Asp Ile
1               5                   10                  15

<210> SEQ ID NO 231
<211> LENGTH: 15
<212> TYPE: PRT
<213> ORGANISM: Artificial Sequence
<220> FEATURE:
```

```
<223> OTHER INFORMATION: >SEQ ID NO: 231 - anti-IL-1Rap-C8-H1A-G3 CDRH3

<400> SEQUENCE: 231

Ala Arg Gly Gln Thr Leu Tyr Asp Ser Gly Arg Gln Phe Asp Ile
1               5                   10                  15

<210> SEQ ID NO 232
<211> LENGTH: 15
<212> TYPE: PRT
<213> ORGANISM: Artificial Sequence
<220> FEATURE:
<223> OTHER INFORMATION: >SEQ ID NO: 232 - anti-IL-1Rap-C8-H1B-A8 CDRH3

<400> SEQUENCE: 232

Ala Arg Gly Gln Thr Leu Tyr Asp Ser Gly Arg Gln Phe Asp Ile
1               5                   10                  15

<210> SEQ ID NO 233
<211> LENGTH: 15
<212> TYPE: PRT
<213> ORGANISM: Artificial Sequence
<220> FEATURE:
<223> OTHER INFORMATION: >SEQ ID NO: 233 - anti-IL-1Rap-C8-H1B-B10 CDRH3

<400> SEQUENCE: 233

Ala Arg Gly Gln Thr Leu Tyr Asp Ser Gly Arg Gln Phe Asp Ile
1               5                   10                  15

<210> SEQ ID NO 234
<211> LENGTH: 15
<212> TYPE: PRT
<213> ORGANISM: Artificial Sequence
<220> FEATURE:
<223> OTHER INFORMATION: >SEQ ID NO: 234 - anti-IL-1Rap-C8-H1B-B8 CDRH3

<400> SEQUENCE: 234

Ala Arg Gly Gln Thr Leu Tyr Asp Ser Gly Arg Gln Phe Asp Ile
1               5                   10                  15

<210> SEQ ID NO 235
<211> LENGTH: 15
<212> TYPE: PRT
<213> ORGANISM: Artificial Sequence
<220> FEATURE:
<223> OTHER INFORMATION: >SEQ ID NO: 235 - anti-IL-1Rap-C8-H1B-D8 CDRH3

<400> SEQUENCE: 235

Ala Arg Gly Gln Thr Leu Tyr Asp Ser Gly Arg Gln Phe Asp Ile
1               5                   10                  15

<210> SEQ ID NO 236
<211> LENGTH: 15
<212> TYPE: PRT
<213> ORGANISM: Artificial Sequence
<220> FEATURE:
<223> OTHER INFORMATION: >SEQ ID NO: 236 - anti-IL-1Rap-C8-H1B-E7 CDRH3

<400> SEQUENCE: 236

Ala Arg Gly Gln Thr Leu Tyr Asp Ser Gly Arg Gln Phe Asp Ile
1               5                   10                  15

<210> SEQ ID NO 237
<211> LENGTH: 15
<212> TYPE: PRT
<213> ORGANISM: Artificial Sequence
<220> FEATURE:
<223> OTHER INFORMATION: >SEQ ID NO: 237 - anti-IL-1Rap-C8-H1B-F3 CDRH3
```

<400> SEQUENCE: 237

Ala Arg Gly Gln Thr Leu Tyr Asp Ser Gly Arg Gln Phe Asp Ile
1               5                   10                  15

<210> SEQ ID NO 238
<211> LENGTH: 15
<212> TYPE: PRT
<213> ORGANISM: Artificial Sequence
<220> FEATURE:
<223> OTHER INFORMATION: >SEQ ID NO: 238 - anti-IL-1Rap-C8-H1B-G10 CDRH3

<400> SEQUENCE: 238

Ala Arg Gly Gln Thr Leu Tyr Asp Ser Gly Arg Gln Phe Asp Ile
1               5                   10                  15

<210> SEQ ID NO 239
<211> LENGTH: 15
<212> TYPE: PRT
<213> ORGANISM: Artificial Sequence
<220> FEATURE:
<223> OTHER INFORMATION: >SEQ ID NO: 239 - anti-IL-1Rap-C8-H1B-H10 CDRH3

<400> SEQUENCE: 239

Ala Arg Gly Gln Thr Leu Tyr Asp Ser Gly Arg Gln Phe Asp Ile
1               5                   10                  15

<210> SEQ ID NO 240
<211> LENGTH: 15
<212> TYPE: PRT
<213> ORGANISM: Artificial Sequence
<220> FEATURE:
<223> OTHER INFORMATION: >SEQ ID NO: 240 - anti-IL-1Rap-C8-H2B-B5 CDRH3

<400> SEQUENCE: 240

Ala Arg Gly Gln Thr Leu Tyr Asp Ser Gly Arg Gln Phe Asp Ile
1               5                   10                  15

<210> SEQ ID NO 241
<211> LENGTH: 15
<212> TYPE: PRT
<213> ORGANISM: Artificial Sequence
<220> FEATURE:
<223> OTHER INFORMATION: >SEQ ID NO: 241 - anti-IL-1Rap-C8-H2B-C10 CDRH3

<400> SEQUENCE: 241

Ala Arg Gly Gln Thr Leu Tyr Asp Ser Gly Arg Gln Phe Asp Ile
1               5                   10                  15

<210> SEQ ID NO 242
<211> LENGTH: 15
<212> TYPE: PRT
<213> ORGANISM: Artificial Sequence
<220> FEATURE:
<223> OTHER INFORMATION: >SEQ ID NO: 242 - anti-IL-1Rap-C8-recA CDRH3

<400> SEQUENCE: 242

Ala Arg Gly Gln Thr Leu Tyr Asp Ser Gly Arg Gln Phe Asp Ile
1               5                   10                  15

<210> SEQ ID NO 243
<211> LENGTH: 15
<212> TYPE: PRT
<213> ORGANISM: Artificial Sequence
<220> FEATURE:
<223> OTHER INFORMATION: >SEQ ID NO: 243 - anti-IL-1Rap-C8-recB CDRH3

```
<400> SEQUENCE: 243

Ala Arg Gly Gln Thr Leu Tyr Asp Ser Gly Arg Gln Phe Asp Ile
1               5                   10                  15

<210> SEQ ID NO 244
<211> LENGTH: 15
<212> TYPE: PRT
<213> ORGANISM: Artificial Sequence
<220> FEATURE:
<223> OTHER INFORMATION: >SEQ ID NO: 244 - anti-IL-1Rap-C8-recC CDRH3

<400> SEQUENCE: 244

Ala Arg Gly Gln Thr Leu Tyr Asp Ser Gly Arg Gln Phe Asp Ile
1               5                   10                  15

<210> SEQ ID NO 245
<211> LENGTH: 15
<212> TYPE: PRT
<213> ORGANISM: Artificial Sequence
<220> FEATURE:
<223> OTHER INFORMATION: >SEQ ID NO: 245 - anti-IL-1Rap-C8-RecC-AA CDRH3

<400> SEQUENCE: 245

Ala Arg Gly Gln Thr Leu Tyr Ala Ala Gly Arg Gln Phe Asp Ile
1               5                   10                  15

<210> SEQ ID NO 246
<211> LENGTH: 15
<212> TYPE: PRT
<213> ORGANISM: Artificial Sequence
<220> FEATURE:
<223> OTHER INFORMATION: >SEQ ID NO: 246 - anti-IL-1Rap-C8-RecC-DA CDRH3

<400> SEQUENCE: 246

Ala Arg Gly Gln Thr Leu Tyr Asp Ala Gly Arg Gln Phe Asp Ile
1               5                   10                  15

<210> SEQ ID NO 247
<211> LENGTH: 15
<212> TYPE: PRT
<213> ORGANISM: Artificial Sequence
<220> FEATURE:
<223> OTHER INFORMATION: >SEQ ID NO: 247 - anti-IL-1Rap-C8-RecC-AS CDRH3

<400> SEQUENCE: 247

Ala Arg Gly Gln Thr Leu Tyr Ala Ser Gly Arg Gln Phe Asp Ile
1               5                   10                  15

<210> SEQ ID NO 248
<211> LENGTH: 15
<212> TYPE: PRT
<213> ORGANISM: Artificial Sequence
<220> FEATURE:
<223> OTHER INFORMATION: >SEQ ID NO: 248 - anti-IL-1Rap-C8-RecC-ES CDRH3

<400> SEQUENCE: 248

Ala Arg Gly Gln Thr Leu Tyr Glu Ser Gly Arg Gln Phe Asp Ile
1               5                   10                  15

<210> SEQ ID NO 249
<211> LENGTH: 15
<212> TYPE: PRT
<213> ORGANISM: Artificial Sequence
<220> FEATURE:
<223> OTHER INFORMATION: >SEQ ID NO: 249 - anti-IL-1Rap-C8-RecC-ET CDRH3

<400> SEQUENCE: 249
```

Ala Arg Gly Gln Thr Leu Tyr Glu Thr Gly Arg Gln Phe Asp Ile
1               5                   10                  15

<210> SEQ ID NO 250
<211> LENGTH: 11
<212> TYPE: PRT
<213> ORGANISM: Artificial Sequence
<220> FEATURE:
<223> OTHER INFORMATION: >SEQ ID NO: 250 - anti-IL-1Rap-C3-MP01-A2 CDRH3

<400> SEQUENCE: 250

Ala Arg Phe Arg Tyr Tyr Thr Ala Phe Asp Tyr
1               5                   10

<210> SEQ ID NO 251
<211> LENGTH: 11
<212> TYPE: PRT
<213> ORGANISM: Artificial Sequence
<220> FEATURE:
<223> OTHER INFORMATION: >SEQ ID NO: 251 - anti-IL-1Rap-C3-MP01-A3 CDRH3

<400> SEQUENCE: 251

Ala Arg Phe Arg Tyr Tyr Thr Ala Phe Asp Tyr
1               5                   10

<210> SEQ ID NO 252
<211> LENGTH: 11
<212> TYPE: PRT
<213> ORGANISM: Artificial Sequence
<220> FEATURE:
<223> OTHER INFORMATION: >SEQ ID NO: 252 - anti-IL-1Rap-C3-MP01-B5 CDRH3

<400> SEQUENCE: 252

Ala Arg Phe Arg Tyr Tyr Thr Ala Phe Asp Tyr
1               5                   10

<210> SEQ ID NO 253
<211> LENGTH: 11
<212> TYPE: PRT
<213> ORGANISM: Artificial Sequence
<220> FEATURE:
<223> OTHER INFORMATION: >SEQ ID NO: 253 - anti-IL-1Rap-C3-MP01-B7 CDRH3

<400> SEQUENCE: 253

Ala Arg Phe Arg Tyr Tyr Thr Ala Phe Asp Tyr
1               5                   10

<210> SEQ ID NO 254
<211> LENGTH: 11
<212> TYPE: PRT
<213> ORGANISM: Artificial Sequence
<220> FEATURE:
<223> OTHER INFORMATION: >SEQ ID NO: 254 - anti-IL-1Rap-C3-MP01-D2 CDRH3

<400> SEQUENCE: 254

Ala Arg Phe Arg Tyr Tyr Thr Ala Phe Asp Tyr
1               5                   10

<210> SEQ ID NO 255
<211> LENGTH: 11
<212> TYPE: PRT
<213> ORGANISM: Artificial Sequence
<220> FEATURE:
<223> OTHER INFORMATION: >SEQ ID NO: 255 - anti-IL-1Rap-C3-MP01-F5 CDRH3

<400> SEQUENCE: 255

```
Ala Arg Phe Arg Tyr Tyr Thr Ala Phe Asp Tyr
1               5                   10

<210> SEQ ID NO 256
<211> LENGTH: 11
<212> TYPE: PRT
<213> ORGANISM: Artificial Sequence
<220> FEATURE:
<223> OTHER INFORMATION: >SEQ ID NO: 256 - anti-IL-1Rap-C3-MP01-G10
      CDRH3

<400> SEQUENCE: 256

Ala Arg Phe Arg Tyr Tyr Thr Ala Phe Asp Tyr
1               5                   10

<210> SEQ ID NO 257
<211> LENGTH: 11
<212> TYPE: PRT
<213> ORGANISM: Artificial Sequence
<220> FEATURE:
<223> OTHER INFORMATION: >SEQ ID NO: 257 - anti-IL-1Rap-C3-MP02-B8 CDRH3

<400> SEQUENCE: 257

Ala Arg Phe Arg Tyr Tyr Thr Ala Phe Asp Tyr
1               5                   10

<210> SEQ ID NO 258
<211> LENGTH: 11
<212> TYPE: PRT
<213> ORGANISM: Artificial Sequence
<220> FEATURE:
<223> OTHER INFORMATION: >SEQ ID NO: 258 - anti-IL-1Rap-C3-MP02-F6 CDRH3

<400> SEQUENCE: 258

Ala Arg Phe Arg Tyr Tyr Thr Ala Phe Asp Tyr
1               5                   10

<210> SEQ ID NO 259
<211> LENGTH: 11
<212> TYPE: PRT
<213> ORGANISM: Artificial Sequence
<220> FEATURE:
<223> OTHER INFORMATION: >SEQ ID NO: 259 - anti-IL-1Rap-C3-MP02-G2 CDRH3

<400> SEQUENCE: 259

Ala Arg Phe Arg Tyr Tyr Thr Ala Phe Asp Tyr
1               5                   10

<210> SEQ ID NO 260
<211> LENGTH: 11
<212> TYPE: PRT
<213> ORGANISM: Artificial Sequence
<220> FEATURE:
<223> OTHER INFORMATION: >SEQ ID NO: 260 - anti-IL-1Rap-C3-UCP01-H4
      CDRH3

<400> SEQUENCE: 260

Ala Arg Phe His Tyr Arg Ser Ala Phe Asp Tyr
1               5                   10

<210> SEQ ID NO 261
<211> LENGTH: 360
<212> TYPE: PRT
<213> ORGANISM: Mus musculus
<220> FEATURE:
<221> NAME/KEY: MISC_FEATURE
<222> LOCATION: (1)..(360)
<223> OTHER INFORMATION: >SEQ ID NO: 261 - mus musculus IL-1RAP
```

<400> SEQUENCE: 261

| | | | | | | | | | | | | | | |
|---|---|---|---|---|---|---|---|---|---|---|---|---|---|---|
| Met | Gly | Leu | Leu | Trp | Tyr | Leu | Met | Ser | Leu | Ser | Phe | Tyr | Gly | Ile | Leu |
| 1 | | | | 5 | | | | | 10 | | | | | 15 | |

Gln Ser His Ala Ser Glu Arg Cys Asp Asp Trp Gly Leu Asp Thr Met
           20                 25               30

Arg Gln Ile Gln Val Phe Glu Asp Glu Pro Ala Arg Ile Lys Cys Pro
        35             40             45

Leu Phe Glu His Phe Leu Lys Tyr Asn Tyr Ser Thr Ala His Ser Ser
  50                 55                60

Gly Leu Thr Leu Ile Trp Tyr Trp Thr Arg Gln Asp Arg Asp Leu Glu
65             70               75            80

Glu Pro Ile Asn Phe Arg Leu Pro Glu Asn Arg Ile Ser Lys Glu Lys
             85             90             95

Asp Val Leu Trp Phe Arg Pro Thr Leu Leu Asn Asp Thr Gly Asn Tyr
          100            105           110

Thr Cys Met Leu Arg Asn Thr Thr Tyr Cys Ser Lys Val Ala Phe Pro
        115           120            125

Leu Glu Val Val Gln Lys Asp Ser Cys Phe Asn Ser Ala Met Arg Phe
130            135             140

Pro Val His Lys Met Tyr Ile Glu His Gly Ile His Lys Ile Thr Cys
145            150           155          160

Pro Asn Val Asp Gly Tyr Phe Pro Ser Ser Val Lys Pro Ser Val Thr
        165           170            175

Trp Tyr Lys Gly Cys Thr Glu Ile Val Asp Phe His Asn Val Leu Pro
        180           185            190

Glu Gly Met Asn Leu Ser Phe Phe Ile Pro Leu Val Ser Asn Asn Gly
        195           200            205

Asn Tyr Thr Cys Val Val Thr Tyr Pro Glu Asn Gly Arg Leu Phe His
        210           215            220

Leu Thr Arg Thr Val Thr Val Lys Val Val Gly Ser Pro Lys Asp Ala
225            230           235          240

Leu Pro Pro Gln Ile Tyr Ser Pro Asn Asp Arg Val Val Tyr Glu Lys
           245           250           255

Glu Pro Gly Glu Glu Leu Val Ile Pro Cys Lys Val Tyr Phe Ser Phe
        260           265           270

Ile Met Asp Ser His Asn Glu Val Trp Trp Thr Ile Asp Gly Lys Lys
         275          280           285

Pro Asp Asp Val Thr Val Asp Ile Thr Ile Asn Glu Ser Val Ser Tyr
        290           295           300

Ser Ser Thr Glu Asp Glu Thr Arg Thr Gln Ile Leu Ser Ile Lys Lys
305            310           315         320

Val Thr Pro Glu Asp Leu Arg Arg Asn Tyr Val Cys His Ala Arg Asn
         325          330           335

Thr Lys Gly Glu Ala Glu Gln Ala Ala Lys Val Lys Gln Lys Gly Asn
        340           345           350

Gly Cys Thr Glu Pro Met Thr Leu
        355           360

<210> SEQ ID NO 262
<211> LENGTH: 10
<212> TYPE: PRT
<213> ORGANISM: Artificial Sequence
<220> FEATURE:
<223> OTHER INFORMATION: > SEQ ID NO: 262 - aanti-human

```
      IL-1RAP_candidate_1 CDRH1
<220> FEATURE:
<221> NAME/KEY: VARIANT
<222> LOCATION: (2)..(2)
<223> OTHER INFORMATION: X at position 2 can be any one of amino acids
      V, G, S, P, E.
<220> FEATURE:
<221> NAME/KEY: VARIANT
<222> LOCATION: (3)..(3)
<223> OTHER INFORMATION: X at position 3 can be any one of amino acids
      I, L, A, G, T, S, P, H, K, R.
<220> FEATURE:
<221> NAME/KEY: VARIANT
<222> LOCATION: (4)..(4)
<223> OTHER INFORMATION: X at position 4 can be any one of amino acids
      L, F, A, S, W, H, N, R.
<220> FEATURE:
<221> NAME/KEY: VARIANT
<222> LOCATION: (5)..(5)
<223> OTHER INFORMATION: X at position 5 can be any one of amino acids
      G, T, S, Y, P, H, E, N, R.
<220> FEATURE:
<221> NAME/KEY: VARIANT
<222> LOCATION: (6)..(6)
<223> OTHER INFORMATION: X at position 6 can be any one of amino acids
      V, A, S, P, Q, N, D.
<220> FEATURE:
<221> NAME/KEY: VARIANT
<222> LOCATION: (7)..(7)
<223> OTHER INFORMATION: X at position 7 can be any one of amino acids
      Y, H.
<220> FEATURE:
<221> NAME/KEY: VARIANT
<222> LOCATION: (10)..(10)
<223> OTHER INFORMATION: X at position 10 can be any one of amino acids
      H, Q.

<400> SEQUENCE: 262

Gly Xaa Xaa Xaa Xaa Xaa Xaa Ala Ile Xaa
1               5                   10

<210> SEQ ID NO 263
<211> LENGTH: 10
<212> TYPE: PRT
<213> ORGANISM: Artificial Sequence
<220> FEATURE:
<223> OTHER INFORMATION: > SEQ ID NO: 263 - aanti-human
      IL-1RAP_candidate_1 CDRH2
<220> FEATURE:
<221> NAME/KEY: VARIANT
<222> LOCATION: (5)..(5)
<223> OTHER INFORMATION: X at position 5 can be any one of amino acids
      T, S.
<220> FEATURE:
<221> NAME/KEY: VARIANT
<222> LOCATION: (6)..(6)
<223> OTHER INFORMATION: X at position 6 can be any one of amino acids
      V, L.
<220> FEATURE:
<221> NAME/KEY: VARIANT
<222> LOCATION: (8)..(8)
<223> OTHER INFORMATION: X at position 8 can be any one of residues Q,
      G.
<220> FEATURE:
<221> NAME/KEY: VARIANT
<222> LOCATION: (9)..(9)
<223> OTHER INFORMATION: X at position 9 can be any one of amino acids
      F, Y.

<400> SEQUENCE: 263

Tyr Ile Ile Pro Xaa Xaa Gly Xaa Xaa Asp
1               5                   10

<210> SEQ ID NO 264
<211> LENGTH: 15
```

```
<212> TYPE: PRT
<213> ORGANISM: Artificial Sequence
<220> FEATURE:
<223> OTHER INFORMATION: > SEQ ID NO: 264 - aanti-human
      IL-1RAP_candidate_1 CDRH3
<220> FEATURE:
<221> NAME/KEY: VARIANT
<222> LOCATION: (8)..(8)
<223> OTHER INFORMATION: X at position 8 can be any one of amino acids
      A, E, D.
<220> FEATURE:
<221> NAME/KEY: VARIANT
<222> LOCATION: (9)..(9)
<223> OTHER INFORMATION: X at position 9 can be any one of amino acids
      A, T, S.

<400> SEQUENCE: 264

Ala Arg Gly Gln Thr Leu Tyr Xaa Xaa Gly Arg Gln Phe Asp Ile
1               5                   10                  15

<210> SEQ ID NO 265
<211> LENGTH: 10
<212> TYPE: PRT
<213> ORGANISM: Artificial Sequence
<220> FEATURE:
<223> OTHER INFORMATION: > SEQ ID NO: 265 - anti-mouse
      IL-1RAP_candidate_1 CDRH1
<220> FEATURE:
<221> NAME/KEY: VARIANT
<222> LOCATION: (3)..(3)
<223> OTHER INFORMATION: X at position 3 can be any one of amino acids
      I, T, P.
<220> FEATURE:
<221> NAME/KEY: VARIANT
<222> LOCATION: (4)..(4)
<223> OTHER INFORMATION: X at position 4 can be any one of amino acids
      L, F, Y.
<220> FEATURE:
<221> NAME/KEY: VARIANT
<222> LOCATION: (5)..(5)
<223> OTHER INFORMATION: X at position 5 can be any one of amino acids
      A, S, P, E, D.
<220> FEATURE:
<221> NAME/KEY: VARIANT
<222> LOCATION: (6)..(6)
<223> OTHER INFORMATION: X at position 6 can be any one of amino acids
      V, G, T, H, Q, E, N, D.
<220> FEATURE:
<221> NAME/KEY: VARIANT
<222> LOCATION: (7)..(7)
<223> OTHER INFORMATION: X at position 7 can be any one of amino acids
      F, A, S, Y.
<220> FEATURE:
<221> NAME/KEY: VARIANT
<222> LOCATION: (8)..(8)
<223> OTHER INFORMATION: X at position 8 can be any one of amino acids
      A, G, S, P.
<220> FEATURE:
<221> NAME/KEY: VARIANT
<222> LOCATION: (9)..(9)
<223> OTHER INFORMATION: X at position 9 can be any one of amino acids
      L, M, A.
<220> FEATURE:
<221> NAME/KEY: VARIANT
<222> LOCATION: (10)..(10)
<223> OTHER INFORMATION: X at position 10 can be any one of amino acids
      G, T, S, N.

<400> SEQUENCE: 265

Gly Phe Xaa Xaa Xaa Xaa Xaa Xaa Xaa Xaa
1               5                   10

<210> SEQ ID NO 266
<211> LENGTH: 20
<212> TYPE: PRT
```

```
<213> ORGANISM: Artificial Sequence
<220> FEATURE:
<223> OTHER INFORMATION: > SEQ ID NO: 266 - anti-mouse
      IL-1RAP_candidate_1 CDRH1

<400> SEQUENCE: 266

Ile Val Leu Phe Cys Met Ala Gly Thr Ser Trp Tyr Pro His Gln Glu
1               5                   10                  15

Asn Asp Lys Arg
            20

<210> SEQ ID NO 267
<211> LENGTH: 11
<212> TYPE: PRT
<213> ORGANISM: Artificial Sequence
<220> FEATURE:
<223> OTHER INFORMATION: > SEQ ID NO: 267 - anti-mouse
      IL-1RAP_candidate_1 CDRH3
<220> FEATURE:
<221> NAME/KEY: VARIANT
<222> LOCATION: (4)..(4)
<223> OTHER INFORMATION: X at position 4 can be any one of amino acids
      R, H.
<220> FEATURE:
<221> NAME/KEY: VARIANT
<222> LOCATION: (6)..(6)
<223> OTHER INFORMATION: X at position 6 can be any one of amino acids
      Y, R.
<220> FEATURE:
<221> NAME/KEY: VARIANT
<222> LOCATION: (7)..(7)
<223> OTHER INFORMATION: X at position 7 can be any one of amino acids
      T, S.

<400> SEQUENCE: 267

Ala Arg Phe Xaa Tyr Xaa Xaa Ala Phe Asp Tyr
1               5                   10

<210> SEQ ID NO 268
<211> LENGTH: 107
<212> TYPE: PRT
<213> ORGANISM: Artificial Sequence
<220> FEATURE:
<223> OTHER INFORMATION: > SEQ ID NO: 268 - anti-IL-1RAP_Light chain
      variable sequence

<400> SEQUENCE: 268

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Trp
                85                  90                  95

Thr Phe Gly Gln Gly Thr Lys Val Glu Ile Lys
            100                 105

<210> SEQ ID NO 269
<211> LENGTH: 5
<212> TYPE: PRT
<213> ORGANISM: Artificial Sequence
```

```
<220> FEATURE:
<223> OTHER INFORMATION: ISB 880-C8_CDRH1_Kabat (31-35)

<400> SEQUENCE: 269

Glu Tyr Ala Ile Gln
1               5

<210> SEQ ID NO 270
<211> LENGTH: 6
<212> TYPE: PRT
<213> ORGANISM: Artificial Sequence
<220> FEATURE:
<223> OTHER INFORMATION: ISB 880-C8_CDRH1_Chothia (26-31)

<400> SEQUENCE: 270

Gly Gly Gln Phe Ser Glu
1               5

<210> SEQ ID NO 271
<211> LENGTH: 8
<212> TYPE: PRT
<213> ORGANISM: Artificial Sequence
<220> FEATURE:
<223> OTHER INFORMATION: ISB 880-C8_CDRH1_IMGT (27-38)

<400> SEQUENCE: 271

Gly Gly Gln Phe Ser Glu Tyr Ala
1               5

<210> SEQ ID NO 272
<211> LENGTH: 17
<212> TYPE: PRT
<213> ORGANISM: Artificial Sequence
<220> FEATURE:
<223> OTHER INFORMATION: ISB 880-C8_CDRH2_Kabat (50-65)

<400> SEQUENCE: 272

Tyr Ile Ile Pro Leu His Gly Gln Val Asp Tyr Ala Gln Lys Phe Gln
1               5                   10                  15

Gly

<210> SEQ ID NO 273
<211> LENGTH: 6
<212> TYPE: PRT
<213> ORGANISM: Artificial Sequence
<220> FEATURE:
<223> OTHER INFORMATION: ISB 880-C8_CDRH2_Chothia (52-56)

<400> SEQUENCE: 273

Ile Pro Leu His Gly Gln
1               5

<210> SEQ ID NO 274
<211> LENGTH: 8
<212> TYPE: PRT
<213> ORGANISM: Artificial Sequence
<220> FEATURE:
<223> OTHER INFORMATION: ISB 880-C8_CDRH2_IMGT (56-65)

<400> SEQUENCE: 274

Ile Ile Pro Leu His Gly Gln Val
1               5

<210> SEQ ID NO 275
<211> LENGTH: 13
<212> TYPE: PRT
```

```
<213> ORGANISM: Artificial Sequence
<220> FEATURE:
<223> OTHER INFORMATION: ISB 880-C8_CDRH3_Kabat (95-102)

<400> SEQUENCE: 275

Gly Gln Thr Leu Tyr Asp Ser Gly Arg Gln Phe Asp Ile
1               5                   10

<210> SEQ ID NO 276
<211> LENGTH: 13
<212> TYPE: PRT
<213> ORGANISM: Artificial Sequence
<220> FEATURE:
<223> OTHER INFORMATION: ISB 880-C8_CDRH3_Chothia (95-102)

<400> SEQUENCE: 276

Gly Gln Thr Leu Tyr Asp Ser Gly Arg Gln Phe Asp Ile
1               5                   10

<210> SEQ ID NO 277
<211> LENGTH: 15
<212> TYPE: PRT
<213> ORGANISM: Artificial Sequence
<220> FEATURE:
<223> OTHER INFORMATION: ISB 880-C8_CDRH3_IMGT (105-117)

<400> SEQUENCE: 277

Ala Arg Gly Gln Thr Leu Tyr Asp Ser Gly Arg Gln Phe Asp Ile
1               5                   10                  15

<210> SEQ ID NO 278
<211> LENGTH: 6
<212> TYPE: PRT
<213> ORGANISM: Artificial Sequence
<220> FEATURE:
<223> OTHER INFORMATION: ISB 880-C8-H1B-B8 _CDRH1_Kabat (31-35)

<400> SEQUENCE: 278

Glu Pro Tyr Ala Ile Gln
1               5

<210> SEQ ID NO 279
<211> LENGTH: 6
<212> TYPE: PRT
<213> ORGANISM: Artificial Sequence
<220> FEATURE:
<223> OTHER INFORMATION: ISB 880-C8-H1B-B8 _CDRH1_Chothia (26-31)

<400> SEQUENCE: 279

Gly Ser Pro Ala Glu Pro
1               5

<210> SEQ ID NO 280
<211> LENGTH: 8
<212> TYPE: PRT
<213> ORGANISM: Artificial Sequence
<220> FEATURE:
<223> OTHER INFORMATION: ISB 880-C8-H1B-B8 _CDRH1_IMGT (27-38)

<400> SEQUENCE: 280

Gly Ser Pro Ala Glu Pro Tyr Ala
1               5

<210> SEQ ID NO 281
<211> LENGTH: 17
<212> TYPE: PRT
<213> ORGANISM: Artificial Sequence
```

<220> FEATURE:
<223> OTHER INFORMATION: ISB 880-C8-H1B-B8 _CDRH2_Kabat (50-65)

<400> SEQUENCE: 281

Tyr Ile Ile Pro Leu His Gly Gln Val Asp Tyr Ala Gln Lys Phe Gln
1               5                   10                  15
Gly

<210> SEQ ID NO 282
<211> LENGTH: 6
<212> TYPE: PRT
<213> ORGANISM: Artificial Sequence
<220> FEATURE:
<223> OTHER INFORMATION: ISB 880-C8-H1B-B8 _CDRH2_Chothia (52-56)

<400> SEQUENCE: 282

Ile Pro Leu His Gly Gln
1               5

<210> SEQ ID NO 283
<211> LENGTH: 8
<212> TYPE: PRT
<213> ORGANISM: Artificial Sequence
<220> FEATURE:
<223> OTHER INFORMATION: ISB 880-C8-H1B-B8 _CDRH2_IMGT (56-65)

<400> SEQUENCE: 283

Ile Ile Pro Leu His Gly Gln Val
1               5

<210> SEQ ID NO 284
<211> LENGTH: 13
<212> TYPE: PRT
<213> ORGANISM: Artificial Sequence
<220> FEATURE:
<223> OTHER INFORMATION: ISB 880-C8-H1B-B8 _CDRH3_Kabat (95-102)

<400> SEQUENCE: 284

Gly Gln Thr Leu Tyr Asp Ser Gly Arg Gln Phe Asp Ile
1               5                   10

<210> SEQ ID NO 285
<211> LENGTH: 13
<212> TYPE: PRT
<213> ORGANISM: Artificial Sequence
<220> FEATURE:
<223> OTHER INFORMATION: ISB 880-C8-H1B-B8 _CDRH3_Chothia (95-102)

<400> SEQUENCE: 285

Gly Gln Thr Leu Tyr Asp Ser Gly Arg Gln Phe Asp Ile
1               5                   10

<210> SEQ ID NO 286
<211> LENGTH: 15
<212> TYPE: PRT
<213> ORGANISM: Artificial Sequence
<220> FEATURE:
<223> OTHER INFORMATION: ISB 880-C8-H1B-B8 _CDRH3_IMGT (105-117)

<400> SEQUENCE: 286

Ala Arg Gly Gln Thr Leu Tyr Asp Ser Gly Arg Gln Phe Asp Ile
1               5                   10                  15

<210> SEQ ID NO 287
<211> LENGTH: 5
<212> TYPE: PRT

-continued

```
<213> ORGANISM: Artificial Sequence
<220> FEATURE:
<223> OTHER INFORMATION: ISB 880-C8-H2B-C10 _CDRH1_Kabat (31-35)

<400> SEQUENCE: 287

Glu Tyr Ala Ile Gln
1               5

<210> SEQ ID NO 288
<211> LENGTH: 6
<212> TYPE: PRT
<213> ORGANISM: Artificial Sequence
<220> FEATURE:
<223> OTHER INFORMATION: ISB 880-C8-H2B-C10 _CDRH1_Chothia (26-31)

<400> SEQUENCE: 288

Gly Gly Gln Phe Ser Glu
1               5

<210> SEQ ID NO 289
<211> LENGTH: 8
<212> TYPE: PRT
<213> ORGANISM: Artificial Sequence
<220> FEATURE:
<223> OTHER INFORMATION: ISB 880-C8-H2B-C10 _CDRH1_IMGT (27-38)

<400> SEQUENCE: 289

Gly Gly Gln Phe Ser Glu Tyr Ala
1               5

<210> SEQ ID NO 290
<211> LENGTH: 17
<212> TYPE: PRT
<213> ORGANISM: Artificial Sequence
<220> FEATURE:
<223> OTHER INFORMATION: ISB 880-C8-H2B-C10 _CDRH2_Kabat (50-65)

<400> SEQUENCE: 290

Tyr Ile Ile Pro Ser Leu Gly Gly Tyr Asp Tyr Ala Gln Lys Phe Gln
1               5                   10                  15

Gly

<210> SEQ ID NO 291
<211> LENGTH: 6
<212> TYPE: PRT
<213> ORGANISM: Artificial Sequence
<220> FEATURE:
<223> OTHER INFORMATION: ISB 880-C8-H2B-C10 _CDRH2_Chothia (52-56)

<400> SEQUENCE: 291

Ile Pro Ser Leu Gly Gly
1               5

<210> SEQ ID NO 292
<211> LENGTH: 8
<212> TYPE: PRT
<213> ORGANISM: Artificial Sequence
<220> FEATURE:
<223> OTHER INFORMATION: ISB 880-C8-H2B-C10 _CDRH2_IMGT (56-65)

<400> SEQUENCE: 292

Ile Ile Pro Ser Leu Gly Gly Tyr
1               5

<210> SEQ ID NO 293
<211> LENGTH: 13
```

```
<212> TYPE: PRT
<213> ORGANISM: Artificial Sequence
<220> FEATURE:
<223> OTHER INFORMATION: ISB 880-C8-H2B-C10 _CDRH3_Kabat (95-102)

<400> SEQUENCE: 293

Gly Gln Thr Leu Tyr Asp Ser Gly Arg Gln Phe Asp Ile
1               5                   10

<210> SEQ ID NO 294
<211> LENGTH: 13
<212> TYPE: PRT
<213> ORGANISM: Artificial Sequence
<220> FEATURE:
<223> OTHER INFORMATION: ISB 880-C8-H2B-C10 _CDRH3_Chothia (95-102)

<400> SEQUENCE: 294

Gly Gln Thr Leu Tyr Asp Ser Gly Arg Gln Phe Asp Ile
1               5                   10

<210> SEQ ID NO 295
<211> LENGTH: 15
<212> TYPE: PRT
<213> ORGANISM: Artificial Sequence
<220> FEATURE:
<223> OTHER INFORMATION: ISB 880-C8-H2B-C10 _CDRH3_IMGT (105-117)

<400> SEQUENCE: 295

Ala Arg Gly Gln Thr Leu Tyr Asp Ser Gly Arg Gln Phe Asp Ile
1               5                   10                  15

<210> SEQ ID NO 296
<211> LENGTH: 6
<212> TYPE: PRT
<213> ORGANISM: Artificial Sequence
<220> FEATURE:
<223> OTHER INFORMATION: ISB 880-C8-recC _CDRH1_Kabat (31-35)

<400> SEQUENCE: 296

Glu Pro Tyr Ala Ile Gln
1               5

<210> SEQ ID NO 297
<211> LENGTH: 6
<212> TYPE: PRT
<213> ORGANISM: Artificial Sequence
<220> FEATURE:
<223> OTHER INFORMATION: ISB 880-C8-recC _CDRH1_Chothia (26-31)

<400> SEQUENCE: 297

Gly Ser Pro Ala Glu Pro
1               5

<210> SEQ ID NO 298
<211> LENGTH: 8
<212> TYPE: PRT
<213> ORGANISM: Artificial Sequence
<220> FEATURE:
<223> OTHER INFORMATION: ISB 880-C8-recC _CDRH1_IMGT (27-38)

<400> SEQUENCE: 298

Gly Ser Pro Ala Glu Pro Tyr Ala
1               5

<210> SEQ ID NO 299
<211> LENGTH: 17
<212> TYPE: PRT
```

```
<213> ORGANISM: Artificial Sequence
<220> FEATURE:
<223> OTHER INFORMATION: ISB 880-C8-recC _CDRH2_Kabat (50-65)

<400> SEQUENCE: 299

Tyr Ile Ile Pro Ser Leu Gly Gly Tyr Asp Tyr Ala Gln Lys Phe Gln
1               5                   10                  15

Gly

<210> SEQ ID NO 300
<211> LENGTH: 6
<212> TYPE: PRT
<213> ORGANISM: Artificial Sequence
<220> FEATURE:
<223> OTHER INFORMATION: ISB 880-C8-recC _CDRH2_Chothia (52-56)

<400> SEQUENCE: 300

Ile Pro Ser Leu Gly Gly
1               5

<210> SEQ ID NO 301
<211> LENGTH: 8
<212> TYPE: PRT
<213> ORGANISM: Artificial Sequence
<220> FEATURE:
<223> OTHER INFORMATION: ISB 880-C8-recC _CDRH2_IMGT (56-65)

<400> SEQUENCE: 301

Ile Ile Pro Ser Leu Gly Gly Tyr
1               5

<210> SEQ ID NO 302
<211> LENGTH: 13
<212> TYPE: PRT
<213> ORGANISM: Artificial Sequence
<220> FEATURE:
<223> OTHER INFORMATION: ISB 880-C8-recC_CDRH3_Kabat (95-102)

<400> SEQUENCE: 302

Gly Gln Thr Leu Tyr Asp Ser Gly Arg Gln Phe Asp Ile
1               5                   10

<210> SEQ ID NO 303
<211> LENGTH: 13
<212> TYPE: PRT
<213> ORGANISM: Artificial Sequence
<220> FEATURE:
<223> OTHER INFORMATION: ISB 880-C8-recC_CDRH3_Chothia (95-102)

<400> SEQUENCE: 303

Gly Gln Thr Leu Tyr Asp Ser Gly Arg Gln Phe Asp Ile
1               5                   10

<210> SEQ ID NO 304
<211> LENGTH: 15
<212> TYPE: PRT
<213> ORGANISM: Artificial Sequence
<220> FEATURE:
<223> OTHER INFORMATION: ISB 880-C8-recC_CDRH3_IMGT (105-117)

<400> SEQUENCE: 304

Ala Arg Gly Gln Thr Leu Tyr Asp Ser Gly Arg Gln Phe Asp Ile
1               5                   10                  15

<210> SEQ ID NO 305
<211> LENGTH: 6
```

```
<212> TYPE: PRT
<213> ORGANISM: Artificial Sequence
<220> FEATURE:
<223> OTHER INFORMATION: ISB 880-C8-recC-AA _CDRH1_Kabat (31-35)

<400> SEQUENCE: 305

Glu Pro Tyr Ala Ile Gln
1               5

<210> SEQ ID NO 306
<211> LENGTH: 6
<212> TYPE: PRT
<213> ORGANISM: Artificial Sequence
<220> FEATURE:
<223> OTHER INFORMATION: ISB 880-C8-recC-AA _CDRH1_Chothia (26-31)

<400> SEQUENCE: 306

Gly Ser Pro Ala Glu Pro
1               5

<210> SEQ ID NO 307
<211> LENGTH: 8
<212> TYPE: PRT
<213> ORGANISM: Artificial Sequence
<220> FEATURE:
<223> OTHER INFORMATION: ISB 880-C8-recC-AA _CDRH1_IMGT (27-38)

<400> SEQUENCE: 307

Gly Ser Pro Ala Glu Pro Tyr Ala
1               5

<210> SEQ ID NO 308
<211> LENGTH: 17
<212> TYPE: PRT
<213> ORGANISM: Artificial Sequence
<220> FEATURE:
<223> OTHER INFORMATION: ISB 880-C8-recC-AA _CDRH2_Kabat (50-65)

<400> SEQUENCE: 308

Tyr Ile Ile Pro Ser Leu Gly Gly Tyr Asp Tyr Ala Gln Lys Phe Gln
1               5                   10                  15

Gly

<210> SEQ ID NO 309
<211> LENGTH: 6
<212> TYPE: PRT
<213> ORGANISM: Artificial Sequence
<220> FEATURE:
<223> OTHER INFORMATION: ISB 880-C8-recC-AA _CDRH2_Chothia (52-56)

<400> SEQUENCE: 309

Ile Pro Ser Leu Gly Gly
1               5

<210> SEQ ID NO 310
<211> LENGTH: 8
<212> TYPE: PRT
<213> ORGANISM: Artificial Sequence
<220> FEATURE:
<223> OTHER INFORMATION: ISB 880-C8-recC-AA _CDRH2_IMGT (56-65)

<400> SEQUENCE: 310

Ile Ile Pro Ser Leu Gly Gly Tyr
1               5

<210> SEQ ID NO 311
```

```
<211> LENGTH: 13
<212> TYPE: PRT
<213> ORGANISM: Artificial Sequence
<220> FEATURE:
<223> OTHER INFORMATION: ISB 880-C8-recC-AA_CDRH3_Kabat (95-102)

<400> SEQUENCE: 311

Gly Gln Thr Leu Tyr Ala Ala Gly Arg Gln Phe Asp Ile
1               5                   10

<210> SEQ ID NO 312
<211> LENGTH: 13
<212> TYPE: PRT
<213> ORGANISM: Artificial Sequence
<220> FEATURE:
<223> OTHER INFORMATION: ISB 880-C8-recC-AA_CDRH3_Chothia (95-102)

<400> SEQUENCE: 312

Gly Gln Thr Leu Tyr Ala Ala Gly Arg Gln Phe Asp Ile
1               5                   10

<210> SEQ ID NO 313
<211> LENGTH: 15
<212> TYPE: PRT
<213> ORGANISM: Artificial Sequence
<220> FEATURE:
<223> OTHER INFORMATION: ISB 880-C8-recC-AA_CDRH3_IMGT (105-117)

<400> SEQUENCE: 313

Ala Arg Gly Gln Thr Leu Tyr Ala Ala Gly Arg Gln Phe Asp Ile
1               5                   10                  15

<210> SEQ ID NO 314
<211> LENGTH: 6
<212> TYPE: PRT
<213> ORGANISM: Artificial Sequence
<220> FEATURE:
<223> OTHER INFORMATION: ISB 880-C8-recC-DA _CDRH1_Kabat (31-35)

<400> SEQUENCE: 314

Glu Pro Tyr Ala Ile Gln
1               5

<210> SEQ ID NO 315
<211> LENGTH: 6
<212> TYPE: PRT
<213> ORGANISM: Artificial Sequence
<220> FEATURE:
<223> OTHER INFORMATION: ISB 880-C8-recC-DA _CDRH1_Chothia (26-31)

<400> SEQUENCE: 315

Gly Ser Pro Ala Glu Pro
1               5

<210> SEQ ID NO 316
<211> LENGTH: 8
<212> TYPE: PRT
<213> ORGANISM: Artificial Sequence
<220> FEATURE:
<223> OTHER INFORMATION: ISB 880-C8-recC-DA _CDRH1_IMGT (27-38)

<400> SEQUENCE: 316

Gly Ser Pro Ala Glu Pro Tyr Ala
1               5

<210> SEQ ID NO 317
<211> LENGTH: 17
```

```
<212> TYPE: PRT
<213> ORGANISM: Artificial Sequence
<220> FEATURE:
<223> OTHER INFORMATION: ISB 880-C8-recC-DA _CDRH2_Kabat (50-65)

<400> SEQUENCE: 317

Tyr Ile Ile Pro Ser Leu Gly Gly Tyr Asp Tyr Ala Gln Lys Phe Gln
1               5                   10                  15
Gly

<210> SEQ ID NO 318
<211> LENGTH: 6
<212> TYPE: PRT
<213> ORGANISM: Artificial Sequence
<220> FEATURE:
<223> OTHER INFORMATION: ISB 880-C8-recC-DA _CDRH2_Chothia (52-56)

<400> SEQUENCE: 318

Ile Pro Ser Leu Gly Gly
1               5

<210> SEQ ID NO 319
<211> LENGTH: 8
<212> TYPE: PRT
<213> ORGANISM: Artificial Sequence
<220> FEATURE:
<223> OTHER INFORMATION: ISB 880-C8-recC-DA _CDRH2_IMGT (56-65)

<400> SEQUENCE: 319

Ile Ile Pro Ser Leu Gly Gly Tyr
1               5

<210> SEQ ID NO 320
<211> LENGTH: 13
<212> TYPE: PRT
<213> ORGANISM: Artificial Sequence
<220> FEATURE:
<223> OTHER INFORMATION: ISB 880-C8-recC-DA_CDRH3_Kabat (95-102)

<400> SEQUENCE: 320

Gly Gln Thr Leu Tyr Asp Ala Gly Arg Gln Phe Asp Ile
1               5                   10

<210> SEQ ID NO 321
<211> LENGTH: 13
<212> TYPE: PRT
<213> ORGANISM: Artificial Sequence
<220> FEATURE:
<223> OTHER INFORMATION: ISB 880-C8-recC-DA_CDRH3_Chothia (95-102)

<400> SEQUENCE: 321

Gly Gln Thr Leu Tyr Asp Ala Gly Arg Gln Phe Asp Ile
1               5                   10

<210> SEQ ID NO 322
<211> LENGTH: 15
<212> TYPE: PRT
<213> ORGANISM: Artificial Sequence
<220> FEATURE:
<223> OTHER INFORMATION: ISB 880-C8-recC-DA_CDRH3_IMGT (105-117)

<400> SEQUENCE: 322

Ala Arg Gly Gln Thr Leu Tyr Asp Ala Gly Arg Gln Phe Asp Ile
1               5                   10                  15

<210> SEQ ID NO 323
```

```
<211> LENGTH: 6
<212> TYPE: PRT
<213> ORGANISM: Artificial Sequence
<220> FEATURE:
<223> OTHER INFORMATION: ISB 880-C8-recC-AS _CDRH1_Kabat (31-35)

<400> SEQUENCE: 323

Glu Pro Tyr Ala Ile Gln
1               5

<210> SEQ ID NO 324
<211> LENGTH: 6
<212> TYPE: PRT
<213> ORGANISM: Artificial Sequence
<220> FEATURE:
<223> OTHER INFORMATION: ISB 880-C8-recC-AS _CDRH1_Chothia (26-31)

<400> SEQUENCE: 324

Gly Ser Pro Ala Glu Pro
1               5

<210> SEQ ID NO 325
<211> LENGTH: 8
<212> TYPE: PRT
<213> ORGANISM: Artificial Sequence
<220> FEATURE:
<223> OTHER INFORMATION: ISB 880-C8-recC-AS _CDRH1_IMGT (27-38)

<400> SEQUENCE: 325

Gly Ser Pro Ala Glu Pro Tyr Ala
1               5

<210> SEQ ID NO 326
<211> LENGTH: 17
<212> TYPE: PRT
<213> ORGANISM: Artificial Sequence
<220> FEATURE:
<223> OTHER INFORMATION: ISB 880-C8-recC-AS _CDRH2_Kabat (50-65)

<400> SEQUENCE: 326

Tyr Ile Ile Pro Ser Leu Gly Gly Tyr Asp Tyr Ala Gln Lys Phe Gln
1               5                   10                  15

Gly

<210> SEQ ID NO 327
<211> LENGTH: 6
<212> TYPE: PRT
<213> ORGANISM: Artificial Sequence
<220> FEATURE:
<223> OTHER INFORMATION: ISB 880-C8-recC-AS _CDRH2_Chothia (52-56)

<400> SEQUENCE: 327

Ile Pro Ser Leu Gly Gly
1               5

<210> SEQ ID NO 328
<211> LENGTH: 8
<212> TYPE: PRT
<213> ORGANISM: Artificial Sequence
<220> FEATURE:
<223> OTHER INFORMATION: ISB 880-C8-recC-AS _CDRH2_IMGT (56-65)

<400> SEQUENCE: 328

Ile Ile Pro Ser Leu Gly Gly Tyr
1               5
```

```
<210> SEQ ID NO 329
<211> LENGTH: 13
<212> TYPE: PRT
<213> ORGANISM: Artificial Sequence
<220> FEATURE:
<223> OTHER INFORMATION: ISB 880-C8-recC-AS_CDRH3_Kabat (95-102)

<400> SEQUENCE: 329

Gly Gln Thr Leu Tyr Ala Ser Gly Arg Gln Phe Asp Ile
1               5                   10

<210> SEQ ID NO 330
<211> LENGTH: 13
<212> TYPE: PRT
<213> ORGANISM: Artificial Sequence
<220> FEATURE:
<223> OTHER INFORMATION: ISB 880-C8-recC-AS_CDRH3_Chothia (95-102)

<400> SEQUENCE: 330

Gly Gln Thr Leu Tyr Ala Ser Gly Arg Gln Phe Asp Ile
1               5                   10

<210> SEQ ID NO 331
<211> LENGTH: 15
<212> TYPE: PRT
<213> ORGANISM: Artificial Sequence
<220> FEATURE:
<223> OTHER INFORMATION: ISB 880-C8-recC-AS_CDRH3_IMGT (105-117)

<400> SEQUENCE: 331

Ala Arg Gly Gln Thr Leu Tyr Ala Ser Gly Arg Gln Phe Asp Ile
1               5                   10                  15

<210> SEQ ID NO 332
<211> LENGTH: 6
<212> TYPE: PRT
<213> ORGANISM: Artificial Sequence
<220> FEATURE:
<223> OTHER INFORMATION: ISB 880-C8-recC-ES _CDRH1_Kabat (31-35)

<400> SEQUENCE: 332

Glu Pro Tyr Ala Ile Gln
1               5

<210> SEQ ID NO 333
<211> LENGTH: 6
<212> TYPE: PRT
<213> ORGANISM: Artificial Sequence
<220> FEATURE:
<223> OTHER INFORMATION: ISB 880-C8-recC-ES _CDRH1_Chothia (26-31)

<400> SEQUENCE: 333

Gly Ser Pro Ala Glu Pro
1               5

<210> SEQ ID NO 334
<211> LENGTH: 8
<212> TYPE: PRT
<213> ORGANISM: Artificial Sequence
<220> FEATURE:
<223> OTHER INFORMATION: ISB 880-C8-recC-ES _CDRH1_IMGT (27-38)

<400> SEQUENCE: 334

Gly Ser Pro Ala Glu Pro Tyr Ala
1               5

<210> SEQ ID NO 335
```

```
<211> LENGTH: 17
<212> TYPE: PRT
<213> ORGANISM: Artificial Sequence
<220> FEATURE:
<223> OTHER INFORMATION: ISB 880-C8-recC-ES _CDRH2_Kabat (50-65)

<400> SEQUENCE: 335

Tyr Ile Ile Pro Ser Leu Gly Gly Tyr Asp Tyr Ala Gln Lys Phe Gln
1               5                   10                  15
Gly

<210> SEQ ID NO 336
<211> LENGTH: 6
<212> TYPE: PRT
<213> ORGANISM: Artificial Sequence
<220> FEATURE:
<223> OTHER INFORMATION: ISB 880-C8-recC-ES _CDRH2_Chothia (52-56)

<400> SEQUENCE: 336

Ile Pro Ser Leu Gly Gly
1               5

<210> SEQ ID NO 337
<211> LENGTH: 8
<212> TYPE: PRT
<213> ORGANISM: Artificial Sequence
<220> FEATURE:
<223> OTHER INFORMATION: ISB 880-C8-recC-ES _CDRH2_IMGT (56-65)

<400> SEQUENCE: 337

Ile Ile Pro Ser Leu Gly Gly Tyr
1               5

<210> SEQ ID NO 338
<211> LENGTH: 13
<212> TYPE: PRT
<213> ORGANISM: Artificial Sequence
<220> FEATURE:
<223> OTHER INFORMATION: ISB 880-C8-recC-ES_CDRH3_Kabat (95-102)

<400> SEQUENCE: 338

Gly Gln Thr Leu Tyr Glu Ser Gly Arg Gln Phe Asp Ile
1               5                   10

<210> SEQ ID NO 339
<211> LENGTH: 13
<212> TYPE: PRT
<213> ORGANISM: Artificial Sequence
<220> FEATURE:
<223> OTHER INFORMATION: ISB 880-C8-recC-ES_CDRH3_Chothia (95-102)

<400> SEQUENCE: 339

Gly Gln Thr Leu Tyr Glu Ser Gly Arg Gln Phe Asp Ile
1               5                   10

<210> SEQ ID NO 340
<211> LENGTH: 15
<212> TYPE: PRT
<213> ORGANISM: Artificial Sequence
<220> FEATURE:
<223> OTHER INFORMATION: ISB 880-C8-recC-ES_CDRH3_IMGT (105-117)

<400> SEQUENCE: 340

Ala Arg Gly Gln Thr Leu Tyr Glu Ser Gly Arg Gln Phe Asp Ile
1               5                   10                  15
```

-continued

```
<210> SEQ ID NO 341
<211> LENGTH: 6
<212> TYPE: PRT
<213> ORGANISM: Artificial Sequence
<220> FEATURE:
<223> OTHER INFORMATION: ISB 880-C8-recC-ET _CDRH1_Kabat (31-35)

<400> SEQUENCE: 341

Glu Pro Tyr Ala Ile Gln
1               5

<210> SEQ ID NO 342
<211> LENGTH: 6
<212> TYPE: PRT
<213> ORGANISM: Artificial Sequence
<220> FEATURE:
<223> OTHER INFORMATION: ISB 880-C8-recC-ET _CDRH1_Chothia (26-31)

<400> SEQUENCE: 342

Gly Ser Pro Ala Glu Pro
1               5

<210> SEQ ID NO 343
<211> LENGTH: 8
<212> TYPE: PRT
<213> ORGANISM: Artificial Sequence
<220> FEATURE:
<223> OTHER INFORMATION: ISB 880-C8-recC-ET _CDRH1_IMGT (27-38)

<400> SEQUENCE: 343

Gly Ser Pro Ala Glu Pro Tyr Ala
1               5

<210> SEQ ID NO 344
<211> LENGTH: 17
<212> TYPE: PRT
<213> ORGANISM: Artificial Sequence
<220> FEATURE:
<223> OTHER INFORMATION: ISB 880-C8-recC-ET _CDRH2_Kabat (50-65)

<400> SEQUENCE: 344

Tyr Ile Ile Pro Ser Leu Gly Gly Tyr Asp Tyr Ala Gln Lys Phe Gln
1               5                   10                  15
Gly

<210> SEQ ID NO 345
<211> LENGTH: 6
<212> TYPE: PRT
<213> ORGANISM: Artificial Sequence
<220> FEATURE:
<223> OTHER INFORMATION: ISB 880-C8-recC-ET _CDRH2_Chothia (52-56)

<400> SEQUENCE: 345

Ile Pro Ser Leu Gly Gly
1               5

<210> SEQ ID NO 346
<211> LENGTH: 8
<212> TYPE: PRT
<213> ORGANISM: Artificial Sequence
<220> FEATURE:
<223> OTHER INFORMATION: ISB 880-C8-recC-ET _CDRH2_IMGT (56-65)

<400> SEQUENCE: 346

Ile Ile Pro Ser Leu Gly Gly Tyr
1               5
```

```
<210> SEQ ID NO 347
<211> LENGTH: 13
<212> TYPE: PRT
<213> ORGANISM: Artificial Sequence
<220> FEATURE:
<223> OTHER INFORMATION: ISB 880-C8-recC-ET_CDRH3_Kabat (95-102)

<400> SEQUENCE: 347

Gly Gln Thr Leu Tyr Glu Thr Gly Arg Gln Phe Asp Ile
1               5                   10

<210> SEQ ID NO 348
<211> LENGTH: 13
<212> TYPE: PRT
<213> ORGANISM: Artificial Sequence
<220> FEATURE:
<223> OTHER INFORMATION: ISB 880-C8-recC-ET_CDRH3_Chothia (95-102)

<400> SEQUENCE: 348

Gly Gln Thr Leu Tyr Glu Thr Gly Arg Gln Phe Asp Ile
1               5                   10

<210> SEQ ID NO 349
<211> LENGTH: 15
<212> TYPE: PRT
<213> ORGANISM: Artificial Sequence
<220> FEATURE:
<223> OTHER INFORMATION: ISB 880-C8-recC-ET_CDRH3_IMGT (105-117)

<400> SEQUENCE: 349

Ala Arg Gly Gln Thr Leu Tyr Glu Thr Gly Arg Gln Phe Asp Ile
1               5                   10                  15
```

ANTIBODIES THAT BIND TO IL1RAP AND USES THEREOF

CROSS REFERENCE TO RELATED APPLICATIONS

This application claims priority to EP Application No. 20195961.6, filed Sep. 14, 2020, the contents of which are incorporated herein by reference in their entirety.

REFERENCE TO A SEQUENCE LISTING SUBMITTED ELECTRONICALLY VIA EFS-WEB

The content of the electronically submitted sequence listing (Name 3305_0350001_Seqlisting_ST25; Size: 270,606 bytes; and Date of Creation: Sep. 14, 2021) is incorporated herein by reference in its entirety.

The present invention relates to antibodies and derivatives which specifically bind to human IL1RAP. The present invention also relates to the use of such antibodies to diagnose and treat human disease.

BACKGROUND OF THE INVENTION

Interleukin-1 receptor accessory protein (IL1RAP or IL1-RAP) is a component of the interleukin 1 receptor complex, which initiates signaling events that result in the activation of interleukin 1-responsive genes. Alternative splicing of this gene results in membrane-bound and soluble isoforms differing in their C-terminus. The ratio of soluble to membrane-bound forms increases during acute-phase induction or stress.

The interleukin-1 (IL-1) family of cytokine ligands and receptors is associated with inflammation, autoimmunity, immune regulation, cell proliferation, and host defense and contributes to the pathology of inflammatory, autoimmune, immune regulatory, degenerative, and cell proliferative (e.g., cancer) diseases and disorders and its cytokine and receptors serve as pathogenic mediators of such diseases and disorders. See, e.g., Garlanda et al., Immunity, 39:1003-1018 (2013).

The IL-1 family of cytokines includes interleukin-1 alpha, interleukin-1 beta, interleukin-33, interleukin-36 alpha, interleukin-36 beta and interleukin-36 gamma. Each of these cytokines serves as a ligand capable of binding a specific IL-1 family cell membrane receptor expressed on the surface of certain cells. Upon binding of an IL-1 family cytokine to its cognate receptor, a co-receptor is recruited to form a ternary complex comprising the cytokine, its cognate membrane receptor, and its co-receptor. The resulting complex facilitates intracellular signal transduction and activation of a set of transcription factors, including NF-κB and AP-1 and mitogen-activated protein kinases, which triggers a cascade of inflammatory and immune responses, including the production of numerous cytokines, chemokines, enzymes, and adhesion molecules.

IL1RAP serves as the common cellular membrane co-receptor for several receptors in the IL-1 family, including interleukin-1 receptor 1, ST2 also known as interleukin-1 receptor-like 1 and interleukin-1 receptor-like 2 (IL1RL2). IL1RAP is a necessary component of the ternary signaling complex formed by one of the IL-1 family cytokines noted above, the cytokine's specific cognate receptor, and the IL1RAP co-receptor. Thus, IL1RAP serves an important function in the IL-1 family signal transduction pathways, since it is required to facilitate particular downstream signaling pathways stimulated by the IL-1 family cytokines IL-1α, IL-1β, IL-33, IL-36α, IL-36β and IL-36γ.

WO2012098407A1 is directed to agents comprising a binding moiety, such as antibodies, with specificity for IL1RAP for use in inducing cell death and/or inhibiting growth and/or proliferation of cells associated with solid tumors that express IL1RAP. WO2012098407A1 discloses a mouse IgG2a monoclonal antibody to human IL1RAP, "mAb 81.2," that when administered in vivo resulted in statistically significant delay of tumor growth in a melanoma mouse model.

WO2015132602A1 is directed to antibodies with specificity for human IL1RAP and their use for treatment of solid tumors. WO2015132602A1 discloses a specific mouse-derived antibody "CAN04" that binds specifically to domain 2 of human IL1RAP with a KD of 200 pM, cross-reacts with cynomolgus monkey IL1RAP, capable of inducing ADCC in one or more cancer cell lines (such as CML) and has some inhibitory effect on IL-1a, IL-1β, and IL-33 stimulated signaling.

WO2016020502A1 discloses two specific mouse-derived antibodies "CAN01" and "CAN03" that bind specifically to domain 3 of human IL1RAP with a KD of 1.4 and 0.9 nM, respectively, cross-react with cynomolgus monkey IL1RAP, and are capable of inducing ADCC in one or more cancer cell lines (such as CML). CAN03 was determined to have some inhibitory effect on IL-1α, IL-1β, and IL-33 stimulated signaling, whereas CAN01 was found to lack appreciable inhibitory action on IL-1α, IL-1β, and IL-33 signaling.

WO2016207304A1 is directed to rabbit-derived antibodies that specifically bind human IL-IRAcP and have some inhibitory effect on NFkB activity stimulated by IL-1α, IL-1β, IL-33, and/or IL-36P.

WO2017191325A9 is directed to humanized IgG1 antibodies that specifically bind human IL-IR3 and have some inhibitory effect on NFkB activity stimulated by IL-1α, IL-1β, IL-33, and/or IL-36β.

WO2020037154A1 is directed to humanized antibodies that specifically bind human IL-1RAP and have some inhibitory effect in limited in vitro models.

There remains a need for therapies to treat, ameliorate, or prevent inflammatory, autoimmune, immune regulatory, degenerative, and cell proliferative diseases or disorders associated with inappropriate signaling through the IL-1 family of cytokine ligands and receptors.

SUMMARY

The present disclosure provides antibodies that specifically bind human IL1RAP with high affinity. The antibodies are capable of decreasing, inhibiting, and/or fully-blocking IL-1, IL-33, and/or IL-36 signaling pathways, including signaling stimulated by binding of one or more of the following agonists: IL-1α, IL-1β, IL-33, IL-36α, IL-36β, and IL-36γ. The present disclosure also provides methods of treating diseases and conditions responsive to inhibition of IL-1, IL-33, and/or IL-36 signaling.

Autoimmune diseases often have multiple causes and can arise from the inappropriate interaction of several signalling pathways. Therefore the present invention relates to anti-IL1RAP antibodies that inhibit all three IL-1, IL-33, and/or IL-36 signaling pathways.

The antibodies according to the claimed invention cause blockade of all three cytokine signalling pathways mediated by IL1RAP for instance on fibroblasts and PBMCs.

By blocking all three pathways this abrogates multiple disease drivers of the IL1 family of proinflammatory cytokines including IL1R, IL33R and IL36R differentiating ISB 880 from single cytokine blockade therapies or earlier anti-IL1RAP antibodies which do not antagonize all three signalling pathways.

In some embodiments, the present disclosure provides an anti-IL1RAP antibody comprising a first heavy chain CDR region (CDR-H1), a second heavy chain CDR region (CDR-H2), and a third heavy chain CDR region (CDR-H3) selected from the group;
(a) CDR-H1 comprises an amino acid sequence GFXXXXXXXX (SEQ ID NO: 265), wherein X at position 3 can be anyone of amino acids I, T, P; X at position 4 can be anyone of amino acids L, F, Y; X at position 5 can be anyone of amino acids A, S, P, E, D; X at position 6 can be anyone of amino acids V, G, T, H, Q, E, N, D. X at position 7 can be anyone of amino acids F, A, S, Y; X at position 8 can be anyone of amino acids A, G, S, P; X at position 9 can be anyone of amino acids L, M, A; X at position 10 can be anyone of amino acids G, T, S, N;
(b) CDR-H2 comprises an amino acid sequence AISYDGEGTL (SEQ ID NO: 266);
(c) CDR-H3 comprises an amino acid sequence ARFXYXXAFDY (SEQ ID NO: 267), wherein X at position 4 can be anyone of amino acids R, H; X at position 6 can be anyone of amino acids Y, R; X at position 7 can be anyone of amino acids T, S;
or
(d) CDR-H1 comprises an amino acid sequence GXXXXXXAIX (SEQ ID NO: 262), wherein X at position 2 can be anyone of amino acids V, G, S, P, E; X at position 3 can be anyone of I, L, A, G, T, S, P, H, K, R; X at position 4 can be anyone of L, F, A, S, W, H, N, R; X at position 5 can be anyone of G, T, S, Y, P, H, E, N, R. X at position 6 be anyone of amino acids V, A, S, P, Q, N, D; X at position 7 be anyone of amino acids Y, H; X at position 10 be anyone of amino acids H, Q;
(e) CDR-H2 comprises an amino acid sequence YIIPXXGXXD (SEQ ID NO: 263), wherein X at position can be anyone of amino acids T, S; X at position 6 can be anyone of amino acids V, L; X at position 8 can be anyone of amino acids G, Q; X at position 9 can be anyone of amino acids F, Y;
(f) CDR-H3 comprises an amino acid sequence ARGQTLYXXGRQFDI (SEQ ID NO: 264), X at position 8 can be anyone of amino acids A, E, D. X at position 9 can be anyone of amino acids A, T, S; and
wherein said anti-IL1 RAP antibody comprises a light chain variable region comprising SEQ ID NO: 268.

In some embodiments, the present disclosure provides an anti-IL1RAP antibody comprising (i) a first heavy chain CDR region (CDR-H1), a second heavy chain CDR region (CDR-H2), and a third heavy chain CDR region (CDR-H3), wherein: (a) CDR-H1 comprises an amino acid sequence selected from SEQ ID NOs: 81-140; (b) CDR-H2 comprises an amino acid sequence selected from SEQ ID NOs: 141-200; (c) CDR-H3 comprises an amino acid sequence selected from SEQ ID NOs: 201-260.

In some embodiments, the anti-IL1RAP antibody of the present disclosure comprises a heavy chain variable domain (VH) amino acid sequence having at least 90% identity to a sequence selected from SEQ ID NO: 8-51, 60-70.

The present invention relates to an anti-IL1RAP antibody comprising the heavy chain CDRs SEQ ID NO:128, 188 and 248.

In various embodiments of the anti-IL1RAP antibody provided by the present disclosure, the antibody is characterized by one or more of the following properties:
(a) the antibody binds to human IL1RAP with a binding affinity of $1\times10^{-8}$ M or less, $1\times10^{-9}$ M or less, $1\times10^{-10}$ M or less, or $1\times10^{-11}$ M or less; optionally, wherein the binding affinity is measured by equilibrium dissociation constant (KD) to IL1RAP polypeptide of SEQ ID NO: I or SEQ ID NO: 6;
(b) the antibody decreases an IL-1 stimulated signal, an IL-33 stimulated signal, and/or an IL-36 stimulated signal by at least 90%, at least 95%, at least 99%, or 100%; optionally, wherein the decrease in signal is measured by a cell-based blocking assay; optionally, wherein the IL-1, IL-33, and/or IL-36 stimulated signals are stimulated by an agonist selected from IL-1α, IL-1β, IL-33, IL-36α, IL-36β, and IL-36γ.
(c) the antibody decreases an intracellular signal initiated by one or more of IL-1α, IL-1, IL-33, IL-36α, IL-36β, and IL-36γ agonist binding to its cognate receptor by at least 90%, at least 95%, at least 99%, or 100%; optionally, wherein the decrease in intracellular signal is measured by a cell-based blocking assay.;
(d) the antibody inhibits IL-1α, IL-1β, and/or IL-36β stimulated release of IL8 from primary HaCaT keratinocytic cell line;
(e) the antibody inhibits IL-1P stimulated release of IL8 from primary human mononuclear cells;
(f) the antibody inhibits IL-33 stimulated release of INF-γ from primary human mononuclear cells;
(g) the antibody inhibits neutrophil activation upon incubation with HaCaT conditioned medium post-stimulation with IL-1P and IL-36γ;
(h) the antibody binds to amino acid residues within domain 2 of human IL1RAP;
(i) the antibody cross-reacts with a cynomolgus monkey IL1RAP polypeptide of SEQ ID NO: 7; and/or
(j) the antibody cross-reacts with a mouse IL1RAP polypeptide of SEQ ID NO: 261.

The present disclosure also provides embodiments of the anti-IL1RAP antibody, wherein: (i) the antibody is a monoclonal antibody; (ii) the antibody is a human, humanized, or chimeric antibody; (iii) the antibody is a full length antibody of class IgG, optionally, wherein the class IgG antibody has an isotype selected from IgG1, IgG2, IgG3, and IgG4; (iv) the antibody is an Fc region variant, optionally an Fc region variant that alters effector function (e.g., a variant resulting in an increase or decrease of effector function), an Fc region variant that exhibits decreased CDC activity, ADCC activity, and/or ADCP activity, an Fc region variant that exhibits decreased cytotoxic activity on human monocytes, neutrophils, and/or Jurkat cells, or an Fc region variant the alters antibody half-life; (v) the antibody is an antibody fragment, optionally selected from the group consisting of F(ab')2, Fab', Fab, Fv, single domain antibody (VHH), and scFv; (vi) the antibody is an immunoconjugate, optionally, wherein the immunoconjugate comprises a therapeutic agent for treatment of an IL1RAP-mediated disease or condition; (vii) the antibody is a multi-specific antibody, optionally a bispecific antibody; and (viii) the antibody is a synthetic antibody, wherein the CDRs are grafted onto a scaffold or framework other than an immunoglobulin scaffold or framework; optionally, a scaffold selected from an alternative protein scaffold and an artificial polymer scaffold.

In other embodiments, the present disclosure provides isolated nucleic acids encoding the anti-IL1RAP antibodies disclosed herein.

In some embodiments, the present disclosure also provides a host cell comprising a nucleic acid encoding an anti-IL1RAP antibody as disclosed herein.

The disclosure also provides a method of producing an anti-IL1RAP antibody, wherein the method comprises culturing a host cell comprising a nucleic acid (or vector) encoding an anti-IL1RAP antibody so that an antibody is produced.

In some embodiments, the disclosure provides a pharmaceutical composition comprising an anti-IL1RAP antibody as disclosed herein and a pharmaceutically acceptable carrier. In some embodiments, the pharmaceutical composition further comprises a therapeutic agent for treatment of an IL-1, IL-33, IL-36, and/or IL1RAP-mediated disease or condition; optionally, wherein the therapeutic agent is a chemotherapeutic agent.

The present disclosure also provides a method of treating an IL1RAP-mediated disease in a subject, comprising administering to the subject a therapeutically effective amount of an anti-IL1RAP antibody as disclosed herein, or a therapeutically effective amount of a pharmaceutical formulation of an anti-IL1RAP antibody as disclosed herein.

The present disclosure also provides a method of treating a disease mediated by IL-1, IL-33, and/or IL-36 signaling in a subject, comprising administering to the subject a therapeutically effective amount of an anti-IL1RAP antibody as disclosed herein, or a therapeutically effective amount of a pharmaceutical composition of an anti-IL1RAP antibody as disclosed herein.

The present disclosure also provides a method of treating a disease mediated by IL-1α, IL-1β, IL-33, IL-36α, IL-36β, and/or IL-36γ stimulated signaling in a subject, comprising administering to the subject a therapeutically effective amount of an anti-IL1RAP antibody as disclosed herein, or a therapeutically effective amount of a pharmaceutical composition of an anti-IL1RAP antibody as disclosed herein.

In the various embodiments of the methods of treatment disclosed herein, the IL1RAP-mediated diseases and conditions, or the diseases mediated by IL-1, IL-33, and/or IL-36 signaling, include inflammatory diseases, autoimmune diseases, auto inflammatory diseases, respiratory diseases, metabolic disorders, infections, and cancers. In some embodiments, the IL1RAP-mediated diseases and conditions can be selected from: acne, pancreatitis, age-related macular degeneration (AMD), airway hyper responsiveness, airway inflammation, allergic conjunctivitis, amyotrophic lateral sclerosis (ALS), allergic rhinitis, allergy, Alzheimer's disease/dementia, neutrophilic dermatoses, Hidradenitis, suppurativa, Ichthyosis, anaphylaxis, arthritis, asthma/atopy/nasal polyps, atherosclerosis, atopic dermatitis, autoimmune/autoinflammatory vasculitides (including but not limited to giant cell arteritis, Takayasu's arteritis, Kawasaki disease), Behcet's disease (including neuro-Bechet's), bone cancer, brain cancer, breast cancer, cachexia/anorexia, cartilage inflammation, cerebral ischemia, chronic fatigue syndrome, chronic obstructive pulmonary disease, *Clostridium* associated illnesses, colon cancer, congestive heart failure, conjunctivitis, coronary artery inflammation, coronary restenosis, diabetes, diabetic macular edema, diabetic retinopathy, dry eye disease, endometriosis, eosinophil-associated gastrointestinal disorder, eosinophilic esophagitis, familial cold auto-inflammatory syndrome, familial Mediterranean fever, fibromyalgia, fibrotic disorder, food allergy, generalized pustular psoriasis, glaucoma, glomerulonephritis, gouty arthritides, graft versus host disease, helminth infection, hemorrhagic shock, hidradenitis suppurativa, hyperalgesia, hyper-IgD syndrome, hyperuricemia, idiopathic pulmonary fibrosis (IPF), cancer-related pain, infection, inflammatory bowel disease (IBD, including but not limited to ulcerative colitis and Crohn's disease), inflammatory conditions resulting from strain, inflammatory eye disease associated with corneal transplant, inflammatory pain, influenza-related sequelae, intestinal cancer, ischemia, juvenile arthritis, Kawasaki's disease, kidney cancer, Leber's congenital amaurosis, liver cancer, liver disease, lung cancer, macrophage activation syndrome (MAS), macular degeneration, Muckle-Wells syndrome, multiple myeloma, multiple sclerosis, musculoskeletal pain, myelogenous and other leukemias, myelodysplastic syndromes (MDS), myocardial dysfunction, myopathies, nasal polyp, neonatal onset multisystem inflammatory disease, neurotoxicity, neutrophilic skin diseases (including palmoplantar pustulosis, pyoderma gangrenosum, psoriasis, Sweet's syndrome, non-infectious conjunctivitis, non-infectious uveitis, non-small cell lung cancer, orthopedic surgery, osteoarthritis, osteoporosis, pain, pancreas cancer, Parkinson's disease, periodontal disease, peripheral vascular disease, polymyalgia rheumatica, polypoidal choroidal vasculopathy (PCV), pre-eclamnpsia or eclampsia, pre-term labor, prostate cancer, protozoan infection, psoriasis, psoriatic arthritis, pyoderna gangrenosum, systemic sclerosis, reperfusion injury, respiratory syncytial virus (RSV), restenosis in particular after angioplasty and stenting, retinal detachment, retinitis pigmentosa, retinopathy of prematurity (ROP), rheumatoid arthritis, septic shock, sickle-cell anemia, side effects from radiation therapy, SAPHO (synovitis, acne, pustulosis, hyperostosis, and osteitis) syndrome, sinusitis, skin cancer, sleep disturbance, inflammation resulting from sprain, Still's disease, stomach cancer, systemic lupus erythematosus (including lupus nephritis), temporomandibular joint disease, TNF receptor associated periodic syndrome and other genetic febrile syndromes, transplant rejection, trauma, traumatic eye injury, type-2 diabetes, and vitiligo.

In some embodiments, the present disclosure also provides a method of treating cancer in a subject, the method comprising administering to the subject a therapeutically effective amount of an antibody of an anti-IL1RAP antibody as disclosed herein, or a therapeutically effective amount of a pharmaceutical formulation of an anti-IL1RAP antibody as disclosed herein. In embodiments, the cancer is selected from breast cancer, colorectal cancer, non-small cell lung cancer, pancreatic cancer.

In some embodiments, the present disclosure also provides a method for detecting the level of IL1RAP in a biological sample, comprising the step of contacting the sample with an anti-IL1RAP antibody as disclosed herein. The anti-IL1RAP antibodies of the present disclosure may be employed in any known assay method, such as competitive binding assays, direct and indirect sandwich assays, immunoprecipitation assays and enzyme-linked immunosorbent assays (ELISA) (See, Sola, 1987, Monoclonal Antibodies: A Manual of Techniques, pp. 147-158, CRC Press, Inc.) for the detection and quantitation of IL1RAP. The antibodies bind human IL1RAP polypeptide (SEQ ID NO: 1 or 6) with high affinity appropriate for a wide range of assays.

BRIEF DESCRIPTION OF THE DRAWINGS

FIG. 1 shows a Surface Plasmon Resonance diagram of the blocking of human IL-1RAP/IL-1R1/IL-1β co-receptor/receptor/cytokine complex formation upon binding of anti-IL-1RAP-C8 Fab and anti-IL-1RAP-C3 Fab to human IL-1RAP. Recombinant human IL-1RAP Fc fusion protein was immobilized on a Series S CM5 sensor CHIP coupled with anti-human IgG Fc. Fab fragment was injected at 300 nM in HBS-EP+ buffer to reach saturation of the immobilized human IL-1RAP, followed by a second injection of a pre-mixed solution of IL-1R1 at 50 nM, IL-1β3 at 100 nM and Fab fragment at 300 nM in HBS-EP+ buffer. Anti-IL-1RAP-E1 Fab was used as non-blocker control. Plot shows data expressed as number of resonance units (abbreviated RU; Y axis) vs. time (X axis). Curves are labelled by saturating Fab clone name.

FIG. 4A shows Surface Plasmon Resonance measurements of anti-IL-1RAP-C8-RecC-ES IgG1 LALA binding to human IL-1RAP. FIG. 4B shows Surface Plasmon Resonance measurements of anti-IL-1RAP-C8-RecC-ES IgG1 LALA binding to cynomolgus monkey IL-1RAP. Anti-IL-1RAP-C8-RecC-ES IgG1 LALA was immobilized on a Series S CM5 sensor CHIP coupled with anti-human IgG Fc. Human IL-1RAP-avi-his or cynomolgus monkey IL-1RAP-avi-his was injected over immobilized IgG1 LALA in concentration series in HBS-EP+ buffer. One representative replicate for human IL-1RAP and cynomolgus monkey IL-1RAP is presented. Plots are showing data expressed as number of resonance units (abbreviated RU; Y axis) vs. time (s, X axis). Dotted lines represent the measured data while solid lines represent simulated fits. KD: equilibrium dissociation constant; Ka: association constant; Kd: dissociation constant.

FIG. 5 shows Surface Plasmon Resonance measurements of anti-IL-1RAP-C3-A3 mouse IgG2a LALA binding to mouse IL-1RAP. Anti-IL-1RAP-C3-A3 mouse IgG2a LALA was immobilized on a Series S CM5 sensor CHIP coupled with anti-mouse IgG Fc. Mouse IL-1RAP-his was injected over immobilized IgG2a LALA in concentration series in HBS-EP+ buffer. One representative replicate is presented. Plots are showing data expressed as number of resonance units (abbreviated RU; Y axis) vs. time (s, X axis). Dotted lines represent the measured data while solid lines represent simulated fits. KD: equilibrium dissociation constant; Ka: association constant; Kd: dissociation constant.

FIG. 9B shows that anti-human IL-1RAP_candidate_1 inhibits MIP-10, IP-10, and IL-6 release in a whole blood restimulation assay upon combined cytokine stimulation with IL-1α, IL-1β, IL-12, IL-33, IL-36α, IL-36β and IL-36γ.

FIG. 12C shows that anti-mouse IL-1RAP_candidate_1 inhibits CXCL-1/GRO-a release in an NIH-3T3 mIL-36s stimulation assay. A dose-response of mouse IL-1RAP_candidate_1 (•) or Isotype control_2 (m) were incubated with mIL-1β, hIL-33 or mIL-36s-stimulated NIH-3T3. The graphs show the nonlinear sigmoidal regression inhibition curves for each stimulus. Each data point represents a measurement.

FIG. 19B shows a table displaying the number of responder donors (SI>3 compared to baseline) included in the graphs for each stimulation and each readout among the 15 donors tested.

DETAILED DESCRIPTION

Figure 2A:
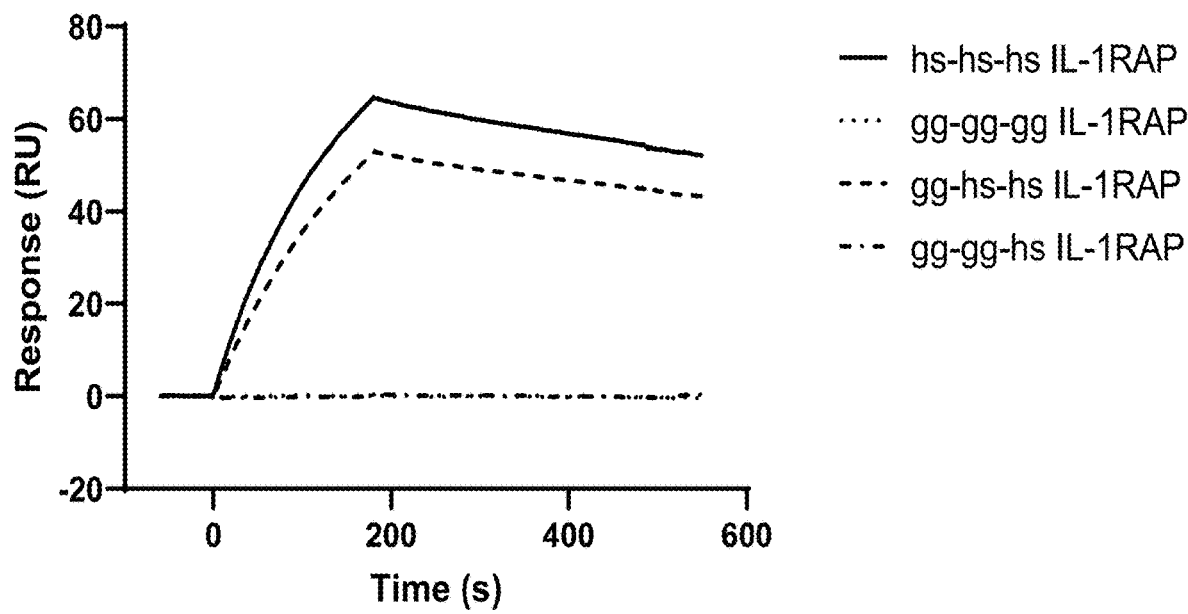
FIG. 2A shows the domain mapping of anti-IL-1RAP-C8 clone to human-chicken IL-1RAP chimeras using Surface Plasmon Resonance with anti-IL-1RAP-C8 IgG1 LALA immobilized on a Series S CM5 sensor CHIP coupled with anti-human IgG Fc.

The present disclosure provides antibodies, including humanized antibodies that specifically bind human IL1RAP with high affinity. The disclosed anti-IL1RAP antibodies are capable of decreasing, inhibiting, and/or fully-blocking intracellular signaling by IL1RAP-mediated pathways, including the IL-1, IL-33, and/or IL-36 signaling pathways. More specifically, the anti-IL1RAP antibodies disclosed herein are capable of decreasing, inhibiting, and/or fully-blocking signaling stimulated by binding of one or more of the following agonists: IL-1α, IL-1β, IL-33, IL-36α, IL-36β, and IL-36γ. The present disclosure also provides uses of the anti-IL1RAP antibodies in methods of treating IL1RAP-mediated diseases, including diseases and conditions responsive to inhibition of IL-1, IL-33, and/or IL-36 signaling, including, but not limited to, various cancers (e.g., breast, colorectal, non-small cell lung, pancreatic), as well as inflammatory, infectious, and autoimmune diseases.

Overview of Terminology and Techniques

For the descriptions herein and the appended claims, the singular forms "a", and "an" include plural referents unless the context clearly indicates otherwise. Thus, for example, reference to "a protein" includes more than one protein, and reference to "a compound" refers to more than one compound. The use of "comprise," "comprises," "comprising" "include," "includes," and "including" are interchangeable and not intended to be limiting. It is to be further understood that where descriptions of various embodiments use the term "comprising," those skilled in the art would understand that in some specific instances, an embodiment can be alternatively described using language "consisting essentially of" or "consisting of."

Where a range of values is provided, unless the context clearly dictates otherwise, it is understood that each intervening integer of the value, and each tenth of each intervening integer of the value, unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of these limits, ranges excluding (i) either or (ii) both of those included limits are also included in the invention. For example, "1 to 50," includes "2 to 25," "5 to 20," "25 to 50," "1 to 10," etc.

Generally, the nomenclature used herein and the techniques and procedures described herein include those that are well understood and commonly employed by those of ordinary skill in the art, such as the common techniques and methodologies described in Sambrook et al., Molecular Cloning-A Laboratory Manual (2nd Ed.), Vols. 1-3, Cold Spring Harbor Laboratory, Cold Spring Harbor, N.Y., 1989 (hereinafter "Sambrook"); Current Protocols in Molecular Biology, F. M. Ausubel et al., eds., Current Protocols, a joint venture between Greene Publishing Associates, Inc. and John Wiley & Sons, Inc. (supplemented through 2011) (hereinafter "Ausubel"); Antibody Engineering, Vols. 1 and 2, R. Kontermann and S. Dubel, eds., Springer-Verlag, Berlin and Heidelberg (2010); Monoclonal Antibodies: Methods and Protocols, V. Ossipow and N. Fischer, eds., 2nd Ed., Humana Press (2014); Therapeutic Antibodies: From Bench to Clinic, Z. An, ed., J. Wiley & Sons, Hoboken, N.J. (2009); and Phage Display, Tim Clackson and Henry B. Lowman, eds., Oxford University Press, United Kingdom (2004).

All publications, patents, patent applications, and other documents referenced in this disclosure are hereby incorporated by reference in their entireties for all purposes to the same extent as if each individual publication, patent, patent application or other document were individually indicated to be incorporated by reference herein for all purposes.

Unless defined otherwise, all technical and scientific terms used herein have the same meaning as commonly understood by one of ordinary skill in the art to which the present invention pertains. It is to be understood that the terminology used herein is for describing particular embodiments only and is not intended to be limiting. For purposes of interpreting this disclosure, the following description of terms will apply and, where appropriate, a term used in the singular form will also include the plural form and vice versa.

"IL1RAP," as used herein, refers to the interleukin-1 receptor accessory protein that is the cellular membrane co-receptor for several receptors in the IL-1 family, including interleukin-1 receptor 1 (IL1R1), ST2 (also known as interleukin-1 receptor-like 1 or IL1RL1), and interleukin-1 receptor-like protein 2 (IL1RL2). It is noted that the interleukin-1 receptor accessory protein, or IL1RAP, is sometimes referred to in the art as "IL-1RAP," "IL-1RAcP," "IL1RAcP" or "IL-1R3." The terms "IL1RAP," "IL-1RAP" and "IL1RAP protein" are used herein interchangeably.

"IL1RAP mediated condition" or "IL1RAP mediated disease," as used herein, encompasses any medical condition associated with aberrant function of the signaling pathways mediated by IL-1 family of cytokines together with IL1RAP acting as a co-receptor, including but not limited to, the downstream signaling pathways stimulated by the IL-1 family cytokines IL-1α, IL-1β, IL-33, IL-36α, IL-36β, and IL-36γ. For example, IL1RAP mediated diseases can include, but are not limited to, diseases mediated by and/or responsive to antagonists or inhibitors of the IL-1, IL-33, and/or IL-36 signaling pathways including cancer, inflammatory, infectious, and autoimmune diseases. More specifically, IL1RAP mediated disease can include but are not limited to acne, acute severe ulcerative colitis, adult-onset Still's disease, allergic rhinitis, gouty arthritis, juvenile arthritis, osteoarthritis, rheumatoid arthritis, systemic sclerosis, arthritis pain, asthma, atherosclerosis, atopic eczema, Behcet's disease, cachexia, breast cancer, colorectal cancer, non-small cell lung cancer, pancreatic cancer, chronic obstructive pulmonary disease, dry eye syndrome, familial cold autoinflammatory syndrome, familial Mediterranean fever, food allergy, generalized pustular psoriasis, hidradenitis suppurativa, hyper-IgD syndrome, hyperuricemia, Muckle-Wells syndrome, neonatal onset multisystem inflammatory disease, musculoskeletal pain, palmoplantar pustulosis, peripheral vascular disease, polymyalgia rheumatica, nasal polyp, psoriasis, pyoderma gangrenosum, restenosis, sickle-cell anemia, sinusitis, TNF receptor associated periodic syndrome, type-2 diabetes, and ulcerative colitis.

"IL-1 stimulated signal," as used herein, refers to an intracellular signal initiated by binding of an IL-1 cytokine, such as IL-1α or IL-1, to its cognate cell surface receptor, IL1R1. Exemplary IL-1 stimulated signals include those measurable using a cell-based blocking assay, such as those disclosed in the Examples herein.

"IL-33 stimulated signal," as used herein, refers to an intracellular signal initiated by binding of an IL-33 cytokine, such as IL-33, to its cognate cell surface receptor, IL1RL1 (also known as ST2). Exemplary IL-33 stimulated signals include those measurable using a cell-based blocking assay, such as those disclosed in the Examples herein.

"IL-36 stimulated signal," as used herein, refers to an intracellular signal initiated by binding of an IL-36 cytokine, such as IL-36α, IL-36β, or IL-36γ, to its cognate cell surface receptor, IL1RL2. Exemplary IL-36 stimulated signals include those measured by surrogate cell-based blocking assays, such as those disclosed in the Examples herein.

"Cell-based blocking assay" refers to an assay in which the ability of an antibody to inhibit or reduce the biological activity of the antigen it binds can be measured. For example, a cell-based blocking assay can be used to measure the concentration of antibody required to inhibit a specific biological or biochemical function, such as IL1RAP-mediated intracellular signaling via the IL-1, IL-33, and IL-36 signaling pathways. In some embodiments, the half maximal inhibitory concentration (IC50) and/or 90% inhibitory concentration (IC90) of an antibody (e.g., an anti-IL1RAP antibody of the disclosure) is measured using a cell-based blocking assay. In some embodiments, the cell-based blocking assay is used to determine whether an antibody blocks the interaction between an agonist (e.g., IL-1α, IL-1β, IL-33, IL-36α, IL-36β, IL-36γ) and its cognate receptor. Cell-based blocking assays useful with the antibodies of the present disclosure can include primary cell assays (e.g., HaCaT cells) as well as reporter or sensor cell assays. Exemplary cell-based blocking assays for the IL-1, IL-33, and IL-36 signaling pathways, such as those described in the Examples provided herein.

"Antibody," as used herein, refers to a molecule comprising one or more polypeptide chains that specifically binds to, or is immunologically reactive with, a particular antigen. Exemplary antibodies of the present disclosure include monoclonal antibodies, polyclonal antibodies, chimeric antibodies, humanized antibodies, human antibodies, multispecific (or heteroconjugate) antibodies (e.g., bispecific antibodies), monovalent antibodies (e.g., single-arm antibodies), multivalent antibodies, antigen-binding fragments (e.g., Fab', F(ab')2, Fab, Fv, rIgG, and scFv fragments), antibody fusions, and synthetic antibodies (or antibody mimetics).

"Anti-IL1RAP antibody" or "antibody that binds IL1RAP" refers to an antibody that binds IL1RAP with sufficient affinity such that the antibody is useful as a diagnostic and/or therapeutic agent in targeting IL1RAP. In some embodiments, the extent of binding of an anti-IL1RAP antibody to an unrelated, non-IL1RAP antigen is less than about 10% of the binding of the antibody to IL1RAP as measured, e.g., by a radioimmunoassay (RIA). In some embodiments, an antibody that binds to IL1RAP has a dissociation constant (KD) of <1 pM, <100 nM, <10 nM, <1 nM, <0.1 nM, <0.01 nM, or <1 pM (e.g., 10-8 M or less, e.g., from 10-8 M to 10-13 M, e.g., from 10-9 M to 10-13 M).

"Full-length antibody," "intact antibody," or "whole antibody" are used herein interchangeably to refer to an antibody having a structure substantially similar to a native antibody structure or having heavy chains that contain an Fc region as defined herein.

"Antibody fragment" refers to a portion of a full-length antibody which is capable of binding the same antigen as the full-length antibody. Examples of antibody fragments include, but are not limited to, Fv, Fab, Fab', Fab'-SH, F(ab')2; diabodies; linear antibodies; monovalent, or single-armed antibodies; single-chain antibody molecules (e.g., scFv); and multispecific antibodies formed from antibody fragments.

"Class" of an antibody refers to the type of constant domain or constant region possessed by its heavy chain. There are five major classes of antibodies: IgA, IgD, IgE, IgG, and IgM, and several of these are further divided into subclasses (isotypes), e.g., IgG1, IgG2, IgG3, IgG4, IgA1, and IgA2. The heavy chain constant domains that correspond to the different classes of immunoglobulins are called α, δ, ε, γ, and α, respectively.

"Variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (CDRs) (see, e.g., Kindt et al., Kuby Immunology, 6th ed., W. H. Freeman and Co., page 91). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively (see, e.g., Portolano et al., J. Immunol., 150: 880-887 (1993); Clarkson et al., Nature, 352:624-628 (1991)).

"Hypervariable region" or "CDR," as used herein, refers to each of the regions of an antibody variable domain which are hypervariable in sequence and/or form structurally defined loops ("hypervariable loops"). Generally, native antibodies comprise four chains with six CDRs; three in the heavy chain variable domain, VH (CDR-H1, CDR-H2, CDR-H3), and three in the light chain variable domain, VL (CDR-L1, CDR-L2, CDR-L3). The CDRs generally comprise amino acid residues from the hypervariable loops and/or from the "complementarity determining regions" (CDRs). Unless otherwise indicated, CDR residues and other residues in the variable domain (e.g., FR residues) are numbered herein according to Kabat et al., Sequences of Proteins of Immunological Interest, 5th Ed. Public Health Service, National Institutes of Health, Bethesda, Md. (1991).

"Complementarity determining region," or "CDR," as used herein, refers to the regions within the CDRs of the variable domain which have the highest sequence variability and/or are involved in antigen recognition. Generally, native antibodies comprise four chains with six CDRs; three in the heavy chain variable domains, VH (H1, H2, H3), and three in the light chain variable domains, VL (L1, L2, L3). Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 26-35 or 31-35 of H1, 50-65 or 50-65 of H2, and 93-102 or 95-102 of H3. (Kabat et al., supra). Alternative methods to Kabat et al., (supra) which collected and aligned the sequences of different members of the immunoglobulin superfamily, have been proposed such as Chothia et al., (Chothia—J Mol Biol. 1987 Aug. 20; 196(4):901-17 and Nature. 1989 Dec. 21-28; 342(6252): 877-83.) and Lefranc et al., (IMGT—Nucleic Acids Res.

1999 Jan. 1; 27(1):209-12.) who proposed a unified numbering scheme for immunoglobulin variable domain germ line sequences. All such alternative definitions are encompassed by the current invention and the sequences provided in this specification are not intended to exclude alternatives defined CDR sequences which may only comprise a portion of the CDR sequences provided in the sequence listing. In particular the CDR sequences in accordance with Chothia et al., occur at amino acid residues 26-31 of H1, 52-65 of H2, and 95-102 of H3; In particular the CDR sequences in accordance with LeFranc et al., occur at amino acid residues 27-38 of H1, 56-65 of H2, and 105-117 of H3.

"Framework" or "FR" refers to variable domain residues other than hypervariable region (CDR) residues. The FR of a variable domain generally consists of four FR domains: FR1, FR2, FR3, and FR4. Accordingly, the CDR and FR sequences generally appear in the following sequence in VH (or VL): FR1-H1 (L1)-FR2-H2(L2)-FR3-H3(L3)-FR4.

"Native antibody" refers to a naturally occurring immunoglobulin molecule. For example, native IgG antibodies are heterotetrameric glycoproteins of about 150,000 Daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

"Monoclonal antibody" as used herein refers to an antibody obtained from a substantially homogeneous population of antibodies, i.e., the individual antibodies comprising the population are identical and/or bind the same epitope, except for possible variant antibodies (e.g., variant antibodies contain mutations that occur naturally or arise during production of a monoclonal antibody, and generally are present in minor amounts). In contrast to polyclonal antibody preparations, which typically include different antibodies directed against different determinants (epitopes), each monoclonal antibody of a monoclonal antibody preparation is directed against a single determinant on an antigen. Thus, the term "monoclonal" indicates the character of the antibody as being obtained from a substantially homogeneous population of antibodies and is not to be construed as requiring production of the antibody by any particular method. For example, the monoclonal antibodies to be used may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

"Chimeric antibody" refers to an antibody in which a portion of the heavy and/or light chain is derived from a particular source or species, while the remainder of the heavy and/or light chain is derived from a different source or species.

"Humanized antibody" refers to a chimeric antibody comprising amino acid sequences from non-human CDRs and amino acid sequences from human FRs. In certain embodiments, a humanized antibody will comprise substantially all of at least one, and typically two, variable domains, in which all or substantially all of the CDRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

"Human antibody" refers to an antibody which possesses an amino acid sequence corresponding to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

"Human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., Sequences of Proteins of Immunological Interest, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

"Acceptor human framework" as used herein is a framework comprising the amino acid sequence of a light chain variable domain (VL) framework or a heavy chain variable domain (VH) framework derived from a human immunoglobulin framework or a human consensus framework. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Fc region," refers to a dimer complex comprising the C-terminal polypeptide sequences of an immunoglobulin heavy chain, wherein a C-terminal polypeptide sequence is that which is obtainable by papain digestion of an intact antibody. The Fc region may comprise native or variant Fc sequences. Although the boundaries of the Fc sequence of an immunoglobulin heavy chain may vary, the human IgG heavy chain Fc sequence is usually defined to stretch from an amino acid residue at about position Cys226, or from about position Pro23, to the carboxyl-terminus of the Fc sequence at Lys447. However, the C-terminal lysine (Lys447) of the Fc sequence may or may not be present in the Fc region of recombinant antibodies due to enzymatic cleavage that can occur in cell culture systems used for recombinant production (e.g., production in CHO cells). The Fc sequence of an immunoglobulin generally comprises two constant domains, a CH2 domain and a CH3 domain, and optionally comprises a CH4 domain.

"Fc receptor" or "FcR," refers to a receptor that binds to the Fc region of an antibody. In some embodiments, an FcR is a native human FcR. In some embodiments, an FcR is one which binds an IgG antibody (a gamma receptor) and includes receptors of the FcγRI, FcγRII, and FcγRIII subclasses, including allelic variants and alternatively spliced forms of those receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain, (see, e.g., Dacron, Annu. Rev. Immunol., 15:203-234 (1997)). FcR, as used herein, also includes the neonatal receptor, FcRn, which is responsible for the transfer of maternal IgGs to the fetus (Guyer et al., J. Immunol., 1 17:587 (1976) and Kim et al., Eur. J. Immunol., 24:2429-2434 (1994)) and regulation of homeostasis of immunoglobulins. FcRs are reviewed, for example, in Ravetch and Kinet, Annu. Rev. Immunol, 9:457-92 (1991); Capel et al., Immunomethods 4:25-34 (1994); and de Haas et al., J. Lab. Clin. Med., 126:330-41 (1995).

"Multivalent antibody," as used herein, is an antibody comprising three or more antigen binding sites. The multivalent antibody is preferably engineered to have the three or more antigen binding sites and is generally not a native sequence IgM or IgA antibody.

"Multispecific antibody" is an antibody having at least two different binding sites, each site with a different binding specificity. A multispecific antibody can be a full-length antibody or an antibody fragment, and the different binding sites may bind each to a different antigen or the different binding sites may bind to two different epitopes of the same antigen.

"Fv fragment" refers to an antibody fragment which contains a complete antigen recognition and binding site. This region consists of a dimer of one heavy and one light chain variable domain in tight association, which can be covalent in nature, for example in scFv. It is in this configuration that the three CDRs of each variable domain interact to define an antigen binding site on the surface of the VH-VL dimer. Collectively, the six CDRs or a subset thereof confer antigen binding specificity to the antibody. However, even a single variable domain (or half of an Fv comprising only three CDRs specific for an antigen) has the ability to recognize and bind antigen, although usually at a lower affinity than the entire binding site.

"Fab fragment" refers to an antibody fragment that contains a variable and constant domain of the light chain and a variable domain and the first constant domain (CH1) of the heavy chain. "F(ab')2 fragments" comprise a pair of Fab fragments which are generally covalently linked near their carboxy termini by hinge cysteines between them. Other chemical couplings of antibody fragments also are known in the art.

"Antigen binding arm," as used herein, refers to a component of an antibody that has an ability to specifically bind a target molecule of interest. Typically, the antigen binding arm is a complex of immunoglobulin polypeptide sequences, e.g., CDR and/or variable domain sequences of an immunoglobulin light and heavy chain.

"Single-chain Fv" or "scFv" refer to antibody fragments comprising the VH and VL domains of an antibody, wherein these domains are present in a single polypeptide chain. Generally, an Fv polypeptide further comprises a polypeptide linker between the VH and VL domains which enables the scFv to form the desired antigen binding structure.

"Diabodies" refers to small antibody fragments with two antigen-binding sites, which fragments comprise a heavy chain variable domain (VH) connected to a light chain variable domain (VL) in the same polypeptide chain (VH and VL). By using a linker that is too short to allow pairing between the two domains on the same chain, the domains are forced to pair with the complementary domains of another chain and create two antigen-binding sites.

"Linear antibodies" refers to the antibodies described in Zapata et al., Protein Eng., 8(10): 1057-1062 (1995). Briefly, these antibodies comprise tandem repeats of a heavy chain fragment (VH-CH1-VH-CH1) which, together with complementary light chain polypeptides, form a pair of antigen binding regions. Linear antibodies can be bispecific or monospecific.

"Naked antibody" refers to an antibody that is not conjugated to a heterologous moiety (e.g., a cytotoxic moiety) or radiolabel.

"Affinity" refers to the strength of the total of noncovalent interactions between a single binding site of a molecule (e.g., an antibody) and its binding partner (e.g., an antigen). "Binding affinity" refers to intrinsic binding affinity which reflects a 1:1 interaction between members of a binding pair (e.g., antibody and antigen). The affinity of a molecule X for its partner Y can generally be represented by the equilibrium dissociation constant (KD). Affinity can be measured by common methods known in the art, including those described herein. Specific illustrative and exemplary embodiments for measuring binding affinity are described in the following.

"Binds specifically" or "specific binding" refers to binding of an antibody to an antigen with an affinity value of no more than about $1 \times 10^{-7}$ M.

"Affinity matured" antibody refers to an antibody with one or more alterations in one or more CDRs, compared to a parent antibody which does not possess such alterations, such alterations resulting in an improvement in the affinity of the antibody for antigen.

"Functional antigen binding site" of an antibody is one which is capable of binding a target antigen. The antigen binding affinity of the antigen binding site is not necessarily as strong as the parent antibody from which the antigen binding site is derived, but the ability to bind antigen must be measurable using any one of a variety of methods known for evaluating antibody binding to an antigen.

"Isolated antibody" refers to an antibody which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic methods (e.g., ion exchange or reverse phase HPLC). For review of methods for assessment of antibody purity, see, e.g., Flatman et al., J. Chromatogr. B Analyt. Technol Biomed Life Sci, 848:79-87.

"Substantially similar" or "substantially the same," as used herein, refers to a sufficiently high degree of similarity between two numeric values (for example, one associated with a test antibody and the other associated with a reference antibody), such that one of skill in the art would consider the difference between the two values to be of little or no biological and/or statistical significance within the context of the biological characteristic measured by said values (e.g., KD values).

"Substantially different," as used herein, refers to a sufficiently high degree of difference between two numeric values (generally one associated with a molecule and the other associated with a reference molecule) such that one of skill in the art would consider the difference between the two values to be of statistical significance within the context of the biological characteristic measured by said values (e.g., KD values).

"Effector functions" refer to those biological activities attributable to the Fc region of an antibody, which vary with the antibody isotype. Examples of antibody effector functions include: Clq binding and complement dependent cytotoxicity (CDC); Fc receptor binding; antibody-dependent cell-mediated cytotoxicity (ADCC); phagocytosis; down regulation of cell surface receptors (e.g., B cell receptor); and B cell activation.

"Immunoconjugate" refers to an antibody conjugated to one or more heterologous molecule(s), including but not limited to a cytotoxic agent.

"Treatment," "treat," or "treating" refers to clinical intervention in an attempt to alter the natural course of a disorder in the individual being treated and can be performed either for prophylaxis or during the course of clinical pathology. Desired results of treatment can include, but are not limited to, preventing occurrence or recurrence of the disorder, alleviation of symptoms, diminishment of any direct or indirect pathological consequences of the disorder, preventing metastasis, decreasing the rate of progression, amelioration or palliation of a disease state, and remission or improved prognosis. For example, treatment can include administration of a therapeutically effective amount of pharmaceutical formulation comprising an anti-IL1RAP antibody to a subject to delay development or slow progression of a disease or condition mediated by IL1RAP.

"Pharmaceutical formulation" refers to a preparation in a form that allows the biological activity of the active ingredient(s) to be effective, and which contain no additional components which are toxic to the subjects to which the formulation is administered.

"Pharmaceutically acceptable carrier" refers to an ingredient in a pharmaceutical formulation, other than an active ingredient, which is nontoxic to the subject to whom it is administered. A pharmaceutically acceptable carrier includes, but is not limited to, a buffer, excipient, stabilizer, or preservative.

"Therapeutically effective amount" refers to the amount of an active ingredient or agent (e.g., a pharmaceutical formulation) to achieve a desired therapeutic or prophylactic result, e.g., to treat or prevent a disease, disorder, or condition in a subject. In the case of a IL1RAP mediated disease or condition, the therapeutically effective amount of the therapeutic agent is an amount that reduces, prevents, inhibits, and/or relieves to some extent one or more of the symptoms associated with the disease, disorder, or condition. For asthma therapy, efficacy in vivo can, for example, be measured by assessing the duration, severity, and/or recurrence of symptoms, the response rate (RR), duration of response, and/or quality of life.

"Concurrently," as used herein to, refers to administration of two or more therapeutic agents, where at least part of the administration overlaps in time. Accordingly, concurrent administration includes a dosing regimen when the administration of one or more agent(s) continues after discontinuing the administration of one or more other agent(s).

"Individual" or "subject" refers to a manual, including but not limited to, domesticated animals (e.g., cows, sheep, cats, dogs, and horses), primates (e.g., humans and non-human primates such as monkeys), rabbits, and rodents (e.g., mice and rats).

Binding Affinity and Cell-Signaling Inhibition of Anti-IL1RAP Antibodies

In some embodiments, the anti-IL1RAP antibodies provided herein have an equilibrium dissociation constant (KD) for binding to human IL1RAP of <100 nM, <10 nM, <1 nM, <0.1 nM, <0.01 nM, or <0.001 nM (e.g., 10-8 M or less, from 10-8 M to 10-13 M, e.g., from 10-9 M to 10-13 M). More specifically, in some embodiments, the anti-IL1RAP antibodies of the present disclosure bind to human IL1RAP with a binding affinity of $1\times10^{-8}$ M or less, 1×10-9 M or less, $1\times10^{-10}$ M or less, or 1×10-11 M or less. In some embodiments, the binding affinity is measured as the equilibrium dissociation constant (KD) for binding to the human IL1RAP polypeptide (SEQ ID NO: 1 or 6). Generally, binding affinity of a ligand to its receptor can be determined using any of a variety of assays and expressed in terms of a variety of quantitative values. Specific IL1RAP binding assays useful in determining affinity of the antibodies are disclosed in the Examples herein. Additionally, antigen binding assays are known in the art and can be used herein including without limitation any direct or competitive binding assays using techniques such as western blots, radioimmunoassays, enzyme-linked immunoabsorbent assay (ELISA), "sandwich" immunoassays, surface plasmon resonance-based assay (such as the BIACORE™ assay as described in WO2005/012359), immunoprecipitation assays, fluorescent immunoassays, and protein A immunoassays.

Accordingly, in some embodiments, the binding affinity is expressed as KD values and reflects intrinsic binding affinity (e.g., with minimized avidity effects). The anti-IL1RAP antibodies of the present disclosure exhibit strong binding affinities to human IL1RAP polypeptide (SEQ ID NO: 1 or 6), for example, exhibiting KD values of between 10 nM and 1 pM.

In some embodiments, the anti-IL1RAP antibodies provided herein decrease, inhibit, and/or fully-block intracellular signaling by IL1RAP-mediated pathways, including the IL-1, IL-33, and/or IL-36 signaling pathways, and more specifically, the signaling pathways that are stimulated by binding of one or more of the following agonists: IL-1α, IL-1β, IL-33, IL-36α, IL-36β, and IL-36γ. The ability of the antibodies to inhibit these IL1RAP-mediated signaling pathways can be assayed in vitro using known cell-based blocking assays including reporter cell assays and primary cell-based blocking assays described in the Examples of the present disclosure. In some embodiments, the ability of the antibody to decrease, inhibit, and/or fully-block intracellular signaling is determined as IC50 of the antibody using a reporter cell-based blocking assay with the agonist(s) IL-1α, IL-1β, IL-33, IL-36α, IL-36β, and/or IL-36γ at concentration of about EC50. The agonist EC50 often can only be estimated prior to the assay and is determined after the assay is completed using nonlinear regression analysis of the data. In such assays, a value of about EC50 typically will be in the range of from EC40-45 to EC55-60.

Accordingly, in some embodiments, the IL 1 RAP antibodies of the present disclosure are characterized by one or more of following functional properties based on the ability to decrease, inhibit, and/or fully-block intracellular signaling by IL1RAP-mediated pathways.

In some embodiments the anti-IL1RAP antibody decreases an IL-1 stimulated signal, an IL-33 stimulated signal, and/or an IL-36 stimulated signal by at least 90%, at least 95%, at least 99%, or 100%. In some embodiments, the decrease in signal can be measured using a reporter cell-based blocking assay. One of ordinary skill can select any of the known reporter cell assays known for use in determining inhibition of cell-signaling in an IL-1 stimulated, an IL-33 stimulated, and/or an IL-36 stimulated pathway. Generally, the anti-IL1RAP antibodies of the present disclosure decrease the IL1RAP-mediated intracellular signal initiated by binding of an agonist at a concentration of about EC50 (e.g., EC40 to EC60) with an IC50 value for the antibody of 10 nM or less, 5 nM or less, or 1 nM.

In some embodiments the anti-IL1RAP antibody decreases an IL-1 stimulated signal, an IL-33 stimulated signal, and an IL-36 stimulated signal by at least 95%, or at least 99%; optionally, wherein the IL-1, IL-33, and/or IL-36 stimulated signals are stimulated by an agonist selected from IL-1α, IL-1β, IL-33, IL-36α, IL-36β, and IL-36γ; optionally, wherein at an agonist concentration of about EC50 the antibody has an IC50 of 10 nM or less, 5 nM or less, or 1 nM or less.

In some embodiments the anti-IL1RAP antibody decreases an intracellular signal initiated by one or more of IL-1α, IL-1D, IL-33, IL-36α, IL-36β, and IL-36γ agonist binding to its cognate receptor by at least 90%, at least 95%, at least 99%, or 100%. In some embodiments the anti-IL1RAP antibody inhibits IL-1α, IL-1D, and/or IL-36P stimulated release of IL8 from primary human lung fibroblasts (PHLF); optionally, wherein at an IL-1α, IL-1β, and/or IL-36R concentration of about EC50 the antibody has an IC50 of 10 nM or less, 5 nM or less, or 1 nM or less. In some embodiments the anti-IL1RAP antibody inhibits IL-1 1 stimulated release of IL6 from primary human monocytes; optionally, wherein at an IL-1β concentration of about EC50 the antibody has an IC50 of 10 nM or less, 5 nM or less, or 1 nM or less. In some embodiments the anti-IL1RAP antibody inhibits IL-33 stimulated release of INF-γ from human natural killer (NK) cells; optionally, wherein at an IL-33 concentration of about EC50 the antibody has an IC50 of 10 nM or less, 5 nM or less, or 1 nM or less. In some embodiments, the antibody inhibits IL-36β stimulated release of IL8 from human epidermal keratinocytes (HEKn); optionally, wherein at an IL-36P concentration of about EC60 the antibody has an IC50 of 10 nM or less, 5 nM or less, or 2 nM or less. In some embodiments, the antibody inhibits IL-33 stimulated phosphorylation in basophils; optionally, wherein at an IL-33 concentration of about EC56 the antibody has an IC50 of 75 nM or less, 50 nM or less, or 45 nM or less. In some embodiments, the antibody inhibits IL-33 stimulated release of INF-γ from CD4+ T cells; optionally, wherein at an IL-33 concentration of about EC34 the antibody has an IC50 of 75 nM or less, 50 nM or less, or 45 nM or less.

Antibody Fragments

In some embodiments, the anti-IL1RAP antibody of the present disclosure can be an antibody fragment. Antibody fragments useful with the binding determinants the present disclosure include, but are not limited to, Fab, Fab', Fab'-SH, F(ab')2, Fv, monovalent, one-armed (or single-armed) antibodies, scFv fragments, and other fragments described herein and known in the art. For a review of various antibody fragments, see e.g., Hudson et al., Nat. Med., 9: 129-134 (2003). For a review of scFv fragments, see, e.g., Pluckthun, in The Pharmacology of Monoclonal Antibodies, vol. 113, Rosenburg and Moore eds., (Springer-Verlag, New York), pp. 269-315 (1994); see also WO93/16185; and U.S. Pat. Nos. 5,571,894 and 5,587,458. For a description of Fab and F(ab')2 fragments comprising salvage receptor binding epitope residues and having increased in vivo half-life, see U.S. Pat. No. 5,869,046. Other monovalent antibody forms are described in, e.g., WO2007/048037, WO2008/145137, WO2008/145138, and WO2007/059782. Monovalent, single-armed antibodies are described, e.g., in WO2005/063816. Diabodies are antibody fragments with two antigen-binding sites that may be bivalent or bispecific (see e.g., EP0404097; WO93/01161; Hudson et al., Nat. Med., 9: 129-134 (2003); and Holliger et al., Proc. Natl. Acad. Sci. USA, 90: 6444-6448 (1993)).

In some embodiments, the antibody fragments are single-domain antibodies which comprise all or a portion of the heavy chain variable domain or all or a portion of the light chain variable domain of an antibody. In some embodiments, a single-domain antibody is a human single-domain antibody (Domantis, Inc., Waltham, Mass.; see, e.g., U.S. Pat. No. 6,248,516).

Antibody fragments can be made by various techniques, including but not limited to proteolytic digestion of an intact antibody as well as production by recombinant host cells (e.g., E. coli or phage), as described herein.

It is contemplated that any of the anti-IL1RAP antibodies of the present disclosure can be prepared as antibody fragments using the methods and techniques known in the art and/or described herein. For example, the preparation and analysis of Fab versions of various anti-IL1RAP antibodies of the present disclosure are described in Example 8.

Chimeric and Humanized Antibodies

In some embodiments, the anti-IL1RAP antibody of the present disclosure can be a chimeric antibody. (See e.g., chimeric antibodies as described in U.S. Pat. No. 4,816,567; and Morrison et al., Proc. Natl. Acad. Sci. USA, 81:6851-6855 (1984)). In one embodiment, a chimeric antibody comprises a non-human variable region (e.g., a variable region derived from a mouse, rat, hamster, rabbit, or non-human primate, such as a monkey) and a human constant region. In some embodiments, a chimeric antibody is a "class switched" antibody in which the class or subclass has been changed from that of the parent antibody. It is contemplated that chimeric antibodies can include antigen-binding fragments thereof.

In some embodiments, the anti-IL1RAP antibody of the present disclosure is a humanized antibody. Typically, a non-human antibody is humanized to reduce immunogenicity to humans, while retaining the specificity and affinity of the parental non-human antibody. Generally, a humanized antibody comprises one or more variable domains in which CDRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the CDR residues are derived) to restore or improve antibody specificity or affinity.

Humanized antibodies and methods of making them are reviewed, e.g., in Almagro and Fransson, Front. Biosci, 13: 1619-1633 (2008), and are further described, e.g., in Riechmann et al., Nature, 332:323-327 (1988); Queen et al., Proc. Nat'l Acad. Sci. USA, 86: 10029-10033 (1989); U.S. Pat. Nos. 5,821,337, 7,527,791, 6,982,321, and 7,087,409; Kashmiri et al., Methods, 36:25-34 (2005) (describing SDR (a-CDR) grafting); Padlan, Mol. Immunol., 28:489-498 (1991) (describing "resurfacing"); Dall'Acqua et al., Methods, 36:43-60 (2005) (describing "FR shuffling"); and Osbourn et al., Methods, 36:61-68 (2005) and Klimka et al., Br. J. Cancer, 83:252-260 (2000) (describing the "guided selection" approach to FR shuffling).

Human framework regions that are useful for humanization include but are not limited to: framework regions selected using the "best-fit" method (see, e.g., Sims et al., J. Immunol., 151:2296 (1993)); framework regions derived from the consensus sequence of human antibodies of a particular subgroup of light or heavy chain variable regions (see, e.g., Carter et al., Proc. Natl. Acad. Sci. USA, 89:4285 (1992); and Presta et al., J. Immunol, 151:2623 (1993));

human mature (somatically mutated) framework regions or human germline framework regions (see, e.g., Almagro and Fransson, Front. Biosci. 13: 1619-1633 (2008)); and framework regions derived from screening FR libraries (see, e.g., Baca et al., J. Biol. Chem. 272: 10678-10684 (1997) and Rosok et al., J. Biol. Chem., 271:22611-22618 (1996)).

It is contemplated that any of the anti-IL1RAP antibodies of the present disclosure can be prepared as humanized antibodies using the methods and techniques known in the art and/or described herein. For example, the preparation and analysis of humanized versions of an anti-IL1RAP antibody of the present disclosure are described in the Examples.

Human Antibodies

In some embodiments, the anti-IL1RAP antibody of the present disclosure can be a human antibody. Human antibodies can be produced using various techniques known in the art. Human antibodies are described generally in van Dijk and van de Winkel, Curr. Opin. Chem. Biol., 5: 368-74 (2001) and Lonberg, Curr. Opin. Immunol., 20:450-459 (2008). Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, Nat. Biotech. 23:1117-1125 (2005). See also, e.g., XENOMOUSE™ technology in U.S. Pat. Nos. 6,075,181 and 6,150,584; transgenic non-human animal capable of producing heterologous antibodies (HUMAB® technology) in U.S. Pat. No. 5,770,429; transgenic transchromosomal rodent technology for making human antibodies (K-M MOUSE® technology) in U.S. Pat. No. 7,041,870; and mice fully derived from gene-targeted ES cells (VELOCIMOUSE® technology) in U.S. Pat. Appl. Pub. No. US 2007/0061900). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. See, e.g., Kozbor, J. Immunol, 133: 3001 (1984); Brodeur et al., Monoclonal Antibody Production Techniques and Applications, pp. 51-63 (Marcel Dekker, Inc., New York, 1987); and Boerner et al., J. Immunol., 147: 86 (1991). Human antibodies generated via human B-cell hybridoma technology are also described in Li et al., Proc. Natl. Acad. Sci. USA, 103:3557-3562 (2006). Additional methods describing production of monoclonal human IgM antibodies from hybridoma cell lines include those described in e.g., U.S. Pat. No. 7,189,826. Human hybridoma technology (i.e., the trioma technique) is described in e.g., Vollmers et al., Histology and Histopathology, 20(3):927-937 (2005) and Vollmers et al., Methods and Findings in Experimental and Clinical Pharmacology, 27(3): 185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

It is contemplated that any of the anti-IL1RAP antibodies of the present disclosure can be prepared as human antibodies using the methods and techniques known in the art and/or described herein.

Library-Derived Antibodies

In some embodiments, the anti-IL1RAP antibody of the present disclosure may be isolated by screening combinatorial libraries for antibodies with the desired activity or activities. For example, a variety of methods are known in the art for generating phage display libraries and screening such libraries for antibodies possessing the desired binding characteristics. The use of phage display for preparation of affinity matured variants of the humanized version of the anti-IL1RAP antibody of the present disclosure are described in the Examples disclosed herein. Other methods for producing such library-derived antibodies can be found in e.g., Hoogenboom et al., Methods in Molecular Biology, 178: 1-37 (O'Brien et al., ed., Antibody Phage Display, Humana Press, Totowa, N.J., 2001); McCafferty et al., Nature, 348:552-554; Clackson et al., Nature, 352: 624-628 (1991); Marks et al., J. Mol. Biol., 222: 581-597 (1992); Marks and Bradbury, Methods in Molecular Biology, 248: 161-175 (Lo, ed., Antibody Engineering, Humana Press, Totowa, N.J., 2003); Sidhu et al., J. Mol. Biol., 338(2): 299-310 (2004); Lee et al., J. Mol. Biol., 340(5): 1073-1093 (2004); Fellouse, Proc. Natl. Acad. Sci. USA, 101 (34): 12467-12472 (2004); and Lee et al., J. Immunol. Methods, 284(1-2): 119-132(2004).

It is contemplated that combinatorial library screening can be used to generate variants of the anti-IL1RAP antibodies of the present disclosure using the methods and techniques known in the art and/or described herein. For example, the use of phage display library generation and screening to prepare a wide-range of affinity matured variants of a humanized anti-IL1RAP antibody of the present disclosure is described in Example 1.

Multispecific Antibodies

In some embodiments, the anti-IL1RAP antibody of the present disclosure is a multispecific antibody, e.g., a bispecific antibody. In some embodiments, the multispecific antibody is a monoclonal antibody having at least two different binding sites, each with a binding specificity for a different antigen, at least one of which specifically binds IL1RAP. In some embodiments, at least one of binding sites specifically binds a cytotoxic agent. In exemplary embodiments, an anti-IL1RAP antibody of the present disclosure is a bispecific antibody and can be used to localize a cytotoxic agent to cells which express IL1RAP.

Techniques for making multispecific antibodies include, but are not limited to, recombinant co-expression of two immunoglobulin heavy chain-light chain pairs having different specificities (see e.g., WO2012131555).

Multispecific antibodies can also be made by engineering "electrostatic steering" effects that favor formation of Fc-heterodimeric antibody molecules rather than homodimers (WO 2009/089004A1); cross-linking two or more antibodies or fragments (see, e.g., U.S. Pat. No. 4,676,980, and Brennan et al., Science, 229: 81 (1985)); using leucine zippers to produce bispecific antibodies (see, e.g., Kostelny et al., J. Immunol, 148(5): 1547-1553 (1992)); using "diabody" technology for making bispecific antibody fragments (see, e.g., Holliger et al., Proc. Natl. Acad. Sci. USA, 90:6444-6448 (1993)); using single-chain Fv (scFv) dimers (see, e.g. Gruber et al., J. Immunol, 152:5368 (1994)); or tri-specific antibodies (see e.g., Tutt et al., J. Immunol., 147:60 (1991).

It is contemplated that any of the anti-IL1RAP antibodies of the present disclosure can be prepared as multispecific antibodies using the methods and techniques known in the art and/or described herein.

Antibody Variants

In some embodiments, variants of the anti-IL1RAP antibody of the present disclosure are also contemplated. For example, antibodies with improved binding affinity and/or other biological properties of the antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristic of IL1RAP antigen binding. It is contemplated that a wide-range of variants of the anti-IL1RAP antibodies of the present disclosure can be prepared using the methods and techniques known in the art and/or described herein, including but not limited to: (i) amino acid substitution, insertion and/or deletion variants; (ii) glycosylation variants; (iii) Fc region variants; (iv) cysteine engineered variants; and (v) derivatized variants.

Substitution, Insertion, and Deletion Variants

In some embodiments, anti-IL1RAP antibody variants having one or more amino acid substitutions in addition to those described herein are provided. Sites for mutagenesis can include the CDRs and FRs. Typical "conservative" amino acid substitutions and/or substitutions based on common side-chain class or properties are well-known in the art and can be used in the embodiments of the present disclosure. The present disclosure also contemplates variants based on non-conservative amino acid substitutions in which a member of one of amino acid side chain class is exchanged for an amino acid from another class.

Amino acid side chains are typically grouped according to the following classes or common properties: (1) hydrophobic: Met, Ala, Val, Leu, Ile, Norleucine; (2) neutral hydrophilic: Cys, Ser, Thr, Asn, Gln; (3) acidic: Asp, Glu; (4) basic: His, Lys, Arg; (5) chain orientation influencing: Gly, Pro; and (6) aromatic: Trp, Tyr, Phe.

Techniques are well-known in the art for amino acid substitution into an antibody and subsequent screening for desired function, e.g., retained/improved antigen binding, decreased immunogenicity, or improved ADCC or CDC.

Amino acid substitution variants can include substituting one or more hypervariable region residues of a parent antibody (e.g., a humanized or human antibody). Generally, the resulting variant(s) selected for further study will have modifications in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described in the Examples herein. Briefly, one or more CDR residues are mutated and the variant antibodies displayed on phage and screened for a particular biological activity (e.g., binding affinity).

A useful method for identifying residues or regions of an antibody that may be targeted for mutagenesis is "alanine scanning mutagenesis" (see e.g., Cunningham and Wells (1989) Science, 244: 1081-1085). In this method, a residue or group of target residues (e.g., charged residues such as Arg, Asp, His, Lys, and Glu) are identified and replaced by a neutral or negatively charged amino acid (e.g., Ala or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen can be determined. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intra-sequence insertions of single or multiple amino acid residues. Examples of terminal insertions include an antibody with an N-terminal methionyl residue. Other insertional variants of the antibody molecule include the fusion to the N-or C-terminus of the antibody to an enzyme or a polypeptide which increases the serum half-life of the antibody.

Substitutions can be made in CDRs to improve antibody affinity. Such alterations may be made in "hotspots," i.e., residues encoded by codons that undergo mutation at high frequency during the somatic maturation process (see, e.g., Chowdhury, Methods Mol., Biol. 207: 179-196 (2008)) with the resulting variant VH or VL being tested for binding affinity. In one embodiment, affinity maturation can be carried out by constructing and reselecting from secondary libraries (see e.g., in Hoogenboom et al., Methods in Molecular Biology, 178: 1-37 (O'Brien et al., ed., Antibody Phage Display, Humana Press, Totowa, N.J., (2001).) Another method to introduce diversity involves CDR-directed approaches, in which several CDR residues (e.g., 4-6 residues at a time) are randomized. CDR residues involved in antigen binding may be specifically identified, e.g., using alanine scanning mutagenesis or modeling. CDR-H3 and CDR-L3 in particular are often targeted.

In some embodiments, substitutions, insertions, or deletions may occur within one or more CDRs so long as such alterations do not substantially reduce the ability of the antibody to bind antigen. For example, conservative alterations (e.g., conservative substitutions as provided herein) that do not substantially reduce binding affinity may be made in CDRs. Such alterations may be outside of CDR "hotspots." In some embodiments of the variant VH and VL sequences provided above, each CDR either is unaltered, or contains no more than one, two or three amino acid substitutions.

Glycosylation Variants

In some embodiments, the anti-IL1RAP antibody of the present disclosure is altered to increase or decrease the extent to which the antibody is glycosylated. Addition or deletion of glycosylation sites to an antibody can be carried out by altering the amino acid sequence such that one or more glycosylation sites is created or removed.

In embodiments where the antibody comprises an Fc region, the carbohydrate attached to the Fc region can be altered. Typically, native antibodies produced by mammalian cells comprise a branched, biantennary oligosaccharide attached by an N-linkage to Asn297 of the CH2 domain of the Fc region (see, e.g., Wright et al., TIBTECH, 15:26-32 (1997)). The oligosaccharide may include various carbohydrates, such as mannose, N-acetyl glucosamine (GlcNAc), galactose, and sialic acid, as well as, a fucose attached to a GlcNAc in the "stem" of the bi-antennary oligosaccharide structure. In some embodiments, the modifications of the oligosaccharide of an Fc region of an antibody can create a variant with certain improved properties.

In some embodiments, the anti-IL1RAP antibody of the present disclosure can be a variant of a parent antibody, wherein the variant comprises a carbohydrate structure that lacks fucose attached (directly or indirectly) to an Fc region. For example, the amount of fucose in such antibody may be from about 1% to about 80%, from about 1% to about 65%, from about 5% to about 65%, or from about 20% to about 40%. The amount of fucose can be determined by calculating the average amount of fucose within the sugar chain at Asn297, relative to the sum of all glyco-structures attached to Asn 297 (e.g., complex, hybrid and high mannose structures) as measured by MALDI-TOF mass spectrometry (see e.g., WO 2008/077546). Asn297 refers to the asparagine residue located at about position 297 in the Fc region (Eu numbering of Fc region residues); however, Asn297 may also be located about 3 amino acids upstream or downstream of position 297, i.e., between positions 294 and 300, due to minor sequence variations in antibodies.

In some embodiments, the fucosylation variants can have improved ADCC function. See, e.g., US Patent Publication Nos. US 2003/0157108, or US 2004/0093621. Examples of "defucosylated" or "fucose-deficient" antibodies and associated methods for preparing them are disclosed in e.g., US2003/0157108; US2003/0115614; US2002/0164328; US2004/0093621; US2004/0132140; US2004/0110704; US2004/0110282; US2004/0109865; WO2000/61739; WO2001/29246; WO2003/085119; WO2003/084570; WO2005/035586; WO2005/035778; WO2005/053742; WO2002/031140; Okazaki et al., J. Mol. Biol., 336: 1239-1249 (2004); Yamane-Ohnuki et al., Biotech. Bioeng. 87: 614 (2004).

Cell lines useful for producing defucosylated antibodies include Led 3 CHO cells deficient in protein fucosylation (see e.g., Ripka et al., Arch. Biochem. Biophys, 249:533-545 (1986); US2003/0157108, and WO2004/056312), and knockout cell lines, such as alpha-1,6-fucosyltransferase gene, FUT8, knockout CHO cells (see, e.g., Yamane-Ohnuki et al., Biotech. Bioeng. 87: 614 (2004); Kanda, Y. et al., Biotechnol. Bioeng., 94(4):680-688 (2006); and WO2003/085107).

Fc Region Variants

In some embodiments, an anti-IL1RAP antibody of the present disclosure can comprise one or more amino acid modifications in the Fc region (i.e., an Fc region variant). The Fc region variant may comprise a human Fc region sequence (e.g., a human IgG1, IgG2, IgG3, or IgG4 Fc region) comprising an amino acid substitution at one or more amino acid residue positions. A wide range of Fc region variants known in the art that are useful with the anti-IL1RAP antibodies of the present disclosure are described below.

In some embodiments, the anti-IL1RAP antibody is an Fc region variant which has altered effector function. In some embodiments, the antibody with altered effector function possesses some (but not all of) the effector functions, decreased effector function, or none of the effector functions (e.g., effectorless) of the parent antibody. Effectorless Fc region variants are more desirable for certain applications where effector function (such as ADCC) is unnecessary or deleterious, and/or in vivo half-life of the antibody is important.

Fc region variant antibodies with reduced effector function, or which are effectorless, can include an amino acid substitution at one or more of the following Fc region positions: 238, 265, 269, 270, 297, 327 and 329. (see, e.g., U.S. Pat. No. 6,737,056). Such Fc region variants can include amino acid substitutions at two or more of positions 265, 269, 270, 297 and 327. Such Fc region variants can also include substitutions of both residues 265 and 297 to alanine (see e.g., U.S. Pat. No. 7,332,581). As disclosed in the Examples and elsewhere herein, in some embodiments, the anti-IL1RAP antibodies of the present disclosure are effectorless Fc region variants. In some embodiments, the effectorless Fc region variants of the anti-IL1RAP antibodies comprise the amino acid substitution N297G.

Fc region variants having improved or diminished binding to FcRs are disclosed in e.g., U.S. Pat. No. 6,737,056; WO 2004/056312; and Shields et al., J. Biol. Chem., 276(9): 6591-6604 (2001). Fc region variants having improved ADCC can comprise one or more amino acid substitutions at e.g., positions 298, 333, and/or 334 of the Fc region (based on EU numbering). Fc region variants having altered (i.e., either improved or diminished) Clq binding and/or Complement Dependent Cytotoxicity (CDC), as described in e.g., U.S. Pat. No. 6,194,551, WO99/51642, and Idusogie et al., J. Immunol., 164: 4178-4184 (2000). Fc region variants with increased half-lives and improved binding to the neonatal Fc receptor (FcRn) are disclosed in e.g., US2005/0014934A1 (Hinton et al.). Such Fc region variants comprise amino acid substitutions at one or more of positions: 238, 256, 265, 272, 286, 303, 305, 307, 311, 312, 317, 340, 356, 360, 362, 376, 378, 380, 382, 413, 424, and 434. Other Fc region variants with increased half-lives include the set of YTE mutations at positions 252, 254, and 256 (i.e., M252Y/S254T/T256E) described in e.g., U.S. Pat. No. 7,658,921 B2 (Dall'Acqua et al.). As disclosed in the Examples and elsewhere herein, in some embodiments, the anti-IL1RAP antibodies of the present disclosure are Fc region variants that include the set of YTE mutations. Other examples of Fc region variants can be found in e.g., U.S. Pat. Nos. 5,648,260 and 5,624,821; and WO94/29351.

As noted elsewhere herein, the Fc region of a naturally occurring antibody typically includes a C-terminal lysine at position 447 (Lys447). This C-terminal lysine, however, is often cleaved from the Fc region during the production of recombinant antibodies in cell culture due to enzymatic cleavage (e.g., production in CIO cells). Accordingly, it is intended that any of the anti-IL1RAP antibodies described herein as comprising an Fc region with a C-terminal lysine, also include the identical anti-IL1RAP antibody comprising an Fc region except without a C-terminal lysine. Similarly, it is intended that any of the anti-IL1RAP antibodies described herein as comprising an Fc region without a C-terminal lysine, also include the identical anti-IL1RAP antibody comprising a Fc region except with a C-terminal lysine.

Generally, in vitro and/or in vivo cytotoxicity assays can be carried out to confirm the reduction/depletion of CDC and/or ADCC activities in an Fc region variant. For example, Fc receptor (FcR) binding assays can be conducted to ensure that the antibody lacks FcγR binding (hence likely lacking ADCC activity) but retains FcRn binding ability. The primary cells for mediating ADCC, NK cells express FcγRIII only, whereas monocytes express FcγRI, FcγRII, and FeγRIII. Non-limiting examples of in vitro assays to assess ADCC activity of a molecule of interest is described in U.S. Pat. No. 5,500,362 (see, e.g. Hellstrom, et al., Proc. Nat'l Acad. Sci. USA, 83:7059-7063 (1986)) and Hellstrom, et al., Proc. Nat'l Acad. Sci. USA, 82: 1499-1502 (1985); U.S. Pat. No. 5,821,337 (see Bruggemann, M. et al., J. Exp. Med., 166:1351-1361 (1987)). Alternatively, non-radioactive assay methods may be employed (see, for example, non-radioactive cytotoxic assay for flow cytometry ACTI™ (CellTechnology, Inc. Mountain View, Calif); and non-radioactive cytotoxicity assay CYTOTOX 96® (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al., Proc. Nat'l Acad. Sci. USA, 95:652-656 (1998). Clq binding assays may also be carried out to confirm that the antibody is unable to bind Clq and hence lacks CDC activity. See, e.g., Clq and C3c binding ELISA in WO2006/029879 and WO2005/100402. To assess complement activation, a CDC assay may be performed (see, e.g., Gazzano-Santoro et al., J. Immunol. Methods, 202: 163 (1997), Cragg, M. S. et al., Blood 101, 1045-1052 (2003); and Cragg, M. S. and M. J. Glennie, Blood, 103:2738-2743 (2004)). FcRn binding and in vivo clearance/half-life determinations can be performed using methods known in the art (see, e.g., Petkova, et al., Intl. Immunol., 18(12): 1759-1769 (2006)).

Cysteine Engineered Variants

In some embodiments, it is contemplated that the anti-IL1RAP antibody described herein can be substituted at specific non-CDR positions with cysteine residues so as to create reactive thiol groups. Such engineered "thioMAbs" can be used to conjugate the antibody to e.g., drug moieties or linker-drug moieties and thereby create immunoconjugates, as described elsewhere herein. Cysteine engineered antibodies can be generated as described in e.g., U.S. Pat. No. 7,521,541. In some embodiments, any one or more of the following antibody residues can be substituted with cysteine: V205 (Kabat numbering) of the light chain; A118 (EU numbering) of the heavy chain; and S400 (EU numbering) of the heavy chain Fc region.

Derivatized Variants

In some embodiments, the anti-IL1RAP antibody of the present disclosure may be further modified (i.e., derivatized) with non-proteinaceous moieties. Non-proteinaceous moieties suitable for derivatization of the antibody include, but are not limited to, water soluble polymers, such as: polyethylene glycol (PEG), copolymers of ethylene glycol and propylene glycol, carboxy-methylcellulose, dextran, polyvinyl alcohol, polyvinyl pyrrolidone, poly-1, 3-dioxolane, poly-1, 3, 6-trioxane, ethylene/maleic anhydride copolymer, poly-amino acid homo-polymers or random co-polymers, and dextran or poly(n-vinyl pyrrolidone)polyethylene glycol, propropylene glycol homo-polymers, polypropylene oxide/ethylene oxide co-polymers, polyoxy-ethylated polyols (e.g., glycerol), polyvinyl alcohol, and mixtures thereof. In some embodiments, modification of the antibody can be carried out using methoxy-polyethylene glycol propionaldehyde. The polymers may be of any molecular weight and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody, e.g., whether the antibody derivative will be used in a therapy under defined conditions.

Immunoconjugates

In some embodiments, the anti-IL1RAP antibody of the present disclosure can also be an immunoconjugate, wherein the immunoconjugate comprises an anti-IL1RAP antibody conjugated to one or more cytotoxic agents. Suitable cytotoxic agents contemplated by the present disclosure include chemotherapeutic agents, drugs, growth inhibitory agents, toxins (e.g., protein toxins, enzymatically active toxins of bacterial, fungal, plant, or animal origin, or fragments thereof), or radioactive isotopes.

In some embodiments, the immunoconjugate is an antibody-drug conjugate (ADC) in which an anti-IL1RAP antibody, as described herein, is conjugated to one or more drugs.

In some embodiments, an immunoconjugate of the present disclosure comprises an anti-IL1RAP antibody as described herein conjugated to a drug or therapeutic agent for the treatment of an IL-1, IL-33, IL-36, and/or IL1RAP-mediated disease or condition.

In some embodiments, an anti-IL1RAP antibody as described herein can be conjugated to an enzymatically active toxin or a fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins, *Momordica charantia* inhibitor, curcin, crotin, *Sapaonaria officinalis* inhibitor, gelonin, mitogellin, restrictocin, phenomycin, enomycin, and the tricothecenes.

In some embodiments, an immunoconjugate of the present disclosure comprises an anti-IL1RAP antibody as described herein conjugated to a radioactive isotope (i.e., a radioconjugate). A variety of radioactive isotopes are available for the production of such radioconjugates. Examples include 211At, 131I, 125I, 90Y, 186Re, 188Re, 153Sm, 212Bi, 32P, 212Pb, and radioactive isotopes of Lu. In some embodiments, the immunoconjugate may comprise a radioisotope for scintigraphic detection, or a spin label for NMR detection or MRI. Suitable radioisotopes or spin labels can include, as 123I, 131I, 111n, 130, 19F, 15N, 170, various isotopes of Gd, Mn, and Fe.

Immunoconjugates of an anti-IL1RAP antibody and a cytotoxic agent, can be made using a variety of well-known bifunctional reagents and chemistries suitable for conjugating to proteins. Such reagents include but are not limited to. N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (e.g., dimethyl adipimidate HQ), active esters (e.g., disuccinimidyl suberate), aldehydes (e.g., glutaraldehyde), bis-azido compounds (e.g., bis-(p-azidobenzoyl)-hexanediamine), bis-diazonium derivatives (e.g., bis-(p-diazoniumbenzoyl)-ethylenediamine), diisocyanates (e.g., toluene-2,6-diisocyanate), and bis-active fluorine compounds (e.g., 1,5-difluoro-2,4-dinitrobenzene).

Reagents for preparing immunoconjugates of the present disclosure can also include commercially available "cross-linking" reagents such as: BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) (see e.g., Pierce Biotechnology, Inc., Rockford, Ill., U.S.A).

Synthetic Antibodies

In some embodiments, the anti-IL1RAP antibody of the present disclosure can be a synthetic antibody comprising a set of CDRs from an anti-IL1RAP immunoglobulin (e.g., CDR-L1, etc.) grafted onto a scaffold or framework other than an immunoglobulin scaffold or framework, such as an alternative protein scaffold, or an artificial polymer scaffold.

Exemplary alternative protein scaffolds contemplated for preparation of synthetic antibodies of the present disclosure can include, but are not limited to: fibronectin, neocarzinostatin CBM4-2, lipocalins, T-cell receptor, protein-A domain (protein Z), Im9, TPR proteins, zinc finger domains, pVIII, avian pancreatic polypeptide, GCN4, WW domain Src homology domain 3, PDZ domains, TEM-1 beta-lactamase, thioredoxin, staphylococcal nuclease, PHD-finger domains, CL-2, BPTI, APPI, HPSTI, ecotin, LACI-D1, LDTI, MTI-II, scorpion toxins, insect defensin-A peptide, EETI-II, Min-23, CBD, PBP, cytochrome b-562, Ldl receptor domains, gamma-crystallin, ubiquitin, transferrin, and/or C-type lectin-like domains.

Exemplary artificial polymer (non-protein) scaffolds useful for synthetic antibodies are described in e.g., Fiedler et al., (2014) "Non-Antibody Scaffolds as Alternative Therapeutic Agents," in Handbook of Therapeutic Antibodies (eds. S. DObel and J. M. Reichert), Wiley-VCH Verlag GmbH & Co.; Gebauer et al., Cuff. Opin. Chem. Biol., 13:245-255 (2009); Binz et al., Nat. Biotech., 23(10): 1257-1268 (2005).

Recombinant Methods and Compositions

The anti-IL1RAP antibody of the present disclosure can be produced using recombinant methods and materials well-known in the art of antibody production. In some embodiments, the present disclosure provides an isolated nucleic acid encoding an anti-IL1RAP antibody. The nucleic acid can encode an amino acid sequence comprising the VL and/or an amino acid sequence comprising the VH of the antibody (e.g., the light and/or heavy chains of the antibody). In some embodiments, one or more vectors (e.g., expression vectors) comprising nucleic acid sequences encoding an anti-IL1RAP antibody of the present disclosure are provided. In some embodiments, a host cell comprising nucleic acid sequences encoding an anti-IL1RAP antibody of the present disclosure are provided. In one embodiment, the host cell has been transformed with a vector comprising a nucleic acid that encodes an amino acid sequence comprising the VL of the antibody and an amino acid sequence comprising the VH of the antibody. In another embodiment, the host cell has been transformed with a first vector comprising a nucleic acid that encodes an amino acid sequence comprising the VL of the antibody and a second vector comprising a nucleic acid that encodes an amino acid sequence comprising the VH of the antibody.

In some embodiments of the recombinant methods, the host cell used is a eukaryotic cell, such as a Chinese Hamster Ovary (CHO) cell, or a lymphoid cell (e.g., YO, NSO, Sp20). In one embodiment, a method of making an anti-IL1RAP antibody is provided, wherein the method comprises culturing a host cell comprising a nucleic acid encoding the antibody, as provided above, under conditions suitable for expression of the antibody, and optionally recovering the antibody from the host cell (or host cell culture medium).

Briefly, recombinant production of an anti-IL1RAP antibody is carried out by isolating a nucleic acid encoding an antibody (e.g., as described herein) and inserting this nucleic acid into one or more vectors for further cloning and/or expression in a host cell. Such nucleic acids are readily isolated and sequenced using conventional procedures well-known in the art (e.g., by using oligonucleotide probes that are capable of binding specifically to genes encoding the heavy and light chains of the desired antibody). Suitable host cells and culturing methods for cloning or expressing the antibody-encoding vectors are well-known in the art and include prokaryotic or eukaryotic cells. Typically, after expression, the antibody may be isolated from cell paste in a soluble fraction and further purified. In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern (see e.g., Gerngross, Nat. Biotech., 22: 1409-1414 (2004), and Li et al., Nat. Biotech., 24:210-215 (2006)).

Suitable host cells for the expression of glycosylated anti-IL1RAP antibodies of the present disclosure can also be derived from multicellular organisms (invertebrates and vertebrates). Examples of invertebrate cells include plant and insect cells. Numerous baculoviral strains have been identified which may be used in conjunction with insect cells, particularly for transfection of Spodoptera frugiperda cells. Plant cell cultures can also be utilized as hosts (see, e.g., U.S. Pat. Nos. 5,959,177, 6,040,498, 6,420,548, and 7,125,978.

Examples of mammalian host cell lines useful for the production of the anti-IL1RAP antibodies of the present disclosure include Chinese hamster ovary (CHO) cells, including DHFR-CHO cells (see e.g., Urlaub et al., Proc. Natl. Acad. Sci. USA, 77:4216 (1980)); myeloma cell lines such as Y0, NS0 and Sp2/0; monkey kidney CV1 line transformed by SV40 (COS-7); human embryonic kidney line (293 or 293 cells as described, e.g., in Graham et al., J. Gen Virol., 36:59 (1977)); baby hamster kidney cells (BHK); mouse Sertoli cells (TM4 cells as described, e.g., in Mather, Biol. Reprod., 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells (see e.g., in Mather et al., Annals N Y. Acad. Sci., 383:44-68 (1982)); MRC 5 cells; and FS4 cells. For a general review of useful mammalian host cell lines suitable for antibody production, see, e.g., Yazaki and Wu, Methods in Molecular Biology, Vol. 248 (B. K. C. Lo, ed., Antibody Engineering, Humana Press, Totowa, N.J.), pp. 255-268 (2003).

Pharmaceutical Compositions and Formulations of Anti-IL1RAP Antibodies

The present disclosure also provides pharmaceutical compositions and pharmaceutical formulations comprising an anti-IL1RAP antibody. In some embodiments, the present disclosure provides a pharmaceutical formulation comprising an anti-IL1RAP antibody as described herein and a pharmaceutically acceptable carrier. Such pharmaceutical formulations can be prepared by mixing an anti-IL1RAP antibody, having the desired degree of purity, with one or more pharmaceutically acceptable carriers. Typically, such antibody formulations can be prepared as an aqueous solution (see e.g., U.S. Pat. No. 6,171,586, and WO2006/044908) or as a lyophilized formulation (see e.g., U.S. Pat. No. 6,267,958).

It is also contemplated that the compositions and formulations comprising an anti-IL1RAP antibody as disclosed herein may further contain other active ingredients (i.e., therapeutic agents) in addition to the anti-IL1RAP, useful for the particular indication being treated in the subject to whom the formulation is administered. Preferably, any additional therapeutic agent has activity complementary to that of the anti-IL1RAP antibody activity and the activities do not adversely affect each other. Accordingly, in some embodiments, the disclosure provides a pharmaceutical composition comprising an anti-IL1RAP antibody as disclosed herein, and a pharmaceutically acceptable carrier, and further comprises a therapeutic agent useful for treatment of an IL-1, IL-33, IL-36, and/or IL1RAP-mediated disease or condition. In some embodiments, for example wherein the disease indication is cancer the therapeutic agent is a chemotherapeutic agent appropriate for the particular cancer. In some embodiments, the further therapeutic agent in the composition is an antagonist of a IL-1, IL-33, IL-36 signaling pathway.

Pharmaceutically acceptable carriers are generally non-toxic to recipients at the dosages and concentrations employed. A wide range of such pharmaceutically acceptable carriers are well-known in the art (see e.g., Remington's Pharmaceutical Sciences 16th edition, Osol, A. Ed. (1980)). Exemplary pharmaceutically acceptable carriers useful in the formulations of the present disclosure can include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as polyethylene glycol (PEG).

Pharmaceutically acceptable carriers useful in the formulations of the present disclosure can also include interstitial drug dispersion agents, such as soluble neutral-active hyaluronidase glycoproteins (sHASEGP) (see e.g., US Pat. Publ. Nos. 2005/0260186 and 2006/0104968), such as human soluble PH-20 hyaluronidase glycoproteins (e.g., rHuPH20 or hyaluronidase human injection HYLENEX), Baxter International, Inc.).

Additional therapeutic agents and active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

In some embodiments, the formulation can be a sustained-release preparation of the antibody and/or other active ingredients. Suitable examples of sustained-release preparations include semipermeable matrices of solid hydrophobic polymers containing the antibody, which matrices are in the form of shaped articles, e.g. films, or microcapsules.

Typically, the formulations of the present disclosure to be administered to a subject are sterile. Sterile formulations may be readily prepared using well-known techniques, e.g., by filtration through sterile filtration membranes.

Uses and Methods of Treatment

It is contemplated that any of the compositions or formulations comprising an anti-IL1RAP antibody of the present disclosure can be used for any methods or uses, such as in therapeutic methods, that utilize their ability to specifically bind to IL1RAP and/or block the activity of IL1RAP, particularly blocking the ability of IL1RAP to mediate intracellular signaling by the IL-1 family cytokines, IL-1α, IL-1β, IL-33, IL-36α. IL-36β, and/or IL-36γ. The intracellular signaling pathways mediated by IL1RAP include the IL-1, IL-33, and IL-36 pathways, and more specifically, include at least the signaling pathways stimulated by the cytokine agonists IL-1α, IL-13, IL-33, IL-36α, IL-36β, and/or IL-36γ. Inhibition of the IL1RAP-mediated signaling pathways can be assayed in vitro using known cell-based blocking assays including reporter cell assays and primary cell-based blocking assays described in the Examples of the present disclosure.

An IL1RAP mediated disease can include any disease or condition associated with elevated levels in bodily fluids or tissue of the IL-1 family of cytokines for which IL1RAP acts as a co-receptor in mediating signaling: IL-1α, IL-1β, IL-33, IL-36α, IL-36β, and/or IL-36γ. Elevated levels of IL-1α, IL-1β, IL-33, IL-36α, IL-36β, and/or IL-36γ can include, for example, levels that exceed those normally found in a particular cell or tissue, or can be any detectable level in a cell or tissue that normally does not express these cytokines. Typically, IL RAP mediated conditions or diseases exhibit the following characteristics: (1) pathologies associated with the condition or disease can be experimentally induced in animals by administration of IL-1α, IL-1β, IL-33, IL-36α, IL-36β, and/or IL-36γ, and/or by up-regulation of expression of IL-1α, IL-1βP. IL-33, IL-36α, IL-36β, and/or IL-36γ; and (2) pathologies associated with the condition or disease generated in experimental animal models can be inhibited by agents that are known inhibit the action of IL-1α, IL-1D, IL-33, IL-36α, IL-363, and/or IL-36γ.

IL-1α, IL-1, IL-33, IL-36α, IL-360, and/or IL-36γ are known to be pro-inflammatory cytokines, however, the aberrant function of the IL-1, IL-33, and/or IL-36 signaling pathways stimulated by these cytokines as mediated by IL RAP as co-receptor, are known to be associated with a wide range of diseases and conditions generally including but not limited to inflammatory diseases, autoimmune diseases, respiratory diseases, metabolic disorders, infections, and cancers.

For example, a wide range conditions and diseases associated with aberrant function of IL-33 signaling, and consequently, also mediated by the co-receptor activity of IL1RAP include but are not limited to: mediated disorder may be an inflammatory condition (e.g., asthma, airway hyperresponsiveness, airway inflammation, sepsis, septic shock, atopic dermatitis, allergic rhinitis, rheumatoid arthritis, or chronic obstructive pulmonary disease (COPD)); an immune disorder (e.g., asthma, rheumatoid arthritis, allergy, atopic allergy, anaphylaxis, anaphylactic shock, allergic rhinitis, psoriasis, systemic sclerosis, inflammatory bowel disease (IBD), Crohn's disease, diabetes, or liver disease); a fibrotic disorder (e.g., idiopathic pulmonary fibrosis (IPF)); an eosinophilic disorder (e.g., eosinophil-associated gastrointestinal disorder, such as eosinophilic esophagitis); an infection (e.g., helminth, protozoan, such as *Leishmania major*, or viral infection, such as RSV or influenza); pain (e.g., inflammatory pain); a central nervous system disorder (e.g., Alzheimer's disease); a solid tumor (e.g., breast tumor, colon tumor, prostate tumor, lung tumor, kidney tumor, liver tumor, pancreas tumor, stomach tumor, intestinal tumor, brain tumor, bone tumor, or skin tumor); or an ophthalmologic disorder. Specific ophthalmologic disorders mediated by IL-33 include but are not limited to: age-related macular degeneration (AMD), including wet AMD, dry AMD, intermediate AMD, advanced AMD, and geographic atrophy (GA)), retinopathy (e.g., diabetic retinopathy (DR), retinopathy of prematurity (ROP), and high-altitude DR), polypoidal choroidal vasculopathy (PCV), diabetic macular edema, dry eye disease, Behcet's disease, retinal detachment, glaucoma, uveitis (e.g., infectious and non-infectious uveitis), retinitis pigmentosa, Leber's congenital amaurosis, Stargardt's disease, traumatic eye injury, and conjunctivitis (e.g., infectious conjunctivitis, non-infectious conjunctivitis, and allergic conjunctivitis).

Similarly, a wide range of conditions and diseases associated with aberrant function of IL-1, and consequently, also mediated by the co-receptor activity of IL1RAP include but are not limited to: acute pancreatitis; amyotrophic lateral sclerosis (ALS); Alzheimer's disease; cachexia/anorexia, including AIDS-induced cachexia; asthma and other pulmonary diseases; atherosclerosis; autoimmune vasculitis; chronic fatigue syndrome; *Clostridium* associated illnesses, including *Clostridium*-associated diarrhea; coronary conditions and indications, including congestive heart failure, coronary restenosis, myocardial infarction, myocardial dysfunction (e.g., related to sepsis), and coronary artery bypass graft; cancer, such as multiple myeloma and myelogenous (e.g., AML or CML) and other leukemias, as well as tumor metastasis; diabetes (e.g., insulin-dependent diabetes); endometriosis; fever, fibromyalgia; glomerulonephritis; graft versus host disease/transplant rejection; hemorrhagic shock; hyperalgesia; inflammatory bowel disease; inflammatory conditions of a joint, including osteoarthritis, psoriatic arthritis and rheumatoid arthritis; inflammatory eye disease, as may be associated with, e.g., corneal transplant; ischemia, including cerebral ischemia (e.g., brain injury as a result of trauma, epilepsy, hemorrhage or stroke, each of which may lead to neurodegeneration); Kawasaki's disease; learning impairment; lung diseases (e.g., ARDS); multiple sclerosis; myopathies (e.g., muscle protein metabolism, especially in sepsis); neurotoxicity (e.g., as induced by HIV); osteoporosis; pain, including cancer-related pain; Parkinson's disease; periodontal disease; pre-term labor; psoriasis; reperfusion injury; septic shock; side effects from radiation therapy; temporal mandibular joint disease; sleep disturbance; uveitis; or an inflammatory condition resulting from strain, sprain, cartilage damage, trauma, orthopedic surgery, infection or other disease processes.

Agents that act as antagonists or inhibitors of the IL-1, IL-33, and/or IL-36 signaling pathways are in clinical development for the treatment of a range of diseases and conditions, including but not limited to the following: acne, acute severe ulcerative colitis, adult-onset Still's disease, allergic rhinitis, systemic sclerosis, arthritis, (including gouty, juvenile, osteo, and rheumatoid), arthritis pain, asthma, atherosclerosis, atopic eczema, Behcet's disease, cachexia, cancer (including breast, colorectal, non-small cell lung, and pancreatic), chronic obstructive pulmonary disease, dry eye syndrome, familial cold autoinflammatory syndrome, familial Mediterranean fever, food allergy, generalized pustular psoriasis, hidradenitis suppurativa, hyper-IgD syndrome, hyperuricemia, Muckle-Wells syndrome, neonatal onset multisystem inflammatory disease, musculoskeletal pain, palmoplantar pustulosis, peripheral vascular disease, polymyalgia rheumatica, nasal polyp, psoriasis, pyoderma gangrenosum, restenosis, sickle-cell anemia, sinusitis, TNF receptor associated periodic syndrome, type-2 diabetes, and ulcerative colitis.

It is contemplated that any of the compositions or formulations comprising an anti-IL1RAP antibody of the present disclosure can be used in a method or use for the treatment of any of the above-listed diseases or conditions associated with aberrant function of the IL-1, IL-33, and/or IL-36 signaling pathway and therefore mediated by the co-receptor activity of IL1RAP. Generally, these conditions and diseases include but are not limited to inflammatory diseases, autoimmune diseases, respiratory diseases, metabolic disorders, infections, and cancers.

Accordingly in some embodiments, the compositions or formulations comprising an anti-IL1RAP antibody of the present disclosure can be used in a method, therapy, medicament, diagnostic, or use for use in the treatment of a condition or disease selected from acne, acute pancreatitis, acute severe ulcerative colitis, adult-onset Still's disease, age-related macular degeneration (AMD), airway hyperresponsiveness, airway inflammation, allergic conjunctivitis, allergic rhinitis, allergy, Alzheimer's disease, amyotrophic lateral sclerosis (ALS), anaphylaxis, arthritis pain, asthma, atherosclerosis, atopic dermatitis, atopic eczema, autoimmune vasculitis, Behcet's disease, bone cancer, brain cancer, breast cancer, cachexia/anorexia, cartilage damage, cerebral ischemia, chronic fatigue syndrome, chronic obstructive pulmonary disease, *Clostridium* associated illnesses, colon cancer, congestive heart failure, conjunctivitis, coronary artery bypass graft, coronary restenosis, Crohn's disease, diabetes, diabetic macular edema, diabetic retinopathy, dry eye disease, endometriosis, eosinophil-associated gastrointestinal disorder, eosinophilic esophagitis, familial cold autoinflammatory syndrome, familial Mediterranean fever, fever, fibromyalgia, fibrotic disorder, food allergy, generalized pustular psoriasis, glaucoma, glomerulonephritis, gouty arthritis, graft versus host disease, helminth infection, hemorrhagic shock, hidradenitis suppurativa, hyperalgesia, hyper-IgD syndrome, hyperuricemia, idiopathic pulmonary fibrosis (IPF), cancer-related pain, infection, inflammatory bowel disease (IBD), inflammatory conditions resulting from strain, inflammatory eye disease associated with corneal transplant, inflammatory pain, influenza, intestinal cancer, ischemia, juvenile arthritis, Kawasaki's disease, kidney cancer, Leber's congenital amaurosis, liver cancer, liver disease, lung cancer, Muckle-Wells syndrome, multiple myeloma, multiple sclerosis, musculoskeletal pain, myelogenous and other leukemias, myocardial dysfunction, myopathies, nasal polyp, neonatal onset multisystem inflammatory disease, neurotoxicity, non-infectious conjunctivitis, non-small cell lung cancer, orthopedic surgery, osteoarthritis, osteoporosis, pain, palmoplantarpustulosis, pancreas cancer, Parkinson's disease, periodontal disease, peripheral vascular disease, polymyalgia rheumatica, polypoidal choroidal vasculopathy (PCV), pre-term labor, prostate cancer, protozoan infection, psoriasis, psoriatic arthritis, pyoderma gangrenosum, reperfusion injury, respiratory syncytial virus (RSV), restenosis, retinal detachment, retinitis pigmentosa, retinopathy of prematurity (ROP), rheumatoid arthritis, septic shock, sickle-cell anemia, side effects from radiation therapy, sinusitis, skin cancer, sleep disturbance, sprain, Stargardt's disease, stomach cancer, temporal mandibular joint disease, TNF receptor associated periodic syndrome, transplant rejection, trauma, traumatic eye injury, type-2 diabetes, ulcerative colitis, and uveitis.

As disclosed herein, including in the Examples below, the anti-IL1RAP antibodies of the present disclosure have the ability to decrease, inhibit, and/or block intracellular signaling mediated by IL1RAP, including the IL-1, IL-33, and IL-36 signaling pathways. Accordingly, in some embodiments, the present disclosure provides a method of treating a IL1RAP-mediated disease or condition in a subject, the method comprising administering to the subject a therapeutically effective amount of an anti-IL1RAP antibody of the present disclosure or administering to a subject in need thereof a therapeutically effective amount of a pharmaceutical composition comprising an anti-IL1RAP antibody of the present disclosure and a pharmaceutically acceptable carrier.

As disclosed elsewhere herein, the anti-IL1RAP antibodies of the present disclosure have the ability to decrease, inhibit, and/or block the IL-1, IL-33, and IL-36 signaling pathways. Accordingly, the present disclosure also provides methods of treating diseases and conditions responsive to a decrease, inhibition, and/or blocking of the IL-1, IL-33, and/or IL-36 signaling pathways.

Additionally, the anti-IL1RAP antibodies of the present disclosure have the ability to decrease, inhibit, and/or block intracellular signaling stimulated by the agonists IL-1α, IL-1β, IL-33, IL-36α, IL-36β, and/or IL-36γ. Accordingly, the present disclosure also provides methods of treating diseases and conditions responsive to a decrease, inhibition, and/or blocking of intracellular signaling stimulated by the agonists IL-1α, IL-1D, IL-33, IL-36α, IL-36, and/or IL-36-γ.

The IL-1 signaling pathways, which are also IL1RAP-mediated pathways, have been associated with many forms of cancer. Accordingly, in some embodiments, the present disclosure provides a method of treating cancer in a subject, the method comprising administering to the subject in need thereof a therapeutically effective amount of an anti-IL1RAP antibody of the present disclosure or administering to a subject a therapeutically effective amount of a pharmaceutical composition comprising an anti-IL1RAP antibody of the present disclosure and a pharmaceutically acceptable carrier.

All three of the IL-1, IL-33, and/or IL-36 signaling pathways, which are also IL1RAP-mediated pathways, have been associated with asthma. Accordingly, in some embodiments, the present disclosure provides a method of treating asthma in a subject, the method comprising administering to the subject in need thereof a therapeutically effective amount of an anti-IL1RAP antibody of the present disclosure or administering to a subject a therapeutically effective amount of a pharmaceutical composition comprising an anti-IL1RAP antibody of the present disclosure and a pharmaceutically acceptable carrier.

In some embodiments, the present disclosure provides a method of treating and/or preventing a IL1RAP-mediated disease, a IL-1, IL-33, and IL-36 signaling pathway mediated disease, and/or a disease mediated by intracellular signaling stimulated by the agonists IL-1α, IL-1D, IL-33, IL-36α, IL-360, and/or IL-36γ. In such method of treatment embodiments, the method comprises administering to a subject in need thereof, a therapeutically effective amount of an anti-IL1RAP antibody, or a composition or pharmaceutical formulation comprising an anti-IL1RAP antibody as described herein.

Administration of the antibody, composition, or pharmaceutical formulation in accordance with the method of treatment provides an antibody-induced therapeutic effect that protects the subject from and/or treats the progression of a IL1RAP-mediated disease in a subject. In some embodiments, the method of treatment can further comprise administration of one or more additional therapeutic agents or treatments known to those of skill in the art to prevent and/or treat the IL1RAP-mediated disease or condition. Such methods comprising administration of one or more additional agents can encompass combined administration (where two or more therapeutic agents are included in the same or separate formulations), and separate administration, in which case, administration of the antibody composition or formulation can occur prior to, simultaneously, and/or following, administration of the additional therapeutic agent.

In some embodiments of the methods of treatment of the present disclosure, the anti-IL1RAP antibody or pharmaceutical formulation comprising an anti-IL1RAP antibody is administered to a subject by any mode of administration that delivers the agent systemically, or to a desired target tissue. Systemic administration generally refers to any mode of administration of the antibody into a subject at a site other than directly into the desired target site, tissue, or organ, such that the antibody or formulation thereof enters the subject's circulatory system and, thus, is subject to metabolism and other like processes.

Accordingly, modes of administration useful in the methods of treatment of the present disclosure can include, but are not limited to, injection, infusion, instillation, and inhalation. Administration by injection can include intravenous, intramuscular, intraarterial, intrathecal, intraventricular, intracapsular, intraorbital, intracardiac, intradermal, intraperitoneal, transtracheal, subcutaneous, subcuticular, intraarticular, subeapsular, subarachnoid, intraspinal, intracerebro spinal, and intrasternal injection and infusion.

In some embodiments, a pharmaceutical formulation of the anti-IL1RAP antibody is formulated such that the antibody is protected from inactivation in the gut. Accordingly, the method of treatments can comprise oral administration of the formulation.

In some embodiments, use of the compositions or formulations comprising an anti-IL1RAP antibody of the present disclosure as a medicament are also provided. Additionally, in some embodiments, the present disclosure also provides for the use of a composition or a formulation comprising an anti-IL1RAP antibody in the manufacture or preparation of a medicament, particularly a medicament for treating, preventing or inhibiting an IL1RAP-mediated disease. In a further embodiment, the medicament is for use in a method for treating, preventing or inhibiting an IL1RAP-mediated disease comprising administering to an individual having an IL1RAP-mediated disease an effective amount of the medicament. In certain embodiments, the medicament further comprises an effective amount of at least one additional therapeutic agent, or treatment.

In a further embodiment, the medicament is for use in treating, inhibiting or preventing an IL1RAP-mediated disease in a subject comprising administering to the subject an amount effective of the medicament to treat, inhibit or prevent the IL1RAP-mediated disease.

For the prevention or treatment of a IL1RAP-mediated disease or condition, the appropriate dosage of the anti-IL1RAP antibody contained in the compositions and formulations of the present disclosure (when used alone or in combination with one or more other additional therapeutic agents) will depend on the specific disease or condition being treated, the severity and course of the disease, whether the antibody is administered for preventive or therapeutic purposes, the previous therapy administered to the patient, the patient's clinical history and response to the antibody, and the discretion of the attending physician. The anti-IL1RAP antibody included in the compositions and formulations described herein, can be suitably administered to the patient at one time, or over a series of treatments. Various dosing schedules including but not limited to single or multiple administrations over various time-points, bolus administration, and pulse infusion are contemplated herein.

Depending on the type and severity of the disease, about 1 pg/kg to 15 mg/kg of anti-IL1RAP antibody in a formulation of the present disclosure is an initial candidate dosage for administration to a human subject, whether, for example, by one or more separate administrations, or by continuous infusion. Generally, the administered dosage of the antibody would be in the range from about 0.05 mg/kg to about 10 mg/kg. In some embodiments, one or more doses of about 0.5 mg/kg, 2.0 mg/kg, 4.0 mg/kg or 10 mg/kg (or any combination thereof) may be administered to a patient.

Dosage administration can be maintained over several days or longer, depending on the condition of the subject, for example, administration can continue until the IL1RAP-mediated disease is sufficiently treated, as determined by methods known in the art. In some embodiments, an initial higher loading dose may be administered, followed by one or more lower doses. However, other dosage regimens may be useful. The progress of the therapeutic effect of dosage administration can be monitored by conventional techniques and assays.

Accordingly, in some embodiments of the methods of the present disclosure, the administration of the anti-IL1RAP antibody comprises a daily dosage from about 1 mg/kg to about 100 mg/kg. In some embodiments, the dosage of anti-IL1RAP antibody comprises a daily dosage of at least about 1 mg/kg, at least about 5 mg/kg, at least about 10 mg/kg, at least about 20 mg/kg, or at least about 30 mg/kg.

Additionally, the anti-IL1RAP antibodies of the present disclosure may be used in assay methods for the detection of IL1RAP. Due to their ability to bind human IL1RAP with high affinity, the anti-IL1RAP antibodies disclosed herein are appropriate for a wide range of assay methods and formats. It is contemplated that the anti-IL1RAP antibodies can be employed in any known assay method, such as competitive binding assays, direct and indirect sandwich assays, immunoprecipitation assays and enzyme-linked immunosorbent assays (ELISA) (See, Sola, 1987, Monoclonal Antibodies: A Manual of Techniques, pp. 147-158, CRC Press, Inc.) for the detection and quantitation of IL1RAP. Accordingly, in some embodiments, the present disclosure provides a method for detecting the level of IL1RAP in a biological sample, the method comprising the step of contacting the sample with an anti-IL1RAP antibody as disclosed herein. Further, in some embodiments, it is contemplated that the method of detecting the level of IL L RAP in a biological sample can be used for detecting and/or diagnosing an IL1RAP-mediated condition or disease in a biological sample, e.g., from a human subject.

EXAMPLES

Example 1: Generation of Anti-IL-1RAP Antibodies

Methods
Recombinant Target Antigens

Human codon-optimized sequences encoding the full-length human IL-1RAP (UniProt accession no: Q9NPH3; SEQ ID NO: 6) and full-length cynomolgus monkey IL-1RAP (accession no: P59822, SEQ ID NO: 7) were synthetized by Twist Biosciences (San Francisco, USA). The soluble extracellular regions of human IL-1RAP (residues 21 to 359; SEQ ID NO: 1) and cynomolgus monkey IL-1RAP (residues 21 to 359; SEQ ID NO: 2) were cloned in a modified expression vector pcDNA™3.1 plasmid (THERMO FISHER SCIENTIFIC®, catalog no. V79020) to generate a protein with a C-terminal biotin tag AVITAG™ (Avidity LLC) followed by a 10-His tag with a Gly$_3$ linker sequence between the two tags (abbreviated human IL-1RAP-ECD-Avi-His and cyno IL-1RAP-ECD-Avi-His).

The expression vector was carrying the murine VJ2C leader peptide to drive product secretion as well as the OriP sequence. For protein expression, the plasmids coding for human IL-1RAP-ECD-Avi-His and cyno IL-1RAP-ECD-Avi-His (residues 21 to 359; SEQ ID NO: 1 and SEQ ID NO: 2, respectively) and a non-coding plasmid were co-transfected into suspension-adapted HEK293-EBNA cells (ATCC®-LGL standards, Teddington, UK; Cat. No: CRL-10852) using Polyethyleneimine (PEI; Polysciences). Briefly, cells were prepared at 8 million cells per ml in RPMI 1640 (Biowest) supplemented with 0.1% Pluronic F-68 (GIBCO®). Cells were then transfected with a DNA-PEI mixture at 37° C. Four hours post-transfection, the cell culture was diluted 1:1 in HEK293 Viral Vector Medium EX-CELL® 293 (SIGMA-ALDRICH®) supplemented with Phenol Red and 4 mM L-Glutamine and incubated for 5 days with orbital shaking at 37° C., 5% C02 and 80% humidity. Post-expression, clarified supernatants were prepared by centrifugation and filtration, pH was adjusted at 7.4 (4° C.) using 1 M sodium hydroxide. Ni-Sepharose Excell beads (General Electric GE® GE HEALTHCARE®) were added to the clarified supernatant and incubated overnight at 4° C. under gentle agitation. Next, the mixtures were loaded on low-pressure chromatography columns ECONO-COL-UMNS® (BIO-RAD® Laboratories) for gravity-flow purification. The beads were first washed in 1× PBS, pH 7.4 (1×10 CV), then 1× PBS supplemented with 20 mM imidazole (2×10 CV) and the proteins were eluted following a step-elution protocol using, sequentially, 1× PBS, pH 7.4 supplemented with 40 mM (10×1 CV), 80 mM (15×1 CV), 250 mM (4×2 CV) and 500 mM (2×2 CV) imidazole. Fractions were analyzed on a SDS-PAGE and selected based on apparent purity. Fractions of interest were then pooled and dialyzed against 1× PBS, pH 7.4 at 4° C. Protein quality was assessed by SDS-PAGE, SE-HPLC and endotoxin measurement. Briefly, SE-HPLC was performed using a TOSOH BIOSC1ENCE® TSKgel G3000SWxl column (catalog no. 08541, TOSOH BIOSCIENCE®) at room temperature with 0.1 M sodium phosphate buffer, 0.15 M sodium chloride, pH 6.8 as eluent at 1 ml/min flow rate, on a Waters Alliance 2695 HPLC system with a Waters 2998 PDA detector (Waters), monitoring at 214 nm and 280 nm. The Multi-Cartridge System Endosafe-MCS from Charles River utilizing a Limulus amebocyte lysate (LAL)-based assay was used to confirm a bacterial endotoxin level inferior to 0.5 EU/mg. Human and cynomolgus monkey IL-1RAP-ECD-Avi-His tagged fusion proteins as described herein have SEQ ID NO: 1 and 2, respectively.

Human codon-optimized sequences encoding the extracellular domains of chicken IL-ARAP (accession no: XP_422719.4; SEQ ID NO: 3) and chicken/human chimeras (SEQ ID NO: 4 and 5) were synthetized by Eurofins (Ebersberg, Germany). The soluble extracellular regions of chicken IL-1RAP (residues 139 to 478; SEQ ID NO: 3) and chicken/human IL-1RAP chimeras (IL-1RAP-ECD(ggD1 (S139-P246)-hsD2(V132-V233)-hsD3(V234-E359))-Avi-His and IL-1RAP-ECD(ggD1(S139-H260)-ggD2(S261-V349)-hsD3(V243-E359))-Avi-His; SEQ ID NO: 4 and 5, respectively) were cloned in an modified expression vector pcDNA™3.1 plasmid (THERMO FISHER SCIENTIFIC®, catalog no. V79020) to generate a protein with a C-terminal AVITAG™ (Avidity LLC) followed by a 10-His tag with a Gly$_3$ linker sequence between the two tags (abbreviated ggIL-1RAP-ECD-Avi-His: IL-1RAP-ECD(ggD1(S139-

P246)-hsD2(V132-V233)-hsD3(V234-E359))-Avi-His and IL-1RAP-ECD(ggD1(S139-H260)-ggD2(S261-V349)-hsD3(V243-E359))-Avi-His). The expression vector was also carrying the murine VJ2C leader peptide to drive product secretion as well as the OriP sequence. For protein expression, the aforementioned plasmids and a non-coding plasmid were co-transfected into suspension-adapted HEK293-EBNA cells (ATCC®-LGL standards, Teddington, UK; Cat. No: CRL-10852) using Polyethyleneimine (PEI; Polysciences). Briefly, cells were prepared at 8 million cells per ml in RPMI 1640 (Biowest) supplemented with 0.1% Pluronic F-68 (GIBCOC). Cells were then transfected with a DNA-PEI mixture at 37° C. Four hours post-transfection, the cell culture was diluted 1:1 in EX-CELL® 293 (SIGMA ALDRICH®) supplemented with Phenol Red and 4 mM L-Glutamine and incubated for 5 days with orbital shaking at 37° C., 5% C02 and 80% humidity. Purification of the recombinant proteins followed the same steps as the ones described above except for the elution step that was performed in 1× PBS supplemented with 500 mM imidazole. Protein quality was assessed by SDS-PAGE, SE-HPLC and endotoxin measurement, as described above. Chicken IL-1RAP-ECD-Avi-His, IL-1RAP-ECD(ggD1(SI39-P246)-hsD2(V132-V233)-hsD3(V234-E359))-Avi-His and IL-1RAP-ECD(ggD1(SI39-H260)-ggD2(S261-V349)-hsD3 (V243-E359))-Avi-His as described herein have SEQ ID NO: 3, 4 and 5, respectively.

Recombinant Cell Lines

The human codon-optimized sequence of, either, full-length human IL-1RAP (UniProt sequence ID Q9NPH3; residues 1 to 570; SEQ ID NO: 6) or full-length cynomolgus monkey IL-1RAP (UniProt sequence ID P59822; residues 1-570; SEQ ID NO: 7) were cloned in a modified expression vector pcDNA™3.1 plasmid (THERMO FISHER SCIENTIFIC®, catalog no. V79020). The vector also contained the enhanced Green Fluorescent Protein (eGFP) and puromycin resistance genes (with intercalated intraribosomal entry sites (IRES) elements). For protein expression, the aforementioned plasmids were transfected into suspension-adapted CHO—S cells (cGMP banked, INVITROGEN®, Cat.-No. A1136401) using Polyethyleneimine (PEI; Polysciences). Briefly, cells were prepared at 2 million cells per ml in CD CHO (GIBCO®). Cells were then transfected with a DNA-PEI mixture at 37° C. Four hours post-transfection, the cell culture was diluted 1:1 POWERCHO™ 2 (Lonza) supplemented with 4 mM L-Glutamine and incubated with orbital shaking at 37° C., 5% C02 and 80% humidity. The expression of human or cyno IL-1RAP was assessed by monitoring the eGFP reporter protein expression with a fluorescence microscope. Human and cynomolgus monkey IL-1RAP-ECD-Avi-His tagged fusion proteins as described herein have SEQ ID NO: 6 and 7, respectively.

Library Generation

The library used herein was from synthetic origin with a diversity restricted to the heavy chain (CDR-H1, CDR-H2 and CDR-H3) and a fixed Vκ3-15/Jκ1 light chain. The library contained 4 different sub libraries based on VH1-69, VH3-23, VH3-15 and VH3-53 antibody germlines. CDRs have been randomized using Trimer oligonucleotides. Primers used for diversifying CDR-H1 and CDR-H2 were designed for each sub libraries and encoded germline-specific naturally occurring diversity at Kabat residues 27-35 and 50-58, respectively. CDR-H3 has been randomized using a pool of oligonucleotides encoding 15 CDR-H3 lengths (6-20) and length-specific naturally occurring diversity at Kabat residues 95-102. Diversified scFv fragments have been pooled to mimic natural CDR-H3 length distribution and cloned into the pNGLEN (in-house modified pUC119 phagemid vector) and the resulting ligation reaction electroporated into E. coli TG1 cells. Each sub-library had diversity between $1.2 \times 10^{10}$ and $1.7 \times 10^{10}$, the four sub-libraries reached a total diversity of $5.6 \times 10^{10}$.

Library Selection

Purified phage particles from each sub-library have been pooled ($2.5 \times 10^{11}$ plaque-forming units/sub-library) and blocked with phosphate buffered saline (PBS) containing 3% (w/v) skimmed milk (3% MPBS) for 1 h at room temperature (RT). MAGNETIC DYNABEADS® Protein G beads (INVITROGEN®, catalog no. 10003D) and 200 nM of human IgG1 were mixed in 3% MPBS and incubated for 1 h at RT. Blocked phage were deselected against IgG1 coated beads for 1 h at RT. Phage were then incubated with 50 nM of recombinant human IL-1RAP Fe fusion protein (Acrobiosystems, catalog no. ILP-H5256) for 2 h at RT. Antigen bound phages were captured on Protein G beads for 30 min at RT and beads were washed five times with PBS containing 0.1% (v/v) Tween (PBS-Tween 0.1%) and twice with PBS. Phages were eluted with 100 mM triethylamine for 10 min at RT and neutralized using Tris-HCl 1 M pH 8. Eluted phages were used to infect 10 ml of exponentially growing E. coli TG1 cells. Infected cells were grown in 2YT medium for 1 h at 37° C. and 100 rotation per minute (RPM), then spread on 2YTAG (2TY medium supplemented with 100 µg/ml ampicillin and 2% glucose) agar plates and incubated overnight (ON) at 30° C. Colonies were scrapped off the plates into 10 ml of 2YT and 15% glycerol (v/v) was added for storage at −80° C. TG1 cells from glycerol stocks were grown at 37° C. and 240 RPM in 2YTAG medium until OD at 600 nm reached 0.5. Cells were then superinfected with the M13K07 helper phage using a multiplicity of infection (MOI) of 10 for 1 h at 37° C. and 100 RPM. Culture medium was then changed for 2YTAK (2YT medium supplemented with 100 g/ml ampicillin and 50 µg/ml kanamycin) and cells were further cultured ON at 30° C. and 280 RPM. The next day, 10 dl of phage containing cell-free supernatant were used for the subsequent round of selection. A total of three rounds of selection were carried out using the same experimental setup.

scFv Screening by SPR

Surface Plasmon Resonance (SPR) analysis was used to confirm specific binding activity of the scFv clones. Measurements were performed on a BIACORE™ 2000 instrument (BIACORE™, GE HEALTHCARE®) using the BIACORE™ 2000 Control Software v3.2 at room temperature and analyzed with the BIACORE™ T200 Evaluation Software (v3.1) from the same manufacturer. Recombinant human IL-1RAP Fc fusion protein (Acrobiosystems, catalog no. ILP-H5256) and recombinant mouse IL-1RAP Fe fusion protein (Sino Biologicals, catalog no. 52657-M02H) were individually diluted to a final concentration of 200 nM in acetate buffer pH 4.5 (BIACORE™, GE HEALTHCARE®, catalog no. BR100350) and subsequently immobilized on Fc2 and Fc4 respectively, to a level of about one thousand resonance units (abbreviated RU) on a CM5 sensor CHIP (BIACORE™, GE HEALTHCARE®, catalog no. BR100012) using an amine coupling kit following manufacturer recommendations. HBS-EP (BIACORE™, GE HEALTHCARE®, catalog no. BR100188) was used as running buffer. Filtered periplasmic extracts were injected directly on the covalently coupled human IL-ARAP Fc and mouse IL-1RAP Fc CM5 sensor chip. Samples were injected on the flow-path 1, 2, 3 and 4 (flow-path 1 and 3 being used as reference) at a 30 µl/min flow rate for 3 min, followed by a dissociation time of 5 min in running buffer. After each binding event, surface was regenerated with 10 mM Glycine pH 1.5 solution (BIACORE™, GE HEALTHCARE®, catalog no. BR100354) injected for 1 min at 30 μl/min. Each measurement included zero-concentration samples as well as irrelevant scFv periplasmic extracts for referencing and specificity, respectively.

scFv Screening by/Low Cytometry

The binding of scFv clones to CHO cells transiently expressing human IL-1RAP protein (SEQ ID NO. 6) or cynomolgus monkey IL-ARAP protein (SEQ ID NO. 7) was assessed by flow cytometry. Individual E. coli colonies from the third round of selection were picked and grown in 2TY medium supplemented with 100 μg/ml ampicillin and 0.1% glucose in 96-well deepwell plates. scFv expression was induced by addition of 0.02 mM of IPTG and incubation ON at 30° C. and 250 RPM. Cells were centrifuged and periplasmic extracts were obtained by resuspending the bacterial pellets in TES buffer (50 mM Tris-HCl pH 8; 1 mM EDTA pH 8; 20% sucrose) followed by incubation on ice for 30 min. Cellular debris were removed by centrifugation, and the seFv containing supernatants were used in flow cytometry experiment. IL-1RAP-expressing and non-transfected CHO cells were seeded at a density of $10^5$ cells/well in microtiter plates. Next, the plates were centrifuged to remove the cell supernatant and 100 μl of periplasmic extract previously diluted 1:1 in PBS containing 3% (w/v) bovine serum albumin (PBS-BSA 3%) was added to each well and the plates further incubated for 30 min at 4° C. Cells were then washed with PBS-BSA 3% and incubated with a biotin-chicken anti-c-Myc antibody (*Gallus* Immunotech catalog no. ACMYC-B) diluted at 1:200 in PBS-BSA 3% for 30 min at 4° C. Next, cells were washed with PBS-BSA 3% and incubated with streptavidin APC (eBioscience, catalog no. 17-4317) diluted at 1:100 in PBS-BSA 3% for 30 min at 4° C. Finally, cell fluorescence was measured using a FACSCALIBUR™ flow cytometer (BD biosciences).

scFv Competition by ELISA

The ability of scFv clones to compete with anti-IL-1RAP antibody was assessed by ELISA. Human IL-1RAP Fc fusion protein (Acrobiosystems, catalog no. ILP-15256) was coated ON at 4° C. onto 96-well microtiter plates at 1.5 μg/ml in PBS. The plates were then washed three times with PBS-Tween 0.05% and blocked with PBS-BSA 3% for 1 h at RT. After blocking and washing, 50 W of Fab at 10 μg/ml were added to the plates and incubated for 30 min at RT. Without washing, 50 μl of periplasmic extract was added and the plates further incubated for 30 min at RT. Plates were then washed and 50 μl of biotin-chicken anti-c-Myc antibody (*Gallus* Immunotech catalog no. ACMYC-B) diluted at 1:5000 in PBS-BSA 3% were added for 1 h at RT. After washing, streptavidin HRP was diluted at 1/8000 in PBS-BSA 0.3% and added to the plate for 30 min at RT. The plate was then washed and the assay was developed using TMB (SIGMA®) for 5 min at RT. After stopping the reaction with H2SO4 (SIGMA®), absorbance at 450 nm was measured using a spectrophotometer.

Fab and IgG1 LALA Expression cDNAs encoding the different antibody constant regions were gene synthetized by GENEART AG (Regensburg, Germany) and modified using standard molecular biology techniques. PCR products were digested with appropriate DNA restriction enzymes, purified and ligated in modified expression vector pcDNA™3.1 plasmids (INVITROGEN®) which carried a CMV promoter and a bovine hormone poly-adenylation (poly(A)). The expression vectors also carried oriP, which is the origin of plasmid replication of Epstein-Barr virus, and the murine V12C leader peptide for secretion of the encoded polypeptide chain. For reformatting scFv library clones into human IgG1 Fab fragments or into human IgG1 LALA (human IgG1 with L234A and L235A substitutions, EU numbering), each scFv clone in its phage library vector was used to amplify its individual VH cDNAs by PCR, next the VH PCR product was cloned in the modified expression vector pcDNA™3.1 vector described above upstream of a cDNA encoding a human IgG1 heavy chain CH1 domain or upstream of a cDNA encoding the human IgG1 heavy chain CH1, hinge, CH2(L234A/L235A) and CH3 domains, whereas the fixed Vx3-15/Jκl light chain (SEQ ID NO. 71) was cloned in the modified expression vector pcDNA™3.1 vector described above upstream of a cDNA encoding a human kappa constant light chain domain.

For Fab and IgG1 LALA expression, equal quantities of heavy chain and light chain vectors were co-transfected into suspension-adapted HEK293-EBNA cells (ATCC®, cat no CRL-10852) using PEI. Typically, cells were prepared at 8 million cells per ml in RPMI supplemented with 0.1% Pluronic F-68. Cells were then transfected with a DNA-PEI mixture. Four hours post-transfection, the cell culture was diluted 1:1 in EX-CELL® 293 supplemented with Phenol Red and 4 mM L-Glutamine and incubated for 5 days with orbital shaking at 37° C., 5% C02 and 80% humidity. Cell-free culture supernatants containing the recombinant proteins were prepared by centrifugation followed by filtration, and used for further purification. Fab proteins were purified using CAPTURESELECT™ IgG-CH1 Affinity Matrix (THERMOSCIENTIFIC®, catalog no. 194320050) and IgG1 LALA proteins were purified using Protein A Affinity Resin CAPTIVA® (Repligen, catalog no. CA-PRI-0100). For both, affinity resin was added to the filtered culture supernatants and incubated ON at 4° C. with gentle mixing. The next day, resin beads were collected into chromatography columns POLY-PREP® columns (BIO-RAD® Laboratories), washed with PBS, and the recombinant proteins eluted with an acidic buffer (typically glycine 0.1 M pH 3). After neutralization with 1/10 volume of Tris-HCl pH 8, preparations were buffer-exchanged into PBS.

Fab Binding Affinities for IL-RAP

Surface plasmon resonance (SPR) was used to measure the binding affinities of the Fab fragments for human, cynomolgus monkey and/or mouse IL-1RAP. Affinities were measured on a BIACORE™ T200 instrument (BIACORE™, GE HEALTHCARE®) at 25° C. and analyzed with the BIACORE™ T200 Evaluation Software (v3.1). Measurements were performed on Series S CM5 sensor chips (BIACORE™ T200, BIACORE™, GE HEALTHCARE®, catalog no. BR100530) coupled with anti-human IgG Fc (BIACORE™, GE HEALTHCARE®, catalog no. BR100839) using a commercial amine coupling kit (BIACORE™, GE HEALTHCARE®, catalog no. BR100050) or on Series S BiotinCAPture chips (BIACORE™, GE HEALTHCARE®, catalog no. 28920234). SPR measurements were performed with commercially available recombinant human IL-1RAP Fc fusion protein (Acrobiosystems, catalog no. ILP-H5256) and recombinant mouse IL-1RAP Fc fusion protein (Sino Biologicals, catalog no. 52657-M02H) or with biotinylated recombinant cynomolgus monkey IL-1RAP-avi-his protein produced in-house (SEQ ID NO. 2).

The affinities to human, cynomolgus monkey and mouse IL-1RAP were assessed by immobilizing IL-1RAP and using Fab fragments as analyte. Around 100 RU of human or mouse IL-1RAP Fc fusion protein were captured on fc2 of a Series S CM5 sensor chip coupled with anti-human IgG Fc and around 150 RU of biotinylated cynomolgus monkey IL-1RAP protein were captured on fc2 of a Series S Biotin-CAPture chip. Fab fragments were injected in single cycle kinetic at different concentrations ranging from 7.8 to 500 nM, in HBS-EP+ buffer (BIACORE™, GE HEALTHCARE®, catalog no. BR100669) at a flow rate of 30 μl/min for 3 min on fc1 and fc2 (fc1 being used as reference). Dissociation was monitored for 5 min. After each cycle, the surface was regenerated with 60 μl of regeneration solution provided with anti-human IgG Fc capture kit (BIACORE™, GE HEALTHCARE®, catalog no. BR100839) or Biotin-CAPture kit (BIACORE™, GE HEALTHCARE®, catalog no. 28920234) respectively. Experimental data were processed using the 1:1 Langmuir kinetic fitting model. Measurements included zero-concentration samples for referencing. $Chi^2$, U— and residual values were used to evaluate the quality of a fit between the experimental data and individual binding models.

IL-1R1/IL-1β/IL-1RAP Blocking Assay

The ability of the Fab fragments to block the interactin between IL-1RAP and IL-1R1/IL-1β receptor/cytokine complexe was assessed by SPR. Around 50 RU of human IL-1RAP Fc fusion protein (Acrobiosystems, catalog no. ILP-H5256) was immobilized on the fc2 of a Series S CM5 sensor chip previously coated with anti-human IgG Fc (BIACORE™, GE HEALTHCARE®, catalog no. BR100839) using a commercial amine coupling kit (BIACORE™, GE HEALTHCARE®, catalog no. BR100050). Fab fragment was injected at 300 nM in HBS-EP+ for 4 min over fc1 and fc2 (fc1 being used as reference) to reach saturation of the immobilized human IL-1RAP, followed by a second injection of a pre-mixed solution of IL-1R1 (R&D Systems, catalog no. 296-IR-100) at 50 nM, IL-1Q (Peprotech, catalog no. 200-01B) at 100 nM and Fab fragment at 300 nM in HBS-EP+ buffer for 2 min. After each cycle, the surface was regenerated with 60 μl of regeneration solution provided with anti-human IgG Fc capture kit (BIACORE™, GE HEALTHCARE®, catalog no. BR100839).

Domain Mapping

Domain of IL-1RAP targeted by IgG1 LALA clones was identified by SPR binding assay. Around 150 RU of IgG1 LALA was immobilized on the fc2 of a Series S CM5 sensor chip previously coated with anti-human IgG Fc (BIACORE™, GE HEALTHCARE®, catalog no. BR100839) using a commercial amine coupling kit (BIACORE™, GE HEALTHCARE®, catalog no. BR100050). Human IL-1RAP-avi-his, chicken IL-1RAP-avi-his, chimeric protein comprising chicken domain 1 of IL-RAP fused to human domain 2 and 3 of IL-RAP (gg-hs-hs-IL-1RAP-ECD-avi-his) and chimeric protein comprising chicken domain 1 and 2 of IL-RAP fused to human domain 3 of IL-RAP (gg-gg-hs-IL-1RAP-avi-his) were injected individually at 50 nM in HBS-EP+ for 3 min over fc1 and fc2 (fc1 being used as reference), followed by dissociation in HBS-EP+ buffer for 5 min. After each binding event, the surface was regenerated with 60 d of regeneration solution provided with anti-human IgG Fc capture kit (BIACORE™, GE HEALTHCARE®, catalog no. BR100839).

Epitope Binning

Epitope binning of Fab fragments on human IL-1RAP was assessed using Bio-Layer Interferometry (BLI). Measurements were done on an OCTETRED96e® instrument (ForteBio) and analyzed using the Data Analyis HT version 11.1 software (OCTET®, ForteBio). Biotinylated human IL-1RAP-avi-his protein produced in house (SEQ ID NO. 1) was loaded at 1 gg/ml in kinetic buffer (ForteBio, catalog no. 18-1105) on a streptavidin OCTET® SA BIOSENSOR® (ForteBio, catalog no. 15-5019) for 5 min. Streptavidin biosensor immobilized with biotinylated human IL-1RAP antigen was dipped into a solution of 200 nM of Fab 1 (saturating Fab) for 10 min, followed by a successive dip into a mixed solution of 200 nM of Fab 1 and 200 nM of Fab 2 (competing Fab) for 5 min. All steps were performed at 25° C. and 1000 RPM shaking. Fresh streptavidin biosensors were immobilized with biotinylated human IL-1RAP before each cycle.

Results

ScFv clones showing specific binding to human IL-1RAP Fc fusion protein by SPR as well as specific binding to both human and cynomolgus IL-1RAP CHO cells, but showing no binding to mouse IL-1RAP Fc fusion protein by SPR were sequenced and unique sequences were reformatted in Fab fragment for further characterization. ScFv clones showing specific binding to both human IL-1RAP Fc fusion protein and mouse IL-1RAP Fc fusion protein by SPR, as well as showing specific binding to both human and cynomolgus IL-1RAP CHO cells and competing to an anti-IL-1RAP antibody known to block the interaction between IL-1RAP and the receptor/cytokine complex IL-1R1/IL-D were sequenced and unique sequences were also reformatted in Fab fragment for further characterization. Biochemical characterization included assessment of binding affinities, functional assessment was performed using IL-1R1/IL-1(3/IL-1RAP blocking assays and epitope targeting was determined using domain mapping and epitope binning assays.

Fab Binding Affinities for IL-RAP

Twenty four Fab clones showed binding affinities to human IL-1RAP with an equilibrium dissociation constant (KD) below 1 μM as determined by SPR. Clone anti-IL-1RAP-UCP02-C8, hereafter also referred to as anti-IL-1RAP-C8, showed highest affinities to both human IL-1RAP (2.2 nM) and cynomolgus monkey IL-1RAP (2.2 nM) but did not bind to mouse IL-1RAP. Clone anti-IL-1RAP-UCP02-C3, hereafter also referred to as anti-IL-1RAP-C3, showed high affinity to mouse IL-1RAP (0.63 nM) and a similar affinity to human IL-1RAP than clone anti-IL-1RAP-C8 (2.8 nM and 2.2 nM respectively). However, anti-IL-1RAP-C3 showed around 40×lower affinity to cynomolgus monkey IL-tRAP (110 nM) than to human IL-1RAP (2.8 nM). Heavy chain sequence identification numbers and binding affinities of the mentioned clones are reported in Table 1.

TABLE 1

Overview of the developed Fab clones and their relative affinity to human, cynomolgus monkey and mouse IL-1RAP

| Clone name | Clone heavy chain SEQ ID NO | Human IL-1RAP KD (nM) | Cynomolgus monkey IL-1RAP KD (nM) | Mouse IL-1RAP KD (nM) |
| --- | --- | --- | --- | --- |
| Anti-IL-1RAP-UCP02-A4-Fab | SEQ ID NO. 8 | 84.3 | 103 | NB |
| Anti-IL-1RAP-UCP02-A6-Fab | SEQ ID NO. 9 | 223 | 197 | NB |
| Anti-IL-1RAP-UCP02-B11-Fab | SEQ ID NO. 10 | 98.1 | 78.7 | NB |
| Anti-IL-1RAP-UCP02-B5-Fab | SEQ ID NO. 11 | 311 | NB | NB |
| Anti-IL-1RAP-UCP02-C3-Fab | SEQ ID NO. 12 | 2.8 | 110 | 0.63 |
| Anti-IL-1RAP-UCP02-C5-Fab | SEQ ID NO. 13 | 368 | 334 | NB |
| Anti-IL-1RAP-UCP02-C8-Fab | SEQ ID NO. 14 | 2.2 | 2.2 | NB |
| Anti-IL-1RAP-UCP02-C9-Fab | SEQ ID NO. 15 | 35.6 | 27.8 | NB |
| Anti-IL-1RAP-UCP02-D2-Fab | SEQ ID NO. 16 | 49 | 50.9 | NB |
| Anti-IL-1RAP-UCP02-G11-Fab | SEQ ID NO. 17 | 260 | 345 | NB |
| Anti-IL-1RAP-UCP02-G3-Fab | SEQ ID NO. 18 | 230 | 296 | NB |
| Anti-IL-1RAP-UCP02-G8-Fab | SEQ ID NO. 19 | 73.5 | 116 | NB |
| Anti-IL-1RAP-UCP02-H8-Fab | SEQ ID NO. 20 | 328 | 297 | NB |
| Anti-IL-1RAP-UCP02-H9-Fab | SEQ ID NO. 21 | 907 | 682 | NB |
| Anti-IL-1RAP-UCP03-A2-Fab | SEQ ID NO. 22 | 582 | 589 | NB |
| Anti-IL-1RAP-UCP03-A3-Fab | SEQ ID NO. 23 | 137 | 177 | NB |
| Anti-IL-1RAP-UCP03-B4-Fab | SEQ ID NO. 24 | 221 | 220 | NB |
| Anti-IL-1RAP-UCP03-B6-Fab | SEQ ID NO. 25 | 545 | 756 | NB |
| Anti-IL-1RAP-UCP03-C1-Fab | SEQ ID NO. 26 | 573 | 761 | NB |
| Anti-IL-1RAP-UCP03-C2-Fab | SEQ ID NO. 27 | 700 | 486 | NB |
| Anti-IL-1RAP-UCP03-F4-Fab | SEQ ID NO. 28 | 888 | 1238 | NB |
| Anti-IL-1RAP-UCP03-G3-Fab | SEQ ID NO. 29 | 279 | 464 | NB |
| Anti-IL-1RAP-UCP03-G4-Fab | SEQ ID NO. 30 | 420 | 378 | NB |
| Anti-IL-1RAP-UCP04-C1-Fab | SEQ ID NO. 31 | 16 | NB | 3.54 |

NB = no detectable binding

IL-1RAP/IL-1R1/IL-1β Blocking Assay

Fab fragments with KD to human IL-1RAP Fc fusion protein below 100 nM as measured by SPR were tested at blocking the human IL-1RAP/IL-R1/IL-11 complex formation using OCTET® Bio-Layer interferometry. Anti-IL-1RAP-E1 Fab was used as non-blocker control. Plot shows data expressed as number of resonance units (abbreviated RU; Y axis) vs. time (X axis). Curves are labelled by saturating Fab clone name. All tested Fab fragments were confirmed to block the interaction between human IL-1RAP and the IL-1R1/IL-1β receptor/cytokine complex. Blocking of the interaction between human IL-1RAP and IL-1R/IL-11 receptor/cytokine complex with clones anti-IL-1RAP-C8 and anti-IL-1RAP-C3 is illustrated in FIG. 1. Clone anti-IL-1RAP-UCP05-E1, hereafter also referred to as anti-IL-1RAP-E1, was used as non-blocker control.

Domain Mapping

Figure 2B:
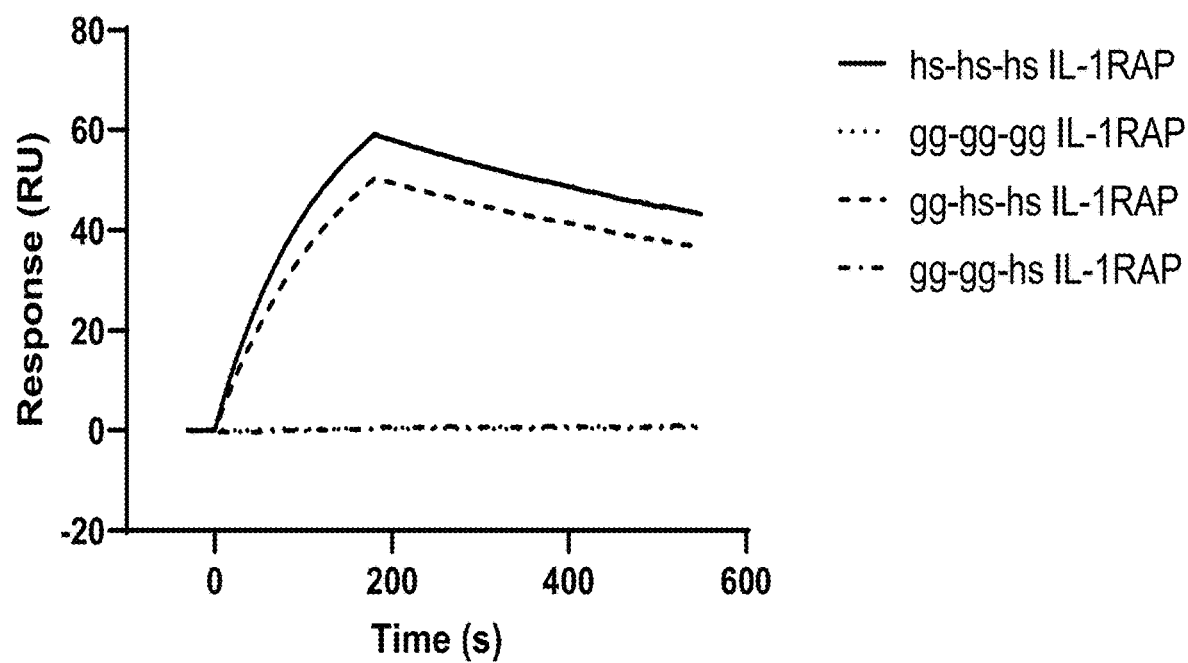
FIG. 2B shows the domain mapping of anti-IL-1RAP-C3 clone to human-chicken IL-1RAP chimeras using Surface Plasmon Resonance with anti-IL-1RAP-C3 IgG1 LALA immobilized on a Series S CM5 sensor CHIP coupled with anti-human IgG Fc. Human-chicken IL-1RAP chimeras were injected over immobilized anti-IL-1RAP IgG1 LALA at 50 nM in HBS-EP+ buffer followed by a dissociation in HBS-EP+ buffer. "hs" stands for a human domain and "gg" stands for a chicken domain. Human-chicken chimeras are then described by their respective human or chicken domains in successive order, e.g. hs-gg-gg IL-1RAP stands for IL-1RAP with human domain 1, chicken domain 2 and chicken domain 3. Plots show data expressed as number of resonance units (abbreviated RU; Y axis) vs. time (X axis).

To get insight into anti-IL-1RAP-C8 mechanism of action and validate anti-IL-1RAP-C3 clone as a relevant mouse surrogate regarding epitope, the domain of IL-1RAP targeted by both antibodies was studied. As described in Table 1, anti-IL-1RAP-C3 Fab binds to human IL-1RAP with a similar affinity than anti-IL-1RAP-C8 Fab. This binding property was used to compare the epitope of both antibodies using human-chicken IL-1RAP chimeras. As shown in FIGS. 2A and 2B, both anti-IL-1RAP-C8 (FIG. 2A) and anti-IL-1RAP-C3 (FIG. 2B) are targeting the domain 2 of IL-1RAP, which is known to be involved in the interaction between IL-1, IL-33, and IL-36, their respective receptors and IL-1RAP. This experiment provides insight into the blocking potency of anti-IL-1RAP-C8 and anti-IL-1RAP-C3 as its mouse surrogate.

Epitope Binning

Figure 3:
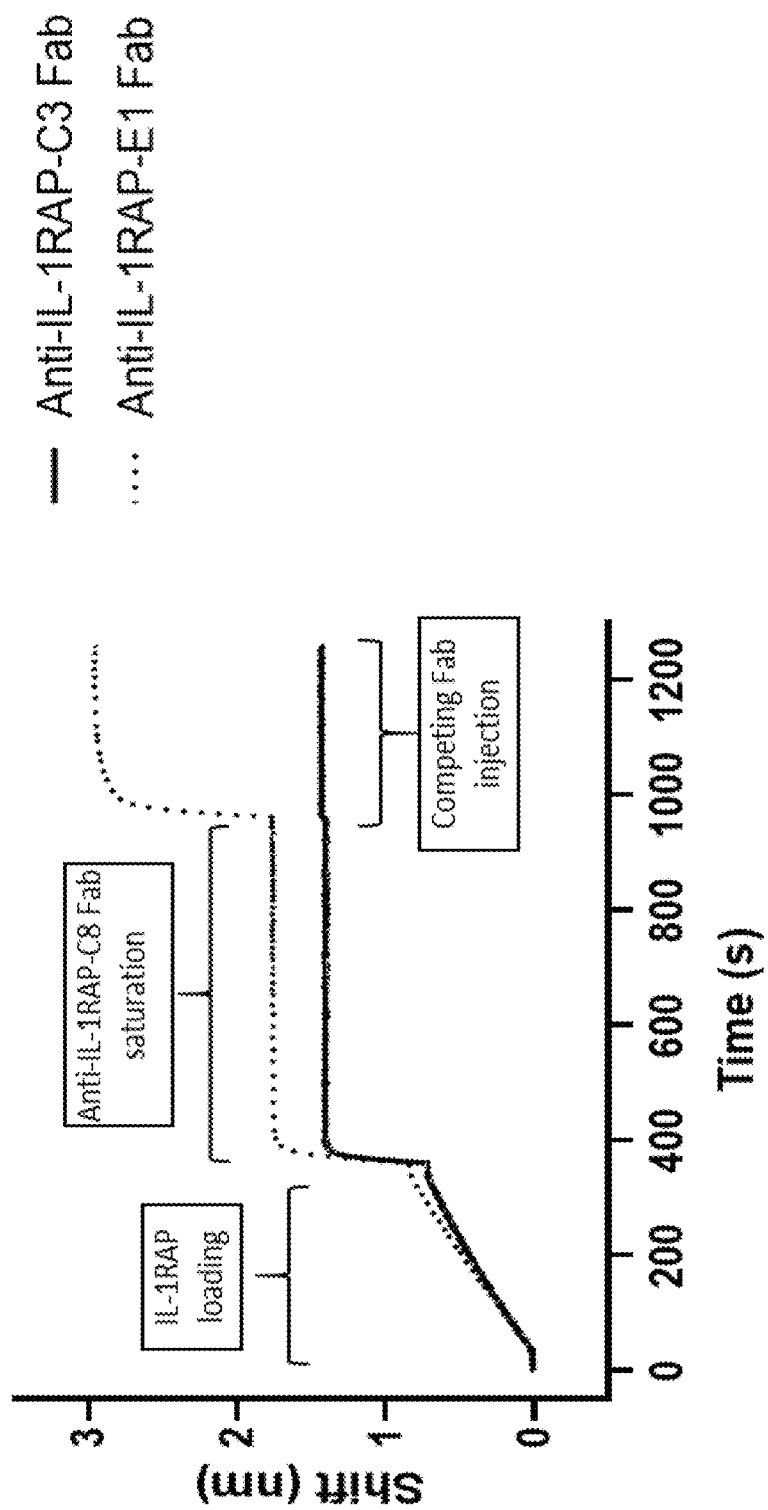
FIG. 3 shows epitope binning of anti-IL-1RAP-C8 clone and anti-IL-1RAP-C3 clone to human IL-1RAP using OCTET® Biolayer Interferometry. Biotinylated human IL-1RAP-avi-his protein was loaded on a streptavidin OCTET® SA BIOSENSOR®. Anti-IL-1RAP-C8 Fab was injected over immobilized human IL-1RAP at 200 nM in kinetic buffer to reach saturation of the surface. Then, a pre-mixed solution of anti-IL-1RAP-C3 Fab and anti-IL-1RAP-C8 Fab at 200 nM final concentration each was injected over saturated surface. Same experimental procedure was performed using anti-IL-1RAP-E1 Fab instead of anti-IL-1RAP-C3 Fab, as non-competing control. Plot shows binding to the sensor tip as a wavelength shift (in nm; Y axis) vs. time (X axis). Curves are labelled by competing Fab clone name.

To further validate anti-IL-1RAP-C3 as relevant mouse surrogate for anti-IL-1RAP-C8, both antibodies were competed with each other using human IL-1RAP. This experiment is presented in FIG. 3 and shows that both antibody compete with each other and recognize overlapping epitope on IL-1RAP. Anti-IL-1RAP-E1, was used as non-competing control.

Example 2: Optimization of Anti-IL-1RAP-C8 Clone

Recombinant Target Antigens

Recombinant human IL-1RAP-ECD(S21-E359)-avi-his protein (SEQ ID NO. 1), hereafter also referred to as recombinant human IL-1RAP-avi-his protein, and recombinant cynomolgus monkey IL-1RAP-ECD(S21-E359)-avi-his protein (SEQ ID NO. 2), hereafter also referred to as recombinant cynomolgus monkey IL-1RAP-avi-his protein, were produced in house as described in Example 1.

Library Generation and Selection

Five affinity maturation libraries were generated by introducing diversity in CDRs' heavy chain. CDR-H1, CDR-H2 and CDR-H3 were randomized using degenerated NNK codon oligonucleotides (wherein N is any of the four deoxyribonucleotides and K is G or T) at Kabat residues 27-35, 50-58, 95-101 minus 2, respectively. Each library was generated using a pool of overlapping oligonucleotides containing 5 consecutive degenerated codons. CDR-H1 and CDR-H2 were also diversified using Trimer oligonucleotide at position Kabat 27-35 and 50-58 respectively. The resulting five library PCR products were cloned into the pNGLEN (in-house modified pUC119 phagemid vector) and the resulting ligation reaction electroporated into *E coli* TG1 cells. Transformed cells were spread on 2YTAG plates and incubated ON at 30° C. Colonies were scrapped off the plates into 10 ml of 2YT medium and 15% glycerol (final concentration) was added for storage at −80° C. Phages were produced and purified by two precipitations steps with one-third v/v of 20% PEG-6000, 2.5 M NaCl and resuspended in PBS.

Phage display selections were performed as described in Example 1 with the following modifications. Each affinity maturation libraries was selected independently. Purified phage particles ($10^{12}$ plaque-forming units) and magnetic DYNABEADS® MYONE™ Streptavidin C1 beads (IN-VITROGEN®, catalog no. 65002) were blocked with 3% MPBS for 1 h at RT. Phage were deselected against pre-blocked beads for 1 h at RT. Deselected phage were incubated with 5 nM, 0.5 nM and 0.1 nM of biotinylated recombinant human IL-1RAP-avi-his protein produced in house (SEQ ID NO. 1) for round 1, round 2 and round 3, respectively. After 1 h incubation, 1 µM of recombinant human IL-1RAP-avi-his protein produced in house (non-biotinylated, SEQ ID NO. 1) was added for 3 h at RT during rounds 2 and 3. Antigen bound phages were captured on Streptavidin beads for 30 min at RT and beads were washed five times with PBS-Tween 0.1% and twice with PBS.

Affinity Screening by SPR

SPR analysis was used to confirm specific binding activity of the new scFv clones and rank the positive clones according to their binding profile. Measurements were performed on a BIACORE™ T200 instrument (BIACORE™, GE HEALTHCARE®) using the BIACORE™ T200 Control Software v2.0 at 25° C. and analyzed with the BIACORE™ T200 Evaluation Software (v3.1) from the same manufacturer. Recombinant human IL-1 RAP-avi-his protein produced in house (SEQ ID NO. 1) or recombinant cynomolgus monkey IL-1RAP-avi-his protein produced in house (SEQ ID NO. 2) was diluted to a final concentration of 200 nM in acetate buffer pH 4.5 (BIACORE™, GE HEALTHCARE®, catalog no. BR-1003-50) and subsequently immobilized on Fc2 or Fc4 respectively, to a level of about one thousand resonance units (abbreviated RU) on a Series S CM5 Sensor Chip (BIACORE™, GE HEALTHCARE®, catalog no. BR100530) using an amine coupling kit (BIACORE™, GE HEALTHCARE®, catalog no. BR100050) following manufacturer recommendations. HBS-EP+(BIACORE™, GE HEALTHCARE®, catalog no. BR100669) was used as running buffer. Filtered periplasmic extracts were injected directly on the covalently coupled human IL-1RAP and cynomolgus monkey IL-1RAP CM5 sensor chip. Samples were injected on the flow-path 1, 2, 3 and 4 (flow-path 1 and 3 being used as reference) at a 30 l/min flow rate for 3 min, followed by a dissociation time of 5 min in running buffer. After each binding event, surface was regenerated with 10 mM Glycine pH 1.5 (BIACORE™, GE HEALTHCARE®, catalog no. BR100354) injected for 1 min at 30 µl/min. Each measurement included zero-concentration samples as well as irrelevant scFv periplasmic extracts for referencing and specificity, respectively. The scFv clones showing the best binding profiles were then reformatted in Fab fragment as described in Example 1. Affinities of the Fab to human IL-1RAP and cynomolgus IL-1RAP were measured as described in Example 1, with modified Fab injection concentration range (from 0.08 nM to 50 nM).

Human IgG1 LALA Expression

Anti-IL-1RAP clones showing highest affinities to human and cynomolgus monkey IL-1RAP after CDR recombination were expressed in human IgG1 LALA format as described in Example 1. To remove a known potential isomerization site (DS) in the CDRH3 (Kabat) of clone anti-IL-1RAP-C8-RecC (SEQ ID NO. 54), D100 and S100a (Kabat) residues were replaced by AA, AS, DA, ES or ET respectively into 5 additional IgG1 LALA heavy chains (SEQ ID NO. 55-59). cDNAs encoding the different antibody variable heavy chain of the anti-IL-1RAP-C8-RecC-AA, anti-IL-1RAP-C8-RecC-AS, anti-IL-1RAP-C8-RecC-DA, anti-IL-1RAP-C8-RecC-ES and anti-IL-IR AP-C8-RecC-ET were constructed by site-directed mutagenesis using standard molecular techniques and cloned in a modified expression vector pcDNA™3.1 vector upstream of a cDNA encoding the CH1, CH2(L234A/L235A) and CH3 domains of a human IgG1 chain as described in Example 1. Human IgG1 LALA molecules were expressed and purified as described in Example 1 or as follows. For expression of Anti-IL1-RAP-C8-RecC-ES-IgG1-LALA (SEQ ID NO: 71 and 72), equal quantities of each engineered chains vectors and a vector encoding Epstein-Barr Virus (EBV) nuclear antigen-1 (EBNA-1) were co-transfected into CHO—S cells (cGMP banked, INVITROGEN®, Cat.-No. A1136401), using Polyethyleneimine (PEI; Polysciences). Typically, cells were prepared at 8 million cells per ml in CD-CHO media (GIBCO®). Cells were then transfected with a DNA-PEI mixture at 37° C. Four hours post-transfection, the cell culture was diluted 1:1 in POWERCHO™ 2 (Lonza) supplemented with 4 mM L-Glutamine and incubated for 14 days with orbital shaking at 32° C., 5% C02 and 80% humidity. Clarified cell culture supernatants containing the recombinant proteins were prepared by centrifugation followed by filtration, and used for further purification. Antibodies were purified by gravity flow mode using protein A chromatography resin KANEKA KANCAPA™ resins (Kaneka) at RT. KANEKA KANCAPA™ beads were added to the clarified supernatant and incubated overnight at 4° C. under gentle agitation. Next, the mixtures were loaded on chromatography POLY-PREP® columns (BIO-RAD@Laboratories) for gravity-flow purification. The beads were first washed in 1× PBS, pH 7.4 (1×10 CV) and the proteins were eluted as described below. For Anti-IL1-RAP-C8-RecC-ES-IgG1-LALA (SEQ ID NO: 71 and 72). proteins were eluted using a step-elution protocol using, sequentially, 50 mM sodium acetate pH 4.3, pH 4.1, pH 3.9 and pH 3.5. Collected fractions were analyzed on a SDS-PAGE and selected based on apparent purity. Fractions of interest were then pooled and dialyzed against 1× PBS, pH 7.4 at 4° C. The purified antibodies were stored at −80° C. after sterile filtration on 0.2 m filter. They were further analyzed by SDS-PAGE (NuPAGE Bis-Tris 4-12% acrylamide, INVITROGEN® AG, Basel, Switzerland) and cGE on a ProteomeLab PA 800 (Beckman Coulter International S.A., Nyon, Switzerland), under reducing and non-reduced conditions to assess purities. In order to determine the content of monomers and aggregate forms, proteins were analyzed by SE-HPLC. Briefly, SE-IPLC was performed using a TOSOH BIOSCIENCE® TSKgel G3000SW×l column (catalog no. 08541, TOSOH BIOSCIENCE®) at room temperature with 0.1 M sodium phosphate buffer, 0.15 M sodium chloride, pH 6.8 as eluent at 1 ml/mm flow rate, on a Waters Alliance 2695 HPLC system with a Waters 2998 PDA detector (Waters), monitoring at 214 nm and 280 nm. The Multi-Cartridge System Endosafe-MCS from Charles River utilizing a Limulus amebocyte lysate (LAL)-based assay was used to confirm a bacterial endotoxin level inferior to 0.5 EU/mg. Typically, for purified antibodies the content of aggregated forms was lower than 5% and the purity measured by SE-HPLC was superior to 95%.

Human IgG1 LALA Binding Affinities to Human and Cynomolgus Monkey IL-1RAP

Surface plasmon resonance (SPR) was used to measure the binding affinities of the human IgG1 LALA molecules for human and cynomolgus monkey IL-1RAP. Affinities were measured on a BIACORE™ T200 instrument (BIACORE™, GE HEALTHCARE®) at 25° C. and analyzed with the BIACORE™ T200 Evaluation Software (v3.1). Measurements were performed on Series S CM5 sensor chips (BIACORE™ T200, BIACORE™, GE HEALTHCARE®, catalog no. BR100530) coupled with anti-human IgG Fc (BIACORE™, GE HEALTHCARE®, catalog no. BR100839) using a commercial amine coupling kit (BIACORE™, GE HEALTHCARE®, catalog no. BR100050). SPR measurements were performed with recombinant human IL-1RAP-avi-his protein produced in house (SEQ ID NO. 1) or recombinant cynomolgus monkey IL-1RAP-avi-his protein produced in house (SEQ ID NO. 2). The affinities to human and cynomolgus monkey IL-1RAP were assessed by immobilizing anti-IL-1RAP IgG1 LALA molecules and using IL-1RAP proteins as analyte. Around 150 RU of human IgG1 LALA were captured on fc2 of a Series S CM5 sensor chip coupled with anti-human IgG Fc. Recombinant human IL-1RAP-avi-his protein or recombinant cynomolgus monkey IL-1RAP-avi-his protein was injected in multi cycle kinetic at different concentrations ranging from 0.14 to 100 nM, in HBS-EP+ buffer (BIACORE™, GE HEALTHCARE®, catalog no. BR100669) at a flow rate of 30 µl/min for 3 min on fc1 and fc2 (fc1 being used as reference). Dissociation was monitored for 12 min. After each cycle, the surface was regenerated with 60 µl of regeneration solution provided with anti-human IgG Fc capture kit (BIACORE™, GE HEALTHCAREC®, catalog no. BR100839). Experimental data were processed using the 1:1 Langmuir kinetic fitting model. Measurements included zero-concentration samples for referencing. Chi$^2$, U— and residual values were used to evaluate the quality of a fit between the experimental data and individual binding models.

Results

Affinity maturation of anti-IL-1RAP-C8 clone (heavy chain SEQ ID NO. 14) involved diversification of CDR-H1 (Kabat positions 27-35), CDR-12 (Kabat positions 50-58) and CDR-H3 (Kabat positions 95-101 minus 2) in five individual libraries. ScFv clones having a slower off-rate than the parental anti-IL-1RAP-C8 clone as measured by SPR were isolated. ScFv clones were reformatted and expressed as Fab fragments and affinities to human and cynomolgus IL-ARAP were measured as described in Example 1. From this assessment, selected mutations originating from the CDR-H1 and CDR-H2 libraries were combined for further off-rate improvement; one clone referred to as Fab clone anti-IL-1RAP-C8-RecC had the highest affinities to human IL-1RAP. Heavy chain sequence identification numbers and binding affinity of the mentioned clones to human IL-1 RAP are reported in Table 2.

TABLE 2

Overview of the developed Fab clones and their relative affinity to human IL-1RAP

| Library | Clone name | Clone heavy chain SEQ ID NO | Human IL-1RAP KD (nM) |
|---|---|---|---|
| CDR-H1 | Anti-IL-1RAP-C8-H1A-C4-Fab | SEQ ID NO. 32 | 0.995 |
| CDR-H1 | Anti-IL-1RAP-C8-H1A-C8-Fab | SEQ ID NO. 33 | 1.237 |
| CDR-H1 | Anti-IL-1RAP-C8-H1A-D8-Fab | SEQ ID NO. 34 | 1.515 |
| CDR-H1 | Anti-IL-1RAP-C8-H1A-F1-Fab | SEQ ID NO. 35 | 0.832 |
| CDR-H1 | Anti-IL-1RAP-C8-H1A-G11-Fab | SEQ ID NO. 36 | 0.742 |
| CDR-H1 | Anti-IL-1RAP-C8-H1A-G1-Fab | SEQ ID NO. 37 | 0.424 |
| CDR-H1 | Anti-IL-1RAP-C8-H1A-G3-Fab | SEQ ID NO. 38 | 0.623 |
| CDR-H1 | Anti-IL-1RAP-C8-H1B-A8-Fab | SEQ ID NO. 39 | 0.522 |
| CDR-H1 | Anti-IL-1RAP-C8-H1B-B10-Fab | SEQ ID NO. 40 | 0.553 |
| CDR-H1 | Anti-IL-1RAP-C8-H1B-B8-Fab | SEQ ID NO. 41 | 0.373 |
| CDR-H1 | Anti-IL-1RAP-C8-H1B-D8-Fab | SEQ ID NO. 42 | 0.476 |
| CDR-H1 | Anti-IL-1RAP-C8-H1B-E7-Fab | SEQ ID NO. 43 | 0.831 |
| CDR-H1 | Anti-IL-1RAP-C8-H1B-F3-Fab | SEQ ID NO. 44 | 0.427 |
| CDR-H1 | Anti-IL-1RAP-C8-H1B-G10-Fab | SEQ ID NO. 45 | 0.313 |
| CDR-H1 | Anti-IL-1RAP-C8-H1B-H10-Fab | SEQ ID NO. 46 | 0.209 |
| CDR-H2 | Anti-IL-1RAP-C8-H2B-B5-Fab | SEQ ID NO. 47 | 1.374 |
| CDR-H2 | Anti-IL-1RAP-C8-H2B-C10-Fab | SEQ ID NO. 48 | 0.589 |
| Combination | Anti-IL-1RAP-C8-recA-Fab | SEQ ID NO. 49 | 0.051 |
| Combination | Anti-IL-1RAP-C8-recB-Fab | SEQ ID NO. 50 | 0.052 |
| Combination | Anti-IL-1RAP-C8-recC-Fab | SEQ ID NO. 51 | 0.038 |

A series of 5 mutated versions of clone anti-IL-1RAP-C8-RecC were expressed in human IgG1 LALA backbone to assess removal of a potential isomerization site (DS) in the CDRH3 (Kabat). Clone anti-IL-1RAP-C8-RecC-ES showed similar affinity to human IL-ARAP and cynomolgus monkey IL-1RAP than parental clone anti-IL-1 RAP-C8-RecC and was further characterized. Heavy chain sequence identification numbers as well as mean binding kinetic constants and standard deviations calculated from at least two independent experiments (when applicable) to human IL-1RAP and cynomolgus monkey IL-1RAP of the mentioned clones are reported in Table 3a. The CDR sequences of the mentioned clones are provided in Table 3b. Representative examples of SPR binding sensorgram of anti-IL-1RAP-CB-RecC-ES IgG1 LALA to human and cynomolgus monkey IL-1RAP are shown in FIGS. 4A and 4B. respectively.

TABLE 3a

SPR binding affinities of IgG1-LALA to human and cynomolgus monkey IL-1RAP

| Clone name | Clone heavy chain SEQ ID NO | Affinity to human IL-1RAP | | | Affinity to cynomolgus monkey IL-1RAP | | |
|---|---|---|---|---|---|---|---|
| | | KD ± SD (nM) | Ka ± SD (1/Ms) | Kd ± SD (1/s) | KD ± SD (nM) | Ka ± SD (1/Ms) | Kd ± SD (1/s) |
| Anti-IL-1RAP-C8-recC IgG1 LALA | SEQ ID NO. 54 | 0.237 ± 0.010 | 8.40E+05 ± 6.73E+04 | 1.99E−04 ± 2.04E−05 | 0.276 ± 0.039 | 8.54E+05 ± 3.77E+04 | 2.36E−04 ± 2.99E−05 |
| Anti-IL-1RAP-C8-RecC-AA-IgG1LALA | SEQ ID NO. 55 | 0.267 ± 0.014 | 6.34E+05 ± 5.66E+02 | 1.69E−04 ± 1.17E−05 | 0.240 | 7.77E+05 | 1.87E−04 |
| Anti-IL-1RAP-C8-RecC-DA-IgG1LALA | SEQ ID NO. 56 | 0.140 ± 0.005 | 1.16E+06 ± 4.45E+04 | 1.62E−04 ± 1.53E−05 | 0.145 | 1.31E+06 | 1.90E−04 |
| Anti-IL-1RAP-C8-RecC-AS-IgG1LALA | SEQ ID NO. 57 | 0.287 ± 0.007 | 5.61E+05 ± 1.44E+04 | 1.61E−04 ± 1.00E−05 | 0.254 | 6.28E+05 | 1.60E−04 |
| Anti-IL-1RAP-C8-RecC-ES-IgG1LALA | SEQ ID NO. 58 | 0.251 ± 0.038 | 6.93E+05 ± 7.09E+04 | 1.72E−04 ± 1.41E−05 | 0.306 ± 0.026 | 6.92E+05 ± 4.94E+04 | 2.12E−04 ± 1.95E−05 |
| Anti-IL-1RAP-C8-RecC-ET-IgG1LALA | SEQ ID NO. 59 | 0.278 ± 0.027 | 9.16E+05 ± 8.51E+04 | 2.53E−04 ± 1.16E−05 | 0.336 | 9.16E+05 | 3.08E−04 |

TABLE 3b

CDR sequences in Kabat, Chothia and IMGT format

| Clone Name | Sequence | SEQ ID NO |
|---|---|---|
| ISB 880-C8_CDRH1_Kabat 26-35 | GGQFSEYAIQ | 87 |
| ISB 880-C8_CDRH1_Kabat (31-35) | EYAIQ | 269 |
| ISB 880-C8_CDRH1_Chothia (26-31) | GGQFSE | 270 |
| ISB 880-C8_CDRH1_IMGT (27-38) | GGQFSEYA | 271 |
| ISB 880-C8_CDRH2_Kabat 50-58 | YIIPLHGQVD | 147 |
| ISB 880-C8_CDRH2_Kabat (50-65) | YIIPLHGQVDYAQKFQG | 272 |
| ISB 880-C8_CDRH2_Chothia (52-56) | IPLHGQ | 273 |
| ISB 880-C8_CDRH2_IMGT (56-65) | IIPLHGQV | 274 |
| ISB 880-C8_CDRH3_Kabat 93-102 | ARGQTLYDSGRQFDI | 207 |
| ISB 880-C8_CDRH3_Kabat (95-102) | GQTLYDSGRQFDI | 275 |
| ISB 880-C8_CDRH3_Chothia (95-102) | GQTLYDSGRQFDI | 276 |
| ISB 880-C8_CDRH3_IMGT (105-117) | ARGQTLYDSGRQFDI | 277 |
| ISB 880-C8-H1B-B8_CDRH1_Kabat 26-35 | GSPAEPYAIQ | 114 |
| ISB 880-C8-H1B-B8_CDRH1_Kabat (31-35) | EPYAIQ | 278 |
| ISB 880-C8-H1B-B8_CDRH1_Chothia (26-31) | GSPAEP | 279 |
| ISB 880-C8-H1B-B8_CDRH1_IMGT (27-38) | GSPAEPYA | 280 |
| ISB 880-C8-H1B-B8_CDRH2_Kabat 50-58 | YIIPLHGQVD | 174 |
| ISB 880-C8-H1B-B8_CDRH2_Kabat (50-65) | YIIPLHGQVDYAQKFQG | 281 |
| ISB 880-C8-H1B-B8_CDRH2_Chothia (52-56) | IPLHGQ | 282 |
| ISB 880-C8-H1B-B8_CDRH2_IMGT (56-65) | IIPLHGQV | 283 |

TABLE 3b-continued

CDR sequences in Kabat, Chothia and IMGT format

| Clone Name | Sequence | SEQ ID NO |
|---|---|---|
| ISB 880-C8-H1B-B8_CDRH3_Kabat 93-102 | ARGQTLYDSGRQFDI | 234 |
| ISB 880-C8-H1B-B8_CDRH3_Kabat (95-102) | GQTLYDSGRQFDI | 284 |
| ISB 880-C8-H1B-B8_CDRH3_Chothia (95-102) | GQTLYDSGRQFDI | 285 |
| ISB 880-C8-H1B-B8_CDRH3_IMGT (105-117) | ARGQTLYDSGRQFDI | 286 |
| ISB 880-C8-H2B-C10_CDRH1_Kabat 26-35 | GGQFSEYAIQ | 121 |
| ISB 880-C8-H2B-C10_CDRH1_Kabat (31-35) | EYAIQ | 287 |
| ISB 880-C8-H2B-C10_CDRH1_Chothia (26-31) | GGQFSE | 288 |
| ISB 880-C8-H2B-C10_CDRH1_IMGT (27-38) | GGQFSEYA | 289 |
| ISB 880-C8-H2B-C10_CDRH2_Kabat 50-58 | YIIPSLGGYD | 181 |
| ISB 880-C8-H2B-C10_CDRH2_Kabat (50-65) | YIIPSLGGYDYAQKFQG | 290 |
| ISB 880-C8-H2B-C10_CDRH2_Chothia (52-56) | IPSLGG | 291 |
| ISB 880-C8-H2B-C10_CDRH2_IMGT (56-65) | IIPSLGGY | 292 |
| ISB 880-C8-H2B-C10_CDRH3_Kabat 93-102 | ARGQTLYDSGRQFDI | 241 |
| ISB 880-C8-H2B-C10_CDRH3_Kabat (95-102) | GQTLYDSGRQFDI | 293 |
| ISB 880-C8-H2B-C10_CDRH3_Chothia (95-102) | GQTLYDSGRQFDI | 294 |
| ISB 880-C8-H2B-C10_CDRH3_IMGT (105-117) | ARGQTLYDSGRQFDI | 295 |
| ISB 880-C8-recC_CDRH1_Kabat 26-35 | GSPAEPYAIQ | 124 |
| ISB 880-C8-recC_CDRH1_Kabat (31-35) | EPYAIQ | 296 |
| ISB 880-C8-recC_CDRH1_Chothia (26-31) | GSPAEP | 297 |
| ISB 880-C8-recC_CDRH1_IMGT (27-38) | GSPAEPYA | 298 |
| ISB 880-C8-recC_CDRH2_Kabat 50-58 | YIIPSLGGYD | 184 |
| ISB 880-C8-recC_CDRH2_Kabat (50-65) | YIIPSLGGYDYAQKFQG | 299 |
| ISB 880-C8-recC_CDRH2_Chothia (52-56) | IPSLGG | 300 |
| ISB 880-C8-recC_CDRH2_IMGT (56-65) | IIPSLGGY | 301 |
| ISB 880-C8-recC_CDRH3_Kabat 93-102 | ARGQTLYDSGRQFDI | 244 |
| ISB 880-C8-recC_CDRH3_Kabat (95-102) | GQTLYDSGRQFDI | 302 |
| ISB 880-C8-recC_CDRH3_Chothia (95-102) | GQTLYDSGRQFDI | 303 |
| ISB 880-C8-recC_CDRH3_IMGT (105-117) | ARGQTLYDSGRQFDI | 304 |

TABLE 3b-continued

CDR sequences in Kabat, Chothia and IMGT format

| Clone Name | Sequence | SEQ ID NO |
|---|---|---|
| ISB 880-C8-recC-AA_CDRH1_Kabat26-35 | GSPAEPYAIQ | 125 |
| ISB 880-C8-recC-AA_CDRH1_Kabat (31-35) | EPYAIQ | 305 |
| ISB 880-C8-recC-AA_CDRH1_Chothia (26-31) | GSPAEP | 306 |
| ISB 880-C8-recC-AA_CDRH1_IMGT (27-38) | GSPAEPYA | 307 |
| ISB 880-C8-recC-AA_CDRH2_Kabat 50-58 | YIIPSLGGYD | 185 |
| ISB 880-C8-recC-AA_CDRH2_Kabat (50-65) | YIIPSLGGYDYAQKFQG | 308 |
| ISB 880-C8-recC-AA_CDRH2_Chothia (52-56) | IPSLGG | 309 |
| ISB 880-C8-recC-AA_CDRH2_IMGT (56-65) | IIPSLGGY | 310 |
| ISB 880-C8-recC-AA_CDRH3_Kabat 93-102 | ARGQTLYAAGRQFDI | 245 |
| ISB 880-C8-recC-AA_CDRH3_Kabat (95-102) | GQTLYAAGRQFDI | 311 |
| ISB 880-C8-recC-AA_CDRH3_Chothia (95-102) | GQTLYAAGRQFDI | 312 |
| ISB 880-C8-recC-AA_CDRH3_IMGT (105-117) | ARGQTLYAAGRQFDI | 313 |
| ISB 880-C8-recC-DA_CDRH1_Kabat 26-35 | GSPAEPYAIQ | 126 |
| ISB 880-C8-recC-DA_CDRH1_Kabat (31-35) | EPYAIQ | 314 |
| ISB 880-C8-recC-DA_CDRH1_Chothia (26-31) | GSPAEP | 315 |
| ISB 880-C8-recC-DA_CDRH1_IMGT (27-38) | GSPAEPYA | 316 |
| ISB 880-C8-recC-DA_CDRH2_Kabat 50-58 | YIIPSLGGYD | 186 |
| ISB 880-C8-recC-DA_CDRH2_Kabat (50-65) | YIIPSLGGYDYAQKFQG | 317 |
| ISB 880-C8-recC-DA_CDRH2_Chothia (52-56) | IPSLGG | 318 |
| ISB 880-C8-recC-DA_CDRH2_IMGT (56-65) | IIPSLGGY | 319 |
| ISB 880-C8-recC-DA_CDRH3_Kabat 93-102 | ARGQTLYDAGRQFDI | 246 |
| ISB 880-C8-recC-DA_CDRH3_Kabat (95-102) | GQTLYDAGRQFDI | 320 |
| ISB 880-C8-recC-DA_CDRH3_Chothia (95-102) | GQTLYDAGRQFDI | 321 |
| ISB 880-C8-recC-DA_CDRH3_IMGT (105-117) | ARGQTLYDAGRQFDI | 322 |
| ISB 880-C8-recC-AS_CDRH1_Kabat 26-35 | GSPAEPYAIQ | 127 |
| ISB 880-C8-recC-AS_CDRH1_Kabat (31-35) | EPYAIQ | 323 |
| ISB 880-C8-recC-AS_CDRH1_Chothia (26-31) | GSPAEP | 324 |

TABLE 3b-continued

CDR sequences in Kabat, Chothia and IMGT format

| Clone Name | Sequence | SEQ ID NO |
|---|---|---|
| ISB 880-C8-recC-AS_CDRH1_IMGT (27-38) | GSPAEPYA | 325 |
| ISB 880-C8-recC-AS_CDRH2_Kabat 50-58 | YIIPSLGGYD | 187 |
| ISB 880-C8-recC-AS_CDRH2_Kabat (50-65) | YIIPSLGGYDYAQKFQG | 326 |
| ISB 880-C8-recC-AS_CDRH2_Chothia (52-56) | IPSLGG | 327 |
| ISB 880-C8-recC-AS_CDRH2_IMGT (56-65) | IIPSLGGY | 328 |
| ISB 880-C8-recC-AS_CDRH3_Kabat 93-102 | ARGQTLYASGRQFDI | 247 |
| ISB 880-C8-recC-AS_CDRH3_Kabat (95-102) | GQTLYASGRQFDI | 329 |
| ISB 880-C8-recC-AS_CDRH3_Chothia (95-102) | GQTLYASGRQFDI | 330 |
| ISB 880-C8-recC-AS_CDRH3_IMGT (105-117) | ARGQTLYASGRQFDI | 331 |
| ISB 880-C8-recC-ES_CDRH1_Kabat 26-35 | GSPAEPYAIQ | 128 |
| ISB 880-C8-recC-ES_CDRH1_Kabat (31-35) | EPYAIQ | 332 |
| ISB 880-C8-recC-ES_CDRH1_Chothia (26-31) | GSPAEP | 333 |
| ISB 880-C8-recC-ES_CDRH1_IMGT (27-38) | GSPAEPYA | 334 |
| ISB 880-C8-recC-ES_CDRH2_Kabat 50-58 | YIIPSLGGYD | 188 |
| ISB 880-C8-recC-ES_CDRH2_Kabat (50-65) | YIIPSLGGYDYAQKFQG | 335 |
| ISB 880-C8-recC-ES_CDRH2_Chothia (52-56) | IPSLGG | 336 |
| ISB 880-C8-recC-ES_CDRH2_IMGT (56-65) | IIPSLGGY | 337 |
| ISB 880-C8-recC-ES_CDRH3_Kabat 93-102 | ARGQTLYESGRQFDI | 248 |
| ISB 880-C8-recC-ES_CDRH3_Kabat (95-102) | GQTLYESGRQFDI | 338 |
| ISB 880-C8-recC-ES_CDRH3_Chothia (95-102) | GQTLYESGRQFDI | 339 |
| ISB 880-C8-recC-ES_CDRH3_IMGT (105-117) | ARGQTLYESGRQFDI | 340 |
| ISB 880-C8-recC-ET_CDRH1_Kabat 26-35 | GSPAEPYAIQ | 129 |
| ISB 880-C8-recC-ET_CDRH1_Kabat (31-35) | EPYAIQ | 341 |
| ISB 880-C8-recC-ET_CDRH1_Chothia (26-31) | GSPAEP | 342 |
| ISB 880-C8-recC-ET_CDRH1_IMGT (27-38) | GSPAEPYA | 343 |
| ISB 880-C8-recC-ET_CDRH2_Kabat 50-58 | YIIPSLGGYD | 189 |
| ISB 880-C8-recC-ET_CDRH2_Kabat (50-65) | YIIPSLGGYDYAQKFQG | 344 |

TABLE 3b-continued

CDR sequences in Kabat, Chothia and IMGT format

| Clone Name | Sequence | SEQ ID NO |
|---|---|---|
| ISB 880-C8-recC-ET_CDRH2_Chothia (52-56) | IPSLGG | 345 |
| ISB 880-C8-recC-ET_CDRH2_IMGT (56-65) | IIPSLGGY | 346 |
| ISB 880-C8-recC-ET_CDRH3_Kabat93-102 | ARGQTLYETGRQFDI | 249 |
| ISB 880-C8-recC-ET_CDRH3_Kabat (95-102) | GQTLYETGRQFDI | 347 |
| ISB 880-C8-recC-ET_CDRH3_Chothia (95-102) | GQTLYETGRQFDI | 348 |
| ISB 880-C8-recC-ET_CDRH3_IMGT (105-117) | ARGQTLYETGRQFDI | 349 |

Example 3: Optimization of Anti-IL-1RAP-C3 Clone

Recombinant Target Antigens

Recombinant human IL-1RAP-ECD(S21-E359)-avi-his protein (SEQ ID NO. 1), hereafter referred to as recombinant human IL-1RAP-avi-his protein, was produced in house as described in Example 1.

Library Generation and Selection

Affinity maturation of anti-IL-1RAP-C3 clone was performed as described in Example 2 with the following modifications. Purified phage particles ($10^{12}$ plaque-forming units) and magnetic DYNABEADS® Protein G beads (Novex, Life technologies) were blocked with 3% MPBS for 1 h at RT. 200 nM of human IgG1 were captured on blocked Protein G beads for 30 min at RT. Next, blocked phages were deselected against IgG1 coated beads for 1 h at RT. Deselected phages were then incubated with 1 nM, 0.5 nM and 0.1 nM of mouse IL-1RAP-Fc (Sino Biological, catalog no.52657-M02H) for round 1, round 2 and round 3, respectively. After 1 h incubation, 1 µM of recombinant human IL-1RAP-avi-his protein produced in house (non-biotinylated, SEQ ID NO. 1) was added for 3 h at RT during rounds 2 and 3. Antigen bound phages were captured on Protein G beads for 30 min at RT and beads were five times with PBS-Tween 0.1% and twice with PBS.

Affinity Screening by SPR

SPR analysis was used to confirm specific binding activity of the new scFv clones and rank the positive clones according to their binding profile. Measurements were performed as described in Example 2 with the following modifications. Recombinant mouse IL-1RAP-Fc (Sino Biological, catalog no.52657-M02H) was diluted to a final concentration of 200 nM in acetate buffer pH 4.5 (BIACORE™, GE HEALTHCARE®, catalog no. BR100350) and subsequently immobilized on fc2 to a level of about 1500 RU on a Series S CM5 sensor CHIP (BIACORE™, GE HEALTHCARE®, catalog no. BR100530) using an amine coupling kit following manufacturer recommendations. Filtered periplasmic extracts were injected directly on the covalently coupled mouse IL-1RAP CM5 sensor chip on the flow-path 1 and 2 (flow-path 1 being used as reference). The scFv clones showing the best binding profiles were reformatted in Fab fragments as described in Example 1.

Affinities of the Fab fragments to mouse IL-1RAP were measured as described in Example 1, with the following modifications. Measurements were performed on Series S CM5 sensor chips (BIACORE™ T200, BIACORE™, GE HEALTHCARE®, catalog no. BR100530) coupled with anti-human IgG Fc (BIACORE™, GE HEALTHCARE®, catalog no. BR100839) using a commercial amine coupling kit (BIACORE™, GE HEALTHCARE®, catalog no. BR100050). SPR measurements were performed with commercially available recombinant mouse IL-1RAP Fc fusion protein (Sino Biologicals, catalog no. 52657-M02H). The affinities to mouse IL-1RAP were assessed by immobilizing mouse IL-1RAP-Fc and using Fab fragments as analyte. Around 60 RUs of mouse IL-1RAP Fc fusion protein were captured on fc2 of a Series S CM5 sensor chip coupled with anti-human IgG Fc. Fab fragments were injected in single cycle kinetic at different concentrations ranging from 0.04 to 5 nM, in HBS-EP+ buffer (BIACORE™, GE HEALTHCARE®, catalog no. BR100669) at a flow rate of 30/min for 3 min on fc1 and fc2 (fc1 being used as reference). Dissociation was monitored for 10 min.

Mouse IgG2a LALA Expression

For expression of Anti-IL-1RAP-C3-A3-mmIgG2a-LALA (SEQ ID NO: 73 and 74), equal quantities of each engineered chains vectors were co-transfected into suspension-adapted HEK293-EBNA cells (ATCC®-LGL standards, Teddington, UK; Cat. No: CRL-10852) using Polyethyleneimine (PEI; Polysciences). Typically, cells were prepared at 8 million cells per ml in RPMI 1640 (Biowest) supplemented with 0.1% Pluronic F-68 (GIBCO®). Cells were then transfected with a DNA-PEI mixture at 37° C. Four hours post-transfection, the cell culture was diluted 1:1 in EX-CELL® 293 supplemented with Phenol Red or BalanCD HEK293 (IRVINE SCIENTIFIC®) and 4 mM L-Glutamine and incubated for 5 days with orbital shaking at 37° C., 5% C02 and 80% humidity. Cell-free culture supernatants containing the recombinant proteins were prepared by centrifugation followed by filtration, and used for further purification. Antibodies were purified as described for Anti-IL1-RAP-C8-RecC-ES-IgG1-LALA in Example 2, with following modifications. For Anti-IL-1RAP-C3-A3-mmIgG2a-LALA (SEQ ID NO: 73 and 74), proteins were eluted with an acidic buffer (typically glycine 0.1 M pH 3.5). Collected fractions were analyzed on a SDS-PAGE and selected based on apparent purity. Fractions of interest were then pooled and dialyzed against 1× PBS, pH 7.4 at 4° C. The purified antibodies were stored at −80° C. after sterile filtration on 0.2 µm filter and further analyzed as described for Anti-IL1-RAP-C8-RecC-ES-IgG1-LALA in Example 2.

Mouse IgG2a LALA Binding Affinities to Mouse IL-1RAP

Surface plasmon resonance (SPR) was used to measure the binding affinities of mouse IgG2a LALA molecules for mouse IL-1RAP. Affinity was measured on a BIACORE™ T200 instrument (BIACORE™, GE HEALTHCARE®) at 25° C. and analyzed with the BIACORE™ T200 Evaluation Software (v3.1). Measurements were performed on Series S CM5 sensor chips (BIACORE™ T200, BIACORE™, GE HEALTHCARE®, catalog no. BR100530) coupled with anti-mouse IgG Fc (BIACORE™, GE HEALTHCARE®, catalog no. BR100838) using a commercial amine coupling kit (BIACORE™, GE HEALTHCARE®, catalog no. BR100050). SPR measurements were performed with commercially available recombinant mouse IL-1RAP-his (Sino Biologicals, catalog no. 52657-M08H). The affinity to mouse IL-1RAP was assessed by immobilizing anti-mouse IL-1RAP mouse IgG2a LALA molecule and using mouse IL-1RAP protein as analyte. Around 150 RU of mouse IgG2a LALA was captured on fc2 of a Series S CM5 sensor chip coupled with anti-mouse IgG Fc. Mouse IL-1RAP-his was injected in multi cycle kinetic at different concentrations ranging from 0.14 to 100 nM, in HBS-EP+ buffer (BIACORE™, GE HEALTHCARE®, catalog no. BR100669) at a flow rate of 30 µl/min for 3 min on fc1 and fc2 (fc1 being used as reference). Dissociation was monitored for 15 min. After each cycle, the surface was regenerated with 60 µl of regeneration solution provided with anti-mouse IgG Fc capture kit (BIACORE™, GE HEALTHCARE®, catalog no. BR100838). Experimental data were processed using the 1:1 Langmuir kinetic fitting model. Measurements included zero-concentration samples for referencing. Chi$^2$. U— and residual values were used to evaluate the quality of a fit between the experimental data and individual binding models.

Results

Affinity maturation of anti-IL-1RAP-C3 clone (SEQ ID NO. 12) involved diversification of CDR-H1 (Kabat positions 27-35), CDR-H2 (Kabat positions 50-53 and 55-58) and CDR-H3 (Kabat positions 95-101 minus 2) in five individual libraries. ScFv clones having a slower off-rate than the parental anti-IL-1RAP-C3 clone as measured by SPR were isolated. Selected scFv clones were reformatted and expressed as Fab fragments and affinities to human and cynomolgus IL-1RAP were measured as described in Example 1. One clone referred to as Fab clone anti-IL-1RAP-C3-A3 had the highest affinity to mouse IL-1RAP. Heavy chain sequence identification numbers and binding affinity of the mentioned clones are reported in Table 4.

TABLE 4

Overview of the developed Fab clones and their relative affinity to mouse IL-1RAP

| Library | Clone name | Clone heavy chain SEQ ID NO | Mouse IL-1RAP KD (nM) |
|---|---|---|---|
| CDR-H1 | Anti-IL-1RAP-C3-MP01-A2 Fab | SEQ ID NO. 60 | 0.68 |
| CDR-H1 | Anti-IL-1RAP-C3-MP01-A3 Fab | SEQ ID NO. 61 | 0.14 |
| CDR-H1 | Anti-IL-1RAP-C3-MP01-B5 Fab | SEQ ID NO. 62 | 0.21 |
| CDR-H1 | Anti-IL-1RAP-C3-MP01-B7 Fab | SEQ ID NO. 63 | 0.17 |
| CDR-H1 | Anti-IL-1RAP-C3-MP01-D2 Fab | SEQ ID NO. 64 | 0.22 |
| CDR-H1 | Anti-IL-1RAP-C3-MP01-F5 Fab | SEQ ID NO. 65 | 0.28 |
| CDR-H1 | Anti-IL-1RAP-C3-MP01-G10 Fab | SEQ ID NO. 66 | 0.21 |
| CDR-H1 | Anti-IL-1RAP-C3-MP02-B8 Fab | SEQ ID NO. 67 | 0.49 |
| CDR-H1 | Anti-IL-1RAP-C3-MP02-F6 Fab | SEQ ID NO. 68 | 0.26 |
| CDR-H1 | Anti-IL-1RAP-C3-MP02-G2 Fab | SEQ ID NO. 69 | 0.32 |
| CDR-H3 | Anti-IL-1RAP-C3-UCP01-H4 Fab | SEQ ID NO. 70 | 0.45 |

Anti-IL-1RAP-C3-A3 clone was selected as potential mouse surrogate for anti-human IL-1RAP candidate and was expressed in mouse IgG2a LALA backbone, equivalent to human IgG1 LALA isotype in mouse. Sequences identification numbers as well as mean binding kinetic constants and standard deviations calculated from at least two independent experiments to human IL-1RAP or mouse IL-1RAP of the mentioned clone are reported in Table 5. Anti-IL-1RAP-C3-A3 clone did not show any detectable binding to cynomolgus monkey IL-1RAP by SPR (data not shown). Sequences identification numbers as well as mean binding kinetic constants and standard deviations calculated from three independent experiments to mouse IL-1RAP of the mentioned clone are reported in Table 5. One representative example of SPR binding sensorgram of anti-IL-1RAP-C3-A3 mmIgG2a LALA to mouse IL-1RAP is shown in FIG. 5.

TABLE 5

SPR binding affinities of mouse IgG2a LALA to mouse IL-1RAP

| Clone name | Clone heavy chain SEQ ID NO | Clone light chain SEQ ID NO | Affinity to human IL-1RAP | | | Affinity to mouse IL-1RAP | | |
|---|---|---|---|---|---|---|---|---|
| | | | KD ± SD (nM) | Ka ± SD (1/Ms) | Kd ± SD (1/s) | KD ± SD (nM) | Ka ± SD (1/Ms) | Kd ± SD (1/s) |
| Anti-IL-1RAP-C3-A3 mmIgG2a LALA | SEQ ID NO. 73 | SEQ ID NO. 74 | 14.0 ± 0.01 | 6.41E+03 ± 1.03E+03 | 8.97E−04 ± 1.42E−04 | 0.545 ± 0.091 | 1.38E+05 ± 6.98E+03 | 7.46E−05 ± 9.24E−06 |

Example 4: In vitro biological characterization of anti-human IL-1RAP_candidate_1

4.1 Anti-human IL-1RAP_candidate_1 binds specifically to human IL-1RAP

Binding of anti-human IL-1RAP_candidate_1 (termed anti-IL1RAP-C8-RecC herein and comprising heavy chain CDRs SEQ ID Nos: 128, 188 and 248 and light chain sequence SEQ ID NO: 71) on membrane-bound human IL-1RAP was evaluated by flow cytometry using multiple human cell lines and human cell types such as HaCaT keratinocytic cell line (AddexBio, T0020001) but also human primary cells (human neutrophils and fibroblast).

In brief, cells were harvested, counted, and plated at 50,000 cells/well in a 96-well round-bottom plate. The plate was centrifuged at 350 g for 3 minutes and the cells were resuspended in 50d of FACS® buffer (PBS (1×)+2.5% FCS+2 mM EDTA+0.05% $NaN_3$) containing various concentrations (ranging from 50 to 0.00003 µg/ml) of either anti-human IL-1RAP_candidate_1 or Isotype control_5 antibodies. Stained cells were incubated for 30 minutes at 4° C., washed twice with FACS® buffer at 350 g for 3 min and resuspended in 100 µl of a monoclonal anti-human IgG PE-Cyanine7 secondary antibody (Biolegend, 409316) diluted 1/200 in FACS® buffer. Cells were then washed twice and resuspended in 200 µl of FACS® buffer containing SYTOX® Green dead cell stain (THERMO FISHER SCIENTIFIC®, S34860) and samples were acquired on a CYTOFLEX® instruments (Beckman Coulter). The cells were gated based on size on FSC vs SSC and analyzed for PE-Cyanine7-geometric mean (geomean) fluorescence intensity using FLOWJO® software. Finally, relative geomean fluorescence intensity was calculated by subtracting fluorescence of anti-human IL-1RAP_candidate 1 per fluorescence of Isotype control_5. As depicted in FIGS. 6A, 6B, 6C, 6D, and 6E, anti-human IL-1RAP_candidate_1 antibody recognizes membrane-bound IL-1RAP expressed on HaCaT cell line and all primary cells. Multiple independent experiments were performed using multiple donors. Associated $K_D$ values are summarized on table 6.

TABLE 6

| Cell type | N | KD +/− SD (nM) |
| --- | --- | --- |
| HaCaT cell line | 4 | 0.75 +/− 0.36 |
| HaCaT IL-1RAP KO | 3 | N/A |
| Human Neutrophils | 6 | 1.67 +/− 0.96 |
| Normal Cynomolgus Fibroblast | 4 | 1.55 +/− 1.45 |
| Normal Human Fibroblast | 4 | 3.1 +/− 2.14 |

Table 6 shows KD values determined from Flow Cytometry experiments in which anti-human IL-1RAP_candidate 1 (•) or Isotype control_3 (■) (FIGS. 6A, 6B, 6C, 6D, and 6E) were incubated with various cell lines and cell types. KD values were extracted from nonlinear sigmoidal regression. Curves showing sufficient goodness of fit ($R^2 > 0.7$) were included in the summary table.

In order to further demonstrate the selective binding of anti-human IL-1RAP_candidate_ito IL-1RAP, the same procedure was performed against HaCaT cell line knocked out of the IL-1RAP gene previously generated and characterized internally. The experiment was conducted following the same protocol described above. Results from FIGS. 6A, 6B, 6C, 6D, and 6E show that anti-human IL-1RAP_candidate_1 antibody binds selectively to membrane-bound IL-1RAP as it does not bind to HaCaT IL-1RAP knockout cell line.

Figure 6A:
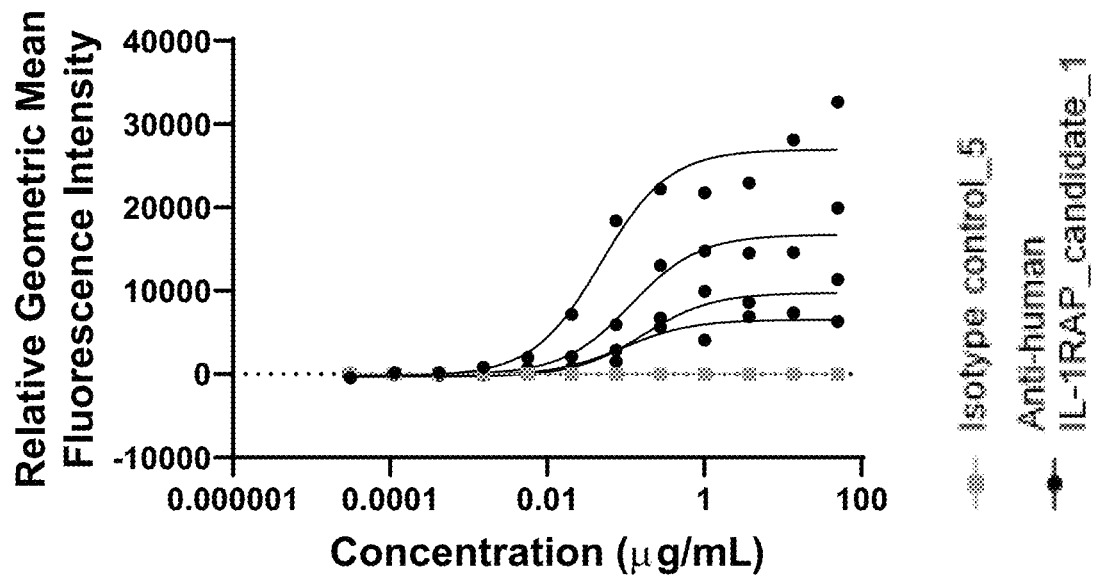
FIG. 6A shows that anti-human IL-1RAP_candidate_1 binds specifically to human IL-1RAP on HaCaT wild-type cells.
Figure 6B:
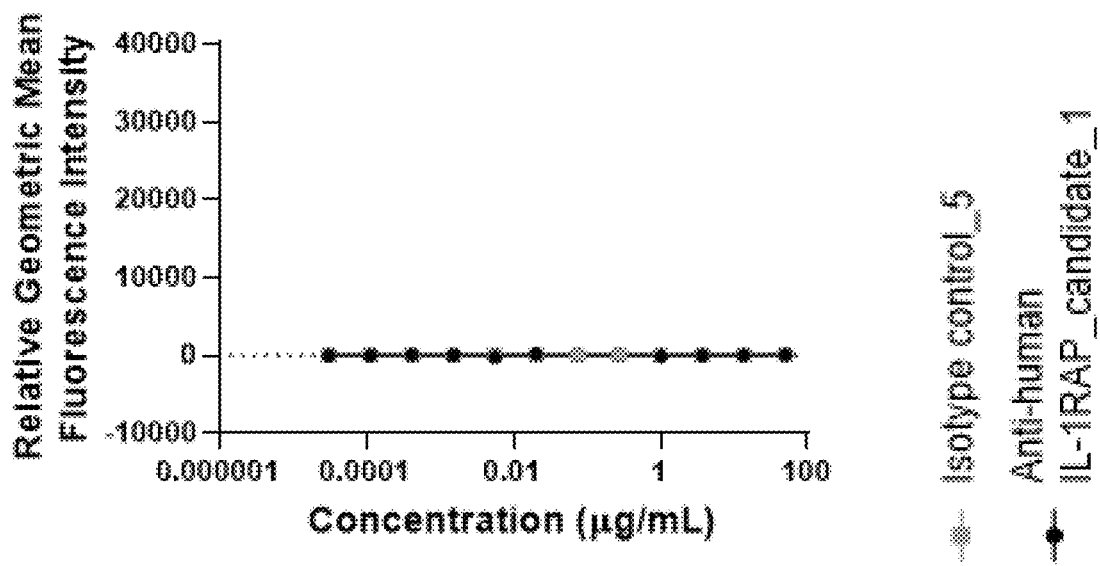
FIG. 6B shows that anti-human IL-1RAP_candidate_1 does not bind to human IL-1RAP on HaCaT IL-1RAP KO cells.
Figure 6C:
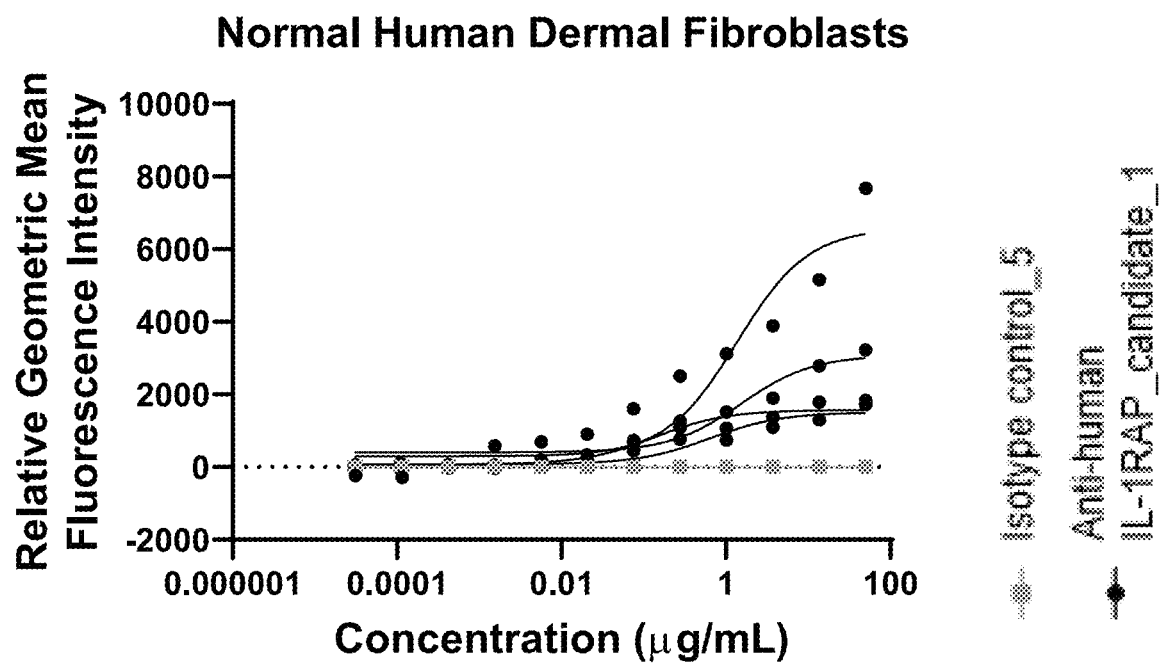
FIG. 6C shows that anti-human IL-1RAP_candidate_1 binds specifically to human IL-1RAP on normal human dermal fibroblasts.
Figure 6D:
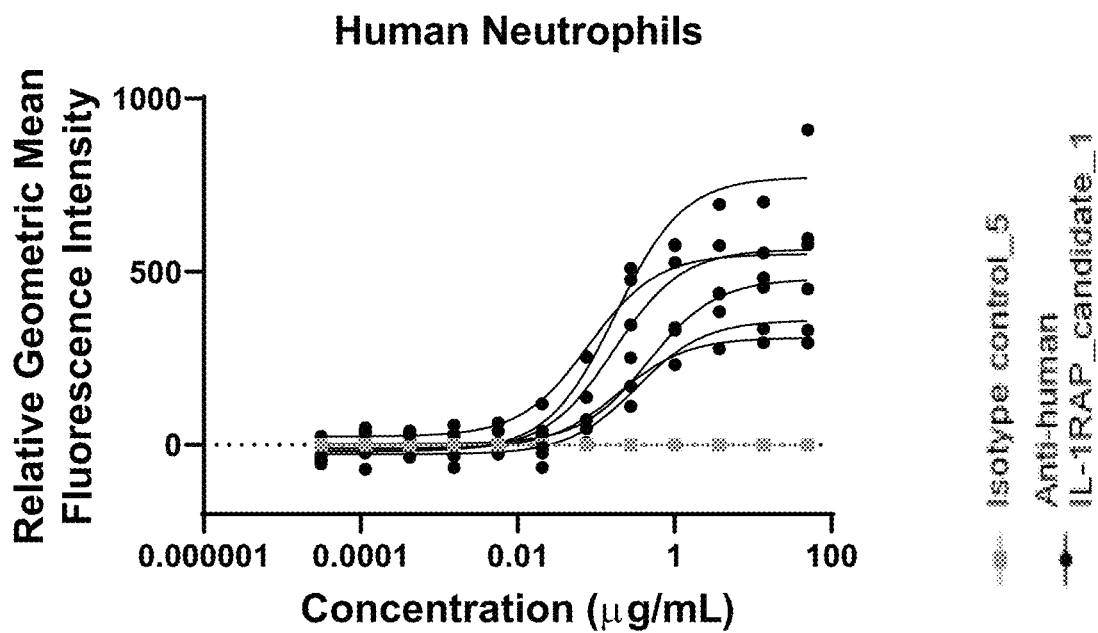
FIG. 6D shows that anti-human IL-1RAP_candidate_1 binds specifically to human IL-1RAP on human neutrophils.
Figure 6E:
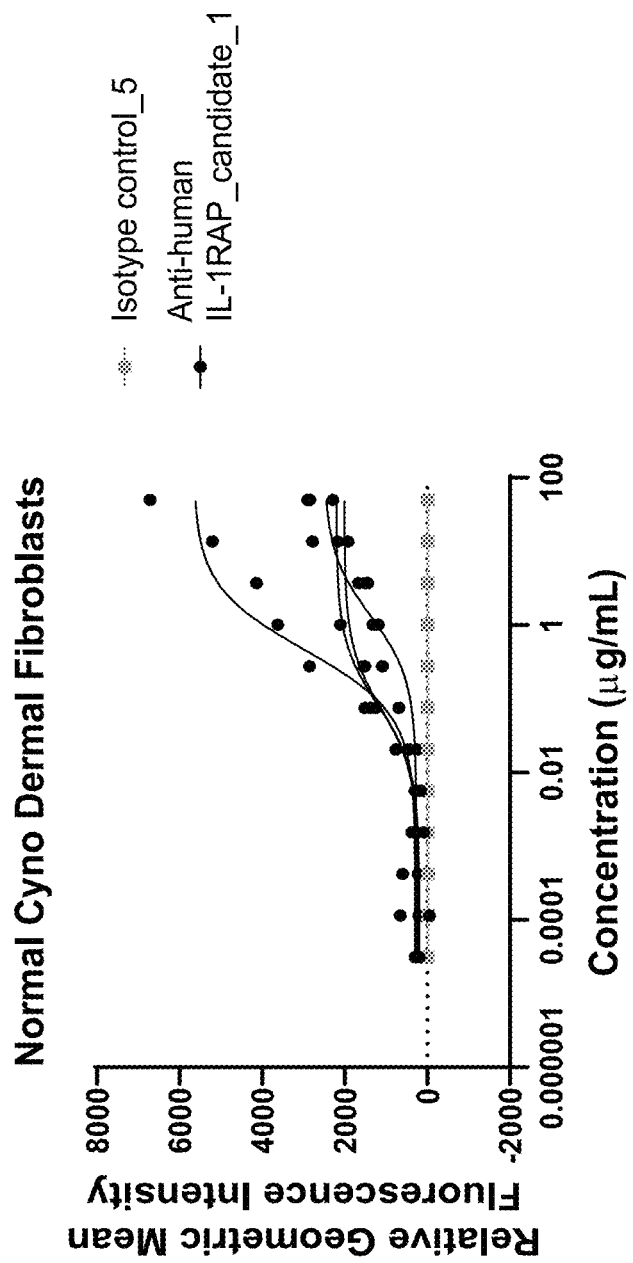
FIG. 6E shows that anti-human IL-1RAP_candidate_1 binds specifically to Cyno IL-1RAP on normal cynomolgus dermal fibroblasts. A dose-response of anti-human IL-1RAP_candidate_1 (•) or Isotype control_5 (■) was incubated with various cell lines and cell types. Bound antibodies were detected with a monoclonal anti-human IgG PE-Cyanine7 secondary antibody. The graphs show the nonlinear sigmoidal regression binding curves (Relative Geometric Mean Fluorescence Intensity) for each cell lines. Each data point is a measurement for a given cell line. Multiple independent experiments were performed across several donors (HaCaT and HaCaT IL-1RAP KO: 4 and 3 independent experiments; Human Dermal Fibroblasts: 2 independent experiments—total of 5 donors; Human Neutrophil: 2 experiments—total of 6 donors; Cyno Dermal Fibroblasts: 2 independent experiment—total of 4 donors).

4.2 Anti-Human IL-1RAP Candidate 1 Binds to Cynomolgus IL-1RAP on Primary Monkey Cells In order to assess the cross-reactivity of anti-human IL-1RAP_candidate_1 to cynomolgus IL-1RAP, the same procedure described above was performed using monkey fibroblasts. In this assay, anti-human IL-1RAP_candidate_1 binds to cynomolgus IL-1RAP-expressing fibroblasts (FIG. 6E). The KD values for the tested cell type is summarized on Table 6.

4.3 Anti-Human IL-1RAP Candidate 1 Inhibits Both IL-1 and IL-36-Induced Cytokine Release in HaCaT Stimulation Assay In order to evaluate the potential of anti-human IL-1RAP_candidate_1 to inhibit IL-1, IL-33 and IL-36 pathways, several assays were developed using different cell systems. The keratinocytic cell line HaCaT was used to test the inhibition of IL-1 and IL-36 pathways as this particular cell line is sensitive to IL-1 and IL-36 but not to IL-33 cytokines as measured by the production of downstream mediators such as IL-6 and IL-8 (CXCL8).

Briefly, HaCaT cells were harvested, counted, and resuspended at $0.05 \times 10^6$ cells/ml in complete DMEM medium (DMEM+10% FBS+1% Glutamine+1% Pen/Strp+1% NEAA+1% NaPyr). Hundred µl of cells were distributed in a 96-well flat-bottom plate and incubated at 37° C., 5% $CO_2$ for 16 h. The next day, cells were incubated with 50 µl of either anti-human IL-1RAP_candidate 1 (ranging from 50 to 0.000005 gg/ml) or Isotype control 5 (unique dose of 50 gg/ml), serially diluted in the assay medium (complete DMEM medium) for 30 minutes. At the end of incubation, 50 µl of either human IL-1β or IL-36γ (both from Peprotech) were supplied to the appropriate wells. After 24 h of incubation at 37° C., 5% $CO_2$, 100 µl of supernatants were transferred to a 96-well round-bottom plate and stored to −80° C. freezer until quantification for cytokine/chemokine. IL-6 and IL-8 productions in the culture supernatants were measured with LUMINEX® using ProcartaPlex kits (THERMO FISHER SCIENTIFIC®, EPX01A-10213-901 and EPX01A-10204-901) following manufacturers' instructions.

Figure 7A:
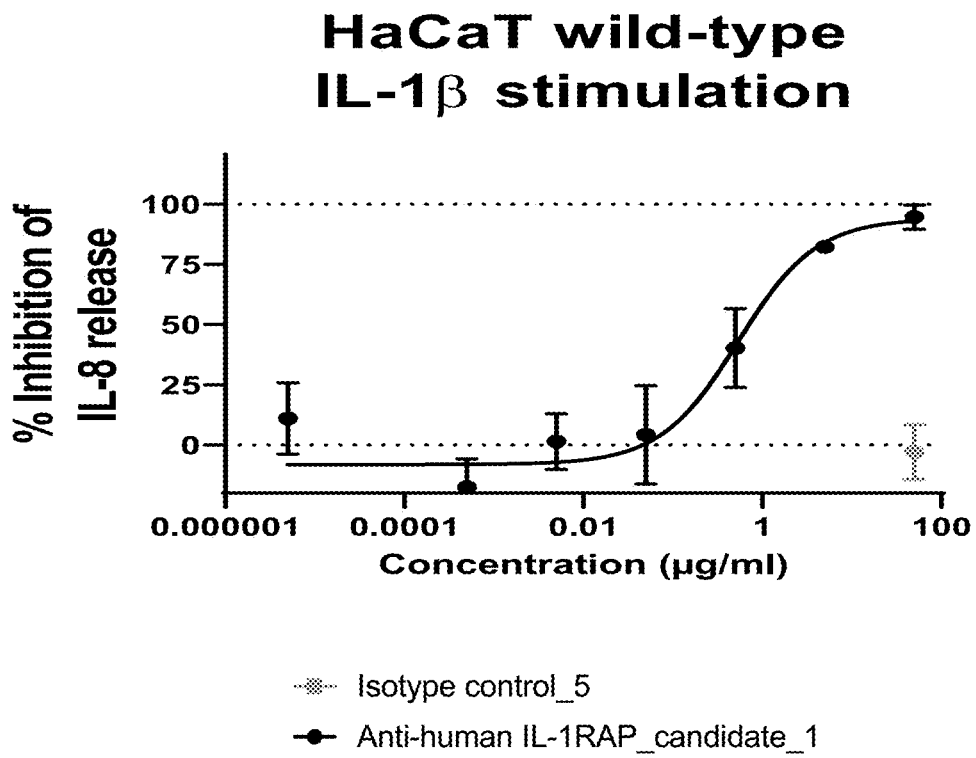
FIG. 7A shows that anti-human IL-1RAP_candidate_1 inhibits IL-1D-induced IL-8 release in a wild-type HaCaT stimulation assay.
Figure 7B:
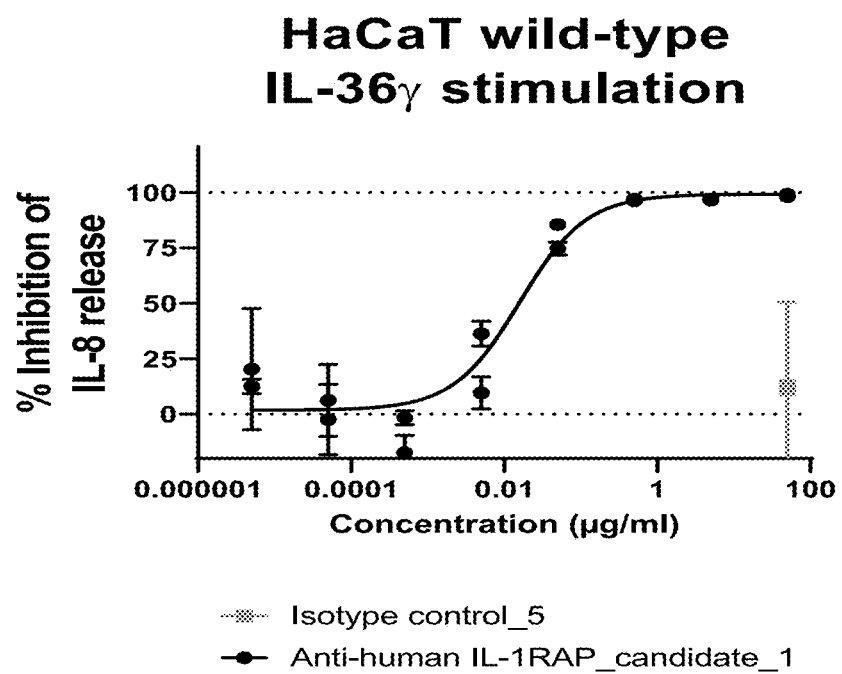
FIG. 7B shows that anti-human IL-1RAP_candidate_1 inhibits IL-36γ-induced IL-8 release in a wild-type HaCaT stimulation assay. A dose-response of anti-human IL-1RAP_candidate_1 (•) or Isotype control_5 (■) were incubated with IL-1β or IL-36γ-stimulated HaCaT wild-type cell line. The graphs show the nonlinear sigmoidal regression inhibition curves for each stimulus (IL-1β or IL-36γ). Each data point is a measurement for an independent experiment. Two independent experiments were performed.

As depicted in FIGS. 7A and 7B, anti-human IL-1RAP_candidate_1 inhibits the release of IL-8 chemokine upon IL-AP (FIG. 7A) or IL-36γ (FIG. 7B) stimulation of HaCaT cells. This effect is dose-dependent for both pathways and even more potent on IL-36γ as the interactions leading to the trimeric complex formation of IL-36/IL-36R/IL-1RAP are weaker than the interactions regulating the formation of IL-1/IL-IR/IL-1RAP complex. Criteria of inclusion were established and applied to all assays to obtain sufficient window of stimulation or Stimulation Index (SI) in order to determine percentages of inhibition.

$$\text{Stimulation Index} = \frac{\text{Cytokine X release}_{Cytokine\ only}}{\text{Cytokine X release}_{Cells\ only}}$$

X is the cytokine considered (IL-6 or IL-8)
"Cytokine only" is the condition where cells were only incubated with stimulator (IL-1β or IL-367)
"Cells only" is the condition where cells were incubated with medium.

Two independent experiments were performed and $EC_{50}$ values of inhibition are summarized on table

TABLE 7

Anti-human IL-1RAP_candidate_1 inhibits both IL-1 and IL-36-induced cytokine release in HaCaT stimulation assay.

| Stimulator | Readout | N | EC20 | EC50 | EC80 | Max Inhibition |
|---|---|---|---|---|---|---|
| IL-1b | IL-6 | 1 | 2.19 | 8.77 | 35.05 | 106.21 |
| IL-1b | IL-8 | 2 | 0.88 +/− 0.34 | 3.53 +/− 1.38 | 14.11 +/− 5.5 | 94.65 +/− 3.5 |
| IL-36g | IL-6 | 2 | 0.04 +/− 0.03 | 0.17 +/− 0.12 | 0.67 +/− 0.5 | 107.6 +/− 3.87 |
| IL-36g | IL-8 | 2 | 0.03 +/− 0.02 | 0.11 +/− 0.07 | 0.45 +/− 0.29 | 98.61 +/− 0.75 |

The table shows EC20, EC50, EC80 and Maximum Inhibition values determined from stimulation as which anti-human IL-1RAP_candidate_1 (•) or Isotype control 5 (m) (FIGS. 7A and 7B), were incubated with IL-1β (FIG. 7A) or IL-36γ (FIG. 7B) stimulated HaCaT. ECx values were extracted from nonlinear sigmoidal regression. Sufficient stimulation conditions (Stimulation Index>1.8) and curves showing sufficient goodness of fit ($R^2$>0.7) were included in the summary table.

4.4 Anti-Human IL-1RAP_Candidate_1 Inhibits IL-33-Induced Cytokine Release in Human Peripheral Blood Mononuclear Cells (PBMC) Stimulation Assay Human peripheral blood mononuclear cells (hPBMC) were used to test the inhibition of IL-33 pathway in IL-12-costimulation assay. It has been reported in the literature that IL-12 or IL-33 alone trigger no to minimal IFN-g production from hPBMC whereas combined treatment with IL-33 and IL-12 resulted in the synergistic production of IFN-g (Smithgall et al., 2008; Ochayon et al., 2019).

Briefly, hPMBCs were harvested from buffy coats obtained from La Chaux-de-Fonds (Switzerland) Transfusion Center using ficoll density gradient isolation. Cells were counted and resuspended at 1×10⁶ cells/ml in complete RPMI medium (RPMI+10% FBS+1% Glutamine+1% Pen/Strep). One hundred µl of hunHundredPBMC were distributed in a 96-well round-bottom plate. Cells were incubated with 50 µl of human IL-12 and IL-33 (both from Peprotech) for 15 minutes. At the end of incubation, 50 µl of either anti-human IL-1RAP_candidate_1 (ranging from 50 to 0.000005 gg/ml) serially diluted in the assay medium (complete RPMI medium) were added to the appropriate wells. An Isotype control_5 antibody was tested at a unique dose of 50 gg/ml. After 48 h of incubation at 37° C., 5% $CO_2$, 100 µl of supernatants were transferred to a 96-well round-bottom plate and stored to −80° C. freezer until quantification for cytokine levels. IFN-g production in the culture supernatants was measured with LUMINEX® using ProcartaPlex kit (THERMO FISHER SCIENTIFIC®, EPX01A-10228-901) following manufacturers' instructions. The same procedure was performed using IL-1β stimulation, instead of IL-33+IL-12, leading to IL-8 release.

Figure 8A:
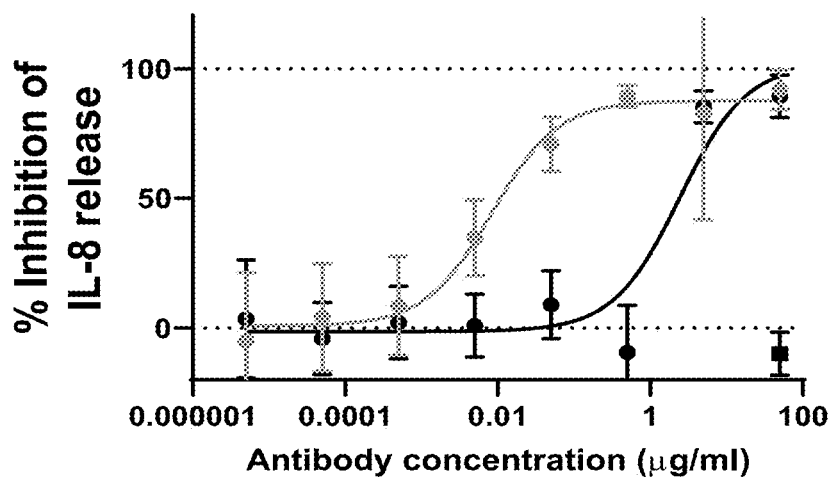
FIG. 8A shows that anti-human IL-1RAP_candidate_1 inhibits IL-1-induced IL-8 release in a Human peripheral blood mononuclear cells (PBMC) stimulation assay.
Figure 8B:
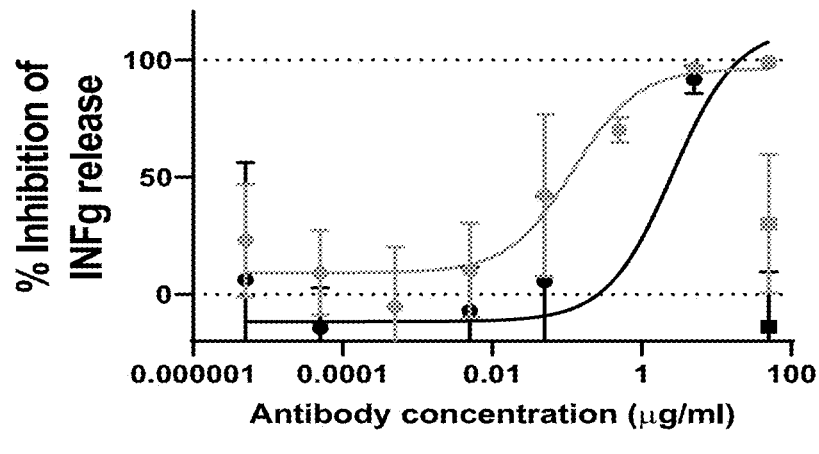
FIG. 8B shows that anti-human IL-1RAP_candidate_1 inhibits IL-12+IL-33-induced IFN-γ release in a Human peripheral blood mononuclear cells (PBMC) stimulation assay. A dose-response of anti-human IL-1RAP_candidate_1 (9) or Isotype control isotype 4 (w) were incubated with IL-1β or IL-12+IL-33-stimulated hPBMC. The graphs show the nonlinear sigmoidal regression inhibition overlay curves for each stimulus (IL-1 or IL-12+IL-33). Each curve represents the overlay of 3 donors. Two independent experiments were performed.
Figure 9A:
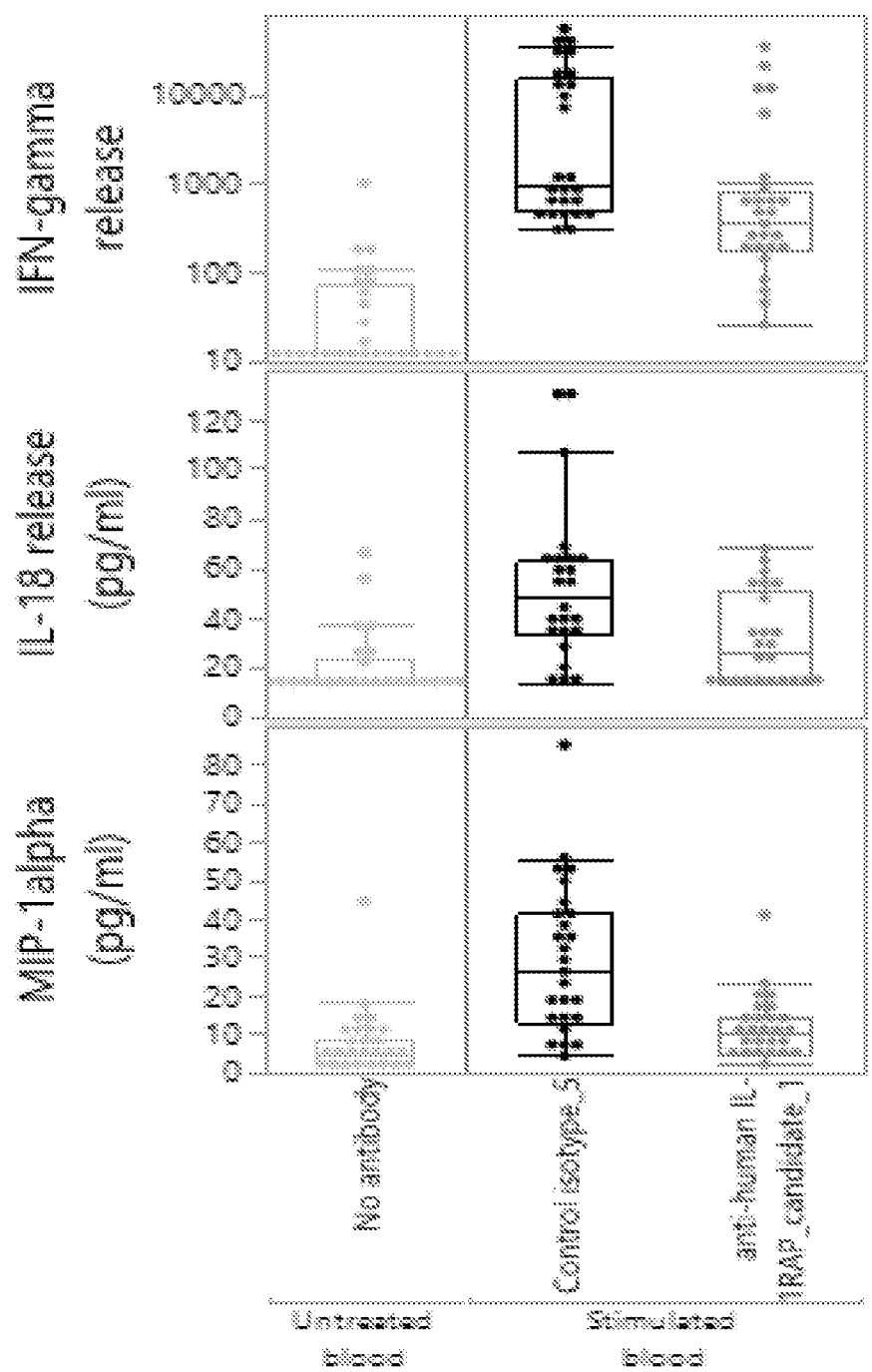
FIG. 9A shows that anti-human IL-1RAP_candidate_1 inhibits MIP-1α, IL-18, and IFN-γ release in a whole blood restimulation assay upon combined stimulation with IL-1α, IL-1β, IL-12, IL-33, IL-36α, IL-36β and IL-36γ.
Figure 9C:
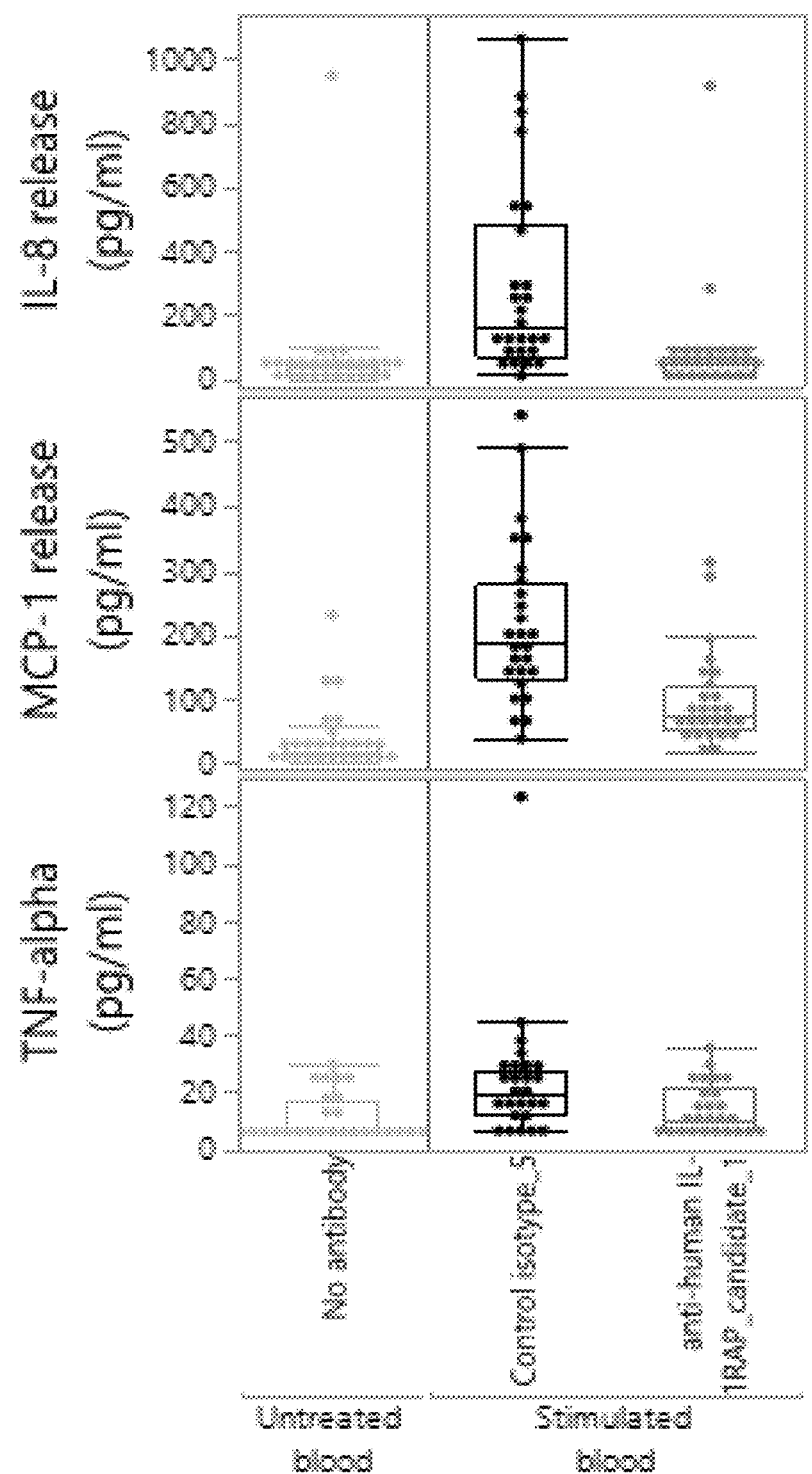
FIG. 9C shows that anti-human IL-1RAP_candidate 1 inhibits TNF-α, MCP-1, and IL-8 release in a whole blood restimulation assay upon combined cytokine stimulation with IL-1α, IL-1β, IL-12, IL-33, IL-36α, IL-36β and IL-36γ.
Figure 9D:
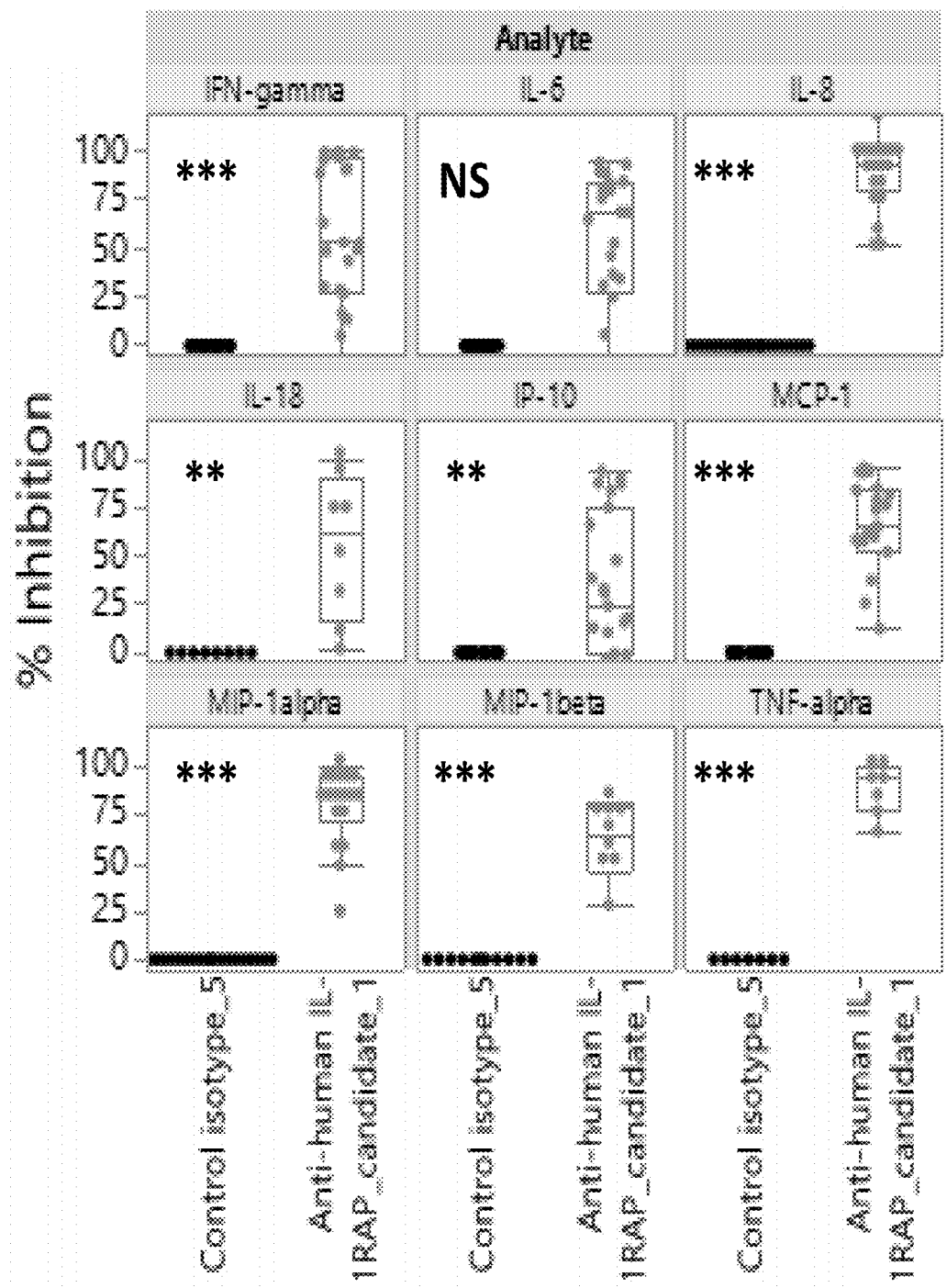
FIG. 9D shows the normalized inhibition data for IFN-γ, IL-6, IL-8, IL-18, IP-10, MCP-1, MIP-1ca, MIP-1, and TNF-α. Anti-human IL-1RAP_candidate_1 (•) or Isotype control 5 (■) were incubated in human whole blood with a combination of IL-1α, IL-1β, IL-12, IL-33, IL-36α, IL-36R and IL-36γ. The graphs show the impact of combination on cytokines and chemokines release and the effect of anti-human IL-1RAP_candidate_1 on each readout either on soluble markers release (FIG. 9A, FIG. 9B, FIG. 9C) and on normalized inhibition data (FIG. 9D). Each point is a measurement for one donor. Eight independent experiments were performed. NS stands for Not significant; * for $0.01<p<0.05$; ** for $0.001<p<0.01$; * for $p<0.001$

As depicted in FIG. 8B (Grey curves, bottom figure), anti-human IL-1RAP_candidate__I inhibits the release of IFN-g cytokine upon concomitant stimulation of IL-12 and IL-33 of PBMC. This effect is dose-dependent.

Additionally, it has been reported that IL-1 RAP could be detected as a soluble molecule in peripheral blood with a concentration reaching approximately 300 ng/ml. In order to assess if anti-human IL-1RAP_candidate_1 was able to inhibit IL-1/IL-33 pathways in the presence of soluble IL-1RAP, the same experimental procedure described above was conducted with the addition of soluble IL-1RAP in the IL-1β or IL-12+IL-33 cytokine mixtures. Results are shown in FIGS. 8A and 8B and demonstrate that anti-human IL-1RAP_candidate_1 can compete with soluble IL-1RAP and retain its ability to block cytokine release upon stimulation of human PBMC with IL-1β (FIG. 8A) and IL-33 (FIG. 8B).

Two independent experiments were performed using a total of 6 donors. The $EC_{50}$ values of inhibition are summarized on table 8.

TABLE 8

Anti-human IL-1RAP_candidate_1 inhibits IL-33-induced cytokine release in Human peripheral blood mononuclear cells (PBMC) stimulation assay.

| Stimulator | Readout | Soluble IL-1RAP | N | EC20 | EC50 | EC80 | Max Inhibition |
|---|---|---|---|---|---|---|---|
| IL-1b | IL-6 | Absence | 6 | 0.01 +/− 0.01 | 0.04 +/− 0.04 | 0.17 +/− 0.15 | 98.82 +/− 2.64 |
| IL-1b | IL-8 | Absence | 6 | 0.02 +/− 0.01 | 0.08 +/− 0.05 | 0.33 +/− 0.18 | 92.19 +/− 3.47 |
| IL-1b | IL-6 | Presence | 6 | 1.94 +/− 1.41 | 7.76 +/− 5.64 | 31.06 +/− 22.60 | 114.25 +/− 1.04 |
| IL-1b | IL-8 | Presence | 6 | 2.61 +/− 2.04 | 10.44 +/− 8.15 | 41.77 +/− 32.60 | 107.62 +/− 10.71 |
| IL-33/IL-12 | IFNg | Absence | 6 | 2.07 +/− 2.91 | 8.28 +/− 11.65 | 33.10 +/− 46.61 | 93.19 +/− 6.78 |
| IL-33/IL-12 | IFNg | Presence | 5 | 14.54 +/− 19.5 | 58.16 +/− 77.82 | 232.56 +/− 311.09 | 143.98 +/− 58.06 |

Table 8 shows $EC_{20}$, $EC_{50}$, $EC_{80}$ and Maximum Inhibition values determined from stnmu ation assay which anti-human IL-1RAP_candidate 1 (•) or Isotype control_4 (■) (FIGS. 8A and 8B) were incubated with IL-1β(FIG. 8A) or IL-12+IL-33 (FIG. 8B) stimulated PBMC. $EC_x$ values were extracted from nonlinear sigmoidal regression. Sufficient stimulation conditions (Stimulation Index>1.8) and curves showing sufficient goodness of fit ($R^2$>0.7) were included in the summary table.

Taken together, these data highlight that anti-human IL-1RAP_candidate_1 is efficiently inhibiting all individual pathways using disease relevant human cellular assays.

4.5 Anti-Human IL-1RAP_Candidate_1 Inhibits Cytokine Release in Whole Blood Restimulation Assay Upon Combined Cytokine Stimulation While previous assays enabled to assess the ability of anti-human IL-1RAP_candidate_1 to inhibit individual pathways, whole blood assay was used to assess the ability of anti-human IL-1RAP_candidate_1 to inhibit combined IL-1, IL-33 and IL-36 stimulated pathways. Freshly harvested human blood from healthy donors (Citrate tubes) were distributed in 15 ml-tubes and pre-incubated with either media alone (RPMI), anti-human IL-1RAP_candidate_1 or Isotype control 5 (saturating dose) for 30 min before stimulation with a combination of IL-1α, IL-1D, IL-12, IL-33, IL-36α, IL-36P and IL-36γ to a final volume of 0.6 ml.

After 24 hrs incubation at 37° C., 5% $CO_2$, supernatants were harvested. Production of various cytokines and chemokines in the culture supernatants was measured with LUMINEX® using multiple ProcartaPlex kits (THERMO FISHER SCIENTIFIC®, 21-plex kit) following manufacturers' instructions. Statistical analysis was conducted across the 26 donors tested from 8 individual experiments. The differences between anti-human IL-1RAP_candidate_1 or Isotype control 5 were calculated within each donor and each analyte to pair all data, then analyzed using a test of mean (t-Test). In this case, H0 or null hypothesis is "the mean of the difference is equal to 0". If p-value of the t-Test is inferior to 0.05; H0 is rejected, meaning a statistical significant difference against the Isotype control_5.

Results depicted in FIGS. 9A, 9B, 9C, and 9D show that anti-human IL-1RAP_candidate_1 inhibits the release of most cytokines and chemokines statistically significantly compared to Isotype control_3.

4.6 Anti-Human IL-1RAP Candidate 1 Inhibits Neutrophil Activation Upon Incubation with Hacat Conditioned Medium Post-Stimulation with IL-1β and IL-367

IL-1 cytokine family members are involved in key inflammatory processes relevant to disease pathophysiology (Migliorini et al., 2020)). In order to further identify the properties of anti-human IL-1RAP_candidate_1, in vitro assays were performed to assess its potential ability to inhibit the cellular crosstalk between Neutrophil and skin cells.

Neutrophils were isolated from freshly harvested human blood from healthy donors (EDTA tubes) using EasySep Direct Human Neutrophil Isolation kit (Stemcell, 19666) following manufacturers' instructions. The purity of isolated Neutrophils was assessed by flow cytometry using CD15 as a specific marker for neutrophils.

HaCaT conditioned medium was prepared by incubating HaCaT cells with medium, anti-human IL-1RAP_candidate_1 or Isotype control_5 (saturating dose) for 30 min at 37° C., 5% $CO_2$. At the end of incubation, simple medium or a combination of human IL-1 P and IL-36γ cytokines (both from Peprotech) were added to the appropriate wells. After 24 h of incubation at 37° C., 5% $CO_2$, supernatants were transferred to a 96-well deep plate and stored to −80° C. freezer until quantification for cytokine/chemokine. IL-8, MCP-1, GRO-a productions in the culture supernatants were measured by LUMINEX® using ProcartaPlex kits (THERMO FISHER SCIENTIFIC®, EPX01A-10204-901, EPX01B-10281-901 and EPX01A-12122-901) following manufacturers' instructions.

Directly after isolation, human neutrophils were incubated with this previously prepared conditioned medium for 3 h at 37° C., 5% $CO_2$. After the incubation, cells were harvested and stained for 20 minutes with labelled-antibodies targeting various surface markers CD45, CD15, CD66b, CD62L, CD11b, CD54 (THERMO FISHER SCIENTIFIC®).

After 3 h of incubation, activated neutrophil were characterized by the following phenotype: CD45+CD15-CD66b+CD54-CD62L. By using the same method described above, stimulation index and percentages of inhibition were calculated for each neutrophil donor:

$$SI\ (sample) = \frac{\%\ \text{active neutrophils}_{sample}}{\text{Average}\ (\%\ \text{active neutrophils}_{HaCaT\ cells\ only})}$$

$$\%\ \text{Inhibition (sample)} = \frac{SI_{sample} - \text{Average}\ (SI)_{HaCaT\ cells\ only}}{\text{Average}\ (SI)_{HaCaT\ stimulated\ with\ cytokine\ combination} - \text{Average}\ (SI)_{HaCaT\ cells\ only}}$$

The differences between anti-human IL-1RAP_candidate_1 or Isotype control_5 were calculated within each donor to pair all data, then analysed using a test of mean (t-Test). In this case, H0 or null hypothesis is "the mean of the difference is equal to 0". If p-value of the t-Test is inferior to 0.05; H0 is rejected, meaning a statistical significant difference against the Isotype control_5.

Figure 10:
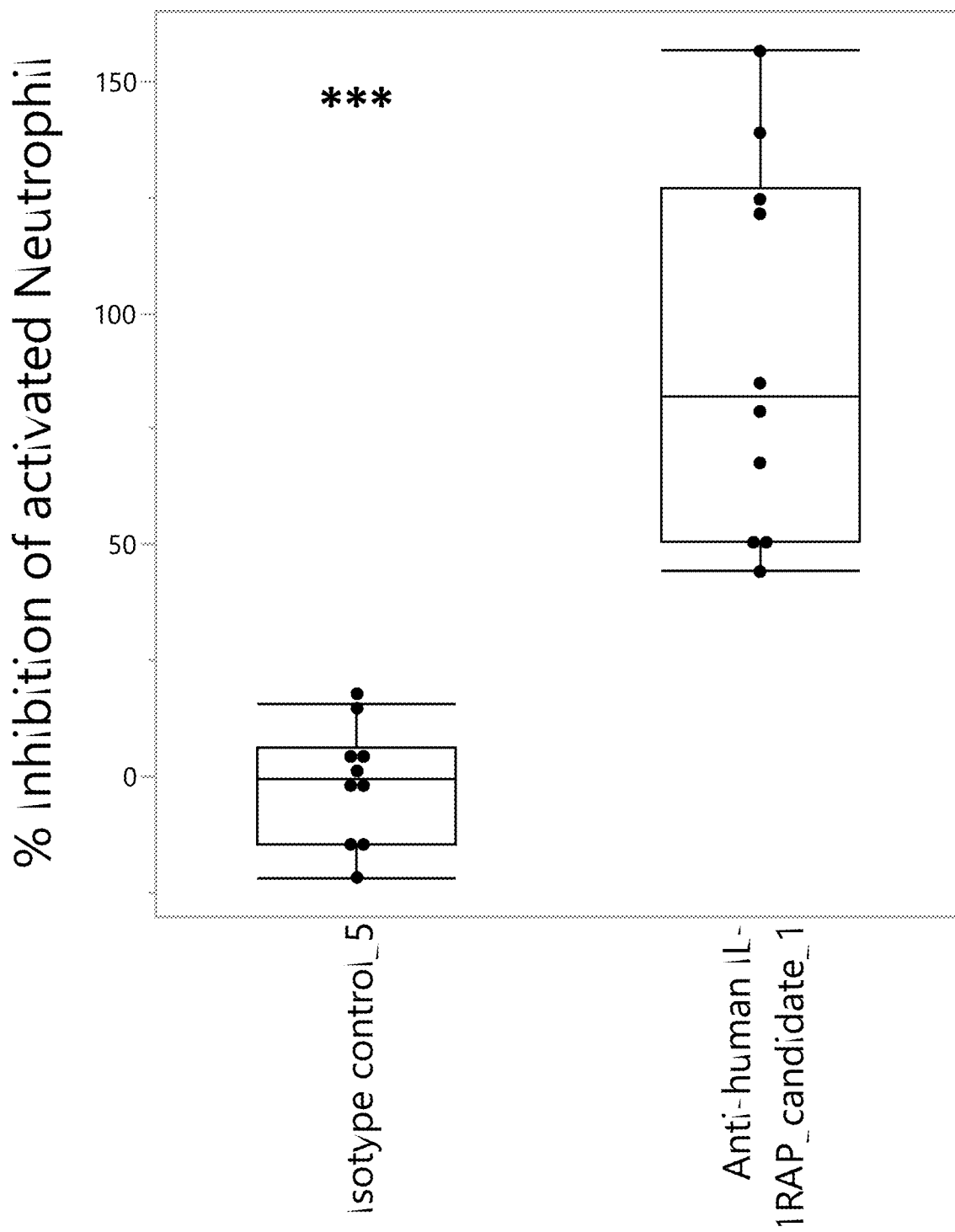
FIG. 10 shows that anti-human IL-1RAP_candidate_1 inhibits neutrophil activation upon incubation with HaCaT conditioned medium post-stimulation with IL-1R and IL-36γ. Anti-human IL-1RAP_candidate_1 (•) or Isotype control_3 (■) were incubated with IL-1β and IL-36γ-stimulated HaCaT wild-type cell line. The conditioned medium 24 h after stimulation were harvested and incubated with freshly isolated neutrophils. The graphs show the effect of anti-human IL-1RAP_candidate_1 on the percentage of activated neutrophil. Each point is a measurement for one donor. Three independent experiments were performed with a total of 9 donors. NS stands for Not significant; * for $0.01<p<0.05$; ** for $0,001<p<0.01$; * for $p<0.001$

Results depicted in FIG. 10 show that anti-human IL-1RAP_candidate 1 inhibits the activation of neutrophil mediated by chemokines released by stimulated HaCaT cells compared to Isotype control_5.

Example 5: In Vitro Biological Characterization of Anti-Mouse IL-1RAP_Candidate_1

5.1.1 Anti-Mouse IL-1RAP_Candidate_1 Binds Specifically to Mouse IL-1RAP

Binding of anti-mouse IL-1RAP_candidate_1 (comprising heavy chain CDRs SEQ ID NO: 265, 266, 267 and light chain sequence SEQ ID NO: 74) on membrane-bound mouse IL-1RAP was evaluated by flow cytometry using relevant cell line such as Murine fibroblastic NIH-3T3 cell line (ATCC®, CRL-1658).

Figure 11:
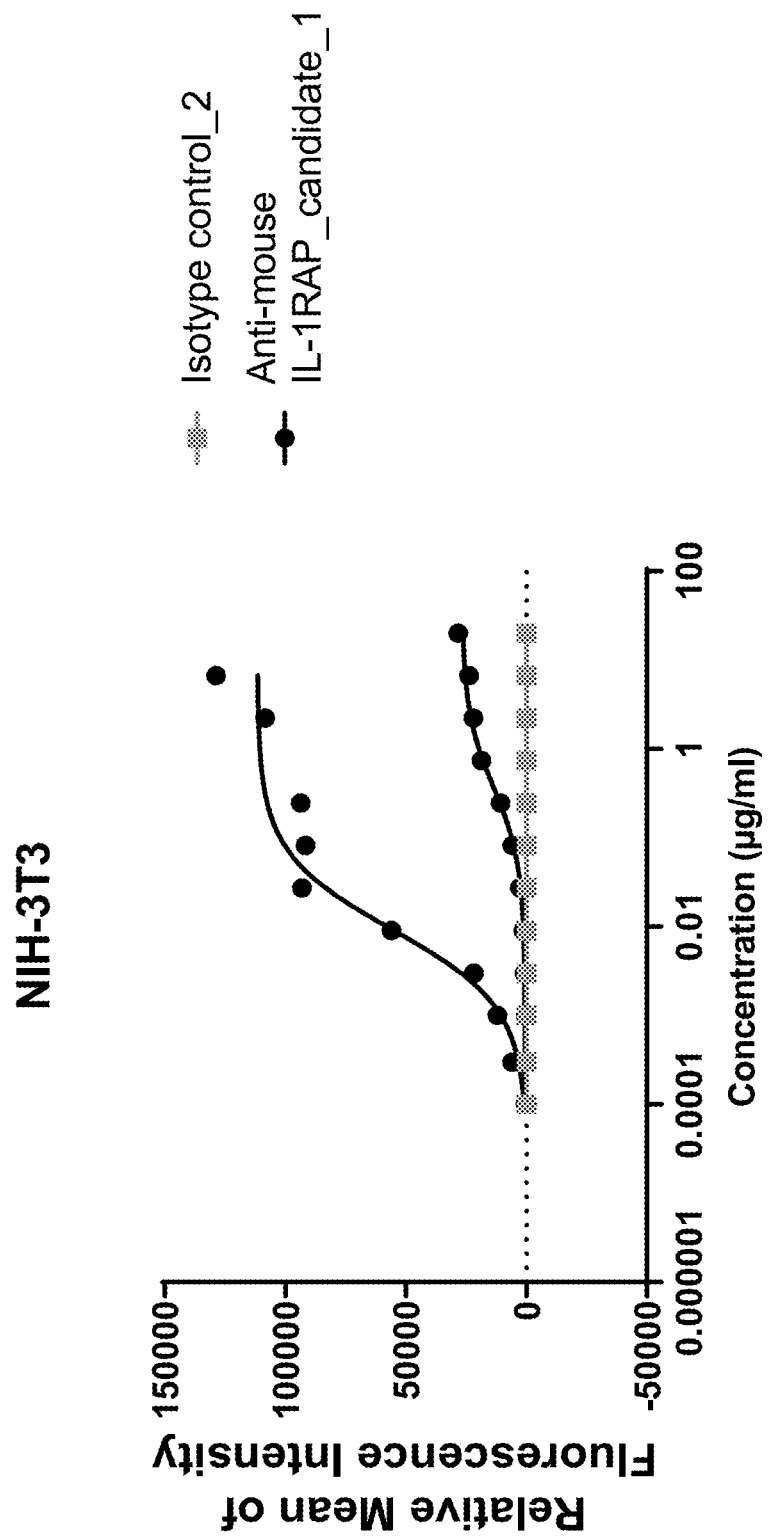
FIG. 11 shows that anti-mouse IL-1RAP_candidate_1 binds membrane-bound IL-1RAP expressed on the NIH-3T3 cell line. A dose-response of anti-human IL-1RAP_candidate_1 (•) or Isotype control_2 (■) was incubated NIH3T3 cells. Bound antibodies were detected with a monoclonal anti-human IgG PE-Cyanine7 secondary antibody.

In brief, cells were harvested, counted, and plated at 50'000 cells/well in a 96-well round-bottom plate. The plate was centrifuged at 350 g for 3 minutes and the cells were resuspended in 50 gl of FACS®7 buffer (PBS (1×)+2.5% FCS+2 mM EDTA+0.05% $NaN_3$) containing various concentrations (ranging from 20 to 0.0001 µg/ml) of either anti-mouse IL-1RAP_candidate_1 or Isotype control_2 antibodies. Stained cells were incubated for 30 minutes at 4° C., washed twice with FACS® buffer at 350 g for 3 min and resuspended in 100 µl of a monoclonal anti-mouse IgG PE-Cyanine7 secondary antibody (Biolegend, 407114) diluted 1/200 in FACS® buffer. Cells were then washed twice, and resuspended in 200 µl of FACS® buffer containing SYTOX® Green dead cell stain (THERMO FISHER SCIENTIFIC®, S34860) and samples were acquired on a CYTOFLEX® instruments (Beckman Coulter). The cells were gated based on size on FSC vs SSC and analysed for PE-Cyanine7-geometric mean (geomean) fluorescence intensity using FLOWJO® software. Finally, relative geomean fluorescence intensity was calculated by subtracting fluorescence of anti-mouse IL-1RAP_candidate 1 per fluorescence of Isotype control_2. As depicted in FIG. 11, anti-mouse IL-1RAP_candidate-1 antibody recognizes membrane-bound IL-1RAP expressed on NIH-3T3 cell line. The graph in FIG. 11 shows the nonlinear sigmoidal regression binding curves (Relative Geometric Mean Fluorescence Intensity) for each cell lines. Each data point is a measurement for a given cell line. Multiple independent experiments were performed across several donors (HaCaT and HaCaT IL-1RAP KO: 4 and 3 independent experiments; Human Dermal Fibroblasts: 2 independent experiments—total of 5 donors; Human Neutrophil: 2 experiments—total of 6 donors; Cyno Dermal Fibroblasts: 2 independent experiment—total of 4 donors). Multiple independent experiments were performed. Associated $K_n$ values are summarized in table 9.

TABLE 9

Anti-mouse IL-1RAP_candidate_1 binds specifically to mouse IL-1RAP

| Cell type | N | KD +/− SD (nM) |
|---|---|---|
| NIH-3T3 | 2 | 1.15 +/− 1.53 |

The table shows KD values determined from Flow Cytometry experiments in which anti-mouse IL-1RAP_candidate 1 (•) or Isotype control_2 (■) (FIG. 11) were incubated with NIH-3T3 cell line. KD values were extracted from nonlinear sigmoidal regression. Curves showing sufficient goodness of fit ($R^2$>0.7) were included in the summary table.

5.1.2 Anti-Mouse IL-1RAP_Candidate_1 Inhibits Both IL-33 and IL-36-Induced Cytokine Release in NIH-3T3 Stimulation Assay The potential of anti-mouse IL-1RAP_candidate 1 to inhibit IL-1, IL-33 and IL-36 pathways was tested with the murine fibroblastic cell line NIH-3T3 (ATCC®, CRL-1658) using the same method described above for HaCaT cell line.

Briefly, cells were harvested, counted, and resuspended at $0.05 \times 10^6$ cells/ml in complete DMEM medium (DMEM+10% FBS+1% Glutamine+1% Pen/Strp+1% HEPES+0.1% β-mercaptoethanol). Hundred µl of cells were distributed in a 96-well flat-bottom plate and incubated at 37° C., 5% $CO_2$ for 16 h. The next day, cells were incubated with 50 µl of either anti-mouse IL-1RAP_candidate 1 (ranging from 50 to 0.000005 gg/ml) or Isotype control_2 (unique dose of 50 µg/ml), serially diluted in the assay medium (complete DMEM medium) for 30 minutes. At the end of incubation, 50 l1 of either mouse IL-13 or human IL-33 or a combination of mouse IL-36α, (3 or 7 (all from Peprotech except for mIL-36 cytokines, R&D Systems) were supplied to the appropriate wells. After 24 h to 48 h of incubation at 37° C., 5% $CO_2$, 100 µl of supernatants were transferred to a 96-well round-bottom plate and stored to −80° C. freezer until quantification for cytokine/chemokine. IL-6 and CXCL-1/GRO-a productions in the culture supernatants were measured with LUMINEX® using ProcartaPlex kits (THERMO FISHER SCIENTIFIC®, EPX01A-20603-901 and EPX01A-26031-901) following manufacturers' instructions.

Figure 12A:
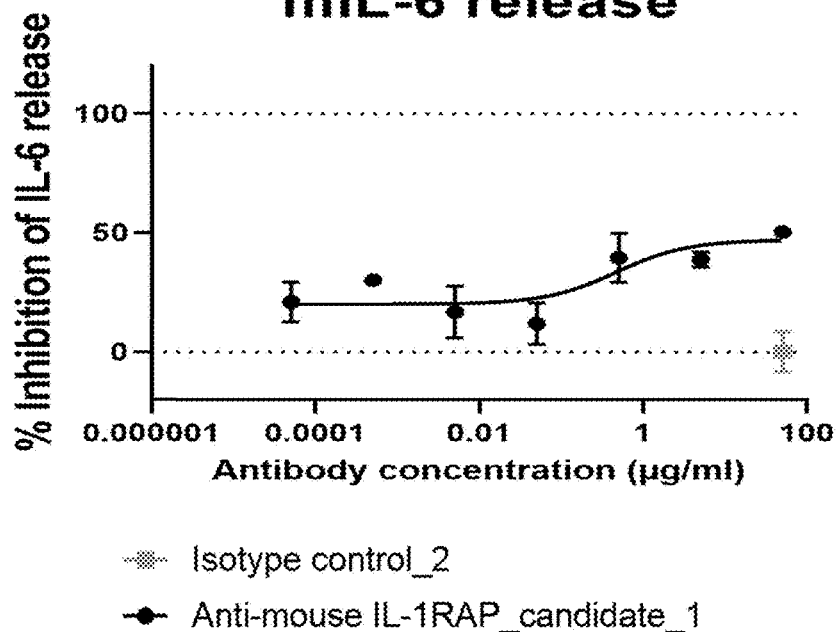
FIG. 12A shows that anti-mouse IL-1RAP_candidate_1 inhibits mIL-6 release in a NIH-3T3 mIL-1β stimulation assay.
Figure 12B:
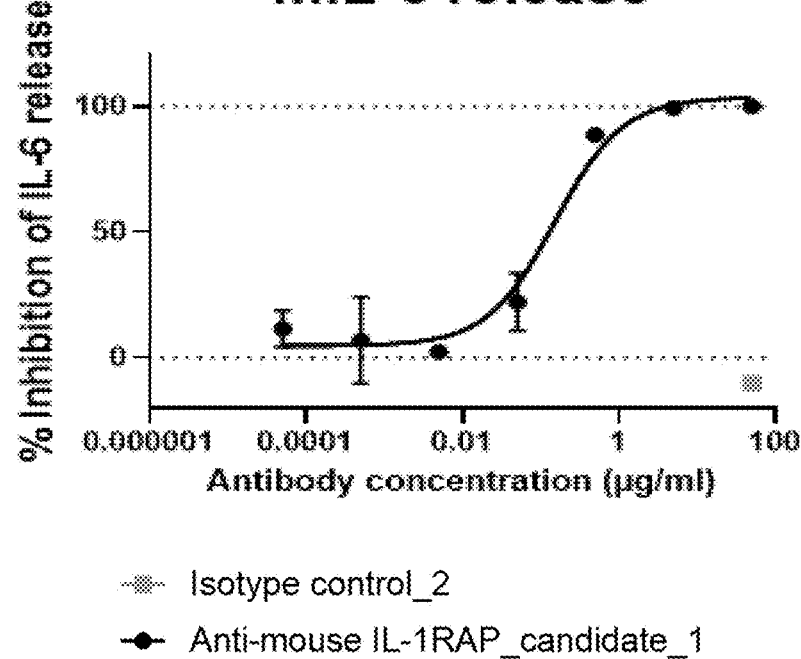
FIG. 12B shows that anti-mouse IL-1RAP_candidate_1 inhibits mIL-6 release in an NIH-3T3 hIL-33 stimulation assay.

As depicted in FIGS. 12A, 12B, and 12C, anti-mouse IL-1RAP_candidate_1 inhibits the release of both IL-6 cytokine and CXCL-1/GRO-a chemokine upon mouse IL-1β(FIG. 12A), human IL-33 (FIG. 12B), or murine IL-36s (FIG. 12C) stimulation of NIH-3T3 cells. The effect of anti-mouse IL-1RAP_candidate_1 on murine IL-1β is very weak as those cells are less sensitive to murine IL-1β stimulation leading to a stimulation window very small. This effect is dose-dependent for IL-33 and IL-36 pathways. Criteria of inclusion were established and applied to all assays to obtain sufficient window of stimulation or Stimulation Index (SI) in order to determine percentages of inhibition.

Multiple experiments were performed with Fe-portion variants of anti-mouse IL-1RAP_candidate_1, the final experiment is consistent with previous findings and depicted in FIGS. 12A, 12B, and 12C and $EC_{50}$ values of inhibition are summarized on table 10.

TABLE 10

Anti-mouse IL-1RAP_candidate_1 inhibits both IL-33 and IL-36-induced cytokine release in NIH-3T3 stimulation assay

| Stimulator | Readout | EC50 (nM) | Max Inhibition (%) |
|---|---|---|---|
| mIL-1b | mIL-6 | 3.14 | 47.1 |
| hIL-33 | mIL-6 | 1.02 | 103.6 |
| mIL-36s | mCXCL-1 | 1.68 | 108.1 |

The table shows $EC_{80}$ and Maximum Inhibition values determined from stimulation assay in which anti-mouse IL-1RAP_candidate_1 (•) or Isotype control_2 (■) (FIGS. 12A, 12B, and 12C), were incubated with mIL-13 (FIG. 12A), hIL-33 (FIG. 12B), or mIL-36s (FIG. 12C)-stimulated NIH-3T3. EC values were extracted from nonlinear sigmoidal regression. Sufficient stimulation conditions (Stimulation Index>1.8) and curves showing sufficient goodness of fit ($R^2$>0.7) were included in the summary table.

Example 6: Efficacy of Anti-Mouse IL-1RAP_Candidate_1 in an In Vivo Acute Inflammation Induced Mouse Model Materials and Methods Animal Husbandry In vivo experiments were performed in female 6-7-week-old immune-competent C57BL/6JRj mice from JANVIER LABS. All mice were maintained under standardized environmental conditions in rodent cages (20±1° C. room temperature, 50±10% relative humidity, 12 hours light dark cycle). Mice received irradiated food and bedding and 0.22 µm-filtered drinking water.

In Vivo Acute Inflammation Induced Mouse Model

Two experiments were conducted and were named respectively Bcly_4 and Bcly_5 studies.

Bcly_4 study. C57BL/6JRj mice were injected intraperitoneal with different treatments at day 0. Two hours post treatments injection, mice were injected intraperitoneal with a mix of interleukins (mouse IL-1 beta, human IL-33 and mouse IL36 alpha, beta and gamma). 24 h after the first injection of treatments, mice were euthanized. Mice serum, splenocytes and intraperitoneal lavage were harvested for ex vivo analysis. LUMINEX® was performed on mice serum. FACS® analysis was performed on splenocytes and intraperitoneal lavage.

Bcly_5 study. C57BL/6JRj mice were injected intraperitoneal with different treatments at day 0, day 1 and day 2. Two hours post treatments injection, mice were injected intraperitoneal with a mix of interleukins (mouse IL-1 beta, human IL-33 and mouse IL36 alpha, beta and gamma). 24 h and/or 72 h after the first injection of treatments, mice were euthanized. Mice serum, splenocytes and intraperitoneal lavage were harvested for ex vivo analysis. LUMINEX® was performed on mice serum. FACS® analysis was performed on splenocytes and intraperitoneal lavage.

Mice Samples Preparation for Flow Cytometry.

For splenocytes, spleens were harvested and mechanically dissociated. Cell suspensions were filtered and centrifuged. Cells were then counted and stained for immune cell profiling. Staining with a complete antibody panel and the relative controls were prepared in FACS® buffer. Samples were analyzed on the Northern lights instrument (CYTEK®). Data were analyzed using KALUZA® and GRAPHPAD PRISM@8.

For intraperitoneal lavage, PBS was injected into the peritoneal cavity. Peritoneum was gently massaged to detach cells and the fluid was then collected by making an incision in the peritoneum. Cell suspensions were filtered and centrifuged. Cells were then counted and stained for immune cell profiling. Staining with a complete antibody panel and the relative controls were prepared in FACS® buffer. Samples were analyzed on the Northern lights instrument (CYTEK®). Data were analyzed using KALUZA® and GRAPHPAD PRISM® 8.

Mice Samples Preparation for LUMINEX® Assay.

Serum samples were assessed by Multiplex LUMINEX® quantification according to the manufacturer's instructions. Beads, in-vivo samples and/or supernatants and diluted standards provided by the kit, were added to the plates, incubated overnight. The detection antibody was added to the plates and incubated for 30 minutes at room temperature. The plates were washed and streptavidin-PE was added and incubated for 30 minutes at room temperature. The plates were washed and the reading buffer was added and incubated at room temperature before reading with the LUMINEX®200 instrument. LUMINEX® data were analyzed using ProcartaPlex 1.0 Analyst software. Cytokines concentration was normalized to the upper (ULOQ) and lower (LLOQ) limit of quantification. All data below LLOQ were set to the lowest point of the standard curves and considered like unanalyzable (for GRAPHPAD PRISM® analysis no zero allowed). Data were analyzed using Excel and GRAPHPAD PRISM® 8.

Statistical Analysis

Data were analyzed using GRAPHPAD PRISIM® 8 software. Statistical analysis performed: one-way analysis of variance (ANOVA) followed by Dunnett's multiple comparison. P<0.05 was considered as statistically significant. Level of significance is represented by asterisks. (** for <0.0001; * for 0.0001; ** for 0.001 and * for 0.01).

Results and Conclusions

The efficacy of anti-mouse IL-1RAP_candidate 1 (comprising SEQ ID NO: 73 and SEQ ID NO: 74) was tested in two independent in vivo acute inflammation induced mouse model. C57BL/6JRj mice were injected intraperitoneal with different treatments at day 0 for the first study and day 0, day 1 and day 2 for the second study. Two hours post each treatments injection, mice were injected intraperitoneal with a mix of interleukins (mouse IL-1 beta, human IL-33 and mouse IL36 alpha, beta and gamma). 24 h after the first injection of treatments for the first study and 72 h after the first injection of treatments for the second study, mice were euthanized. Mice serum, splenocytes and intraperitoneal lavage were harvested for ex vivo analysis.

24 h after the first injection, anti-mouse IL-1RAP_candidate_1 showed a significant down modulation of IL-5 (FIG. 1) compared to control group (pvalue=0.0018). No significant down modulation of IL-5 induced by benchmarks Anakinra (pvalue=0.1611) and mIL36Ra (pvalue=0.4719).

TABLE 11

Figure 13:
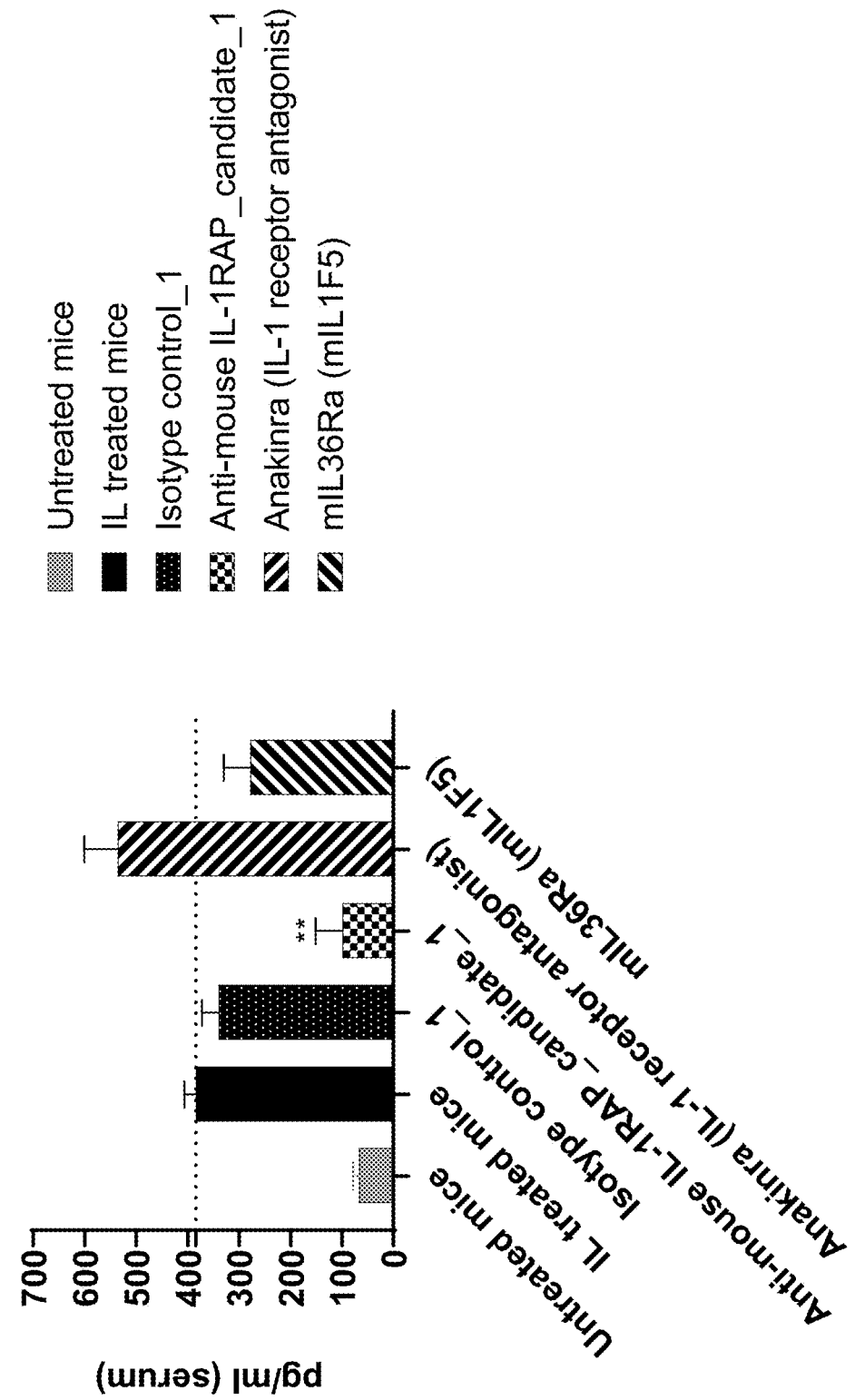
FIG. 13 shows that anti-mouse IL-1RAP_candidate_1 inhibits IL-5 release in mice serum 24 h post injection of a mix of interleukins mouse IL-1 beta, human IL-33 and mouse IL36 alpha, beta and gamma. C57BL/6JRj mice were injected intraperitoneal with different treatments at day 0. Two hours post treatments injection, mice were injected intraperitoneal with a mix of interleukins (mouse IL-1 beta, human IL-33 and mouse IL36 alpha, beta and gamma). 24 h after the first injection of treatments, mice were euthanized. Mice serum was harvested for LUMINEX® analysis. Quantification of IL-5 release. Data from Bcly_4 study.

Statistical analysis of FIG. 13

| Dunnett's multiple comparisons test | Mean Diff. | 95.00% CI of diff. | Significant? | Summary | Adjusted P Value |
|---|---|---|---|---|---|
| IL treated mice vs. Untreated mice | 317.4 | 126.1 to 508.6 | Yes | *** | 0.0006 |
| IL treated mice vs. Isotype control_1 | 44.69 | −146.5 to 235.9 | No | ns | 0.97 |
| IL treated mice vs. Anti-mouse IL-1RAP_candidate_1 | 285.5 | 94.24 to 476.7 | Yes | ** | 0.0018 |
| IL treated mice vs. Anakinra (IL-1 receptor antagonist) | −151.6 | −342.8 to 39.61 | No | ns | 0.1611 |
| IL treated mice vs. mIL36Ra (mIL1F5) | 106.1 | −85.13 to 297.3 | No | ns | 0.4719 |

72 h after the first injection, anti-mouse IL-1RAP_candidate_1 showed a significant down modulation of IL-5 (FIG. 14) and Gro-alpha (FIG. 15) compared to control group (respectively pvalue=0.0356 and pvalue=0.0009). No significant down modulation of IL-5 induced by benchmarks Anakinra (pvalue=0.5413) and mIL36Ra (pvalue=0.1337). Significant down modulation of Gro-alpha induced by Anakinra (pvalue=0.0162) but not by mIL36Ra (pvalue=0.933).

TABLE 12

Figure 14:
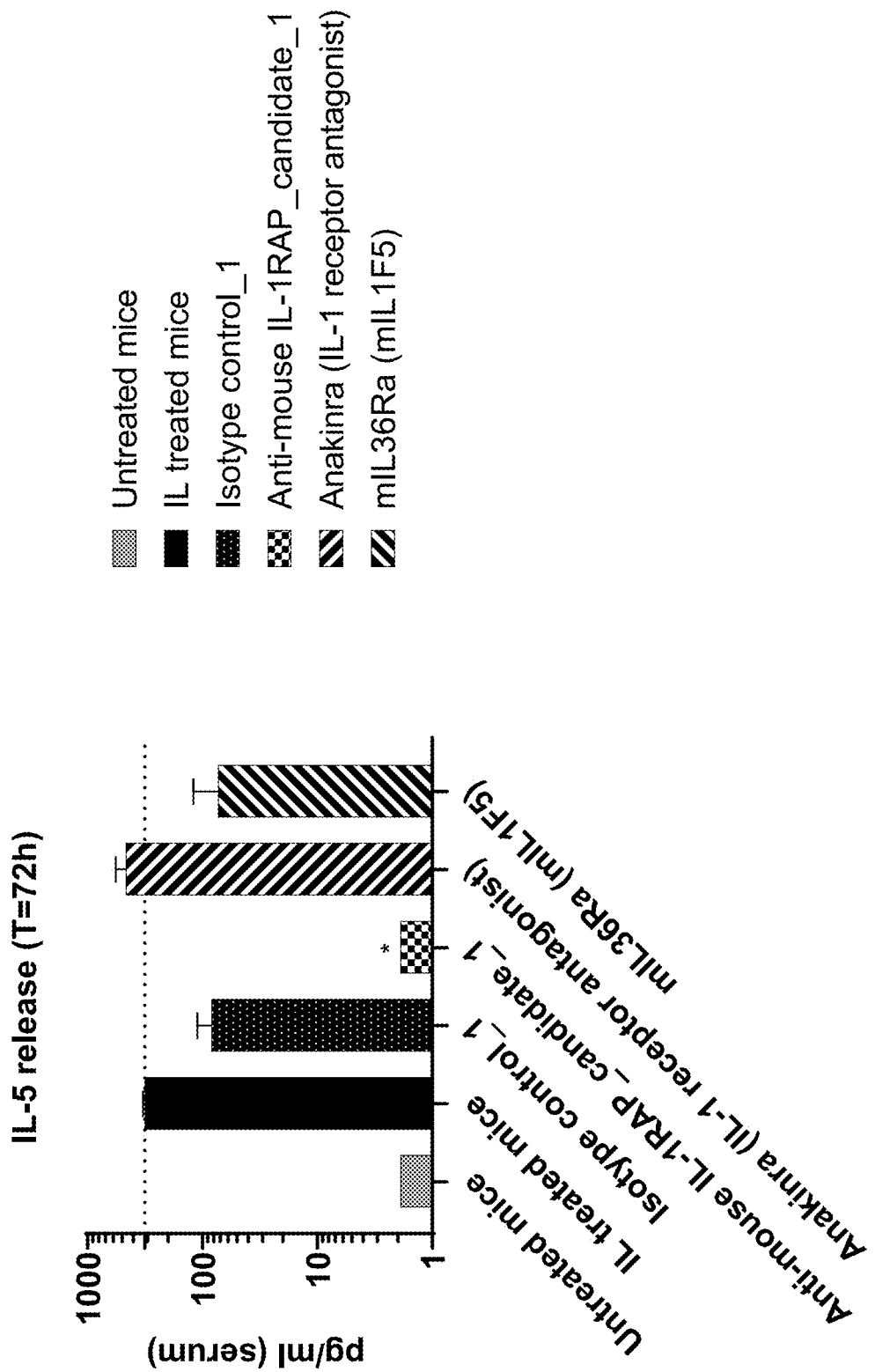
FIG. 14 shows that anti-mouse IL-1RAP_candidate_1 inhibits IL-5 release in mice serum 72 h post injection of a mix of interleukins mouse IL-1 beta, human IL-33 and mouse IL36 alpha, beta and gamma. C57BL/6JRj mice were injected intraperitoneal with different treatments at day 0, day 1 and day 2. Two hours post treatments injection, mice were injected intraperitoneal with a mix of interleukins (mouse IL-1 beta, human IL-33 and mouse IL36 alpha, beta and gamma). 72 h after the first injection of treatments, mice were euthanized. Mice serum was harvested for LUMINEX® analysis. Quantification of IL-5 release. Data from Bcly 5 study.

Statistical analysis of FIG. 14

| Dunnett's multiple comparisons test | Mean Diff. | 95.00% CI of diff. | Significant? | Summary | Adjusted P Value |
|---|---|---|---|---|---|
| IL treated mice vs. Untreated mice | 317.4 | 17.36 to 617.3 | Yes | * | 0.0356 |
| IL treated mice vs. Isotype control_1 | 235.5 | −64.48 to 535.5 | No | ns | 0.1589 |
| IL treated mice vs. Anti-mouse IL-1RAP_candidate_1 | 317.4 | 17.36 to 617.3 | Yes | * | 0.0356 |
| IL treated mice vs. Anakinra (IL-1 receptor antagonist) | −148.2 | −448.2 to 151.8 | No | ns | 0.5413 |
| IL treated mice vs. mIL36Ra (mIL1F5) | 245.8 | −54.19 to 545.8 | No | ns | 0.1337 |

TABLE 13

Figure 15:
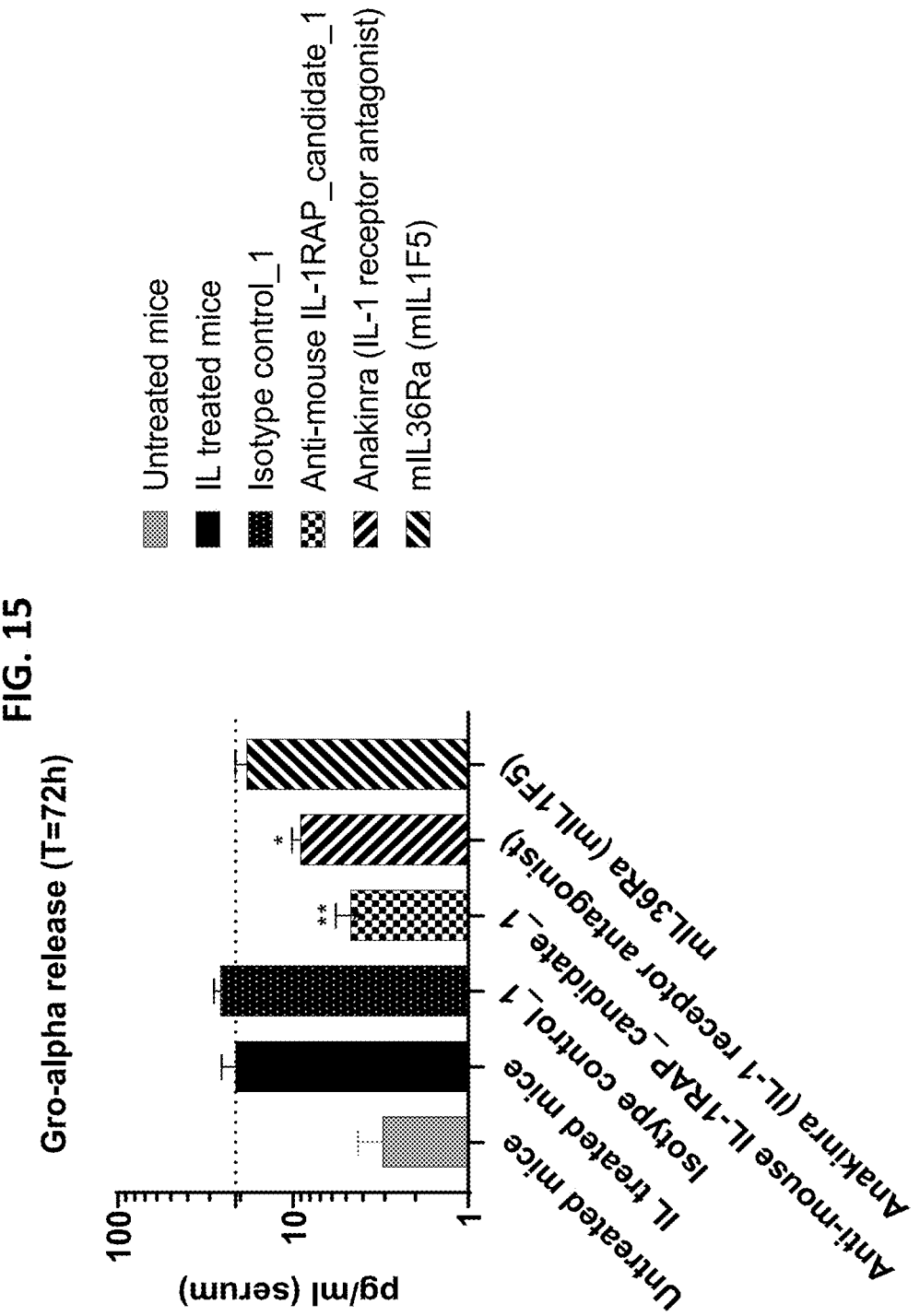
FIG. 15 shows that anti-mouse IL-1RAP_candidate_1 inhibits Gro-alpha release in mice serum 72 h post injection of a mix of interleukins mouse IL-1 beta, human IL-33 and mouse IL36 alpha, beta and gamma. C57BL/6JRj mice were injected intraperitoneal with different treatments at day 0, day 1 and day 2. Two hours post treatments injection, mice were injected intraperitoneal with a mix of interleukins (mouse IL-1 beta, human IL-33 and mouse IL36 alpha, beta and gamma). 72 h after the first injection of treatments, mice were euthanized. Mice serum was harvested for LUMINEX® analysis. Quantification of Gro-alpha release. Data from Bcly_5 study.

Statistical analysis of FIG. 15

| Dunnett's multiple comparisons test | Mean Diff. | 95.00% CI of diff. | Significant? | Summary | Adjusted P Value |
|---|---|---|---|---|---|
| IL treated mice vs. Untreated mice | 18.25 | 7.852 to 28.65 | Yes | *** | 0.0003 |
| IL treated mice vs. Isotype control_1 | −4.666 | −15.06 to 5.731 | No | ns | 0.6704 |
| IL treated mice vs. Anti-mouse IL-1RAP_candidate_1 | 16.64 | 6.242 to 27.04 | Yes | *** | 0.0009 |
| IL treated mice vs. Anakinra (IL-1 receptor antagonist) | 12.24 | 1.845 to 22.64 | Yes | * | 0.0162 |

TABLE 13-continued

Statistical analysis of FIG. 15

| Dunnett's multiple comparisons test | Mean Diff. | 95.00% CI of diff. | Significant? | Summary | Adjusted P Value |
|---|---|---|---|---|---|
| IL treated mice vs. mIL36Ra (mIL1F5) | 2.92 | −7.477 to 13.32 | No | ns | 0.933 |

Anti-mouse IL-1RAP_candidate_1 inhibit IL-5 release in mouse serum 24 h and 72 h post interleukins injection and inhibit Gro-alpha release in mouse serum 72 h post interleukins injection. These data confirmed that compared to benchmarks, targeting IL-1RAP allowed the blocking of IL-36, IL-33 and IL1 signaling pathway in vivo.

Example 7: Efficacy of Anti-Mouse IL-1RAP_Candidate_1 in an In Vivo Chronic Inflammation Induced Mouse Model Material and Method
Animal Husbandry In vivo experiments were performed in female 8-9-week-old immune-competent C57BL/6J mice (JR #00664) inbred strain developed by the Jackson Laboratories (Bar Harbor, ME). All mice were maintained under standardized environmental conditions in rodent cages (20±1° C. room temperature, 50±10% relative humidity, 12 hours light dark cycle). Mice received irradiated food and bedding and 0.22 µm-filtered drinking water.

Psoriasis Like Mouse Models

In-life observations and procedures. Mice were weighted three days before the beginning of the study and all along the in life phase. Mice were shaved 48 hours prior to IMQ application. Backs of shaved mice and both ears received daily topical application of 5% IMQ cream (Imiquimod, ALDARA®). IMQ treated skin areas were covered with TEGADERM™ sterile opaque dressing as a means to safeguard the topical application. Treatments were administered on mice through intraperitoneal routes once every three days for all molecules except for Anakinra, injected through intraperitoneal routes every day. Mice were physically examined daily and a PASI (Psoriasis Area and Severity Index) score was applied as follows: Erythema (irritation/reddening of skin) and eschar (scab) formation (1-4 score)/Scaling and lesion severity scale (1-4 score). At the end of the study, dorsal skin was harvested for ex vivo analysis. Histology was performed on dorsal skin.

Mice Samples Preparation for Ex Vivo Experiments

The left side of dorsal skin was cut into 1 cm wide strips (transversal section) prior fixation in 4% Formalin.

Histology Assays

Dorsal skin (4 samples per slide) was stained for hematoxylin. Slides were analyzing using cellSens standard software. Rete pegs formation quantification (named Acanthosis) was done on 4 skin samples per slide per mouse/10 pictures per slide/6 mice per group. Double scoring was performed. Data were analyzed using Excel and GRAPH-PAD PRISM® 8.

Statistical Analysis

Data were analyzed using GRAPHPAD PRISM® 8 software. Statistical analysis performed: one-way analysis of variance (ANOVA) followed by Dunnett's multiple comparison test for multiple comparisons. P<0.05 was considered as statistically significant. Level of significance is represented by asterisks (** for <0.0001; * for 0.0001; ** for 0.001 and * for 0.01).

Results and Conclusions Psoriasis is an inflammatory skin disease with accelerated epidermal cell turnover. Circulating neutrophils migrate to the psoriatic lesions and induce respiratory burst, degranulation, and formation of neutrophil extracellular trap, thereby contributing to the immuno pathogenesis of psoriasis which involves T cell imbalance, keratinocyte proliferation, angiogenesis, and auto-antigen formation. Neutrophil accumulation in the skin is one of the histological characteristics of psoriasis. IL-36, produced and secreted at high level, has a key role in psoriasis form skin disease induced by Imiquimod. IL-36 may promote neutrophil recruitment. IL-36 and IL-1 cooperate to drive psoriasis form skin inflammation though mutual regulation. Efficacy of anti-mouse IL-1RAP_candidate 1 was tested in an in vivo chronic inflammation induced mouse model: Psoriasis-Like Skin Inflammation mouse model.

Backs of shaved mice and both ears received daily topical application of 5% IMQ cream (Imiquimod, ALDARA®). IMQ treated skin areas were covered with TEGADERM™ sterile opaque dressing as a means to safeguard the topical application. Treatments were administered on mice through intraperitoneal routes once every three days for all molecules except for Anakinra, injected through intraperitoneal routes every day. Mice were physically examined daily and a PASI (Psoriasis Area and Severity Index) score applied as follows: Erythema (irritation/reddening of skin) and eschar (scab) formation (1-4 score)/Scaling and lesion severity scale (1-4 score).

At day 10, anti-mouse IL-1RAP_candidate_1 induced a significant decrease of scaling and lesion score (pvalue=0.0141 at 1 mg and pvalue=0.0025 at 250 ug) in Psoriasis-Like Skin Inflammation model (FIG. 16) compared to control group.

TABLE 14

Figure 16:
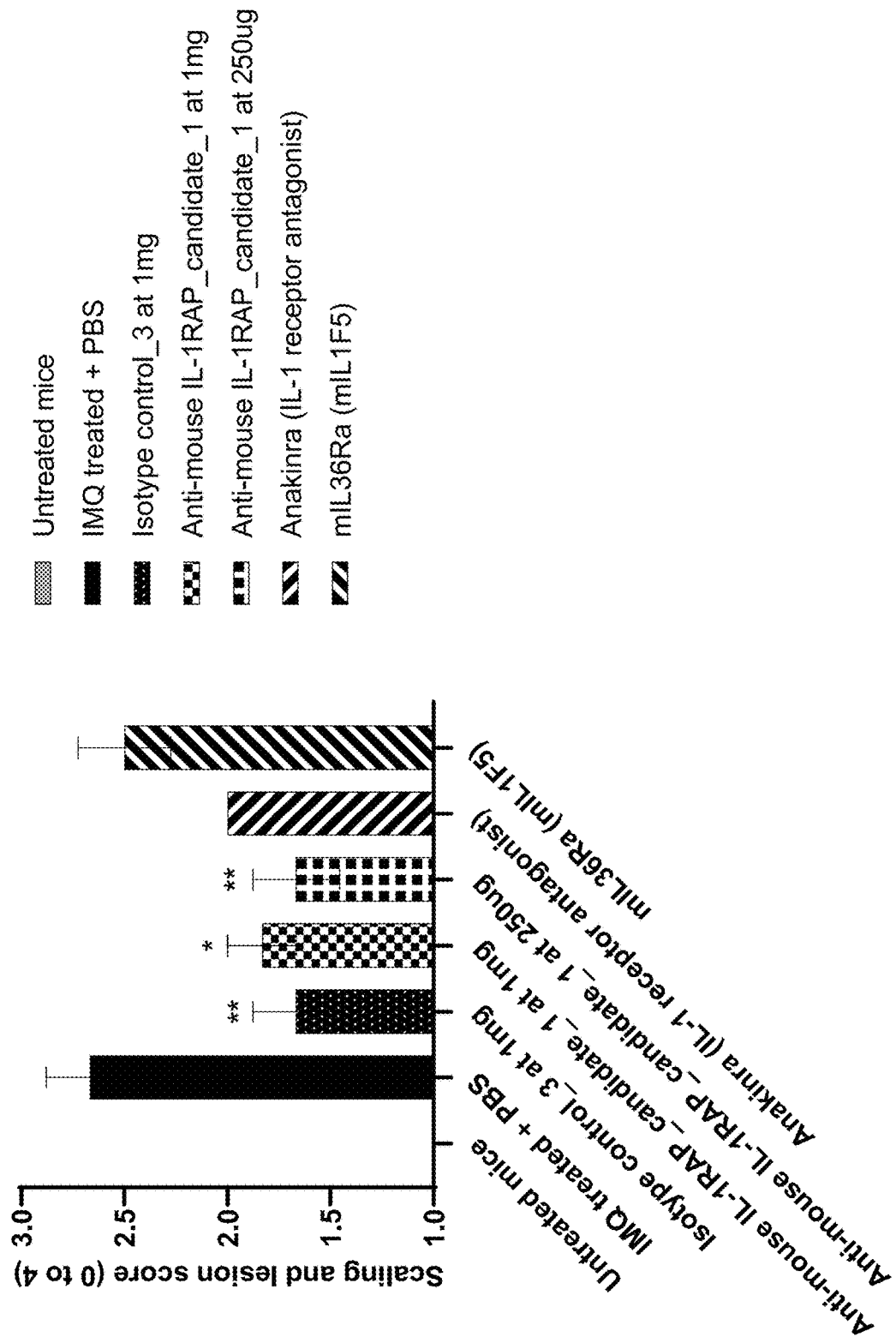
FIG. 16 shows that anti-mouse IL-1RAP_candidate_1 induced a significant decrease of scaling and lesion score in a Psoriasis-Like Skin Inflammation model. Backs of shaved mice and both ears received daily topical application of 5% IMQ cream (Imiquimod, ALDARA®) to dose IMQ for 7 to 14 consecutive days. IMQ treated skin areas were covered with TEGADERM™ sterile opaque dressing as a means to safeguard the topical application. Treatments were administrated on mice through intraperitoneal routes once every three days for all molecules except for Anakinra, injected through intraperitoneal routes every day. Mice were physically examined daily and a PASI (Psoriasis Area and Severity Index) score applied as follows: Erythema (irritation/reddening of skin) and eschar (scab) formation (1-4 score)/Scaling and lesion severity scale (1-4 score). Data from IMQ_s2 study.

Statistical analysis of FIG. 16

| Dunnett's multiple comparisons test | Mean Diff. | 95.00% CI of diff. | Significant? | Summary | Adjusted P Value |
|---|---|---|---|---|---|
| IMQ treated + PBS vs. Untreated mice | 2.667 | 1811 to 3.522 | Yes | **** | <0.0001 |
| IMQ treated + PBS vs. Isotype control_3 at 1 mg | 1 | 0.3015 to 1.699 | Yes | ** | 0.0025 |
| IMQ treated + PBS vs. Anti-mouse IL-1RAP_candidate_1 at 1 mg | 0.8333 | 0.1348 to 1.532 | Yes | * | 0.0141 |
| IMQ treated + PBS vs. Anti-mouse IL-1RAP_candidate_1 at 250 µg | 1 | 0.3015 to 1.699 | Yes | ** | 0.0025 |
| IMQ treated + PBS vs. Anakinra (IL-1 receptor antagonist) | 0.6667 | 0.03187 to 1.365 | No | ns | 0.0661 |
| IMQ treated + PBS vs. mIL36Ra (mIL1F5) | 0.1667 | −0.5319 to 0.8652 | No | ns | 0.9704 |

Histology data demonstrated that anti-mouse IL-1RAP_candidate_1 could inhibit the formation of rete pegs (pvalue=0.0001), also called acanthosis, in Psoriasis-Like Skin Inflammation model (FIGS. 17 and 18) compared to control and isotype group. Significant decrease of acanthosis formation with mIL36Ra (pvalue=0.0006) but not with Anakinra (pvalue=0.0702).

Figure 18A:
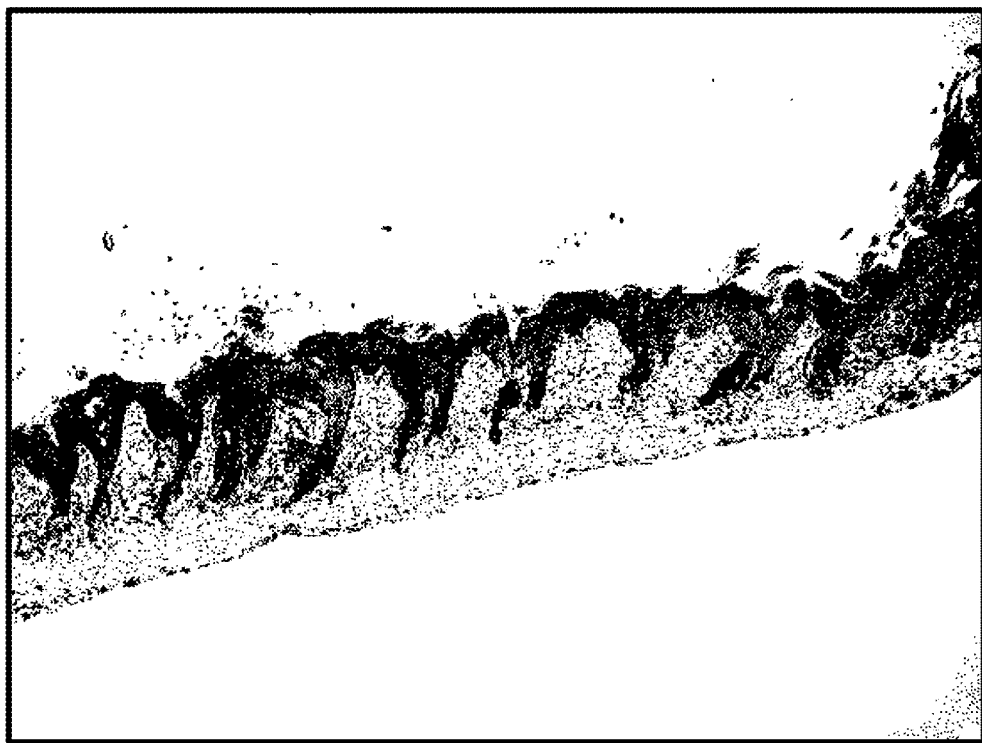
FIG. 18A shows a picture of histology performed on mice dorsal skin treated with Imiquimod and PBS.
Figure 18B:
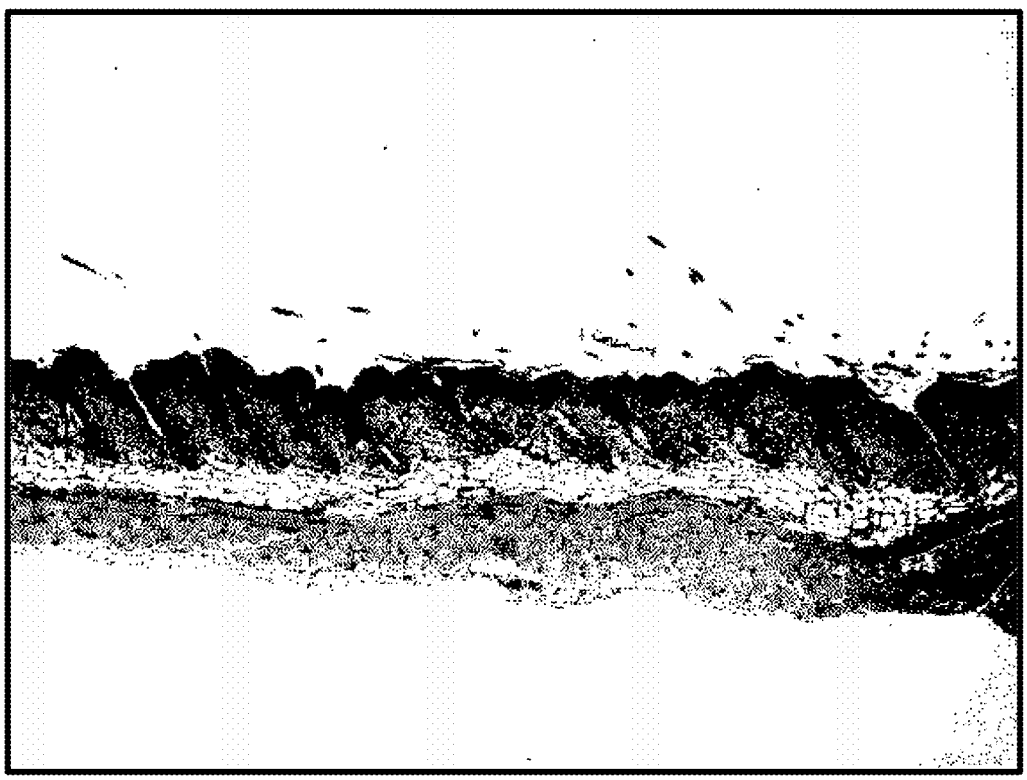
FIG. 18B shows a picture of histology performed on mice dorsal skin treated with Isotype control_3.
Figure 18C:
FIG. 18C shows a picture of histology performed on mice dorsal skin treated with anti-mouse IL-1RAP_candidate_1 at 1 mg.
Figure 18D:
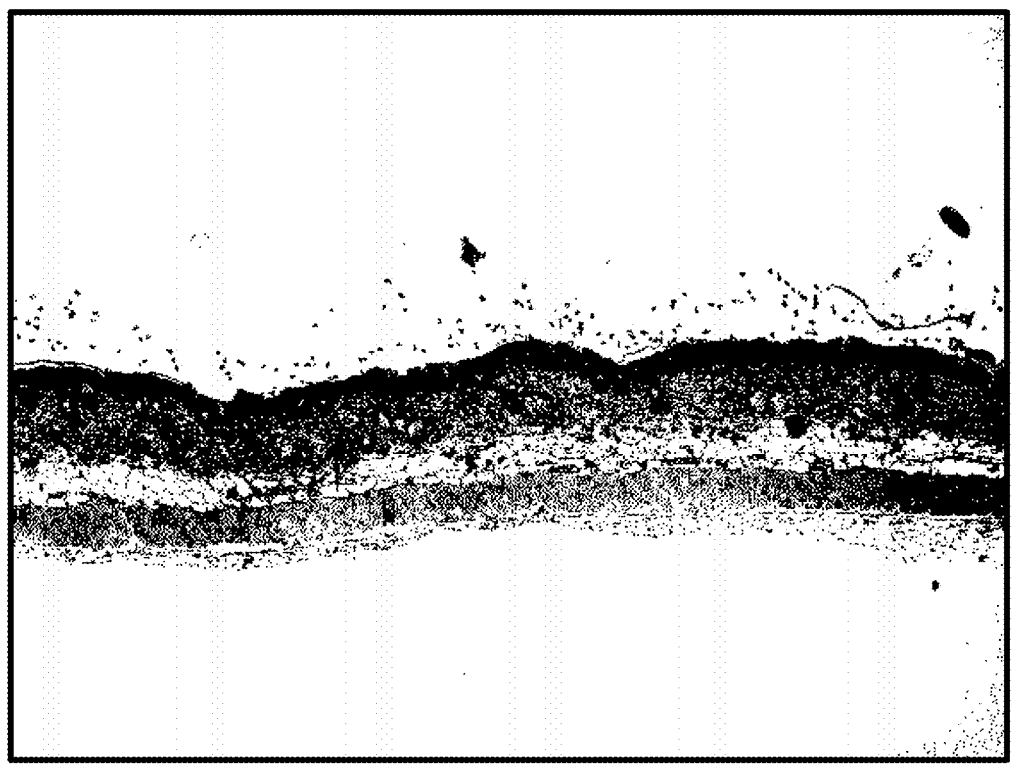
FIG. 18D shows a picture of histology performed on mice dorsal skin treated with anti-mouse IL-1RAP_candidate_1 at at 250 ug.
Figure 18E:
FIG. 18E shows a picture of histology performed on mice dorsal skin treated with Anakinra.
Figure 18F:
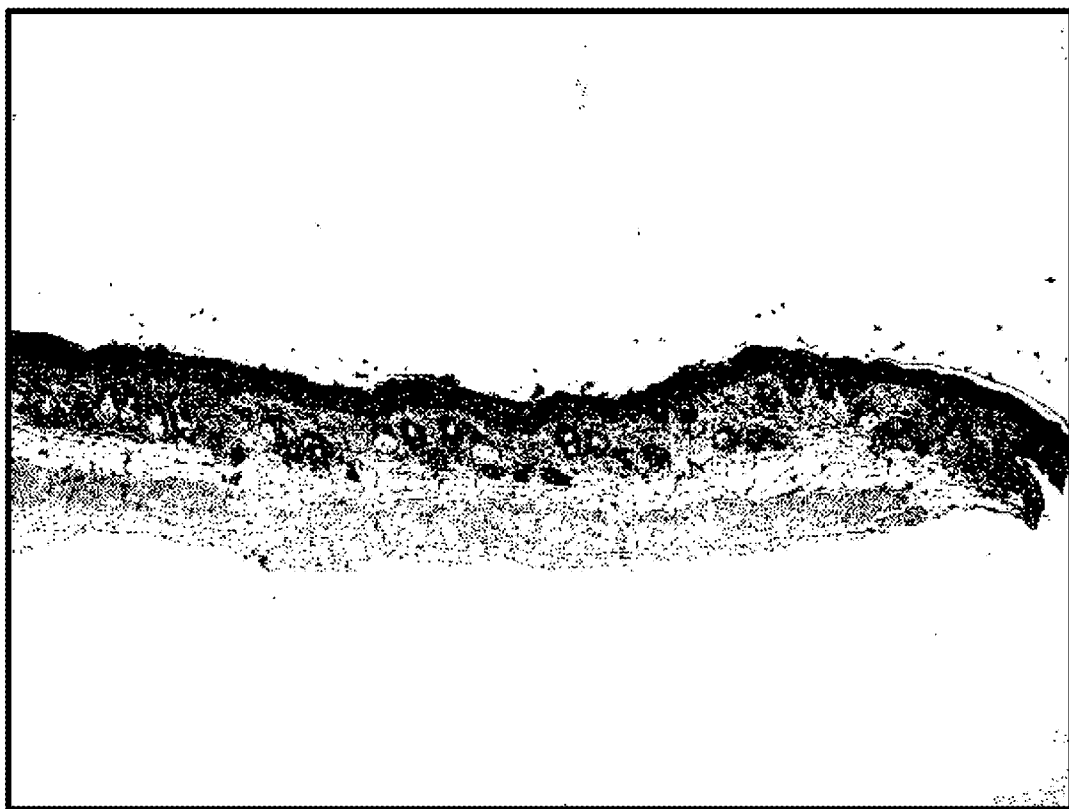
FIG. 18F shows a picture of histology performed on mice dorsal skin treated with mIL36Ra.
Figure 18G:
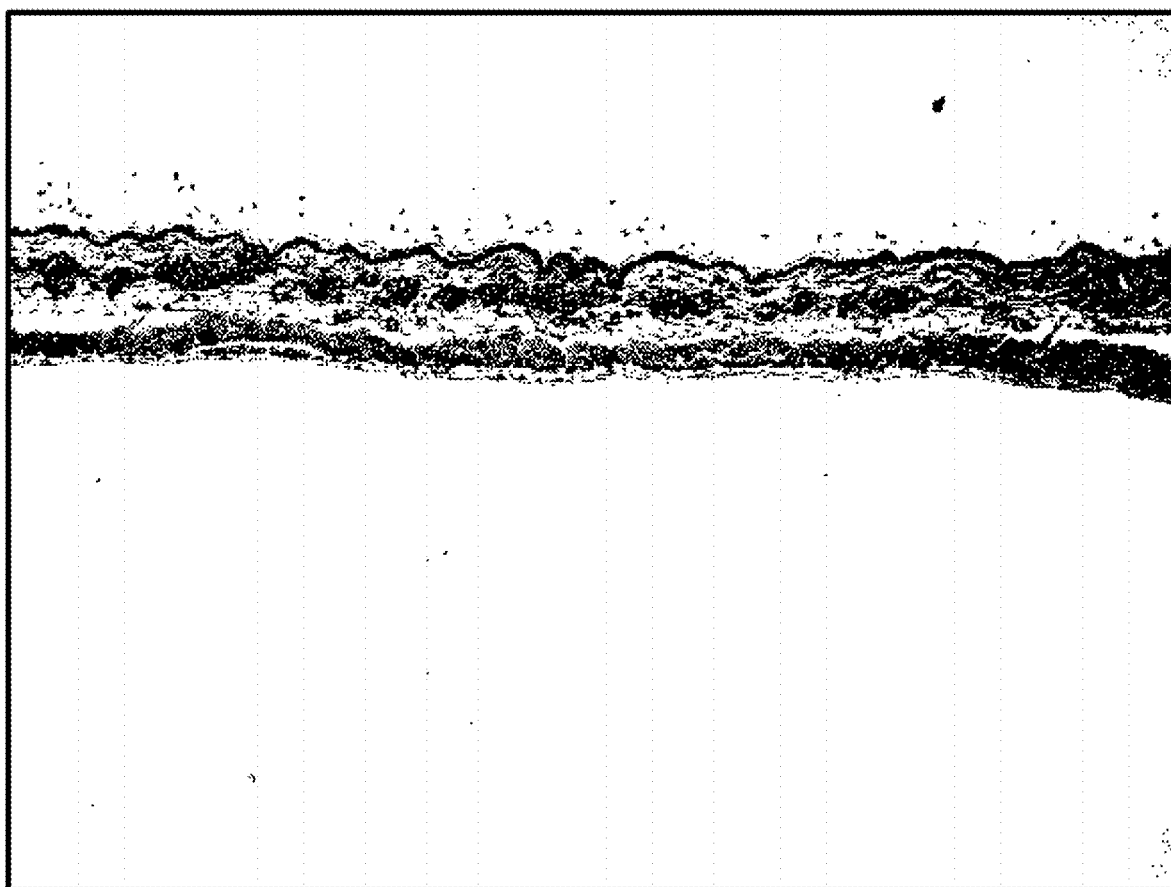
FIG. 18G shows a picture of histology performed on mice dorsal skin of untreated mice. Data from IMQ_s2 study.

Pictures of histology performed on mice dorsal skin are shown in FIGS. 18A, 18B, 18C, 18D, 18E, 18F, and 18G. Briefly mice were treated with Imiquimod and PBS (FIG. 18A), Isotype control_3 (FIG. 18B), Anti-mouse IL-1RAP_candidate_1 at 1 mg (FIG. 18C), Anti-mouse IL-1RAP_candidate_1 at 250 ug (FIG. 18D), Anakinra (FIG. 18E), mIL36Ra (FIG. 18F) or untreated mice (FIG. 18G). Administration of Anti-Mouse IL-1RAP_candidate_1 inhibited neutrophils infiltration in Psoriasis-Like Skin Inflammation mouse model.

Data from IMQ_s2 study.

TABLE 15

Figure 17:
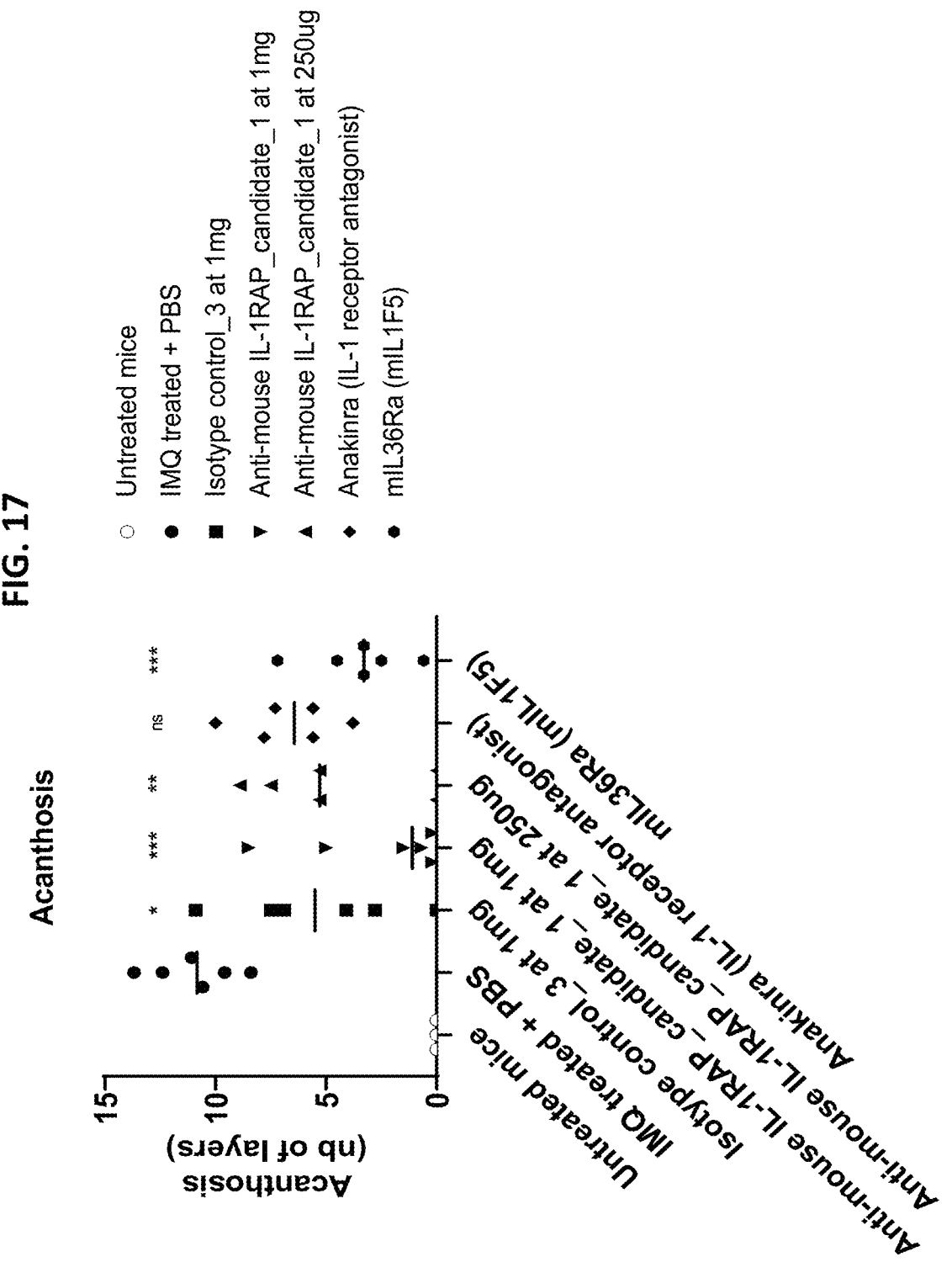
FIG. 17 shows that anti-mouse IL-1RAP_candidate_1 inhibits neutrophil infiltration in a Psoriasis-Like Skin Inflammation mouse model. Backs of shaved mice and both ears received daily topical application 5% IMQ cream (Imiquimod, ALDARA®) to dose IMQ for twelve consecutive days. IMQ treated skin areas were covered with sterile opaque dressing (TEGADERM™) as a means to safeguard the topical application. Treatments were administrated on mice through intraperitoneal routes once every three days for all molecules except for Anakinra, injected through intraperitoneal routes every day. Mice were physically examined daily and a PASI (Psoriasis Area and Severity Index) score applied as follows: Erythema (irritation/reddening of skin) and eschar (scab) formation (1-4 score)/Scaling and lesion severity scale (1-4 score). At the end of the study, IHC was performed on dorsal skin. Acanthosis quantification was done on 4 skin samples per slide per mouse/10 pictures per slide. Data from IMQ_s2 study.

Statistical analysis of FIG. 17

| Dunnett's multiple comparisons test | Mean Diff. | 95.00% Cl of diff. | Significant? | Summary | Adjusted P Value |
|---|---|---|---|---|---|
| IMQ treated + PBS vs. Untreated mice | 10.97 | 5.411 to 16.52 | Yes | **** | <0.0001 |
| IMQ treated + PBS vs. Isotype control_3 at 1 mg | 5.6 | 1.064 to 10.14 | Yes | * | 0.0106 |
| IMQ treated + PBS vs. Anti-mouse IL-1RAP_candidate_1 at 1 mg | 8.283 | 3.747 to 12.82 | Yes | *** | 0.0001 |
| IMQ treated + PBS vs. Anti-mouse IL-1RAP_candidate_1 at 250 µg | 6.467 | 1.930 to 11.00 | Yes | ** | 0.0027 |
| IMQ treated + PBS vs. Anakinra (IL-1 receptor antagonist) | 4.283 | −0.2530 to 8.820 | No | ns | 0.0702 |
| IMQ treated + PBS vs. mIL36Ra (mIL1F5) | 7.4 | 2.864 to 11.94 | Yes | *** | 0.0006 |

Anti-mouse IL-1RAP_candidate 1 inhibit neutrophils infiltration in Psoriasis-Like Skin Inflammation mouse model. These data confirmed that compared to benchmarks, targeting IL-1RAP allowed the blocking of IL-36, IL-33 and IL1 signalling pathway in vivo.

Example 8: In Vitro Biological Characterization of Anti-Human IL-1RAP_Candidate_1

Anti-human IL-1RAP_candidate_1 inhibits cytokine release in whole blood restimulation assay upon IL-1 stimulation in a dose-dependent manner. While previous assays enabled the assessment of the ability of anti-human IL-1RAP_candidate_1 to inhibit the combined pathways mediated by IL1RAP in the context of whole blood assay, here separated IL-1α or IL-1P were used to assess the ability of anti-human IL-1RAP_candidate_1 to inhibit IL-1 stimulated pathways and determine the Half maximal effective concentration (or EC50) of inhibition.

Materials and Methods

Freshly harvested human blood from healthy donors (Citrate tubes) were distributed in 15 ml-tubes and pre-incubated with either media alone (RPMI), serial dilutions of anti-human IL-1RAP_candidate_1 ranging from 25 ug/ml to 0.00032 µg/mL, or Isotype control_4 (25 µg/ml) for 30 min before stimulation with 5 ng/ml of IL-1α or 5 ng/ml of IL-1P to a final volume of 0.6 ml. After 24 hrs incubation at 37° C., 5% C02, supernatants were harvested. Production of various cytokines and chemokines in the culture supernatants was measured with LUMINEX® using multiple ProcartaPlex kit (THERMO FISHER SCIENTIFIC®, 9-plex kit) following manufacturers' instructions. The analytes quantification was normalized to stimulation index:

Stimulation Index (Sample), $(SI)\_X = ((Cytokine\ release)\_X$ $(Sample)/((Average\ Cytokine\ release)\_X\ (Unstimulated\ blood))$ Stimulation Index (Stimulated/Unstimulated blood) below 3 (3-fold compared to baseline) were excluded for the determination of percentage of inhibition.

% Inhibition (Sample) =

$(1 - ((SI)\_X\ (Sample) - (SI)\_X\ Average\ (Unstimulated\ blood))/$ $((Average\ SI)\_X\ (Stimulated) -$ $(Average\ SI)\_X\ (Unstimulated\ blood))) \times 100$ Where "×" is the cytokine/chemokine considered, "Stimulated" corresponds to the values obtained for the whole blood pre-incubated with Isotype control then Cytokine X and "Unstimulated blood" corresponds to the values obtained for the whole blood without any stimulation. Each calculation is donor and cytokine specific.

Half maximal effective concentration (EC50) values were extracted from nonlinear sigmoidal regression. Sufficient stimulation conditions (Stimulation Index>3) and curves showing sufficient goodness of fit ($R^2$>0.7 and Span>50%) were included in the summary table.

Three independent experiments were performed with a total of 15 donors tested. The Table in FIG. 19B and Table 16 described the number of included donors showing sufficient stimulation conditions (Stimulation Index>3).

Figure 19A:
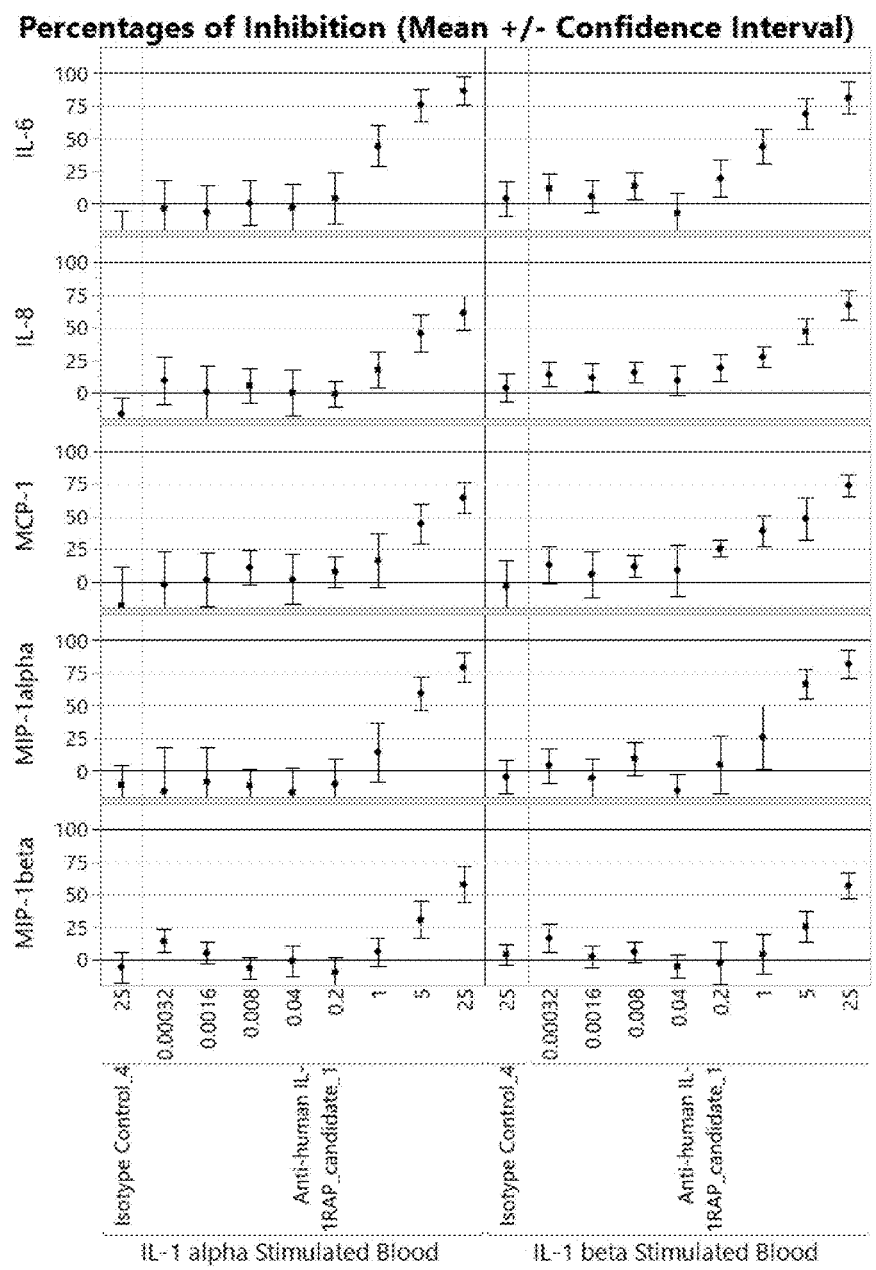
FIG. 19A shows a dose-response of anti-human IL-1RAP_candidate 1 (•) or a maximum dose of Isotype control_4 (■) incubated in human whole blood with 5 ng/ml of IL-1α or 5 ng/ml of IL-1β. The graphs show the inhibitory effect of anti-human IL-1RAP_candidate_1 on each readout. Each point is the mean of percentages of inhibition +/− Confidence Interval for donors that have shown stimulation index superior to 3-fold compared to baseline (SI>3). Three independent experiments were performed with a total of 15 donors tested.

Results depicted in FIGS. 19A and 19B and table 16 show that anti-human IL-1RAP_candidate_1 demonstrates a concentration dependent inhibition IL-6, IL-8, MCP-1, MIP-1a and MIP-1(releases following stimulation with IL-1α or IL-113 in a human whole blood restimulation assay with a mean EC50 in the nanomolar range for both IL-1α and IL-1β.

TABLE 16

| STIMULATION | READOUT | N Included donors | Mean $EC_{50}$ +/− SD |
|---|---|---|---|
| IL-1alpha | IL-6 | 11/13 | 9.5 +/− 8.6 nM |
| IL-1alpha | IL-8 | 4/11 | 14.2 +/− 7 nM |
| IL-1alpha | MCP-1 | 5/10 | 11.1 +/− 13.5 nM |
| IL-1alpha | MIP-1alpha | 6/8 | 15 +/− 14 nM |
| IL-1alpha | MIP-1beta | 7/10 | 89 +/− 153.8 nM |
| IL-1beta | IL-6 | 12/15 | 8.8 +/− 7.7 nM |
| IL-1beta | IL-8 | 9/15 | 24.7 +/− 22.3 nM |
| IL-1beta | MCP-1 | 4/10 | 17.7 +/− 21.1 nM |
| IL-1beta | MIP-1alpha | 8/10 | 16 +/− 23.8 nM |
| IL-1beta | MIP-1beta | 6/11 | 53.3 +/− 49.9 nM |

A dose-response of anti-human IL-1RAP_candidate 1 or a maximum dose of Isotype control_4 were incubated in human whole blood with 5 ng/ml of IL-1α or 5 ng/ml of IL-1β.

Table 16 displays the EC50 of inhibition for all included donors for each stimulation and each readout. ECx values were extracted from nonlinear sigmoidal regression. Sufficient stimulation conditions (Stimulation Index>3) and curves showing sufficient goodness of fit ($R^2$>0.7 and Span>50%) were included in the summary table. Three independent experiments were performed with a total of 15 donors tested. X/Y represent the X donors in which the anti-human IL-1RAP_candidate_1 show inhibition amongst the Y donors that responded to the IL-1 stimulation.

In auto-immune disorders, the anti-human IL-1RAP_candidate_1 could down modulate the IL-1 driven inflammatory response that amplifies pathogenic cytokine production and exacerbates disease pathophysiology.

Data were also generated using IL-12/IL-33 and IL-36α/IL-36β/IL-36γ as stimulators and show dose dependent modulation of cytokine and chemokine releases (data not shown).

The invention claimed is:

1. An anti-IL1RAP antibody comprising a first heavy chain CDR region (CDR-H1), a second heavy chain CDR region (CDR-H2), and a third heavy chain CDR region (CDR-H3), wherein:
   (a) CDR-H1 comprises the amino acid sequence of SEQ ID NO: 128;
   (b) CDR-H2 comprises the amino acid sequence of SEQ ID NO: 188; and
   (c) CDR-H3 comprises the amino acid sequence of SEQ ID NO: 248, and wherein said anti-IL1RAP antibody comprises a light chain variable region comprising the amino acid sequence of SEQ ID NO: 268.

2. The antibody of claim 1, wherein said antibody comprises a heavy chain variable region comprising the amino acid sequence of SEQ ID NO: 58.

3. The antibody of claim 1, wherein said antibody binds to human IL1RAP with a binding affinity from $1 \times 10^{-8}$ M to $10^{-13}$ M.

4. The antibody of claim 1, wherein said antibody decreases an IL-1 stimulated signal, an IL-33 stimulated signal, and/or an IL-36 stimulated signal by at least 90%, at least 95%, at least 99%, or 100%; wherein the decrease in signal is measured by a cell-based blocking assay.

5. The antibody of claim 1, wherein said antibody cross-reacts with a cynomolgus monkey IL1RAP polypeptide of SEQ ID NO: 2.

6. The antibody of claim 1, wherein said antibody cross-reacts with a mouse IL1RAP polypeptide of SEQ ID NO: 261.

7. The antibody of claim 1, wherein said antibody is a full-length antibody of class IgG and in particular wherein the class IgG antibody has an isotype selected from lgG1, lgG2, lgG3 and lgG4.

8. The antibody of claim 2, wherein said antibody is a multispecific antibody.

9. The antibody of claim 1, wherein the antibody specifically binds to one or more amino acid residues within domain 2 of IL1RAP.

10. The antibody of claim 3, wherein the binding affinity is measured by equilibrium dissociation constant (KD) to human IL1RAP polypeptide of SEQ ID NO: 1 or 6.

11. A pharmaceutical composition comprising an antibody of claim 1 and a pharmaceutically acceptable carrier.

* * * * *